United States Patent
Anthony et al.

(10) Patent No.: US 6,248,756 B1
(45) Date of Patent: *Jun. 19, 2001

(54) INHIBITORS OF FARNESYL-PROTEIN TRANSFERASE

(75) Inventors: Neville J. Anthony, Hatfield; Christopher Dinsmore, Schwenksville; Robert P. Gomez, Perkasie; John H. Hutchinson, Philadelphia; John S. Wai, Harleysville; Theresa M. Williams, Harleysville; Ian M. Bell, Harleysville; Mark W. Embrey, North Wales; Thorsten E. Fisher, Hatfield, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/248,883

(22) Filed: Feb. 11, 1999

Related U.S. Application Data

(62) Division of application No. 08/831,308, filed on Apr. 1, 1997, now Pat. No. 5,891,889.

(60) Provisional application No. 60/014,791, filed on Apr. 3, 1996.

(51) Int. Cl.$^7$ .................... A61K 31/4468; C07D 401/12
(52) U.S. Cl. ............................................. 514/326; 546/210
(58) Field of Search ............................. 514/326; 546/210

(56) References Cited

U.S. PATENT DOCUMENTS

| | | | |
|---|---|---|---|
| 5,159,083 | * 10/1992 | Thurkauf et al. | 548/335.5 |
| 5,478,934 | * 12/1995 | Yuan et al. | 540/546 |
| 5,817,678 | * 10/1998 | Kim et al. | 514/326 |
| 5,965,578 | * 10/1999 | Grham et al. | 514/326 |
| 6,001,835 | * 12/1999 | Dinsmore et al. | 514/255 |

* cited by examiner

*Primary Examiner*—Jane Fan
(74) *Attorney, Agent, or Firm*—J. Antonio Garcia-Rivas; Mark R. Daniel

(57) ABSTRACT

The present invention is directed to compounds which inhibit farnesyl-protein transferas (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

11 Claims, No Drawings

INHIBITORS OF FARNESYL-PROTEIN TRANSFERASE

This is a division of application Ser. No. 08/831,308 filed Apr. 1, 1997 now U.S. Pat No 5,891,889 which claim domestic priority under 119e the provisional application 60/014,791, filed Apr. 3, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biot. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Famesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne etal., *Proc. Natl. Acad. Sci USA*, 87:7541–7545 (1990)). Inhibition of famesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of famesyl-protein transferase (FPTase) have been described in two general classes. The first are analogs of famesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the famesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises piperidine-containing compounds which inhibit the famesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula A:

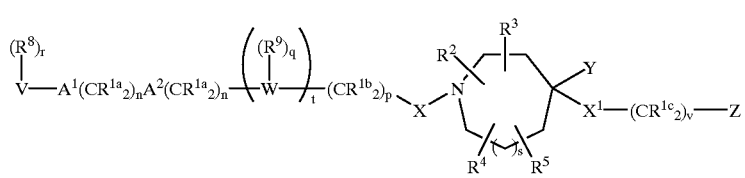

A

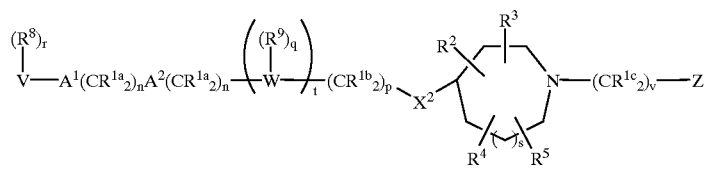

B

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

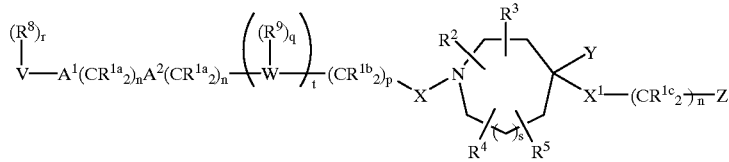

A wherein:

$R^{1a}$ and $R^{1b}$ are independently selected from:
 a) hydrogen,
 b) aryl, heterocycle, $C_3$–$C_{10}$ cycloalkyl, $C_2$–$C_6$ alkenyl, $C_6$–$C_6$ alkynyl, $R^{10}O$—, $R^{11}S(O)_m$—, $R^{10}C(O)NR^{10}$—, $(R^{10})_2N$—$C(O)$—, $CN$, $NO_2$, $(R^{10})_2N$—$C(NR^{10})$—, $R^{10}C(O)$—, $N_3$, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, $CN$, $(R^{10})_2N$—$C(NR^{10})$—, $R^{10}C(O)$—, $N_3$, —$N(R^{10})_2$, and $R^{11}OC(O)$—$NP^{10}$—;

$R^{1c}$ is selected from:
 a) hydrogen,
 b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, $CN$, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—, and
 c) unsubstituted or substituted aryl;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or

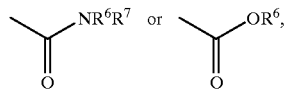

substituted heterocycle, $OR^{10}$, wherein the substituted group is substituted with one or more of:
 1) aryl or heterocycle, unsubstituted or substituted with:
  a) $C_1$–$C_4$ alkyl,
  b) $(CH_2)_pOR^6$,
  c) $(CH_2)_pNR^6R^7$,
  d) halogen,
  e) CN,
  f) aryl or heteroaryl,
  g) perfluoro-$C_{1-4}$ alkyl,
  h) $SR^{6a}$, $S(O)R^{6a}$, $SO_2R^{6a}$,
 2) $C_{3-6}$ cycloalkyl,
 3) $OR^6$,
 4) $SR^{6a}$, $S(O)R^{6a}$, or $SO_2R^{6a}$,
 5) 
  —$NR^6R^7$,
 6) 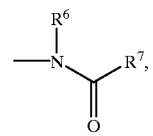

-continued

7) 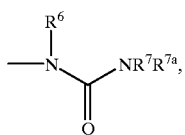

8) 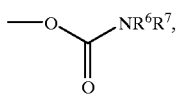

9) 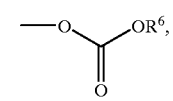

10) 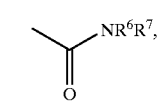

11) —SO$_2$—NR$^6$R$^7$,

12) 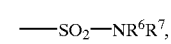

13) 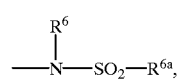

14) 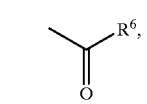

15) N$_3$,

16) F, or 17) perfluoro-C$_{1-4}$-alkyl; or

R$^2$ and R$^3$ are attached to the same C atom and are combined to form (CH$_2$)$_u$—wherein one of the carbon atoms is optionally replaced by a moiety selected from: O, S(O)$_m$, —NC(O)—, and —N(COR$^{10}$)—;

R$^4$ and R$^5$ are independently selected from H and CH$_3$;

and any two of R$^2$, R$^3$, R$^4$ and R$^5$ are optionally attached to the same carbon atom;

R$^6$, R$^7$ and R$^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:

a) C$_{1-4}$ alkoxy,
b) unsubstituted aryl, substituted aryl, unsubstituted heteroaryl or substituted heteroaryl,
c) halogen,
d) HO, e) 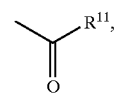

f) —SO$_2$R$^{11}$, or
g) N(R$^{10}$)$_2$; or

R$^6$ and R$^7$ may be joined in a ring;
R$^7$ and R$^{7a}$ may be joined in a ring;
R$^{6a}$ is selected from: C$_{1-4}$ alkyl, C$_{3-6}$ cycloalkyl, heterocycle, aryl, unsubstituted or substituted with:
a) C$_{1-4}$ alkoxy,
b) aryl or heterocycle,
c) halogen,
d) HO, e) 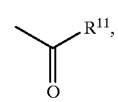

f) —SO$_2$R$^{11}$, or
g) N(R$^{10}$)$_2$;

R$^8$ is independently selected from:
a) hydrogen,
b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$OC(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{10}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_{14}$ alkyl, substituted or unsubstituted benzyl and substituted or unsubstituted aryl;

R$^{11}$ is independently selected from C$_1$–C$_6$ alkyl and substituted or unsubstituted aryl;

R$^{12}$ is selected from: H; unsubstituted or substituted C$_{1-8}$ alkyl, unsubstituted or substituted aryl or unsubstituted or substituted heterocycle, wherein the substituted alkyl, substituted aryl or substituted heterocycle is substituted with one or more of:
1) aryl or heterocycle, unsubstituted or substituted with:
a) C$_{1-4}$ alkyl,
b) (CH$_2$)$_p$OR$^6$,
c) (CH$_2$)$_p$NR$^6$R$^7$,
d) halogen,
e) CN, f) aryl or heteroaryl,
g) perfluoro-$C_{1-4}$ alkyl,
h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,

5) —$NR^6R^7$

6) 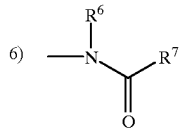

7) 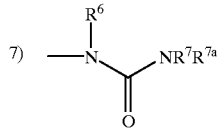

8) 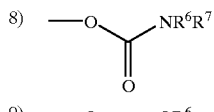

9) 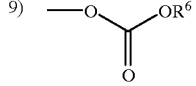

10) 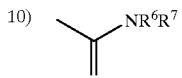

11) —$SO_2$—$NR^6R^7$

12) 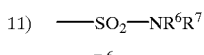

13) 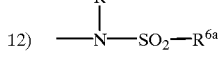

14) 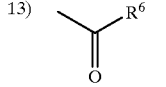

15) $N_3$,
16) F,
17) perfluoro-$C_{1-4}$—alkyl, or
18) $C_{1-6}$—alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or $S(O)_m$;
V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl,
provided that V is not hydrogen if $A^1$ is $S(O)m$ and V is not hydrogen if $A^1$ is a bond, n is 0 and $A^2$ is $S(O)_m$;
W is a heterocycle;
X is a bond, —CH$_2$—, —C(=O)—, —NR$^6$C(=O)—or—S(=O)$_m$—;
$X^1$ is a bond, —C(=O)—, —NR$^6$C(=O)—, —NR$^6$—, —O—or —S(=O)$_m$—;
Y is selected from:

a) hydrogen,
b) $R^{10}O$—, $R^{11}S(O)_m$—, $R^{10}C(O)NR^{10}$—, $(R^{10})_2N$—C(O)—, CN, NO$_2$, $(R^{10})_2N$—C(NR$^{10}$)—, $R^{12}C(O)$—, $R^{10}OC(O)$—, $N_3$, F, —N(R$^{10}$)$_2$, or $R^{11}OC(O)NR^{10}$—, and
c) unsubstituted or substituted $C_1$–$C_6$ alkyl wherein the substitutent on the substituted $C_1$–$C_6$ alkyl is selected from unsubstituted or substituted aryl, $R^{10}O$—, $R^{10}C(O)NR^{10}$—, $(R^{10})_2N$—C(O)—, $R^{10}C(O)$—and $R^{10}OC(O)$—;

Z is an unsubstituted or substituted group selected from aryl and heterocycle, wherein the substituted group is substituted with one or more of the following:
1) $C_{1-4}$ alkyl, unsubstituted or substituted with:
a) $C_{1-4}$ alkoxy,
b) $NR^6R^7$,
c) $C_{3-6}$ cycloalkyl,
d) aryl, substituted aryl or heterocycle,
e) HO,
f) —$S(O)_mR^{6a}$, or
g) -$C(O)NR^6R^7$,
2) aryl or heterocycle,
3) halogen,
4) $OR^6$,
5) $NR^6R^7$,
6) CN,
7) NO$_2$,
8) CF$_3$;
9) —$S(O)_mR^{6a}$,
10) —$C(O)NR^6R^7$, or
11) $C_3$–$C_6$ cycloalkyl;
m is 0,1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1;
u is 4 or 5; and
v is 0,1 or 2;
or a pharmaceutically acceptable salt thereof.

In a second embodiment of this invention, the inhibitors of farnesyl-protein transferase are illustrated by the formula B:

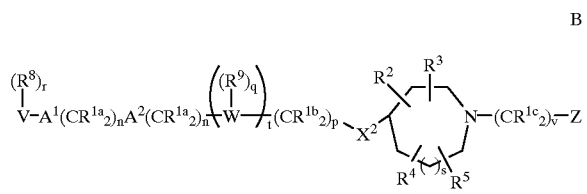

wherein:
$R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, NO$_2$, $(R^{10})_2N$—C(NR$^{10}$)—, $R^{10}C(O)$—, $N_3$, —N(R$^{10}$)$_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C (O)—, CN, $(R^{10})_2N$—C(NR$^{10}$)—, $R^{10}C(O)$—, N$_3$, —N(R$^{10}$)$_2$, and $R^{11}OC(O)$—NR$^{10}$—;

$R^{1c}$ is selected from:
  a) hydrogen,
  b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, N$_3$, —N(R$^{10}$)$_2$, and $R^{11}OC(O)$—NR$^{10}$—, and
  c) unsubstituted or substituted aryl;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or

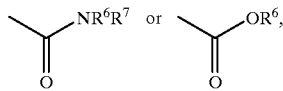

substituted heterocycle, OR$^{10}$,
  wherein the substituted group is substituted with one or more of:
  1) aryl or heterocycle, unsubstituted or substituted with:
    a) $C_{1-4}$ alkyl,
    b) $(CH_2)_pOR^6$,
    c) $(CH_2)_pNR^6R^7$,
    d) halogen,
    e) CN,
    f) aryl or heteroaryl,
    g) perfluoro-$C_{1-4}$ alkyl,
    h) SR$^{6a}$, S(O)R$^{6a}$, SO$_2$R$^{6a}$,
  2) $C_{3-6}$ cycloalkyl,
  3) OR$^6$,
  4) SR$^{6a}$, S(O)R$^{6a}$, or SO$_2$R$^{6a}$, 5) 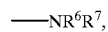

6) 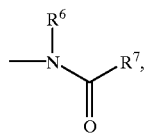

7) 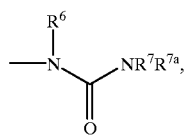

8) 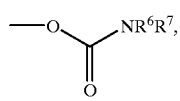

9) 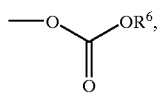

10) 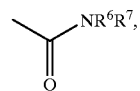

11) —SO$_2$—NR$^6$R$^7$,

12) 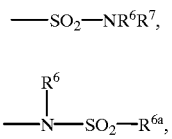

13) 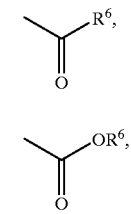

14) 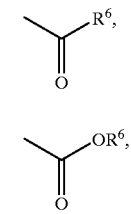

15) N$_3$,

16) F, or 17) perfluoro-$C_{1-4}$-alkyl; or $R^2$ and $R^3$ are attached to the same C atom and are combined to form—(CH$_2$)$_u$—wherein one of the carbon atoms is optionally replaced by a moiety selected from: O, S(O)$_m$, —NC(O)—, and —N(COR$^{10}$)—;

$R^4$ and $R^5$ are independently selected from H and CH$_3$;
  and any two of $R^2$, $R^3$, $R^4$ and $R^5$ are optionally attached to the same carbon atom;

$R^6$, $R^7$ and $R^{7a}$ are independently selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) unsubstituted aryl, substituted aryl, unsubstituted heteroaryl or substituted heterocycle,
  c) halogen,
  d) HO,
  e) 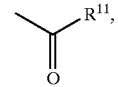
  f) —SO$_2$R$^{11}$ or
  g) N(R$^{10}$)$_2$; or $R^6$ and $R^7$ may be joined in a ring;
$R^7$ and $R^{7a}$ may be joined in a ring;

$R^{6a}$ is selected from: $C_{1-4}$ alkyl, $C_{3-6}$ cycloalkyl, heterocycle, aryl, unsubstituted or substituted with:
  a) $C_{1-4}$ alkoxy,
  b) aryl or heterocycle,
  c) halogen,
  d) HO, e)

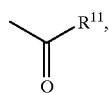

f) —SO$_2$R$^{11}$, or
g) N(R$^{10}$)$_2$;

R$^8$ is independently selected from:
  a) hydrogen,
  b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
  c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:
  a) hydrogen,
  b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
  c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_{14}$ alkyl, substituted or unsubstituted benzyl and substituted or unsubstituted aryl;

R$^{11}$ is independently selected from C$_1$–C$_6$ alkyl and substituted or unsubstituted aryl;

A$^1$ and A$^2$ are independently selected from: a bond, —CH═CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
  a) hydrogen,
  b) heterocycle,
  c) aryl,
  d) C$_1$–C$_{20}$ alkyl wherein from 0 to 4 carbon atoms are replaced with a heteroatom selected from O, S, and N, and
  e) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is a heterocycle;

X$^2$ is a bond, —CH$_2$—, —C(═O)—, —NR$^6$C(═O)—, —C(═O)NR$^6$—, —NR$^6$—, —O— or —S(═O)$_m$—;

Z is an unsubstituted or substituted group selected from aryl and heterocycle, wherein the substituted group is substituted with one or more of the following:

1) C$_{1\text{-}4}$ alkyl, unsubstituted or substituted with:
     a) C$_{1\text{-}4}$ alkoxy,
     b) NR$^6$R$^7$,
     c) C$_{3\text{-}6}$ cycloalkyl,
     d) aryl, substituted aryl or heterocycle,
     e) HO,
     f) —S(O)$_m$R$^{6a}$, or
     g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$;
  9) —S(O)$_m$R$^{6a}$,
  10) —C(O)NR$^6$R$^7$, or
  11) C$_3$–C$_6$ cycloalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1;
u is 4 or 5; and
v is 0, 1 or 2;

or a pharmaceutically acceptable salt thereof.

A preferred embodiment of the compounds of this invention is illustrated by the following formula A:

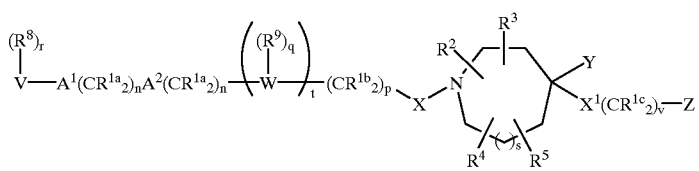

A wherein:
R$^{1a}$ is independently selected from: hydrogen or C$_1$–C$_6$ alkyl;
R$^{1b}$ is independently selected from:
  a) hydrogen,
  b) aryl, heterocycle, cycloalkyl, R$^{10}$O—, —N(R$^{10}$)$_2$ or C$_2$–C$_6$ alkenyl,
  c) unsubstituted or substituted C$_1$–C$_6$ alkyl wherein the substitutent on the substituted C$_1$–C$_6$ alkyl is selected from unsubstituted or substituted aryl, heterocycle, cycloalkyl, alkenyl, R$^{10}$O— and —N(R$^{10}$)$_2$;
R$^{1c}$ is selected from:
  a) hydrogen,
  b) unsubstituted or substituted C$_1$–C$_6$ alkyl wherein the substitutent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—, and
  c) unsubstituted or substituted aryl;

$R^3$, $R^4$ and $R^5$ are independently selected from H and $CH_3$;

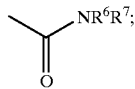

$R^2$ is H; $OR^{10}$,
or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

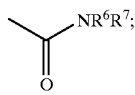

and any two of $R^2$, $R^3$, $R^4$, and $R^5$ are optionally attached to the same carbon atom;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}O$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$R^{12}$ is selected from: H; unsubstituted or substituted $C_{1-8}$ alkyl, unsubstituted or substituted aryl or unsubstituted or substituted heterocycle,
wherein the substituted alkyl, substituted aryl or substituted heterocycle is substituted with one or more of:
1) aryl or heterocycle, unsubstituted or substituted with:
    a) $C_{1-4}$ alkyl,
    b) $(CH_2)_pOR^6$,
    c) $(CH_2)_pNR^6R^7$,
    d) halogen,
    e) CN,
    f) aryl or heteroaryl,
    g) perfluoro-$C_{1-4}$ alkyl,
    h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$, 5) —$NR^6R^7$ 6) 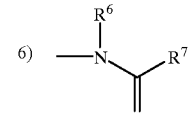

7) 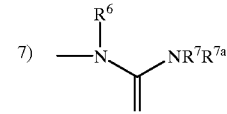

8) 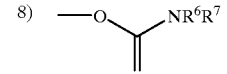

9) 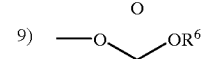

10) 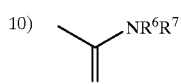

11) 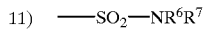—$SO_2$—$NR^6R^7$

12) 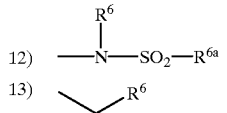—N—$SO_2$—$R^{6a}$

13) 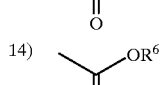

14) 

15) $N_3$,
16) F,
17) perfluoro-$C_{1-4}$—alkyl, or
18) $C_{1-6}$—alkyl;

15) $N_3$,
16) F,
17) perfluoro-$C_{1-4}$-alkyl, or
18) $C_{1-6}$-alkyl;

$A^1$ and $A^2$ are independently selected from: a bond, —CH=CH—, —C≡C—, —C(O)—, —C(O)NR^{10}—, —NR^{10}C(O)—, O, —N(R^{10})—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X is —$CH_2$— or —C(=O)—;

$X^1$ is a bond, —C(=O)—, —$NR^6$C(=O)—, —$NR^6$—, —O— or —$S(=O)_m$—;

Y is selected from:
  a) hydrogen,
  b) $R^{10}$O—, $R^{11}$S(O)$_m$—, $R^{10}$C(O)$NR^{10}$—, $(R^{10})_2$N—C(O)—, CN, $NO_2$, $(R^{10})_2$N—C($NR^{10}$)—, $R^{12}$C(O)—, $R^{10}$OC(O)—, $N_3$, F, —$N(R^{10})_2$, or $R^{11}$OC(O)$NR^{10}$—, and
  c) unsubstituted or substituted $C_1$–$C_6$ alkyl wherein the substitutent on the substituted $C_1$–$C_6$ alkyl is selected from unsubstituted or substituted aryl, $R^{10}$O—, $R^{10}$C(O)$NR^{10}$—, $(R^{10})_2$N—C(O)—, $R^{10}$C(O)— and $R^{10}$OC(O)—;

Z is an unsubstituted or substituted group selected from aryl and heterocycle, wherein the substituted group is substituted with one or more of the following:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl, substituted aryl or heterocycle,
    e) HO,
    f) —S(O)$_m$$R^{6a}$, or
    g) —C(O)$NR^6R^7$,
  2) aryl or heterocycle,
  3) halogen,
  4) $OR^6$,
  5) $NR^6R^7$,
  6) CN,
  7) $NO_2$,
  8) $CF_3$;
  9) —S(O)$_m$$R^{6a}$,
  10) —C(O)$NR^6R^7$, or
  11) $C_3$–$C_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 1; and
v is 0, 1 or 2;

or a pharmaceutically acceptable salt thereof.

In a another preferred embodiment of this invention, the inhibitors of farnesyl—protein transferase are illustrated by the formula B:

a) hydrogen,
b) aryl, heterocycle, cycloalkyl, $R^{10}$O—, —$N(R^{10})_2$ or $C_2$–$C_6$ alkenyl,
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}$O— and —$N(R^{10})_2$;

$R^{1c}$ is selected from:
  a) hydrogen,
  b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}$O—; $R^{11}$S(O)$_m$—, $R^{10}$C(O)$NR^{10}$—, $(R^{10})_2$N—C(O)—, CN, $(R^{10})_2$N—C($NR^{10}$)—, $R^{10}$C(O)—, $R^{10}$OC(O)—, $N_3$, —$N(R^{10})_2$, and $R^{11}$OC(O)—$NR^{10}$—, and
  c) unsubstituted or substituted aryl;

$R^3$, $R^4$ and $R^5$ are independently selected from H and $CH_3$;

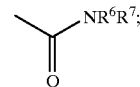

$R^2$ is H;
or $C_{1-5}$ alkyl, unbranched or branched, unsubstituted or substituted with one or more of:
  1) aryl, 2) heterocycle,
  3) $OR^6$,
  4) $SR^{6a}$, $SO_2R^{6a}$, or

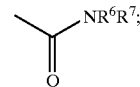

and any two of $R^2$, $R^3$, $R^4$, and $R^5$ are optionally attached to the same carbon atom;

$R^6$, $R^7$ and $R^{7a}$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

$R^8$ is independently selected from:
  a) hydrogen,

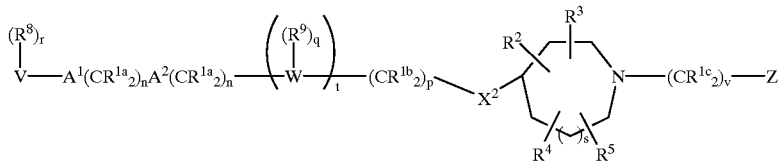

wherein:
$R^{1a}$ is independently selected from: hydrogen or $C_1$–$C_6$ alkyl;
$R^{1b}$ is independently selected from:

b) $C_1$–$C_6$ alkyl, $C_2$–$C_6$ alkenyl, $C_2$–$C_6$ alkynyl, $C_1$–$C_6$ perfluoroalkyl, F, Cl, $R^{10}$O—, $R^{10}$C(O)$NR^{10}$—, CN, $NO_2$, $(R^{10})_2$N—C($NR^{10}$)—, $R^{10}$C(O)—, —$N(R^{10})_2$, or $R^{11}$OC(O)$NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by Cl –$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_{14}$ alkyl, substituted or unsubstituted benzyl and substituted or unsubstituted aryl; $R^{11}$ is independently selected from $C_1$–$C_6$ alkyl and substituted or unsubstituted aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $Al^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

$X^2$ is a bond, —CH$_2$—, —C(=O)—, —NR$^6$C(=O)—, —C(=O)NR$^6$—, —NR$^6$—, —O— or —S(=O)$_m$—;

Z is an unsubstituted or substituted aryl, wherein the substituted aryl is substituted with one or more of the following:
1) $C_{1-4}$ alkyl, unsubstituted or substituted with:
   a) $C_{1-4}$ alkoxy,
   b) NR$^6$R$^7$,
   c) $C_{3-6}$ cycloalkyl,
   d) aryl, substituted aryl or heterocycle,
   e) HO,
   f) —S(O)$_m$R$^{6a}$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^{6a}$,
10) —C(O)NR$^6$R$^7$, or
11) $C_3$–$C_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 1; and
v is 0, 1 or 2;

or a pharmaceutically acceptable salt thereof.

A further preferred embodiment of the compounds of this invention are illustrated by the formula C:

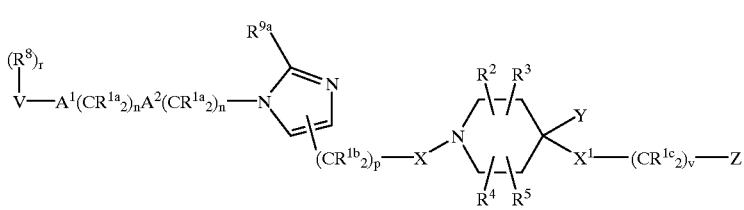

C wherein:

$R^{1a}$ is selected from: hydrogen or $C_1$–$C_6$ alkyl;

$R^{1b}$ is independently selected from:
a) hydrogen,
b) aryl, heterocycle, cycloalkyl, $R^{10}O$—, —$N(R^{10})_2$ or $C_2$–$C_6$ alkenyl,
c) $C_1$–$C_6$ alkyl unsubstituted or substituted by unsubstituted or substituted aryl, heterocycle, cycloalkyl, alkenyl, $R^{10}O$—, or —$N(R^{10})_2$;

$R^{1c}$ is selected from:
a) hydrogen,
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, N$_3$, —$N(R^{10})_2$, and $R^{11}OC(O)$—NR$^{10}$—, and
c) unsubstituted or substituted aryl;

$R^3$ and $R^4$ independently selected from H and CH$_3$;
$R^2$ is selected from H; OR$^{10}$;

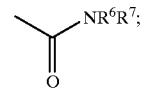

or $C_{1-5}$ alkyl, unbranched or branched, unsubstituted or substituted with one or more of:

1) aryl,
2) heterocycle,
3) OR$^6$,

4) $SR^{6a}$, $SO_2R^{6a}$, or

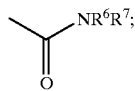

and $R^2$, $R^3$ and $R^4$ are optionally attached to the same carbon atom;

$R^6$ and $R^7$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is selected from: H; unsubstituted or substituted $C_{1-8}$ alkyl, unsubstituted or substituted aryl or unsubstituted or substituted heterocycle, wherein the substituted alkyl, substituted aryl or substituted heterocycle is substituted with one or more of:
1) aryl or heterocycle, unsubstituted or substituted with:
a) $C_{1-4}$ alkyl,
b) $(CH_2)_pOR^6$,
c) $(CH_2)_pNR^6R^7$,
d) halogen,
e) CN,
f) aryl or heteroaryl,
g) perfluoro-$C_{1-4}$ alkyl,
h) $SR^{6a}$, $S(O)R^{6a}$, $SO_2R^{6a}$,
2) $C_{3-6}$ cycloalkyl,
3) $OR^6$,
4) $SR^{6a}$, $S(O)R^{6a}$, or $SO_2R^{6a}$,

5) —$NR^6R^7$,

6) 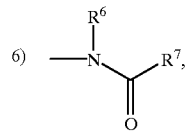

-continued

7) 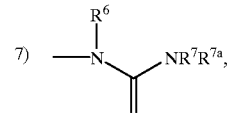

8) 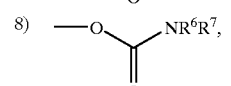

9) 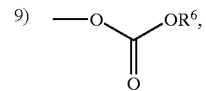

10) 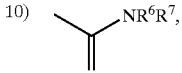

11) —$SO_2$—$NR^6R^7$,

12) 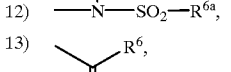

13) 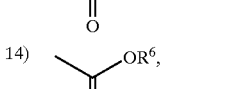

14) 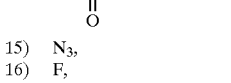

15) $N_3$,
16) F,
17) perfluoro-$C_{1-4}$-alkyl, or
18) $C_{1-6}$-alkyl;

15) $N_3$,
16) F,
17) perfluoro-$C_{1-4}$-alkyl, or 18) $C_{1-6}$-alkyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

X is —$CH_2$— or —C(=O)—;

$X^1$ is a bond, —C(=O)—, —$NR^6C(=O)$—, —$NR^6$—, —O— or —$S(=O)_m$—;

Y is selected from:
:a) hydrogen,
b) $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{12}C(O)$—, $R^{10}OC(O)$—, $N_3$, F, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, $R^{10}O$—, $R^{10}C(O)NR^{10}$—, $(R^{10})_2N$—C(O)—, $R^{10}C(O)$— and $R^{10}C(O)$—;

Z is an unsubstituted or substituted aryl, wherein the substituted aryl is substituted with one or more of the following:

1) C$_{1-4}$ alkyl, unsubstituted or substituted with:
  a) C$_{1-4}$ alkoxy,
  b) NR$^6$R$^7$,
  c) C$_{3-6}$ cycloalkyl,
  d) aryl, substituted aryl or heterocycle,
  e) HO,
  f) —S(O)$_m$R$^{6a}$, or
  g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^{6a}$,
10) —C(O)NR$^6$R$^7$, or
11) C$_3$–C$_6$ cycloalkyl;
m is 0, 1 or 2;
n is 0, 1, 2, 3 or 4;
p is 0, 1, 2, 3 or 4; and
r is 0 to 5, provided that r is 0 when V is hydrogen; and
v is 0, 1 or 2;
or a pharmaceutically acceptable salt thereof.

Another further preferred embodiment of the compounds of this invention are illustrated by the formula D:

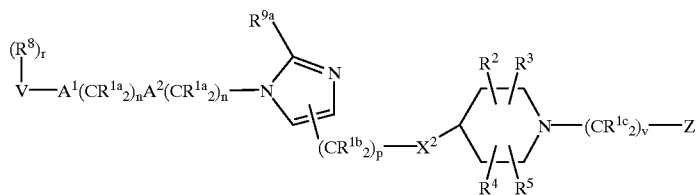

D wherein:

R$^{1a}$ is selected from: hydrogen or C$_1$–C$_6$ alkyl;

R$^{1b}$ is independently selected from:
  a) hydrogen,
  b) aryl, heterocycle, cycloalkyl, R$^{10}$O—, —N(R$^{10}$)$_2$ or C$_2$–C$_6$ alkenyl,
  c) C$_1$–C$_6$ alkyl unsubstituted or substituted by unsubstituted or substituted aryl, heterocycle, cycloalkyl, alkenyl, R$^{10}$O—, or —N(R$^{10}$)$_2$;

R$^{1c}$ is selected from:
  a) hydrogen,
  b) unsubstituted or substituted C$_1$–C$_6$ alkyl wherein the substitutent on the substituted C$_1$–C$_6$ alkyl is selected from unsubstituted or substituted aryl, heterocyclic, C$_3$–C$_{10}$ cycloalkyl, C$_2$–C$_6$ alkenyl, C$_2$–C$_6$ alkynyl, R$^{10}$O—R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—, and
  c) unsubstituted or substituted aryl;

R$^3$ and R$^4$ independently selected from H and CH$_3$;

R$^2$ is selected from H; OR$^{10}$;

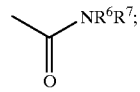

or C$_{1-5}$ alkyl,—unbranched or branched, unsubstituted or substituted with one or more of:
  1) aryl,
  2) heterocycle,
  3) OR$^6$,
  4) SR$^{6a}$, SO$_2$R$^{6a}$, or

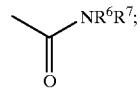

and R$^2$, R$^3$ and R$^4$ are optionally attached to the same carbon atom;

R$^6$ and R$^7$ are independently selected from:
  H; C$_{1-4}$ alkyl, C$_{3-6}$ cycloalkyl, aryl, heterocycle, unsubstituted or substituted with:
  a) C$_{1-4}$ alkoxy,
  b) halogen, or
  c) aryl or heterocycle;

R$^{6a}$ is selected from:
  C$_{1-4}$ alkyl or C$_{3-6}$ cycloalkyl, unsubstituted or substituted with:
  a) C$_{1-4}$ alkoxy,
  b) halogen, or
  c) aryl or heterocycle;

R$^8$ is independently selected from:
  a) hydrogen,
  b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$OC(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ is independently selected from hydrogen, C$_1$–C$_{14}$ alkyl, substituted or unsubstituted benzyl and substituted or unsubstituted aryl;

R$^{11}$ is independently selected from C$_1$–C$_6$ alkyl and substituted or unsubstituted aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

$X^2$ is a bond, —$CH_2$—, —$C(=O)$—, —$NR^6C(=O)$—, —$C(=O)NR^6$—, —$NR^6$—, O—or —$S(=O)_m$—;

Z is an unsubstituted or substituted aryl, wherein the substituted aryl is substituted with one or more of the following:
1) $C_{1-4}$ alkyl, unsubstituted or substituted with:
 a) $C_{1-4}$ alkoxy,
 b) $NR^6R^7$,
 c) $C_{3-6}$ cycloalkyl,
 d) aryl, substituted aryl or heterocycle,
 e) HO,
 f) —$S(O)_mR^{6a}$, or
 g) —$C(O)NR^6R^7$,
2) aryl or heterocycle,
3) halogen,
4) $OR^6$)
5) $NR^6R^7$,
6) CN,
b 7) $N_2$,
8) $CF_3$;
9) —$S(O)_mR^{6a}$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4; and
r is 0 to 5, provided that r is 0 when V is hydrogen; and
v is 0, 1 or 2;
or a pharmaceutically acceptable salt thereof.

In another embodiment of this invention, the inhibitors of farnesyl-protein transferase are illustrated by the formula E:

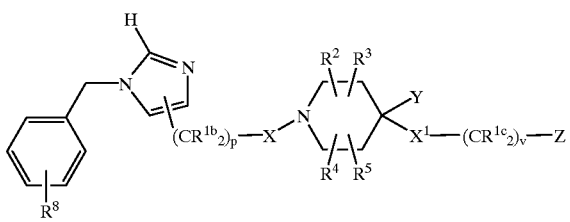

E wherein:
$R^{1b}$ is independently selected from:
 a) hydrogen,
 b) aryl, heterocycle, cycloalkyl, $R^{10}O$—, —$N(R^{10})_2$ or $C_2$–$C_6$ alkenyl,
 c) $C_1$–$C_6$ alkyl unsubstituted or substituted by unsubstituted or substituted aryl, heterocycle, cycloalkyl, alkenyl, $R^{10}O$—, or —$N(R^{10})_2$;
$R^{1c}$ is selected from:
 a) hydrogen,
 b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—, and
 c) unsubstituted or substituted aryl;
$R^3$ and $R^4$ independently selected from H and $CH_3$;
$R^2$ is selected from H; $OR^{10}$;

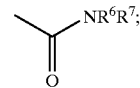

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or

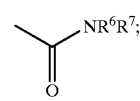

and $R^2$, $R^3$ and $R^4$ are optionally attached to the same carbon atom;
$R^6$, $R^7$ and $R^7a$ are independently selected from:
 H; $C_{1-4}$ alkyl, $C_{3-6}$ cycloalkyl, aryl, heterocycle, unsubstituted or substituted with:
 a) $C_{1-4}$ alkoxy,
 b) halogen, or
 c) aryl or heterocycle;
$R^{6a}$ is selected from:
 $C_{1-4}$ alkyl or $C_{3-6}$ cycloalkyl, unsubstituted or substituted with:
 a) $C_{1-4}$ alkoxy,
 b) halogen, or
 c) aryl or heterocycle;
$R^8$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;
$R^{10}$ is independently selected from hydrogen, $C_1$–$C_{14}$ alkyl, substituted or unsubstituted benzyl and substituted or unsubstituted aryl;
$R^{11}$ is independently selected from $C_1$–$C_6$ alkyl and substituted or unsubstituted aryl;
$R^{12}$ is selected from: H; unsubstituted or substituted $C_{1-8}$ alkyl, unsubstituted or substituted aryl or unsubstituted or substituted heterocycle,
 wherein the substituted alkyl, substituted aryl or substituted heterocycle is substituted with one or more of:
 1) aryl or heterocycle, unsubstituited or substituted with:
  a) $C_{1-4}$ alkyl,
  b) halogen,
  c) CN,
  d) perfluoro-$C_{1-4}$ alkyl,
 2) $C_{3-6}$ cycloalkyl,
 3) $OR^6$, 4) $SR^{6a}$, $S(O)R^{6a}$, or $SO_2R^{6a}$, 5) 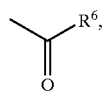

6) 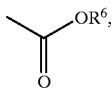

7) $N_3$,

8) F, 9) perfluoro-$C_{1-4}$-alkyl, or

10) $C_{1-6}$-alkyl;

7) $N_3$,
    8) F,
    9) perfluoro-$C_{1-4}$-alkyl, or
    10) $C_{1-6}$-alkyl;

X is —$CH_2$— or —$C(=O)$—;

$X^1$ is a bond, —$C(=O)$— or —$S(=O)_m$—;

Y is selected from:
  a) hydrogen,
  b) $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{12}C(O)$—, $R^{10}OC(O)$—, $N_3$, F, —$N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, $R^{10}O$—, $R^{10}C(O)NR^{10}$—, $(R^{10})_2N$—C(O)—, $R^{10}C(O)$— and $R^{10}OC(O)$—;

Z is an unsubstituted or substituted aryl, wherein the substituted aryl is substituted with one or more of the following:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl, substituted aryl or heterocycle,
    e) HO,
    f) —$S(O)_mR^{6a}$, or
    g) —$C(O)NR^6R^7$,
  2) aryl or heterocycle,
  3) halogen,
  4) $OR^6$,
  5) $NR^6R^7$,
  6) CN,
  7) $NO_2$,
  8) $CF_3$;
  9) —$S(O)_mR^{6a}$,
  10) —$C(O)NR^6R^7$, or
  11) $C_3$–$C_6$ cycloalkyl;

m is 0, 1 or 2;

p is 0, 1, 2, 3 or 4; and

V is 0, 1 or 2;

or a pharmaceutically acceptable salt thereof.

In another embodiment of this invention, the inhibitors of farnesyl-protein transferase are illustrated by the formula F:

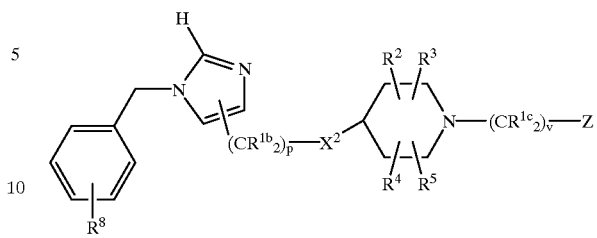

wherein:

$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by unsubstituted or substituted aryl, heterocycle, cycloalkyl, alkenyl, $R^{10}O$—, or —$N(R^{10})_2$;

$R^{1c}$ is selected from:
  a) hydrogen,
  b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}C(O)$—, $N_3$, —$N(R^{10})_2$, and $R^{11}OC(O)$—$NR^{10}$—, and
  c) unsubstituted or substituted aryl;

$R^3$ and $R^4$ independently selected from H and $CH_3$;

$R^2$ is selected from H; $OR^{10}$;

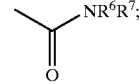

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or

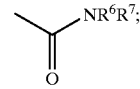

and $R^2$, $R^3$ and $R^4$ are optionally attached to the same carbon atom;

$R^6$, $R^7$ and $R_{7a}$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

R⁸ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$—$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$X^2$ is —$CH_2$—, —$C(=O)$—, —$C(=O)NR^6$— or —NR6—;

Z is an unsubstituted or substituted aryl, wherein the substituted aryl is substituted with one or more of the following:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl, substituted aryl or heterocycle,
    e) HO,
    f) —$S(O)_mR^{6a}$, or
    g) —$C(O)NR^6R^7$,
  2) aryl or heterocycle,
  3) halogen,
  4) $OR^6$,
  5) $NR^6R^7$,
  6) CN,
  7) $NO_2$,
  8) $CF_3$;
  9) —$S(O)_mR^{6a}$,
  10) —$C(O)NR^6R^7$, or
  11) $C_3$–$C_6$ cycloalkyl;

m is 0, 1 or 2;
p is 0, 1, 2, 3 or 4; and
v is 0, 1 or 2;
or the pharmaceutically acceptable salts thereof.

The preferred compounds of this invention are as follows:
N-{[1-(4-Cyanobenzyl)-1H-imidazol-5-yl]methyl}-4-(3-methylphenyl)-4-hydroxy piperidine,
N-{[1-(4-Cyanobenzyl)-1H-imidazol-5-yl]methyl}-4-(3-chlorophenyl)-4 hydroxy piperidine,
N-{[1-(4-Cyanobenzyl)-1H-imidazol-5-yl]methyl}-4-(2-methylbenzyl)isonipecotic acid methyl ester,
N-{[1-(4-Cyanobenzyl)-1H-imidazol-5-yl]methyl }-4-(3-methylphenyl)-4-hydroxy piperidine,
N-{[1-(4-Cyanobenzyl)-1H-imidazol-5-yl]acetyl}-4-(2-methylbenzyl)isonipecotic acid methyl ester,
N-{[1-(4-Cyanobenzyl)-1H-imidazol-5-yl]acetyl}-4-(4-methylbenzyl))isonipecotic acid methyl ester,
N-{[1-(4-Cyanobenzyl)-1H-imidazol-5-yl]acetyl}-4-(3-methylbenzyl))isonipecotic acid methyl ester,
N-{[1-(4-Cyanobenzyl)-1H-imidazol-5-yl]acetyl}-4-(2,4-dichlorobenzyl))isonipecotic acid methyl ester,
N-{[1-(4-Cyanobenzyl)-1H-imidazol-5-yl]acetyl}-4-(3-methoxybenzyl)isonipecotic acid methyl ester,
N-{[1-(4-Cyanobenzyl)-1H-imidazol-5-yl]acetyl]}-4-(I1-naphthylmethyl)isonipecotic acid methyl ester,
N-{[1-(4-Cyanobenzyl)-1H-imidazol-5-yl]acetyl}-4-(4-chlorobenzyl)isonipecotic acid methyl ester,
N-{[1-(4-Cyanobenzyl)-1H-imidazol-5-yl]acetyl}-4-(2,3-dichlorobenzyl)isonipecotic acid methyl ester,
N-{1-(4-Cyanobenzyl)-1H-imidazol-5-yl-aminocarbonyl}-4-(2-methylbenzyl) isonipecotic acid methyl ester,
2(R,S)-N{-2-{[1-(4-Cyanobenzyl)-1H-imidazol-5-yl]2-(4-cyanobenzyl)}acetyl-4-(2-methylbenzyl)-isonipecotic acid methyl ester,
N-{[1-(Naphth-2-ylmethyl)-1H-imidazol-5-yl]acetyl}-4-(2-methylbenzyl)isonipecotic acid methyl ester,
N-{[1-(4-Cyanobenzyl)-1H-imidazol-5-yl]methyl}-4-methoxymethyl-4-(2-methylbenzyl) piperidine,
N-{[1-(4-Cyanobenzyl)-1H-imidazol-5-yl]acetyl}-4-methoxymethyl-4-(2-methylbenzyl) piperidine,
N-{[1-(4-Cyanobenzyl)-1H-imidazol-5-yl]acetyl}-4-hydroxymethyl-4-(2-methylberizyl) piperidine,
N-{[1-(4-Cyanobenzyl)-1H-imidazol-5-yl]ethyl}-4-(2-methylbenzyl)isonipecotic acid methyl ester,
N-{[1-(4-Cyanobenzyl)-1H-imidazol-5-yl]methyl}-trans-4-(3-methylphenyl)-3-hydroxypiperidine,
N-{[1-(4-Cyanohenzyl)-1H-imidazol-5-yl]methyl}-trans-4-(3-methylphenyl)-3 methoxy piperidine,
N-{[1-(4-cyanobenzyl)-1H-imidazol-5-yl]methyl}-trans-4-(3-methylphenyl)-3 benzyloxy piperidine,
1-[2(R,S)-Amino-3-(2-tetradecyloxyphenyl)propyl]-4-(2-methylbenzyl)isonipecotic acid methyl ester,
N-2-(S)-aminolauroyl-4-(1-napthylmethyl) isonipecotic acid methyl ester,
4-(Benzoxazolidin-2-one-1-yl)-1-[1-(4-cyanobenzyl)-5-imidazolylacetyl]piperidine,
4-(1,2-Dihydro-4(H)-3,1 -benzoxazin-2-one-1-yl)-1-[1-(4-cyanobenzyl)-5-imidazolylacetyl]piperidine,
4-(1,2-Dihydro-4(H)-3,1 -benzoxazin-2-one-1-yl)-1-[1-(4-cyanobenzyl)-5-imidazolylmethyl]piperidine,
N-[2-{(4-Cyanobenzyl)-5-imidazolyl}ethyl]-4-carbamoyl-1-phenylpiperidine
4-[2-{1-(4-Cyanobenzyl)-5-imidazolyl}ethyl]-1-phenylpiperidine
4-{5-[4-Hydroxymethyl-4-(3-trifluoromethoxybenzyl)-piperidine-1-ylmethyl]imidazol-1-ylmethyl}benzonitrile
4-{5-[4-Hydroxymethyl-4-(3-trifluoromethoxybenzyl)-piperidine-1-ylmethyl]-2-methylimidazol-1-ylmethyl}benzonitrile
4-{5-[4-Hydroxymethyl-4-(3-trifluoromethylbenzyl)-piperidine-1-ylmethyl]imidazol-1-ylmethyl}benzonitrile
4-{5-[4-Hydroxymethyl-4-(3-trifluoromethylbenzyl)-piperidine-1-ylmethyl]-2-methylimidazol-1-ylmethyl}benzonitrile
4-{5-[4-Hydroxymethyl-4-(2-trifluoromethylbenzyl)-piperidine-1-ylmethyl]imidazol-1-ylmethyl}benzonitrile
4-{5-[4-Hydroxymethyl-4-(2-methylbenzyl)piperidine-1-ylmethyl]imidazol-1-ylmethyl}benzonitrile
4-{5-[4-Hydroxymethyl-4-(3-methylbenzyl)piperidine-1-ylmethyl]imidazol-1-ylmethyl}benzonitrile
4-{-5-[4-Hydroxymethyl-4-(3-methylbenzyl)piperidine-1-ylmethyl]-2-methylimidazol-1-ylmethyl}benzonitrile
4-(5-{2-[4-Hydroxymethyl-4-(3-methylbenzyl)piperidine-1-yl]-2-oxoethyl}imidazol-1-ylmethyl)benzonitrile
4-{-(5-[4-Hydroxymethyl-4-(3-methylbenzyl)piperidine-1-carbonyl]imidazol-1-ylmethyl}benzonitrile
4-{-5-[4-Hydroxymethyl-4-(2-methylbenzyl)piperidine-1-carbonyl]imidazol-1-ylmethyl}benzonitrile
4-{-5-[4-Hydroxymethyl-4-(3-chlorobenzyl)-piperidine-1-ylmethyl]-2-methylimidazol-1-ylmethyl}benzonitrile
4-{5-[4-Hydroxymethyl-4-(2-cyanobenzyl)-piperidine-1-ylmethyl]-2-methylimidazol-1-ylmethyl}benzonitrile
4-{5-[4-Hydroxymethyl-4-(3-cyanobenzyl)-piperidine-1-ylmethyl]-2-methylimidazol-1-ylmethyl}benzonitrile
4-{5-[4-Hydroxymethyl-4-(4-cyanobenzyl)piperidine-1-ylmethyl]-2-methylimidazol-1-ylmethyl}benzonitrile
4-{5-[4-Hydroxymethyl -4-(2,5 -dimethylbenzyl) piperidine-1-ylmethyl1]-2-methylimidazol-1-ylmethyl}benzonitrile 4-{5-[4-Hydroxymethyl-4-(2,5-dichlorobenzyl)piperidine-1-ylmethyl]-2-methylimidazol-1-ylmethyl}benzonitrile
4-{5-[4-Hydroxymethyl-4-(3,5-dimethylbenzyl)piperidine-11-ylmethyl]-2-methylimidazol-1-ylmethyl}benzonitrile
4-(5-{4-Hydroxymethyl-4-[3,5-bis(trifluoromethyl)benzyl]piperidine-1-ylmethyl}-2-methylimidazol-1-ylmethyl)benzonitrile
4-{5-[4-Hydroxymethyl-4-(2,3-dichlorobenzyl)piperidine-1-ylmethyl]-2-methylimidazol-1-ylmethyl}benzonitrile
4-[5-(4-Hydroxymethyl-4-benzylpiperidine-1-ylmethyl)-2-methylimidazol-1-ylmethyl]benzonitrile
4-{5-[4-Hydroxymethyl-4-(3-trifluoromethoxybenzyl)-piperidine-1-ylmethyl]-2-methylimidazol-1-ylmethyl}benzamide
4-{5-[4-Methoxymethyl-4-(3-methylbenzyl)-piperidine-1-ylmethyl]imidazol-1-ylmethyl}benzonitrile
4-{5-[4-Methoxymethyl-4-(3-methylbenzyl)-piperidine-1-ylmethyl]-2-methylimidazol-1-ylmethyl}benzonitrile
4-{5-[4-Methoxymethyl-4-(3-trifluoromethoxybenzyl)-piperidine-1-ylmethyl]imidazol-1-ylmethyl}benzonitrile
4-{5-[4-Methoxymethyl-4-(3-trifluoromethoxybenzyl)-piperidine-1-ylmethyl]-2-methylimidazol-1-ylmethyl}benzonitrile
4-{5-[4-Methoxymethyl-4-(2-trifluoromethoxybenzyl)-piperidine-1-ylmethyl]imidazol-1-ylmethyl}benzonitrile
4-{5-[4-Methoxymethyl-4-(2-trifluoromethoxybenzyl)-piperidine-1-ylmethyl]-2-methylimidazol-1-ylmethyl}benzonitrile
4-{5-[4-Methoxymethyl-4-(3-cyanobenzyl)-piperidine-1-ylmethyl]-2-methylimidazol-1-ylmethyl}benzonitrile
4-(5-{2-[4-Methoxymethyl-4-(3-methylbenzyl)-piperidine-1-yl]-2-oxoethyl}imidazol-1-ylmethyl)benzonitrile
4-{5-[4-Methoxymethyl-4-(3-methylbenzyl)piperidine-1-carbonyl]imidazol-1-ylmethyl}benzonitrile
Methyl 1-[3-(4-cyanobenzyl)-3H-imidazol-4-ylmethyl]-4-(3-methylbenzyl)piperidine-4-carboxylate
Methyl 1-[3-(4-cyanobenzyl)-3H-imidazol-4-ylmethyl]-4-(3-trifluoromethoxybenzyl)piperidine-4-carboxylate
Methyl 1-[3-(4-cyanobenzyl)-2-methyl-3H-imidazol-4-ylmethyl]-4-(3-trifluoromethoxybenzyl)piperidine-4-carboxylate
Methyl 1-[3-(4-cyanobenzyl)-3H-imidazol-4-ylmethyl]-4-(2-trifluoromethoxybenzyl)piperidine-4-carboxylate
Methyl 1-[3-(4-cyanobenzyl)-3H-imidazol-4-ylmethyl]-4-(3-cyanobenzyl)piperidine-4-carboxylate
Methyl 1-[3-(4-cyanobenzyl)-3H-imidazol-4-ylmethyl]-4-[3-(benzyloxycarbonylaminomethyl)benzyl]piperidine-4-carboxylate
Methyl 1-[3-(4-cyanobenzyl)-3H-imidazol-4-ylmethyl]-4-[3-(aminomethyl)benzyl]piperidine-4-carboxylate
Ethyl 1-[3-(4-cyanobenzyl)-2-methyl-3H-imidazol-4-ylmethyl]-4-[3-(methanesulfonylaminomethyl)benzyl]piperidine-4-carboxylate
Ethyl 1-[3-(4-cyanobenzyl)-2-methyl-3H-imidazol-4-ylmethyl]-4-(3-nitrobenzyl)piperidine-4-carboxylate
Ethyl 1-[3-(4-cyanobenzyl)-2-methyl-3H-imidazol-4-ylmethyl]-4-(3-methanesulfonylaminobenzyl)piperidine-4-carboxylate
Ethyl 1-[3-(4-cyanobenzyl)-3H-imidazol-4-ylmethyl]-4-benzylpiperidine-4-carboxylate
Methyl 1-[3-(4-cyanobenzyl)-3H-imidazol-4-ylmethyl]-4-cyclopropylmethylpiperidine-4-carboxylate
Methyl 1-[3-(4-cyanobenzyl)-3H-imidazol-4-ylcarbonyl]-4-(3-methylbenzyl)piperidine-4-carboxylate
Methyl 1-[3-(4-cyanobenzyl)-3H-imidazol4-ylcarbonyl]-4-(2-methylbenzyl)piperidine-4-carboxylate
Methyl 1-[3-(4-cyanobenzyl)-3H-imidazol-4-ylacetyl]-4-(3-trifluoromethoxybenzyl)piperidine-4-carboxylate
Methyl 1-[3-(4-cyanobenzyl)-3H-imidazol-4-ylacetyl]-4-(2-trifluoromethoxybenzyl)piperidine-4-carboxylate
Methyl 1-[3-(4-cyanobenzyl)-3H-imidazol-4-ylacetyl]-4-(3-cyanobenzyl)piperidine-4-carboxylate
Methyl 1-[3-(4-cyanobenzyl)-3H-imidazol-4-ylacetyl]-4-(3-methylbenzyl)piperidine-4-carboxylate
(±)Methyl 2-(n-butyl)-1-[3-(4-cyanobenzyl)-3H-imidazol-4-ylmethyl]-4-(3-methylbenzyl)piperidine-4-carboxylate
1-[3-(4-Cyanobenzyl)-3H-imidazol-4-ylmethyl]-4-(3-methylbenzyl)isonipecotamide
1-[3-(4-Cyanobenzyl)-3H-imidazol-4-ylmethyl]-4-(2-methylbenzyl)isonipecotamide
1-[3-(4-Cyanobenzyl)-3H-imidazol-4-ylacetyl]-4-(3-methyl-benzyl)isonipecotamide
1-[3-(4-Cyanobenzyl)-3H-imidazol-4-ylacetyl]-4-(2-methyl-benzyl)isonipecotamide
1-[3-(4-Cyanobenzyl)-3H-imidazol-4-ylcarbonyl]-4-(3-methyl-benzyl)isonipecotamide
1-[3-(4-Cyanobenzyl)-3H-imidazol-4-ylcarbonyl]-4-(2-methyl-benzyl)isonipecotamide
1-[3-(4-Cyanobenzyl)-3H-imidazol-4-ylmethyl]-4-(3-methylbenzyl)piperidine-4-carbonitrile
1-[3-(4-Cyanobenzyl)-3H-imidazol-4-ylmethyl]-4-(2-methylbenzyl)piperidine-4-carbonitrile
1-[3-(4-Cyanobenzyl)-3H-imidazol-4-ylmethyl]-4-(4-methylbenzyl)piperidine-4-carbonitrile
1-[3-(4-Cyanobenzyl)-2-methyl-3H-imidazol-4-ylmethyl]-4-(3-methylbenzyl)piperidine-4-carbonitrile
1-[3-(4-Cyanobenzyl)-3H-imidazol-4-ylcarbonyl]-4-(3-methylbenzyl)piperidine-4-carbonitrile
1-[3-(4-Cyanobenzyl)-3H-imidazol-4-ylcarbonyl]-4-(2-methylbenzyl)piperidine-4-carbonitrile
1-[3-(4-Cyanobenzyl)-3H-imidazol-4-ylacetyl]-4-(3-methylbenzyl)piperidine-4-carbonitrile
1-[3-(4-Cyanobenzyl)-3H1-imidazol-4-ylacetyl]-4-(2-methylbenzyl)piperidine-4-carbonitrile
1-[3-(4-Cyanobenzyl)-3H-imidazol-4-ylethyl]-4-(3-methylbenzyl)piperidine-4-carbonitrile
1-[3-(4-Cyanobenzyl)-3H-imidazol-4-ylethyl]-4-(2-methylbenzyl)piperidine-4-carbonitrile
4-{5-[4-Hydroxymethyl-4-(4-methylpyridin-2-ylmethyl)-piperidine-1ylmethyl]-2-methylimidazol-1-ylmethyl}benzonitrile
4-{5-[4-Hydroxymethyl-4-(6-methylpyridin-2-ylmethyl)-piperidine-1-ylmethyl]-2-methylimidazol-1-ylmethyl}benzonitrile
4-{5-[4-Hydroxymethyl-4-(2-methylpyridin-4-ylmethyl)-piperidine-1-ylmethyl]-2-methylimidazol-1-ylmethyl}benzonitrile
4-{5-[4-Hydroxymethyl-4-(4-chloropyridin-2-ylmethyl)-piperidine-1-ylmethyl]-2-methylimidazol-1-ylmethyl}benzonitrile
4-{5-[4-Methoxymethyl-4-(6-methylpyridin-2-ylmethyl)-piperidine-1-ylmethyl]imidazol-1-ylmethyl}benzonitrile
4-{5-[4-Hydroxymethyl-4-(6-hydroxypyridin-2-ylmethyl)-piperidine-1-ylmethyl]-2-methylimidazol-1-ylmethyl}benzonitrile
4-[5-(4-Hydroxymethyl-4-quinolin-2-ylmethyl-piperidine-1-ylmethyl)-2-methylimidazol-1-ylmethyl]benzonitrile
Methyl 1-[3-(4-cyanobenzyl)-3H-imidazol-4-ylmethyl]-4-(3-methylbenzoyl)piperidine-4-carboxylate
1-[3-(4-Cyanobenzyl)-3H-imidazol-4-ylmethyl]-4-(3-methylbenzoyl)piperidine
1-[3-(4-Cyanobenzyl)-3H-imidazol-4-ylmethyl]-4-(hydroxy-m-tolylmethyl)piperidine
4-{5-[4-Hydroxymethyl-4-(3-tolylsulfanyl)piperidine-1-ylmethyl]imidazol-1-ylmethyl}benzonitrile 4-{5-[4-Methoxymethyl-4-(3-tolylsulfanyl)piperidine-1-ylmethyl]imidazol-1-ylmethyl}benzonitrile
4-{5-[4-Methoxymethyl-4-(3-tolylsulfinyl)piperidine-1-ylmethyl]imidazol-1-ylmethyl}benzonitrile
4-{5-[4-Methoxymethyl-4-(3-tolylsulfonyl)piperidine-1-ylmethyl]imidazol-1-ylmethyl}benzonitrile
1-[3-(4-Cyanobenzyl)-3H-imidazol4-ylmethyl]-4-(3-methylphenylamino)isonipecotamide
Ethyl 1-[3-(4-Cyanobenzyl)-3H-imidazol-4-ylmethyl]-4-(3-methylphenylamino)piperidine-4-carboxylate
1-[3-(4-Cyanobenzyl)-3H-imidazol-4-ylmethyl]-4-hydroxymethyl-4-(3-methylphenylamino)piperidine
O-{1-[3-(4-Cyanobenzyl)-3H-imidazol-4-ylmethyl]-4-(3-methylphenylamino)piperidyl-4-methyl}carbamate
1-[3-(4-Cyanobenzyl)-3H-imidazol-4-ylmethyl]-4-(3-methylphenylamino)piperidyl-4-methylurea
1-[3-(4-Cyanobenzyl)-3H-imidazol-4-ylmethyl]-4-(3-methylphenylamino)piperidyl-4-methylsulfamide
4-{5-[4-(Hydroxydiphenylmethyl)piperidin-1-ylmethyl]imidazol-1-ylmethyl}benzonitrile
4-{5-[4-(Hydroxydiphenylmethyl)piperidine-1-carbonyl]imidazol-1-ylmethyl}benzonitrile
4-(5-{2-[4-(Hydroxydiphenylmethyl)piperidin-1-yl]-2-oxoethyl-}-3H-imidazol-1-ylmethyl)benzonitrile
1-(Piperidin-4-ylmethyl)-5-(4-cyanobenzyl)imidazole
1-(1-Phenylpiperidin-4-ylmethyl)-5-(4-cyanobenzyl)imidazole
1-(1-(2-Methylphenyl)piperidin-4-ylmethyl)-5-(4-cyanobenzyl)imidazole
1-(1-(2-Chlorobenzoyl)piperidin-4-ylmethyl)-5-(4-cyanobenzyl)imidazole
1-(1-(3-Chlorobenzoyl)piperidin-4-ylmethyl)-5-(4-cyanobenzyl)imidazole
1-(1-(3-Chlorobenzenesulfonyl)piperidin-4-ylmethyl)-5-(4-cyanobenzyl)imidazole
1-(1-(3-Chlorobenzyl)piperidin-4-ylmethyl)-5-(4-cyanobenzyl)imidazole
2-[3-(4-Cyanobenzyl)-3H-imidazol-1-yl]-N-(1-phenylpiperidin-4-yl)acetamide
2-[3-(4-Cyanobenzyl)-3H-imidazol-1-yl]-N-benzyl-N-(1-phenylpiperidin-4-yl)acetamide
2-[3-(4-Cyanobenzyl)-3H-imidazol-1-yl]-N-(1-phenylpiperidin-4-yl)-N-pyridin-4-ylmethylacetamide
2-[3-(4-Cyanobenzyl)-3H-imidazol-1-yl]-N-phenethyl-N-(-phenylpiperidin-4-yl)acetamide
4-{5-[(1-Phenylpiperidin-4-ylamino)methyl]imidazol-1-ylmethyl}benzonitrile
4-(5-{[Benzyl(1-phenylpiperidin-4-yl)amino]methyl}imidazol-1-ylmethyl)benzonitrile
4-(5-{[(1-Phenylpiperidin-4-yl)pyridin-4-ylmethylamino]methyl-}-imidazol-1-ylmethyl)benzonitrile
4-(5-{[Phenethyl(1-phenylpiperidin-4-yl)amino]methyl}imidazol-1-ylmethyl)benzonitrile
4-{5-[2-(1-Phenylpiperidin-4-ylamino)ethyl]imidazol-1-ylmethyl}benzonitrile
4-(5-{2-[Benzyl(1-phenylpiperidin-4-yl)amino]ethyl}imidazol-1-ylmethyl)benzonitrile
2-[3 -(4-Cyanobenzyl)-3H-imidazol-1-yl]-N-(4-cyanobenzyl)-N-(1-phenylpiperidin-4-yl)acetamide
N-(1-Benzylpiperidin-4-yl)-2-[3-(4-cyanobenzyl)-3H-imidazol-4-yl]acetamide and
4{-5-[(1-Benzylpiperidin-4-ylamino)methyl]imidazol-1-ylmethyl}benzonitrile
or a pharmaceutically acceptable salt thereof.

Specific examples of the compounds of the invention are:
N-{[1-(4-Cyanobenzyl)-1H-imidazol-5-yl]methyl}-4-(3-methylphenyl)-4-hydroxy piperidine

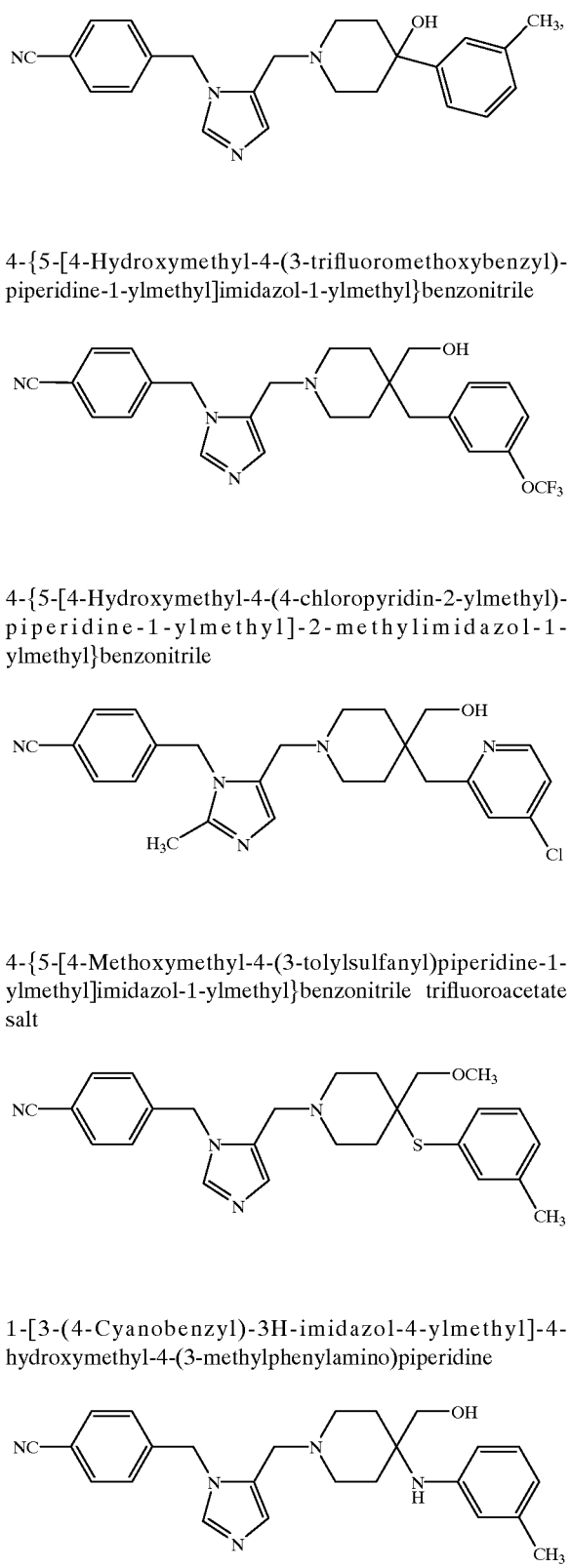

4-{5-[4-Hydroxymethyl-4-(3-trifluoromethoxybenzyl)-piperidine-1-ylmethyl]imidazol-1-ylmethyl}benzonitrile 4-{5-[4-Hydroxymethyl-4-(4-chloropyridin-2-ylmethyl)-piperidine-1-ylmethyl]-2-methylimidazol-1-ylmethyl}benzonitrile 4-{5-[4-Methoxymethyl-4-(3-tolylsulfanyl)piperidine-1-ylmethyl]imidazol-1-ylmethyl}benzonitrile trifluoroacetate salt 1-[3-(4-Cyanobenzyl)-3H-imidazol-4-ylmethyl]-4-hydroxymethyl-4-(3-methylphenylamino)piperidine 1-[3-(4-Cyanobenzyl)-3H-imidazol-4-ylmethyl]-4-(3-methylphenylamino)-piperidyl-4-methylcarbamate

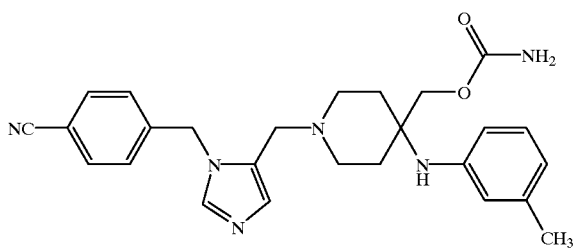

1-(1-(3-Chlorobenzoyl)piperidin-4-ylmethyl)-5-(4-cyanobenzyl)imidazole

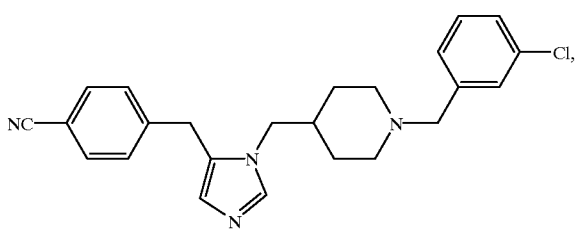

4-{5-[(1-Benzylpiperidin-4-ylamino)methyl]imidazol-1-ylmethyl}benzonitrile

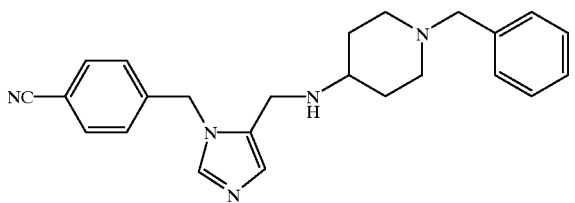

or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurrence is independent at every other occurrence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, benzoxazolidinonyl, benzoxazinonyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein in the definition of $R^6$, $R^7$ and $R^{7a}$, the substituted $C_{1-8}$ alkyl, substituted $C_{3-6}$ alkenyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substitutents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O-$, $-OH$, $(C_1-C_6 \text{ alkyl})S(O)m-$, $(C_1-C_6 \text{ alkyl})C(O)NH-$, $H_2N-C(NH)-$, $(C_1-C_6 \text{ alkyl})C(O)-$, $(C_1-C_6 \text{ alkyl})OC(O)-$, $N_3$, $(C_1-C_6 \text{ alkyl})OC(O)NH-$, phenyl, pyridyl, imidazolyl, oxazolyl, isoxazolyl, thiazolyl, thienyl, furyl, isothiazolyl and $C_1-C_{20}$ alkyl.

When $R^2$ and $R^3$ are combined to form —$(CH_2)_u$—, cyclic moieties are formed. Examples of such cyclic moieties include, but are not limited to:

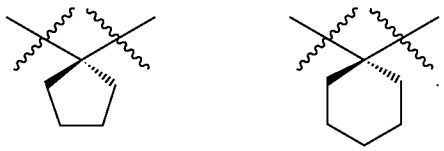

In addition, such cyclic moieties may optionally include a heteroatom(s). Examples of such heteroatom-containing cyclic moieties include, but are not limited to:

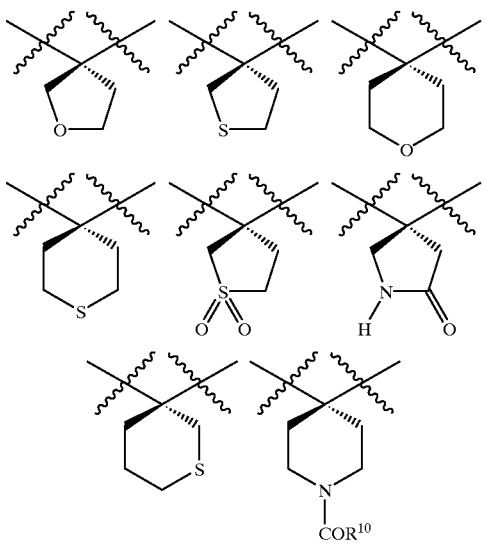

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, —$N(R^{10})_2$, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—. More preferably, $R^{1a}$ and $R^{1b}$ are independently selected from: hydrogen or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^2$ is selected from: H, $OR^{10}$,

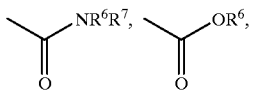

and an unsubstituted or substituted group, the group selected from $C_{1-8}$ alkyl, $C_{2-8}$ alkenyl and $C_{2-8}$ alkynyl;
wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl,
3) $OR^6$,
4) $SR^{6a}$, $S(O)R^{6a}$, $SO_2R^{6a}$,

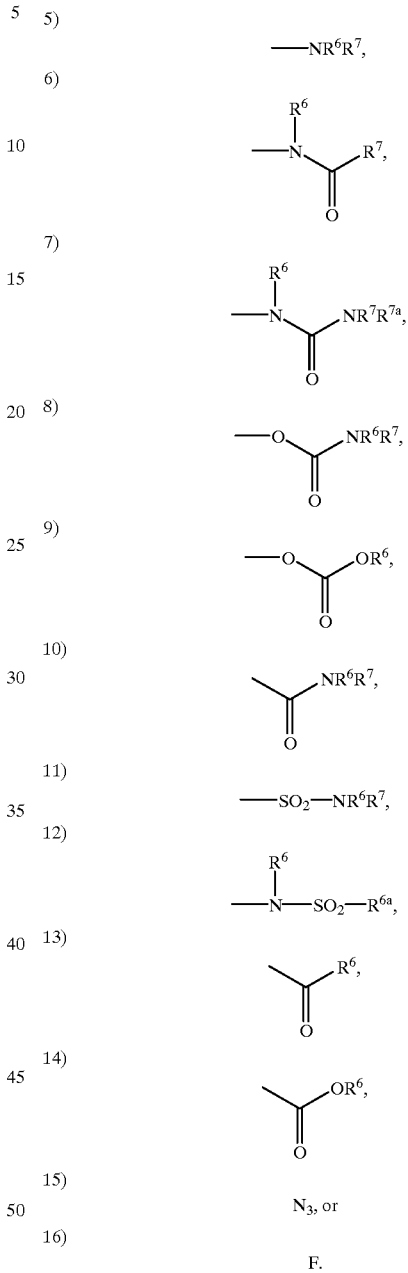

Preferably, $R^3$ is selected from: hydrogen and $C_1$–$C_6$ alkyl.

Preferably, $R^4$ and $R^5$ are hydrogen.

Preferably, $R^6$, $R^7$ and $R^{7a}$ is selected from: hydrogen, unsubstituted or substituted $C_1$–$C_6$ alkyl, unsubstituted or substituted aryl and unsubstituted or substituted cycloalkyl.

Preferably, $R^{6a}$ is unsubstituted or substituted $C_1$–$C_6$ alkyl, unsubstituted or substituted aryl and unsubstituted or substituted cycloalkyl.

Preferably, $R^9$ is hydrogen or methyl. Most preferably, $R^9$ is hydrogen.

Preferably, $R^{10}$ is selected from H, $C_1$–$C_6$ alkyl and substituted and unsubstituted benzyl.

Preferably, $R^{12}$ is selected from: H; unsubstituted or substituted $C_{1-8}$ alkyl, unsubstituted or substituted aryl or unsubstituted or substituted heterocycle, wherein the substituted alkyl, substituted aryl or substituted heterocycle is substituted with one or more of:
1) aryl or heterocycle, unsubstituted or substituted with:
   a) $C_{1-4}$ alkyl,
   b) halogen,
   c) CN,
   d) perfluoro-$C_{1-4}$ alkyl,
2) $C_{3-6}$ cycloalkyl,
3) $OR^6$,
4) $SR^{6a}$, $S(O)R^{6a}$, or $SO_2R^{6a}$, 5) 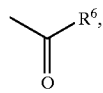

6) 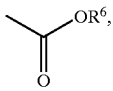

7) 

8) F, 9) perfluoro-$C_{1-4}$-alkyl, or

10) $C_{1-6}$-alkyl.

Preferably, $A^1$ and $A^2$ are independently selected from: a bond, —C(O)$NR^{10}$—, —$NR^{10}$C(O)—, O, —N($R^{10}$)—, —S(O)$_2$N($R^{10}$)— and —N($R^{10}$)S(O)2—.

Preferably, V is selected from hydrogen, heterocycle and aryl. More preferably, V is phenyl.

Preferably, $X^1$ is a bond.

Preferably, $X^2$ is a bond, —CH2—, —C(=O)—, —$NR^6$C(=O)—, —C(=O)$NR^6$— or —S(=O)$_m$—.

Preferably, Y is selected from hydrogen, $R^{10}$O—, $R^{10}$C(O)$NR^{10}$—, ($R^{10}$)$_2$N—C(O)—, $R^{12}$C(O)—, $R^{10}$OC(O)—, —N($R^{10}$)$_2$, and unsubstituted or substituted $C_1$-$C_6$ alkyl. More preferably, Y is $R^{10}$O—, $R^{10}$OC(O)— and unsubstituted or substituted $C_1$-$C_6$ alkyl.

Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Z is unsubstituted or substituted phenyl or unsubstituted or substituted naphthyl.

Preferably, W is selected from imidazolinyl, imidazolyl, oxazolyl, pyrazolyl, pyrrolidinyl, thiazolyl and pyridyl. More preferably, W is selected from imidazolyl and pyridyl.

Preferably, n and r are independently 0, 1, or 2.

Preferably p is 1, 2 or 3.

Preferably s is 0.

Preferably t is 1.

Preferably, the moiety

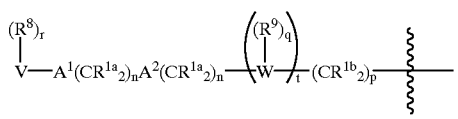

is selected from:

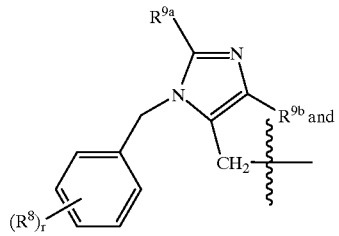

and

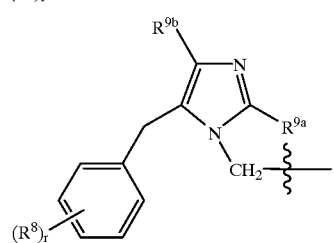

It is intended that the definition of any substituent or variable (e.g., $R^{1a}$, $R^9$, n, etc.) at a particular location in a molecule be independent of its definitions elsewhere in that molecule. Thus, —N($R^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–29, in addition to other standard manipulations such as ester hydrolysis, cleavage of protecting groups, etc., as may be known in the literature or exemplified in the experimental procedures. Substituents $R^a$ and $R^b$, as shown in the Schemes, represent the substituents $R^2$, $R^3$, $R^4$, and $R^5$; substituent "sub" represents a suitable substitutent on the substituent Z. The point of attachment of such substituents to a ring is illustrative only and is not meant to be limiting.

These reactions may be employed in a linear sequence to provide the compounds of the invention or they may be used to synthesize fragments which are subsequently joined by the alkylation reactions described in the Schemes.

Synopsis of Schemes 1–29

The requisite intermediates utilized as starting material in the Schemes hereinbelow are in some cases commercially available, or can be prepared according to literature procedures. In Scheme 1, for example, a suitably substituted Boc protected isonipecotate I may be deprotonated and then treated with a suitably substituted alkylating group, such as a suitably substituted benzyl bromide, to provide the gem disubstituted intermediate III. Deprotection and reduction provides the hydroxymethyl piperidine IV which can be utilized is synthesis of compounds of the invention or which may be nitrogen-protected and methylated to give the intermediate V.

As shown in Scheme 2, the protected piperidine intermediate III can be deprotected and reductively alkylated with aldehydes such as 1-trityl-4-imidazolyl-carboxaldehyde or 1-trityl-4-imidazolylacetaldehyde, to give products such as VI. The trityl protecting group can be removed from VI to give VII, or alternatively, VI can first be treated with an alkyl halide then subsequently deprotected to give the alkylated imidazole VIII.

The deprotected intermediate IIIa can also be reductively alkylated with a variety of other aldehydes, such as IX, as shown in Scheme 3. The aldehydes can be prepared by standard procedures, such as that described by O. P. Goel, U. Krolls, M. Stier and S. Kesten in *Organic Syntheses*, 1988, 67, 69–75, from the appropriate amino acid (Scheme 3). The reductive alkylation can be accomplished at pH 5–7 with a variety of reducing agents, such as sodium triacetoxyborohydride or sodium cyanoborohydride in a solvent such as dichloroethane, methanol or dimethylformamide. The product X can be deprotected with trifluoroacetic acid in methylene chloride to give the final compound XI. The final product XI is isolated in the salt form, for example, as a trifluoroacetate, hydrochloride or acetate salt, among others. The product diamine XI can further be selectively protected to obtain XII, which can subsequently be reductively alkylated with a second aldehyde to obtain XIII. Removal of the protecting group, and conversion to cyclized products such as the dihydroimidazole XV can be accomplished by literature procedures.

Alternatively, the intermediate IIIa can be acylated or sulfonylated by standard techniques. The imidazole acetic acid XIX can be converted to the acetate XXI by standard procedures shown in Scheme 4, and XXI can be first reacted with an alkyl halide, then treated with refluxing methanol to provide the regiospecifically alkylated imidazole acetic acid ester XXII. Hydrolysis and reaction with piperidine IIIa in the presence of condensing reagents such as 1-(3-dimethylaminopropyl)-3-ethylcarbodiimide (EDC) leads to acylated products such as XXIV.

An alternative synthesis of the hydroxymethyl intermediate IV and utilization of that intermediate in the synthesis of the instant compounds which incorporate the preferred imidazolyl moiety is illustrated in Scheme 4a. Scheme 4b illustrates the reductive alkylation of intermediate IV to provide a 4-cyanobenzylimidazolyl substituted piperidine.

The cyano moiety may be selectively oxidized with sodium borate to provide the corresponding amido compound of the instant invention.

Scheme 4c alternative preparation of the methyl ether intermediate V and the alkylation of V with a suitably substituted imidazolylmethyl chloride to provide the instant compound. Preparation of the homologous 1-(imidazolylethyl)piperidine is illustrated in Scheme 4d.

Specific substitution on the piperidine of the compounds of the instant invention may be accomplished as illustrated in Scheme 4e. Thus, metal-halogen exchange coupling of a butynyl moiety to an isonicotinate, followed by hydrogenation, provides the 2-butylpiperidine intermediate that can then undergo the reactions previously described to provide the compound of the instant invention.

Incorporation of a 4-amido moiety for Y is illustrated in Scheme 4f.

If the piperidine IIIa is reductively alkylated with an aldehyde which also has a protected hydroxyl group, such as XXV in Scheme 5, the protecting groups can be subsequently removed to unmask the hydroxyl group (Schemes 5, 6). The alcohol can be oxidized under standard conditions to e.g. an aldehyde, which can then be reacted with a variety of organometallic reagents such as Grignard reagents, to obtain secondary alcohols such as XXIX. In addition, the fully deprotected amino alcohol XXX can be reductively alkylated (under conditions described previously) with a variety of aldehydes to obtain secondary amines, such as XXXI (Scheme 6), or tertiary amines.

The Boc protected amino alcohol XXVII can also be utilized to synthesize 2-aziridinylmethylpiperidine such as XXXII (Scheme 7). Treating XXVII with 1,1'-sulfonyldiimidazole and sodium hydride in a solvent such as dimethylformamide led to the formation of aziridine XXXII. The aziridine reacted in the presence of a nucleophile, such as a thiol, in the presence of base to yield the ring-opened product XXXIII.

In addition, the piperidine IIIa can be reacted with aldehydes derived from amino acids such as O-alkylated tyrosines, according to standard procedures, as shown in Scheme 8, to obtain compounds such as XXXIX. When R' is an aryl group, XXXIX can first be hydrogenated to unmask the phenol, and the amine group deprotected with acid to produce XL. Alternatively, the amine protecting group in XXXIX can be removed, and O-alkylated phenolic amines such as XLI produced.

Scheme 9 illustrates the synthesis of the instant compounds wherein the moiety Z is attached directly to the piperidine ring. Thus the piperidone XLII is treated with a suitably substituted phenyl Grignard reagent to provide the gem disubstituted piperidine XLIII. Deprotection provides the key intermediate XLIV. Intermediate XLIV may be acetylated as described above to provide the instant compound XLV (Scheme 10).

As illustrated in Scheme 11, the protected piperidine XLIII may be dehydrated and then hydroborated to provide the 3-hydroxypiperidine XLVI. This compound may be deprotected and further derivatized to provide compounds of the instant invention (as shown in Scheme 12) or the hydroxyl group may be alkylated, as shown in Scheme 11, prior to deprotection and further manipulation.

The dehydration product may also be catalytically reduced to provide the des-hydroxy intermediate XLVIII, as shown in Scheme 13, which can be processed via the reactions illustrated in the previous Schemes.

Schemes 14 and 15 illustrate further chemical manipulations of the 4-carboxylic acid functionality to provide instant compounds wherein the substituent Y is an acetylamine or sulfonamide moiety.

Scheme 16 illustrates incorporation of a nitrile moiety in the 4-position of the piperdine of the compounds of formula A. Thus, the hydroxyl moiety of a suitably substituted 4-hydroxypiperidine is substituted with nitrile to provide intermediate IL, which can undergo reactions previously described in Schemes 1–8.

Scheme 17 illustrates the preparation of several pyridyl intermediates that may be utilized with the piperdine intermediates such as compound I in Scheme 1 to provide the instant compounds. Scheme 18 shows a generalllized reaction sequence which utilizes such pyridyl intermediates.

Compounds of the instant invention wherein $X^1$ is a carbonyl moiety may be prepared as shown in Scheme 19. Intermediate L may undergo subsequent reactions as illustrated in Schemes 1–8 to provide the instant compounds. Preparation of the instant compounds wherein $X^1$ is sulfur in its various oxidation states is shown in Scheme 20. Intermediates LI–LIV may undergo the previously described reactions to provide the instant compounds.

Scheme 21 illustrated preparation of compounds of the formula A wherein Y is hydrogen. Thus, suitably substituted isonipecotic acid may be treated with N,O-dimethylhydroxylamine and the intermediate LV reacted with a suitably substituted phenyl Grignard reagent to provide intermediate LVI. That intermediate may undergo the reactions previously described in Schemes 1–8 and may be further modified by reduction of the phenyl ketone to provide the alcohol LVII.

Compounds of the instant invention wherein $X^1$ is an amine moiety may be prepared as shown in Scheme 22. Thus the N-protected 4-piperidinone may be reacted with a suitably substituted aniline in the presence of trimethylsilylcyanide to provide the 4-cyano-4-aminopiperidine LVIII. Intermediate LVIII may then be converted in sequence to the corresponding amide LIX, ester LX and alcohol LXI. Intermediates LIX–LXI can be deprotected and can then undergo the reactions previously described in Schemes 1–8 to provide the compounds of the instant invention.

Preparations of compounds of formula B wherein $X^2$ is an amido or an amine moiety are illustrated in Schemes 23, 24 and 25. As is clear from the reaction illustrated, the intermediate LXIII can undergo any of the piperidine nitrogen reactions illustrated in Schemes 1–8 to provide the instant compounds.

Schemes 26–29 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

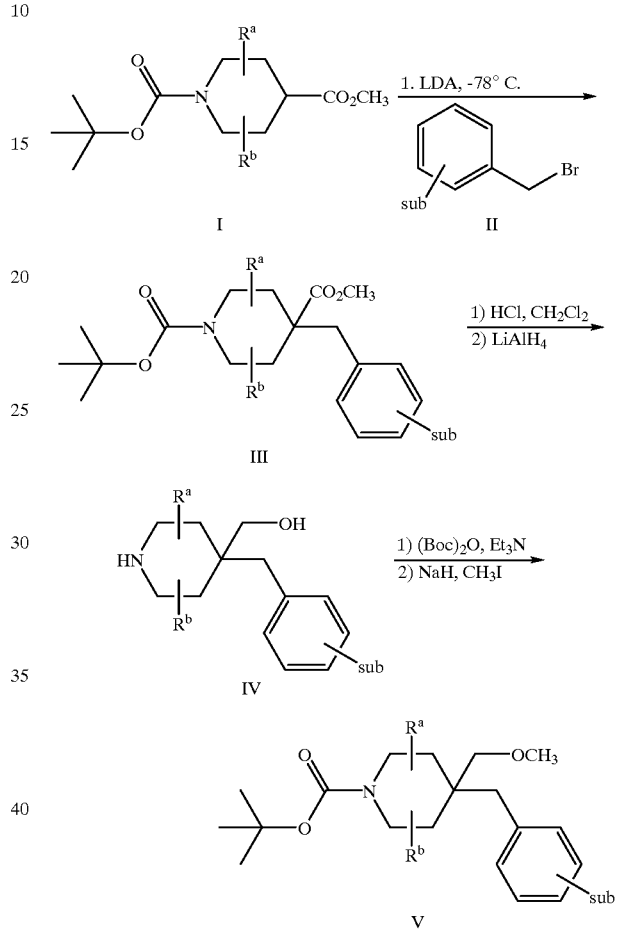

SCHEME 1

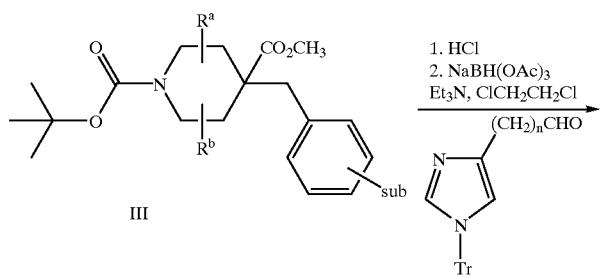

SCHEME 2

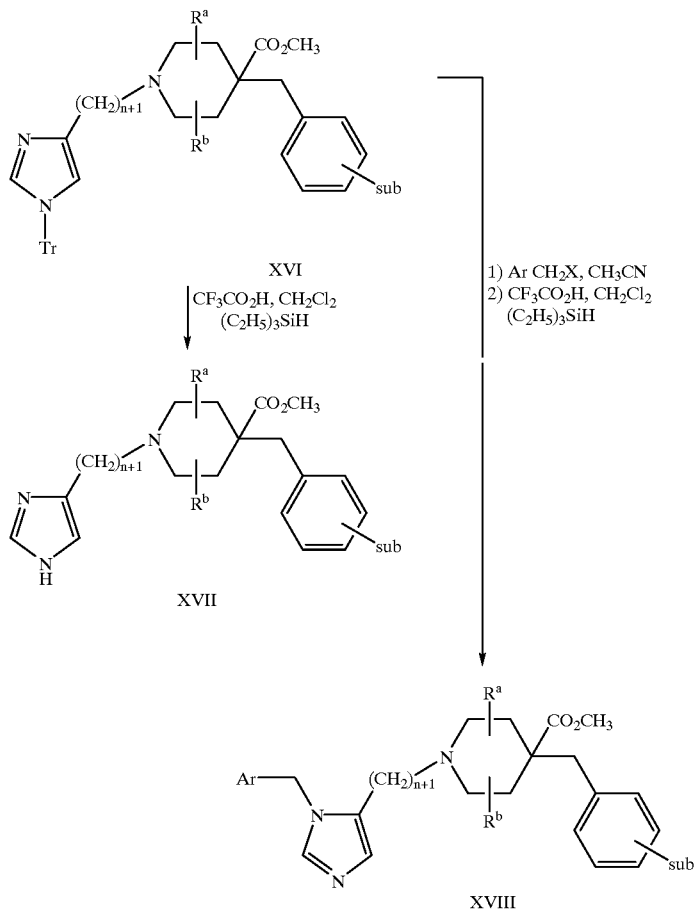
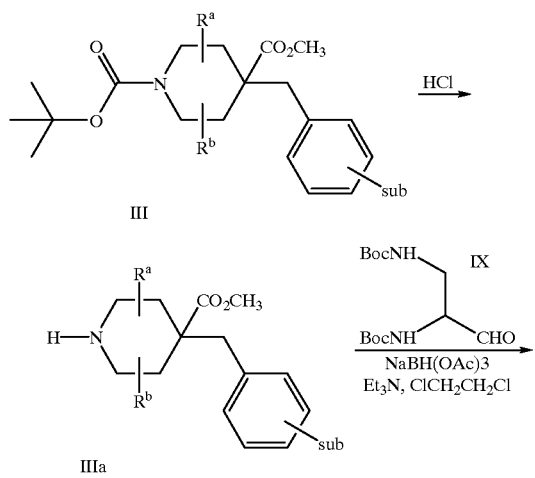
SCHEME 3
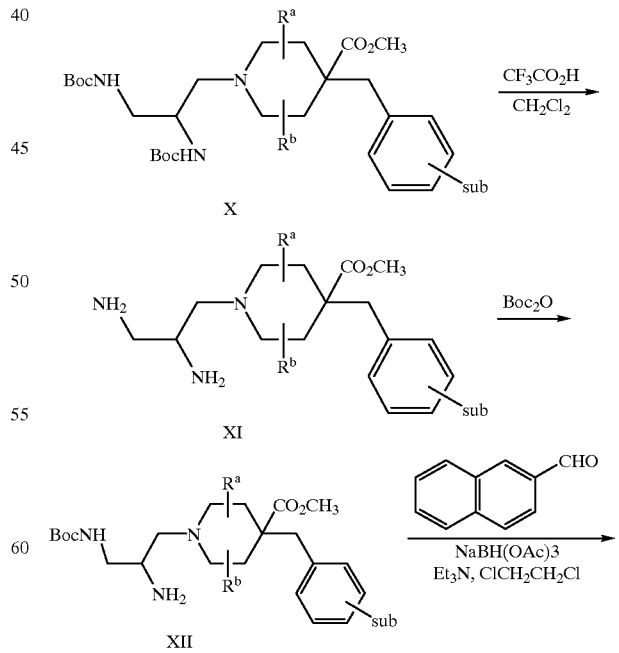

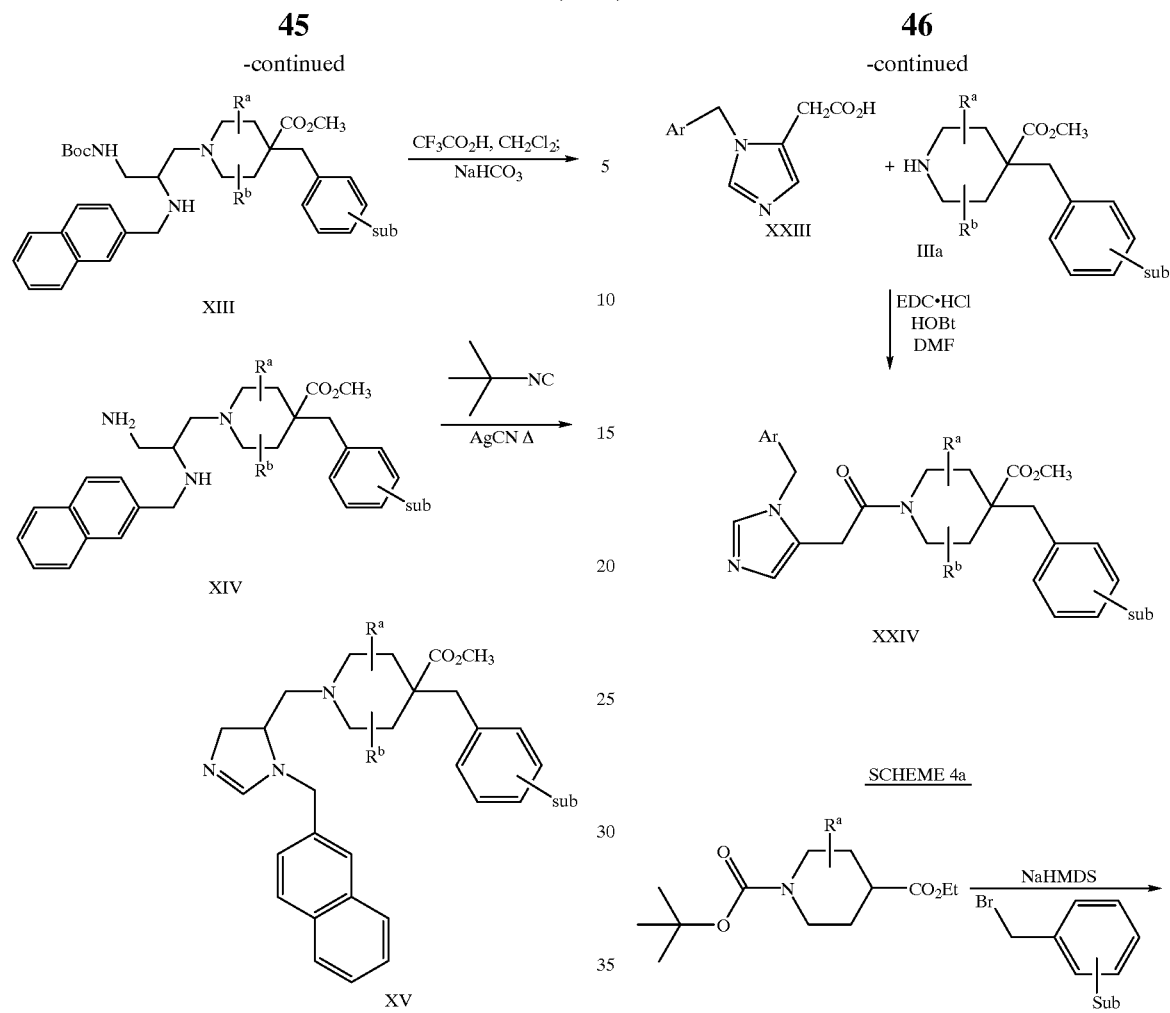
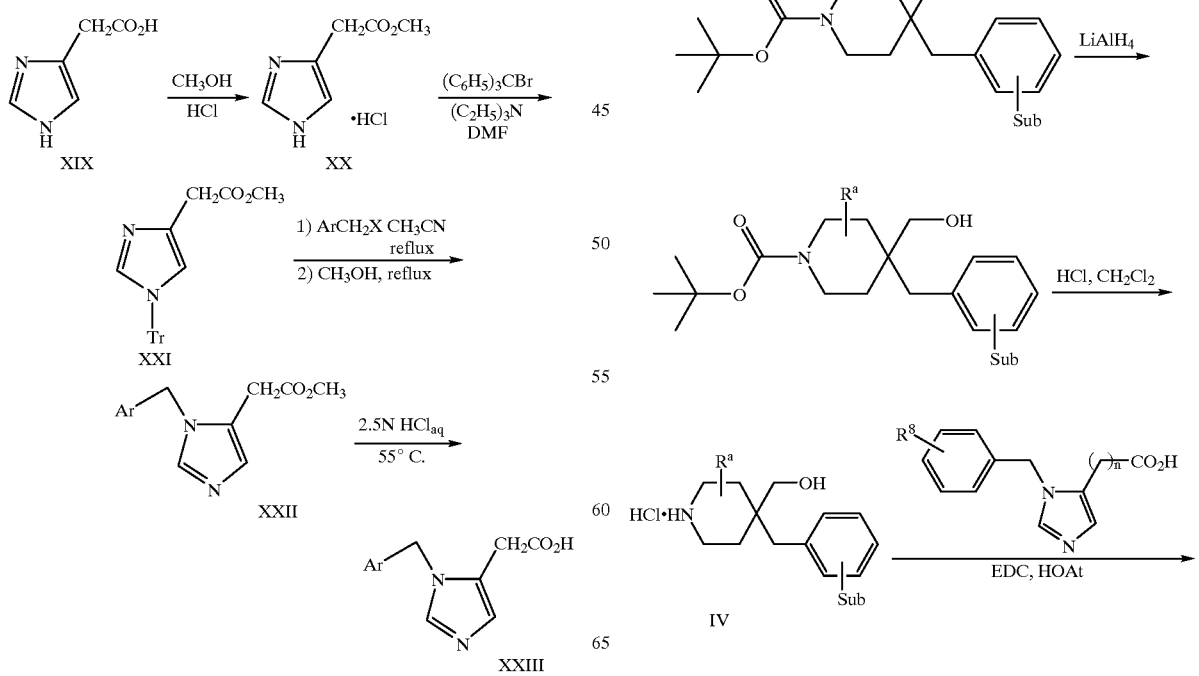

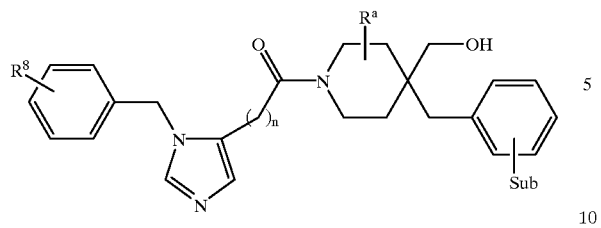
SCHEME 4b
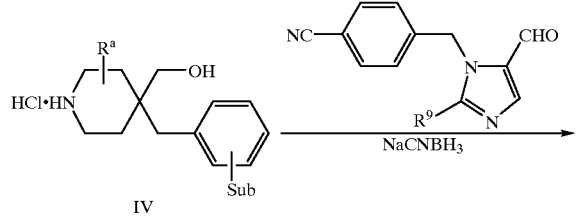
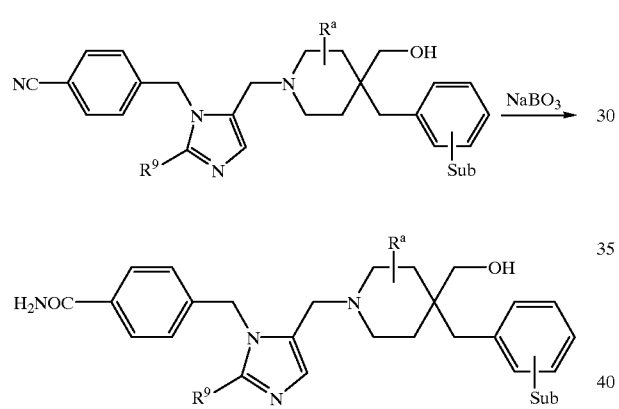
SCHEME 4c
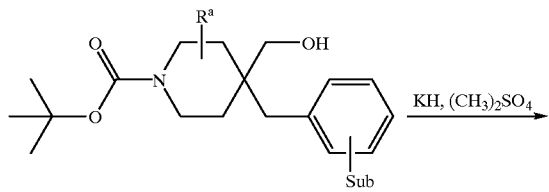
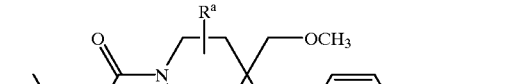
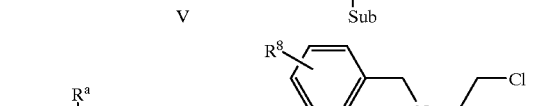
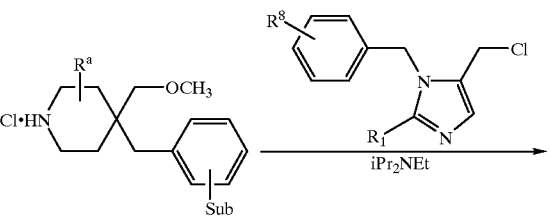
SCHEME 4d
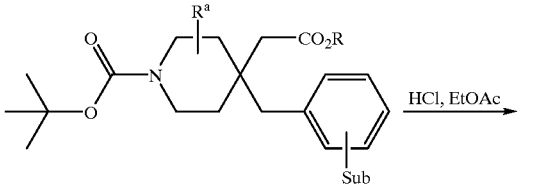
R = CH$_3$, CH$_3$CH$_2$
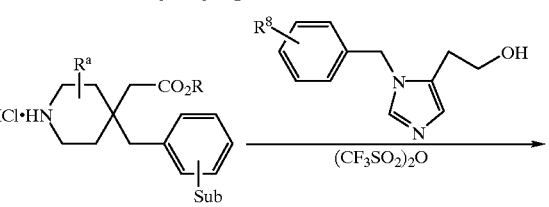
SCHEME 4e
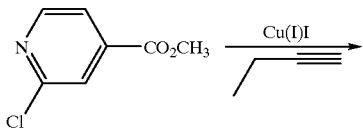

-continued
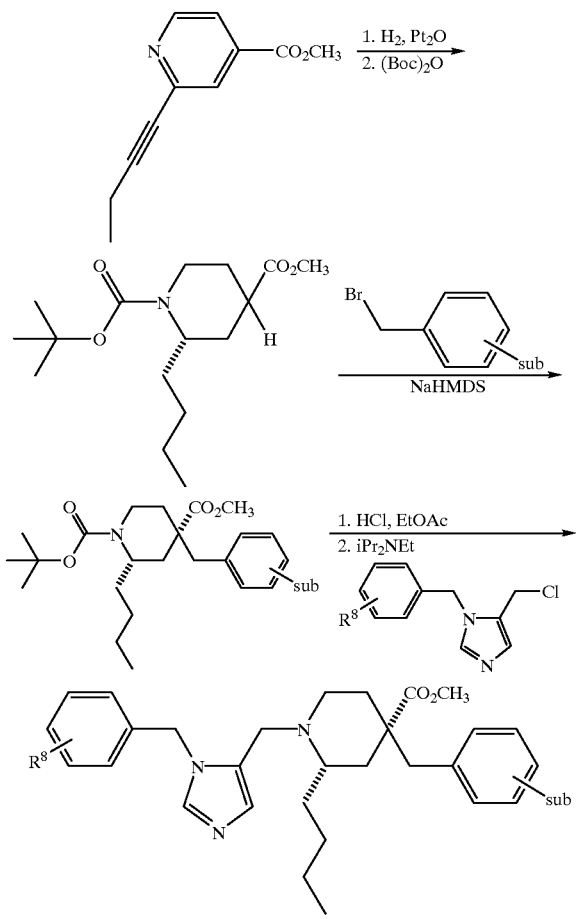
SCHEME 4f
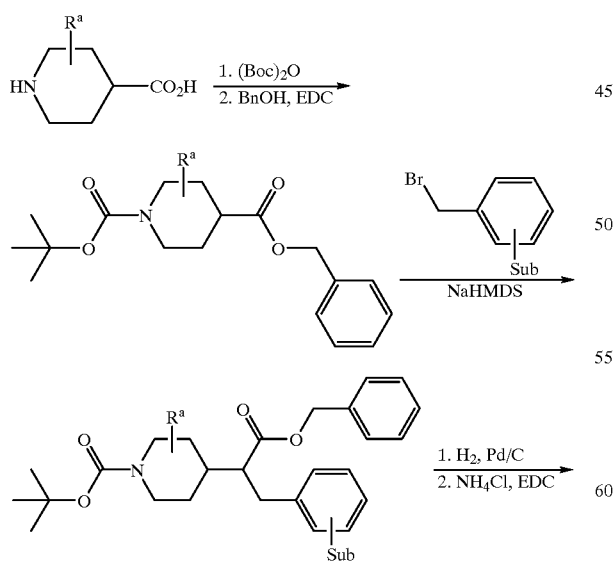
SCHEME 5
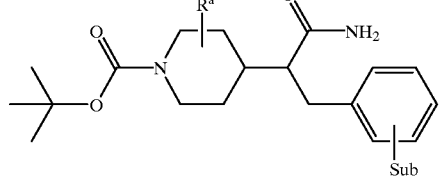

-continued
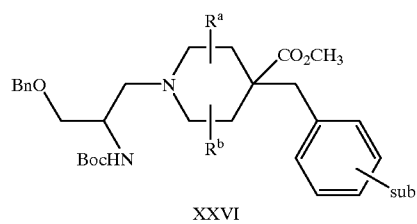
XXVI
20% Pd(OH)₂ H₂
CH₃OH
CH₃CO₂H
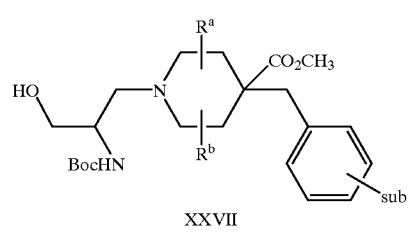
XXVII
ClCOCOCl
DMSO CH₂Cl₂
(C₂H₅)₃N
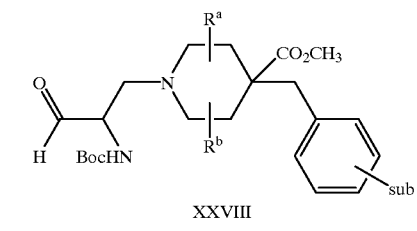
XXVIII
1. R'MgX
   (C₂H₅)₂O
2. TFA,
   CH₂Cl₂
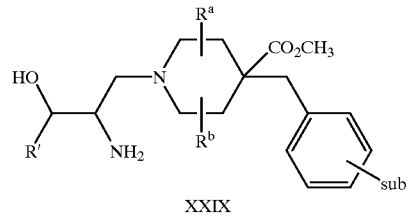
XXIX
SCHEME 6
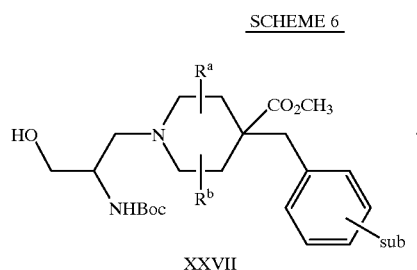
XXVII
CF₃CO₂H
CH₂Cl₂
-continued
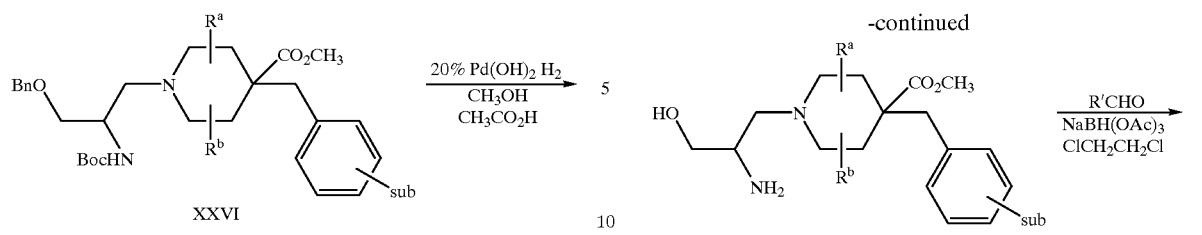
XXX
R'CHO
NaBH(OAc)₃
ClCH₂CH₂Cl
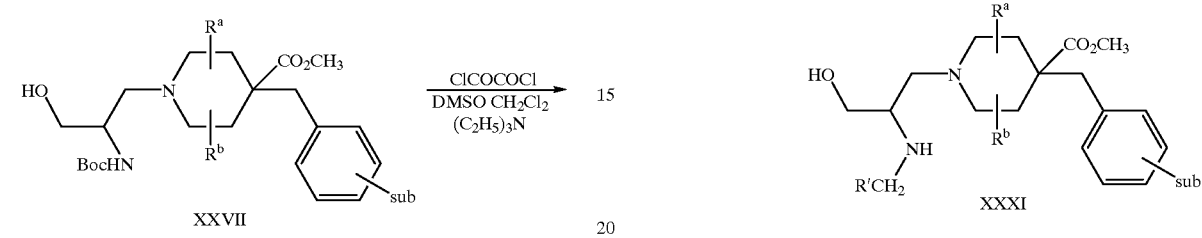
XXXI
SCHEME 7
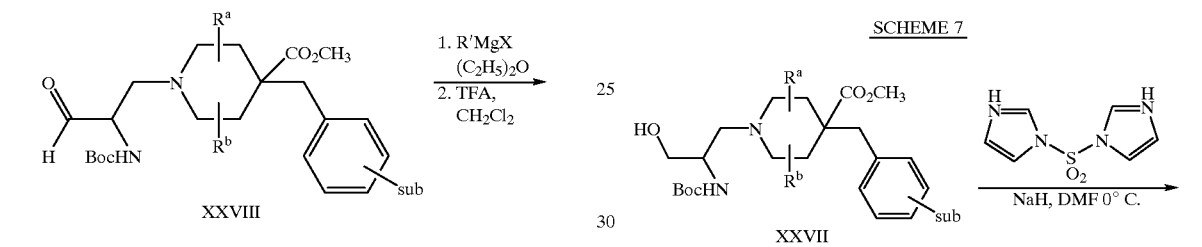
XXVII
imidazole-SO₂-imidazole
NaH, DMF 0° C.
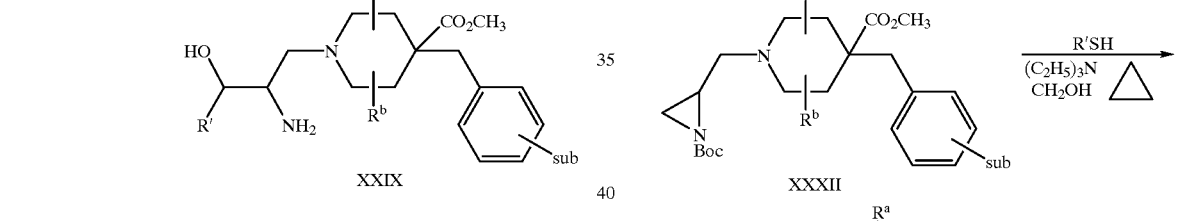
XXXII
R'SH
(C₂H₅)₃N
CH₃OH
Δ
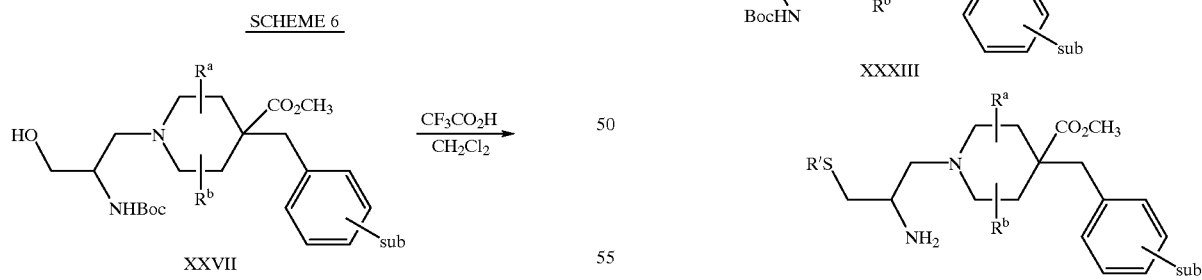
XXXIII
HCl

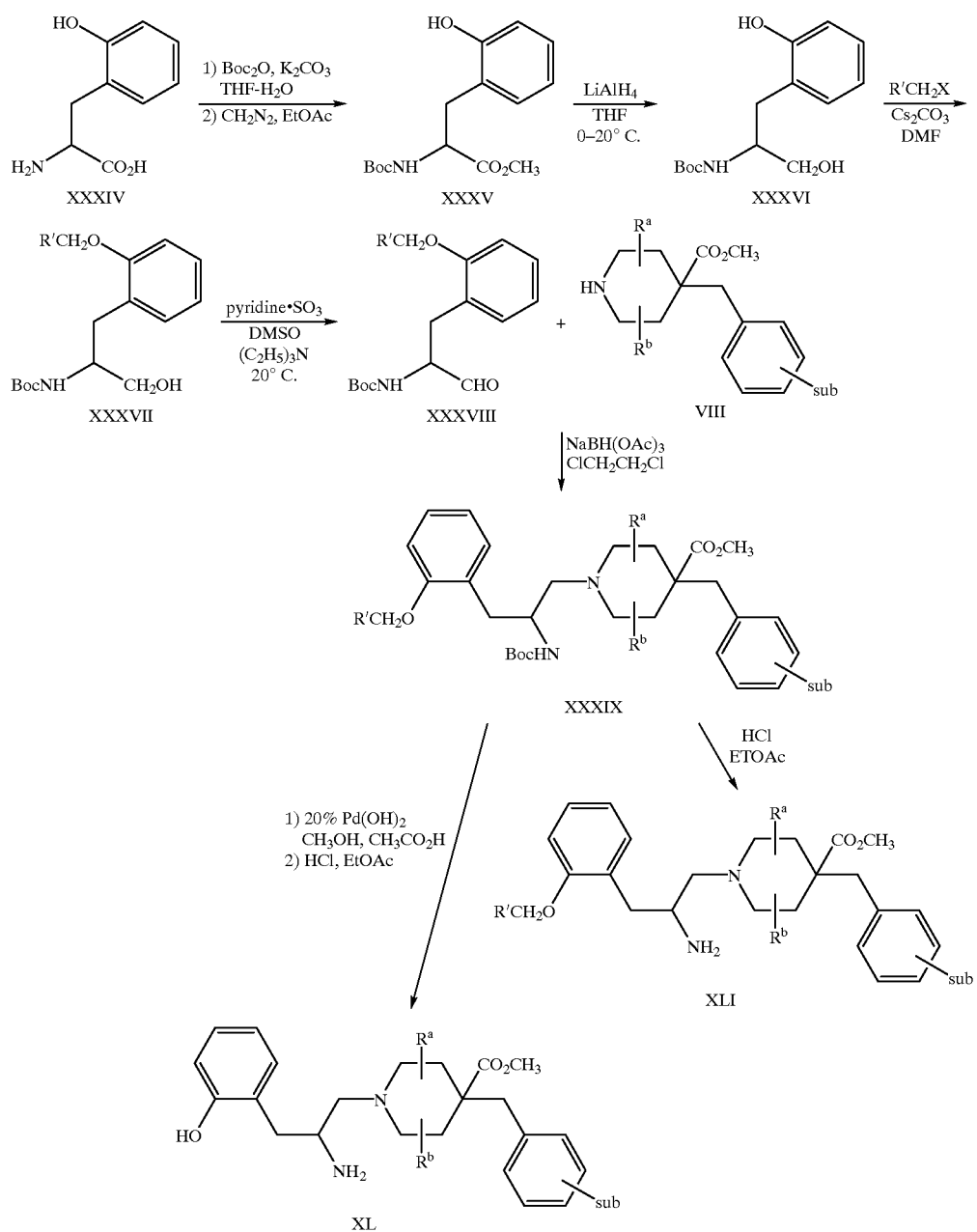
SCHEME 9
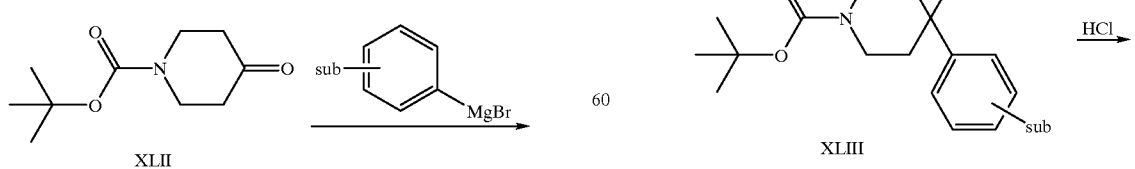

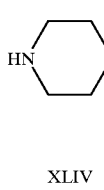
XLIV
SCHEME 10
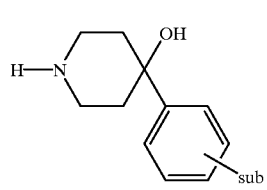
XLIV
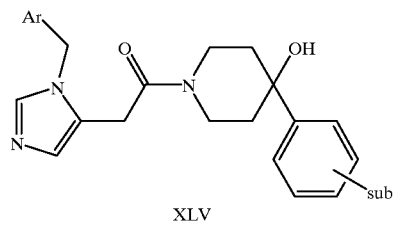
XXIII
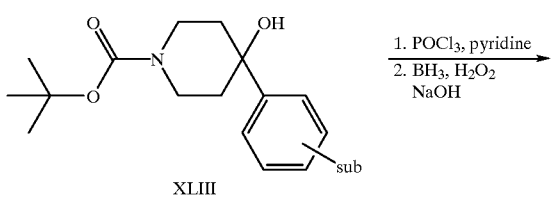
XLV
SCHEME 11
XLIII
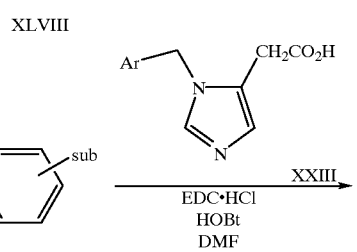
XLVI
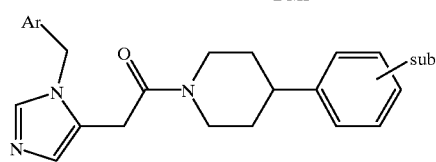
XLVII
SCHEME 12
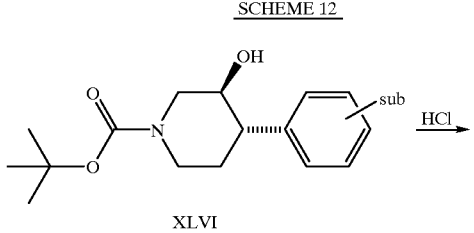
XLVI
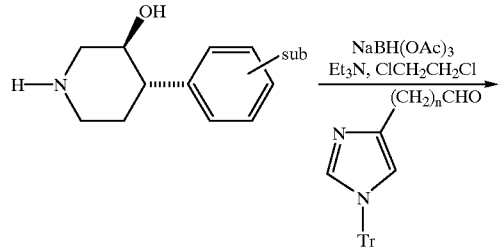
SCHEME 13
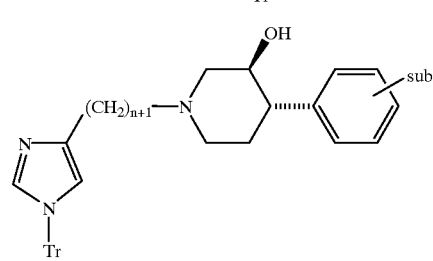

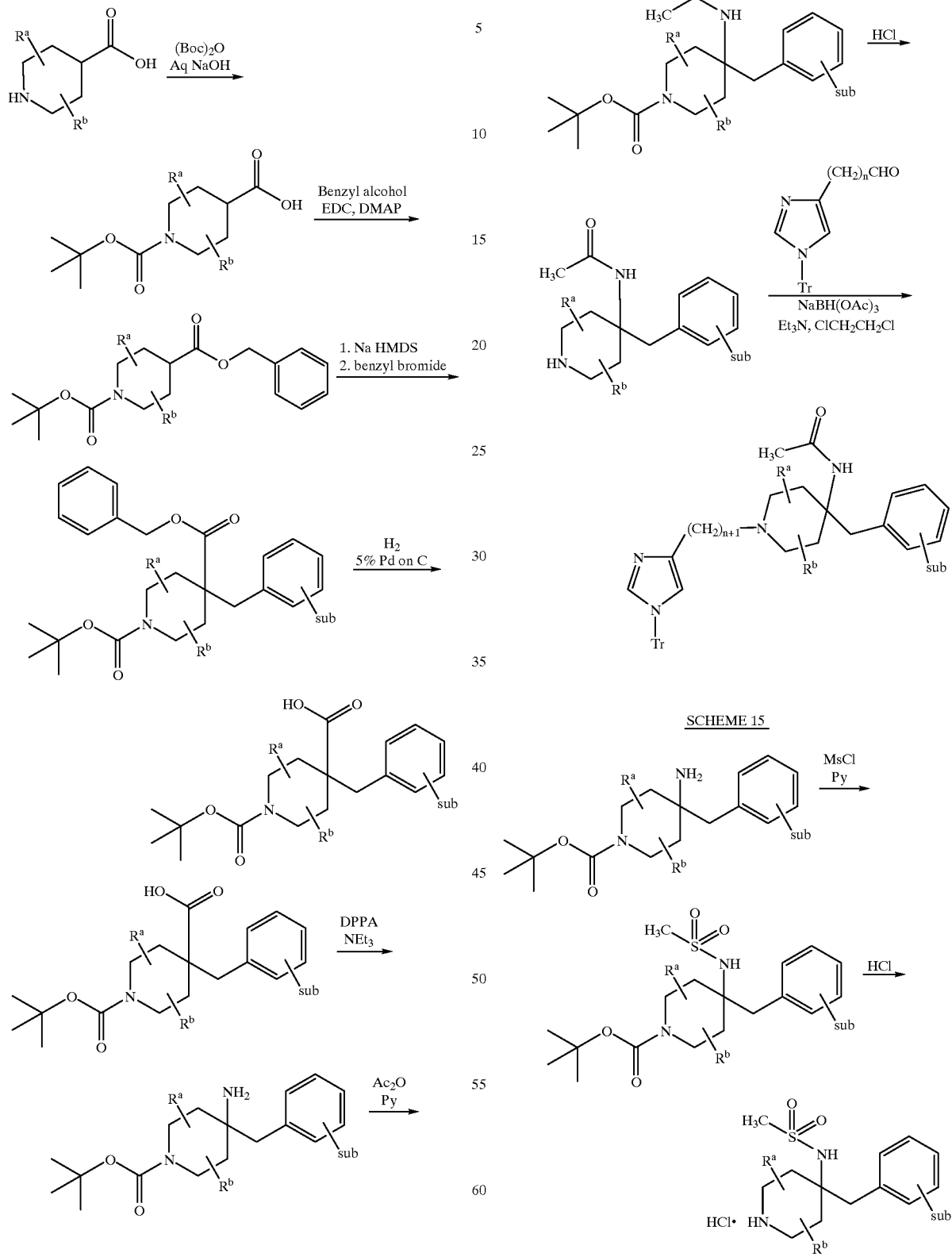

SCHEME 16
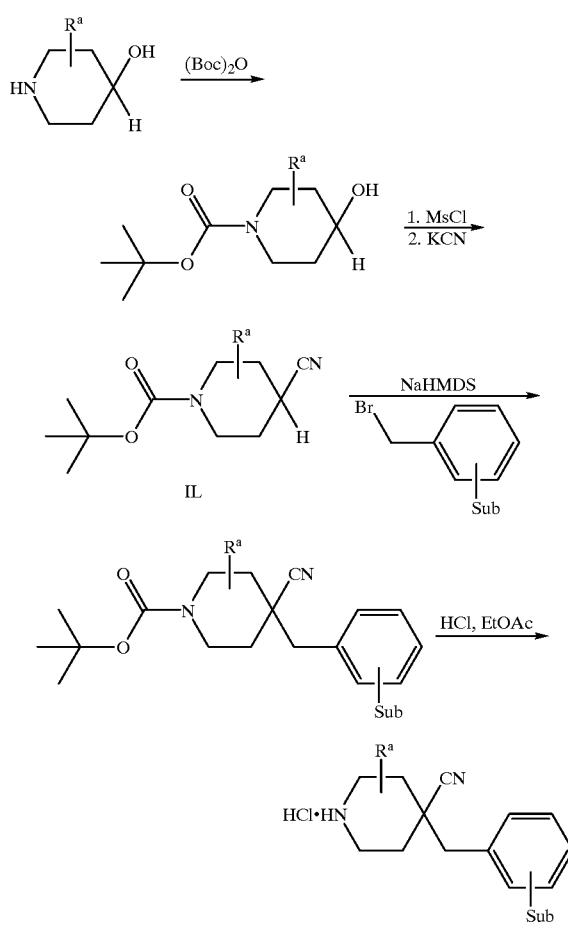
SCHEME 17
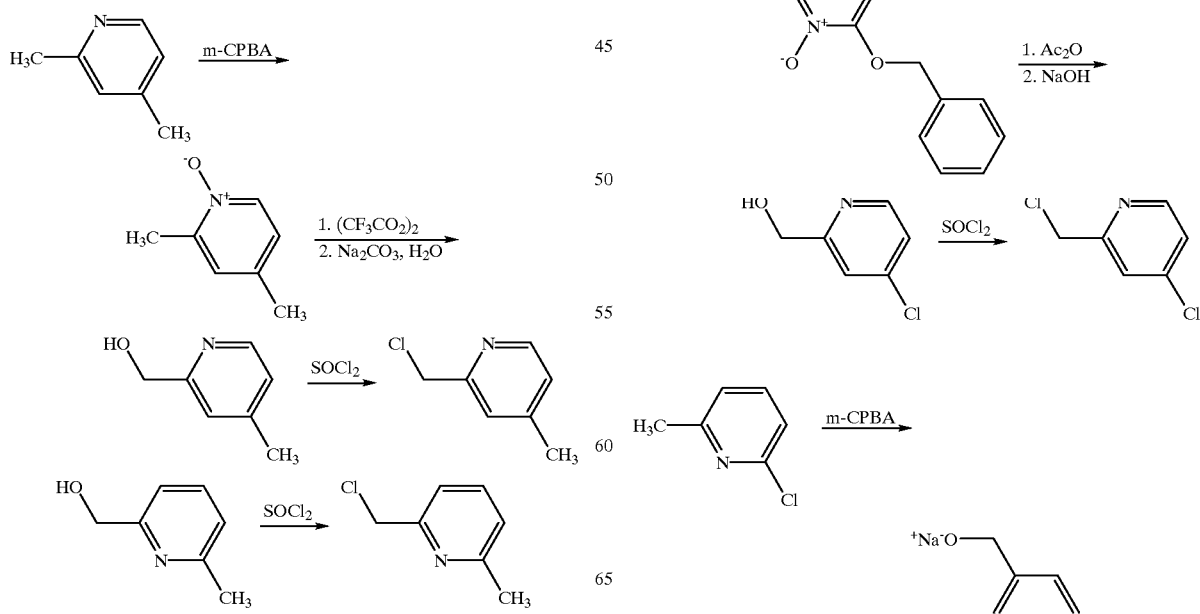

-continued
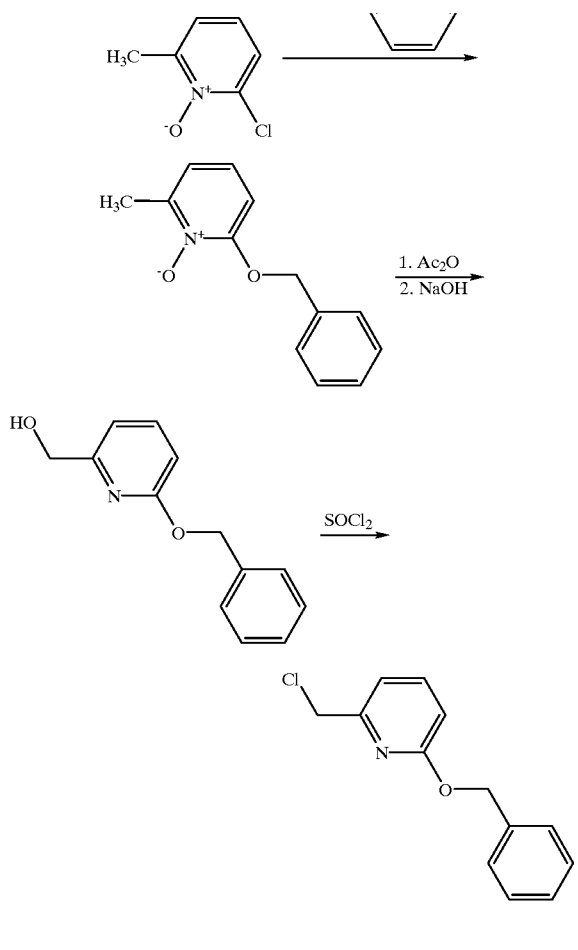
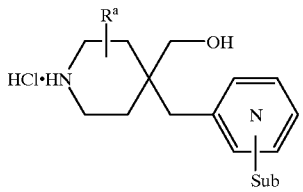
SCHEME 18
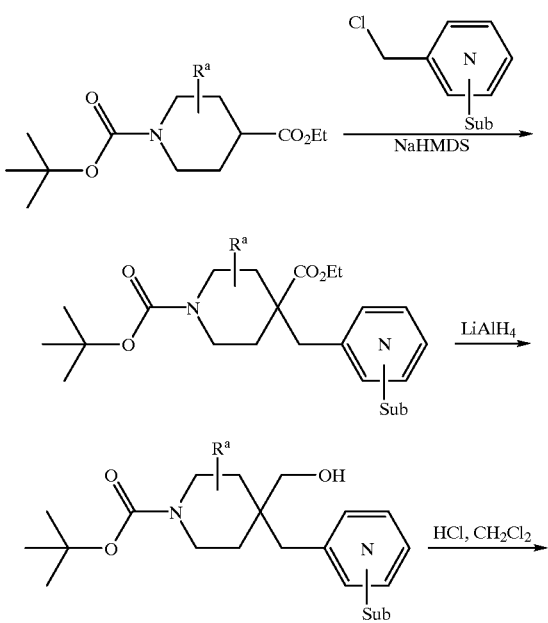
SCHEME 19
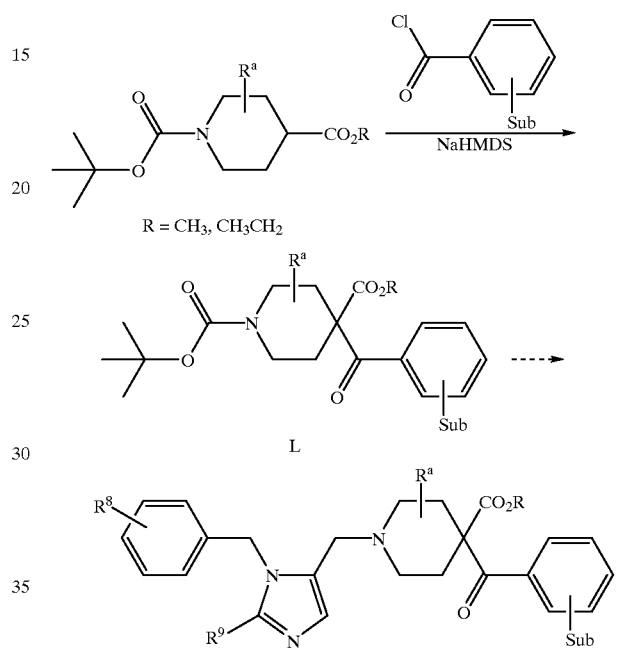
SCHEME 20
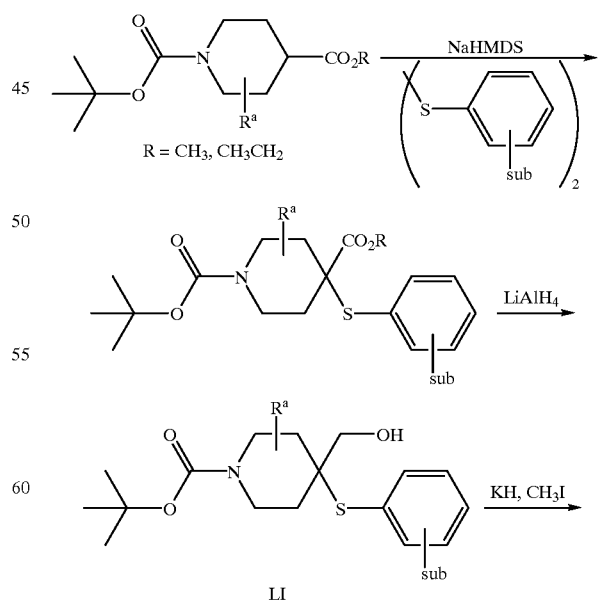

-continued
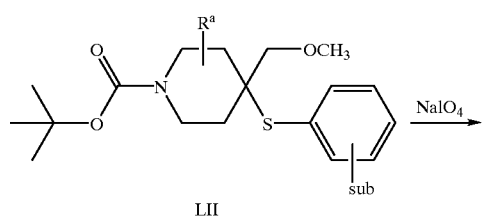
LII
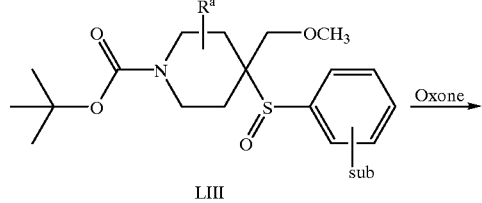
LIII
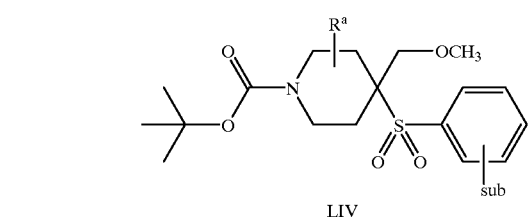
LIV
SCHEME 21
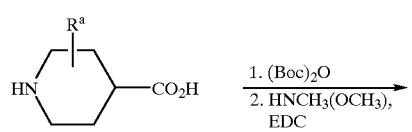
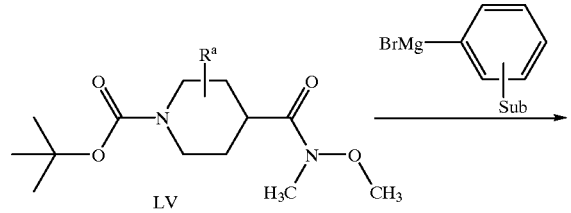
LV
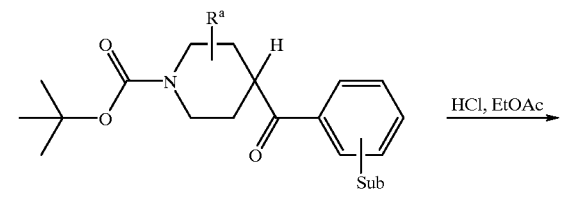
LVI
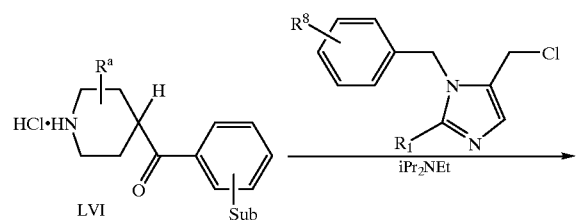
-continued
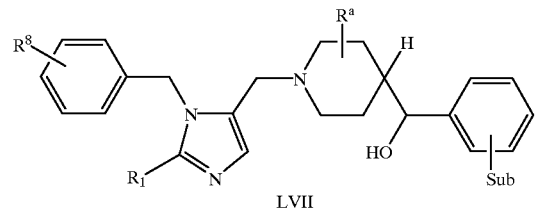
LVII
SCHEME 22
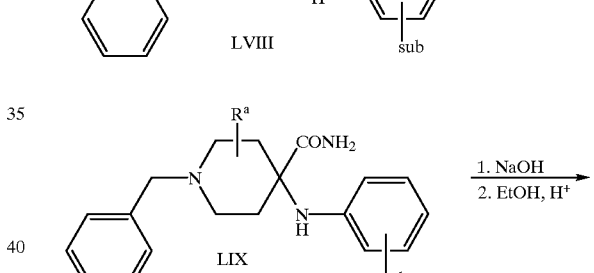
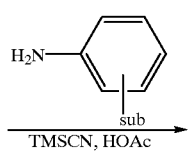
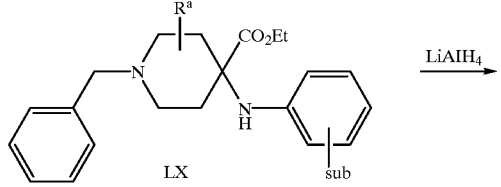
LVIII
LIX
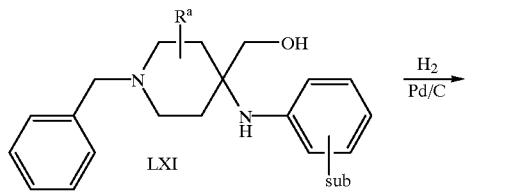
LX
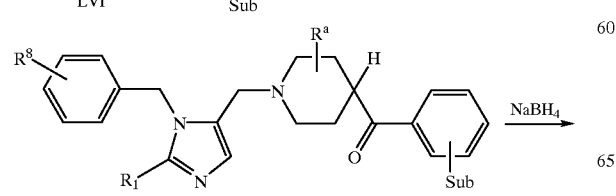
LXI
LXII

SCHEME 23
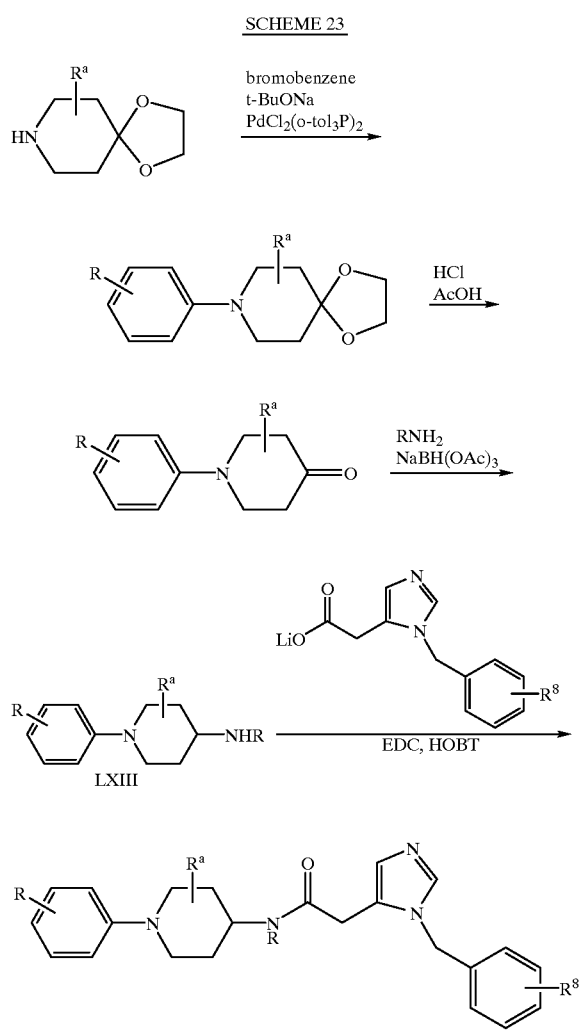
SCHEME 24
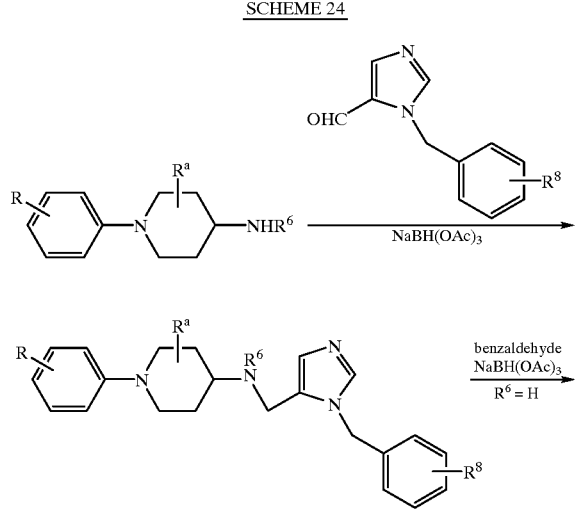
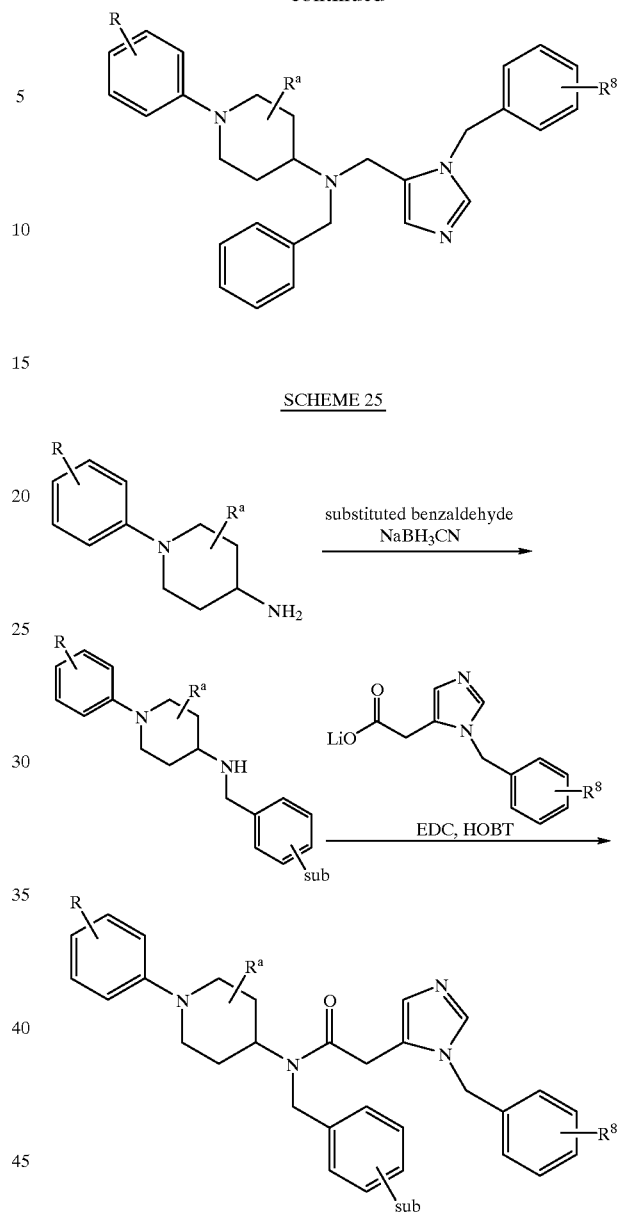
SCHEME 25
SCHEME 26
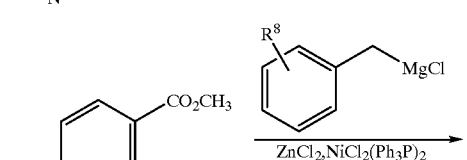

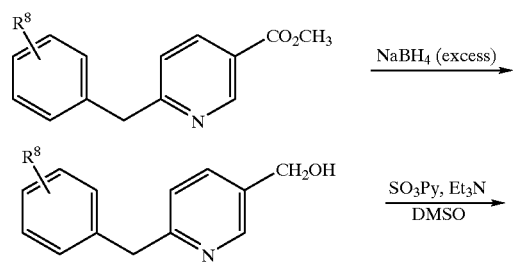
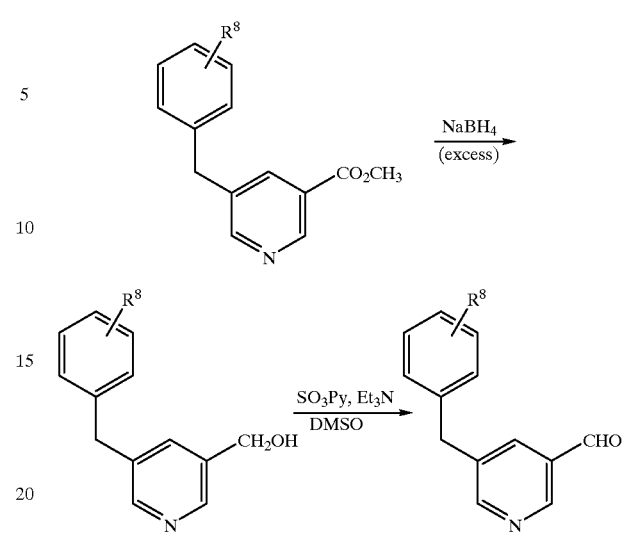
SCHEME 27
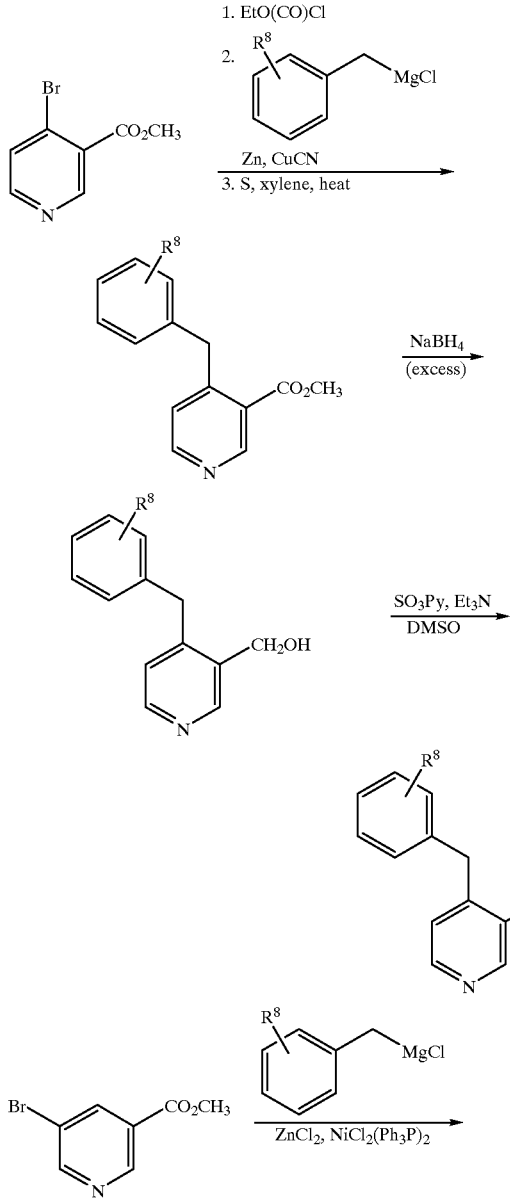
SCHEME 28
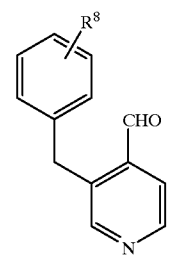

SCHEME 29

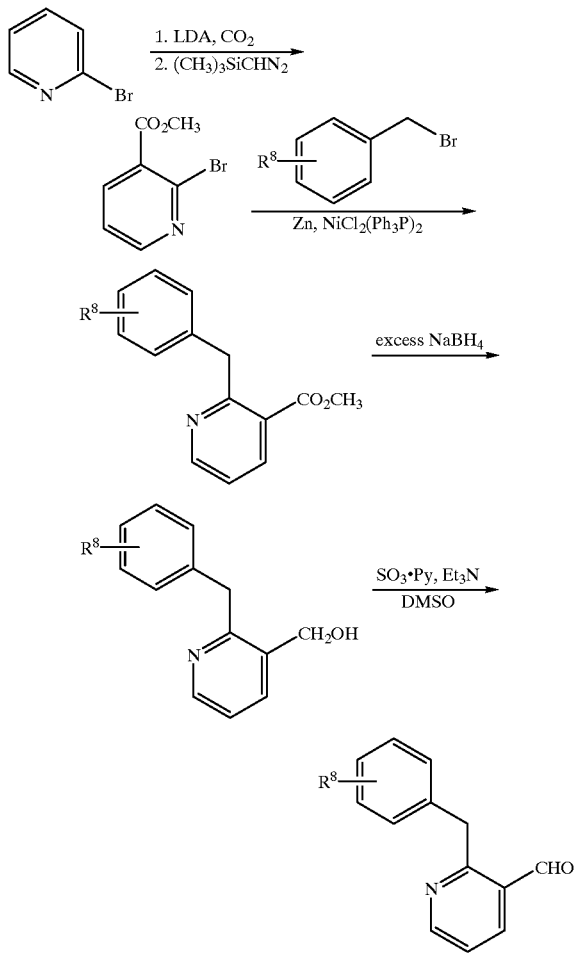

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al.*FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of N-{[1-(4-cyanobenzyl)-1H-imidazol-5-yl]methyl}-4-(3-methylphenyl)-4-hydroxy piperidine Step A: 1-Triphenylmethyl-4-(hydroxymethyl)-imidazole To a solution of 4-(hydroxymethyl)imidazole hydrochloride (35.0 g, 260 mmol) in dry DMF (250 ml) at room temperature was added triethylamine (90.6 ml, 650 mmol). A white solid precipitated from the solution. Chlorotriphenylmethane (76.1 g, 273 mmol) in of DMF (500 ml) was added dropwise. The reaction mixture was stirred for 20 hrs, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl)-imidazole

The alcohol from Step A (260 mmol, prepared above) was suspended in pyridine (500 ml). Acetic anhydride (74 ml, 780 mmol) was added dropwise, and the reaction was stirred for 48 hrs during which it became homogeneous. The solution was poured into EtOAc, washed sequentially with water, 5% aqueous HCl solution, saturated aqueous $NaHCO_3$, solution, and brine, the organic extracts were dried ($Na_2SO_4$), and concentrated in vacuo to provide the product as a white powder, which was sufficiently pure for use in the next reaction.

Step C: 1-(4-Cyanobenzyl)-5-(acetoxymethyl)-imidazole hydrobromide

A solution of the product from Step B (85.8 g, 225 mmol) and 4-cyano benzyl bromide (50.1 g, 232 mmol) in EtOAc (500 ml) was stirred at 60° C. for 20 hrs, during which a pale yellow precipitate formed. The reaction was cooled to room temperature and filtered to provide the solid imidazolium bromide salt. The filtrate was concentrated in vacuo to a volume (200 ml), reheated at 60° C. for 2 hrs, cooled to room temperature, and filtered again. The filtrate was concentrated in vacuo to a volume (100 m), reheated at 60° C. for another 2 hrs, cooled to room temperature, and concentrated in vacuo to provide a pale yellow solid. All of the solid material was combined, dissolved in methanol (500 ml), and warmed to 60° C. After 2 hrs, the solution was concentrated in vacuo to provide a white solid which was triturated with hexane to remove soluble materials. Removal of residual solvents in vacuo provided the titled product hydrobromide as a white solid which was used in the next step without further purification.

Step D: 1-(4-Cyanobenzyl)-5-(hydroxymethyl)-imidazole

To a solution of the acetate from Step C (50.4 g, 150 mmol) in 3:1 THF/water (1.5 l) at 0° C. was added lithium hydroxide monohydrate (18.9 g, 450 mmol). After 1 hr, the reaction was concentrated in vacuo, diluted with EtOAc (3 l), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E: 1-(4-Cyanobenzyl)-5-imidazole carboxaldehyde

To a solution of the alcohol from Step D (21.5 g, 101 mmol) in DMSO (500 ml) at room temperature was added triethylamine (56 ml, 402 mmol), then $SO_3$-pyridine complex (40.5 g, 254 mmol). After 45 min, the reaction was poured into EtOAc, washed with water and brine, dried ($Na_2SO_4$), and concentrated in vacuo to provide the aldehyde as a white powder which was sufficiently pure without further purification.

Step F: N-t-Butoxycarbonyl-4-(3-methylphenyl)-4-hydroxy piperidine

To a solution of 3-methylphenyl magnesium bromide (58 ml of a 1M solution in THF, 58.0 mmol) at 0° C. was added a solution of N-t-butoxycarbonyl piperidin-4-one (10.0 g, 53 mmol) in THF (30 ml) dropwise over 20 min, and the reaction stirred under argon for a further 30 min. The reaction was quenched by addition of sat $NH_4Cl$ solution (100 ml), and diluted with EtOAc. The organic extracts were dried, ($MgSO_4$) and the solvent evaporated in vacuo to afford the title compound of sufficient purity to be used in the next step.

$^1$H NMR $CD_3OD$ δ7.31 (1H, s), 7.28–7.16(2H, m), 7.05 (1H, brd, J=7.1 Hz), 3.97(2H, d, J=13 Hz), 3.40–3.10(2H, m), 2.35(3H, s), 1.94(2H, dt, J=4.4 and 12.7 Hz), 1.70(2H, d, J=12.7 Hz) and 1.49(9H, s)ppm.

Step G: 4-(3-Methylphenyl)-4-hydroxypiperidine hydrochloride

To a solution of N-t-butoxycarbonyl-4-(3-methylphenyl)-4-hydroxy piperidine (0.546 mg, 1.87 mmol) in EtOAc (30 ml) at 0° C. was bubbled gasseous HCl until saturated. After 10 min the solvent was evaporated in vacuo to afford the title compound of sufficient purity to be used in the next step.

$^1$H NMR $CD_3OD$ δ7.33 (1H, s), 7.32–7.16(2H, m), 7.10 (1H, brd, J=7.0 Hz), 3.44(2H, t, J=14 Hz), 3.40–3.20(2H, m), 2.36(3H, s), 2.24(2H, dt, J=4.4 and 13.5 Hz) and 1.92(2H, d, J=13.5 Hz)ppm.

Step H: N-{[1-(4-Cyanobenzyl)-1H-imidazol-5-yl]methyl}-4-(3-methylphenyl)-4 hydroxy piperidine To a mixture of 4-(3-methylphenyl)-4-hydroxypiperidine hydrochloride (457 mg, 2.00 mmol), the aldehyde from step E (508 mg, 2.41 mmol), and 3A molecular sieves (2.0 g) in methanol (20 ml) was added sodium cyanoborohydride (2.20 ml of a 1M solution in THF, 2.20 mmol). The pH was adjusted to 5 by addition of acetic acid and the reaction stirred under argon for 48 hrs at room temperature. The solids were removed by filtration and the filtrate partitioned between EtOAc and saturated $NaHCO_3$ solution, the organic extracts were dried ($MgSO_4$), and the solvent evaporated in vacuo. The residue was purified by chromatography ($SiO_2$, gradient elution, 5 to 7% MeOH in methylene chloride. The residue was converted to the corresponding hydrochloride salt by its treatment with a solution of two equivalents of HCl in aqueous acetonitrile and subsequent evaporation of solvents in vacuo.

Anal. Calcd for $C_{24}H_{26}N_4O.2.0HCl.0.95H_2O$: C, 60.49; H, 6.32; N, 11.76. Found: C, 60.32; H, 6.42; N, 11.95.

FAB HRMS exact mass calcd for $C_{24}H_{27}N_4O$: 387.218487 (MH$^+$); found 387.218317.

$^1$H NMR $CD_3OD$ δ9.00 (1H, s), 8.09 (1H, s), 7.84 (2H, d, J=8.4 Hz), 7.56 (2H, d, J=8.4 Hz), 7.35 (1H, s), 7.30 (1H, d, J=7.7 Hz), 7.24 (1H, t, J=7.4 Hz), 7.10 (1H,d, J=7.4 Hz), 5.82 (2H, s), 4.56 (2H, s), 3.65–3.45 (4H, m), 2.52 (2H, m), 2.35 (3H, s) and 1.94 (2H, d, J=14.4 Hz) ppm.

Example 2

Preparation of N-{[1-(4-Cyanobenzyl)-1H-imidazol-5-yl]methyl}-4-(3-chlorophenyl)-4 hydroxy piperidine The title compound was prepared according to the procedure in Example 1, Steps F–H replacing 3-methylphenyl magnesium bromide with 3-chlorophenyl magnesium bromide.

Anal. Calcd for $C_{23}H_{23}N_4OCl.2.0HCl.0.35H_2O.0.20CH_3CN$: C, 56.85; H, 5.36; N, 11.90. Found: C, 56.83; H, 5.38; N, 11.89.

FAB MS 407 (MH$^+$).

$^1$H NMR δ$CD_3OD$ 9.02 (1H, s), 8.15 (1H, s), 7.84 (2H, d, J=8.0 Hz), 7.60 (2H, d, J=8.0 Hz), 7.59 (1H, s), 7.45 (1H, d, J=7.7 Hz), 7.36 (1H, t, J=7.0 Hz), 7.29 (1H, d, J=7.7 Hz), 5.87 (2H, s), 4.58 (2H, s), 3.65–3.45 (4H, m), 2.59 (2H, m) and 1.94 (2H, d, J=14.3 Hz) ppm.

Example 3

Preparation of N-{[1-(4-Cyanobenzyl)-1H-imidazol-5-yl]methyl}-4-(2-methylbenzyl)isonipecotic acid methyl ester

Step A: N-t-Butoxycarbonyl isonipecotic acid

To a solution of isonipecotic acid (25.8 g, 200 mmol) in 1 M aqueous NaOH (223 ml, 223 mmol) was added a solution of di-t-butyl dicarbonate in THF (200 ml) over 1 hr. The resulting solution was stirred at room temperature for 16 hrs. The reaction mixture was then concentrated in vacuo to remove the THF and the residual aqueous solution extracted with hexane. The hexane extracts were combined and back extracted with saturated $NaHCO_3$. All of the basic aqueous solutions were combined and cooled to 0° C. and then acidified with a 15% aqueous $KHSO_4$ solution to a pH of 1–2. The resulting thick slurry was extracted with EtOAc (4×), combined and washed with brine, dried ($MgSO_4$) and concentrated in vacuo to afford the product as a white solid.

Step B: N-t-Butoxycarbonyl isonipecotic acid methyl ester

To an ice cold solution of N-t-butoxycarbonyl isonipecotic acid (8.8 g, 34.9 mmol), in a 10% mixture of methanol in benzene (250 ml), was added a 2.0 M solution of trimethylsilyldiazomethane in hexanes, dropwise, until a consistent yellow color was obtained (~30 ml). After vigorous gas evolution had ceased, the reaction mixture was stirred for 1 hr at room temperature. The mixture was then treated dropwise with glacial acetic acid until the yellow color had dissipated. The reaction was stirred 15 min. and concentrated in vacuo to a pale yellow oil. The residue was purified by chromatography (SiO2,eluting with 20% EtOAc in hexanes). Evaporation of the solvent in vacuo afforded the product as a colorless oil.

Step C: N-t-Butoxycarbonyl-4-(2-methylbenzyl)-isonipecotic acid methyl ester To a solution of N-t-butoxycarbonyl isonipecotic acid methyl ester (10.1 g 41.8 mmol) in 140 ml of dry THF at −78° C. was added LDA (59 ml of a 1.0 M solution in THF, 59 mmol) over 15 min. The resulting orange solution was stirred at −78° C. for 1 hr and then treated dropwise with 2-methylbenzyl bromide (6.80 ml, 50.7 mmol) and then allowed to warm slowly to room temperature over 16 hrs. The reaction was quenched with saturated aqueous NH$_4$Cl, diluted with H$_2$O, and extracted with EtOAc. The combined organic extracts were washed with brine, and concentrated in vacuo to an orange gum. Chromatography (SiO2, eluting with 20 to 30% EtOAc in hexanes) and evaporation of solvent in vacuo, afforded the product as a white solid.

Step D: 4-(2-Methylbenzyl)-isonipecotic acid methyl ester hydrochloride salt

To a solution of N-t-butoxycarbonyl-4-(2-methylbenzyl)-isonipecotic acid methyl ester (7.13 g, 20.5 mmol) in EtOAc (100 ml) at 0° C. was bubbled HCl gas until saturated. The reaction was stirred for 10 min at 0° C. and the solvent evaporated in vacuo to afford the product as a white solid.

$^1$H NMR CD$_3$OD, δ7.25–7.00(4H, m), 3.70(3H, s), 3.30 (2H, m), 2.98(2H, s), 2.85(2H, dt, J=2.5 and 13.5 Hz), 2.36(2H, d, J=15.0 Hz), 2.29(3H, s) and 1.76(2H, m)ppm.

Step E: N-{[1-(4-Cyanobenzyl)-1H-imidazol-5-yl] methyl}-4-(2-methylbenzyl)isonipecotic acid methyl ester The title compound was prepared using the procedure from example 1 step H and the hydrochloride salt from Step D.

FAB HRMS exact mass calcd for C$_{27}$H$_{31}$N$_4$O$_2$443.244702(MH$^+$); found 443.245590.

Anal. Calcd for C$_{27}$H$_{30}$N$_4$O$_2$.2.95TFA: 0.35H$_2$O: C, 50.32 H, 4.32; N, 7.14. Found: C, 50.30; H, 4.28; N, 7.10.

Example 4

Preparation of N-{[1-(4-Cyanobenzyl)-1H-imidazol-5-yl]methyl}-4-(3-methylphenyl)-4 hydroxy piperidine Step A: 1H-Imidazole-4- acetic acid methyl ester hydrochloride A solution of 1H-imidazole-4-acetic acid hydrochloride (400 g, 24.6 mmol) in methanol (100 ml) was saturated with gaseous hydrogen chloride. The resulting solution was allowed to stand at room temperature for 18 hrs. The solvent was evaporated in vacuo to afford the title compound as a white solid.

$^1$H NMR CDCl$_3$, δ8.85(1H, s), 7.45(1H, s), 3.89(2H, s) and 3.75(3H, s) ppm.

Step B: 1-(Triphenylmethyl)-1H-imidazol-4-ylacetic acid methyl ester

To a solution of the product from Step A (24.85 g, 0.141 mol) in DMF (115 ml) was added triethylamine (57.2 ml, 0.412 mol) and triphenylmethyl bromide (55.3 g, 0.171 mol) and the suspension was stirred for 24 hrs. After this time, the reaction mixture was diluted with EtOAc and water. The organic phase was washed with saturated aqueous NaHCO$_3$, dried (Na$_2$SO$_4$) and the solvent evaporated in vacuo. The residue was purified by chromatography (SiO$_2$, gradient elution, 0–100% EtOAc in hexanes;) to provide the title compound as a white solid.

$^1$H NMR CDCl$_3$, δ7.35(1H, s), 7.31(9H, m), 7.22(6H, m), 6.76(1H, s), 3.68(3H, s) and 3.60(2H, s) ppm.

Step C: [1-(4-Cyanobenzyl)-1H-imidazol-5-yl]acetic acid methyl ester

To a solution of the product from Step B (8.00 g, 20.9 mmol) in acetonitrile (70 ml) was added 4-cyanobenzyl bromide (4.10g, 20.92 mmol) and heated at 55° C. for 3 hr. After this time, the reaction was cooled to room temperature and the resulting imidazolium salt was collected by filtration. The filtrate was heated at 55° C. for 18 hrs. The reaction mixture was cooled to room temperature and evaporated in vacuo. To the residue was added EtOAc (70 ml) and the resulting precipitate collected by filtration. The precipitated imidazolium salts were combined, suspended in methanol (100 ml) and heated to reflux for 30 min. After this time, the solvent was removed in vacuo,. The resulting residue was suspended in EtOAc (75 ml) and the solid isolated by filtration and washed with EtOAc. The solid was treated with saturated aqueous NaHCO$_3$ solution (300 ml) and CH$_2$Cl$_2$ (300 ml) and stirred at room temperature for 2 hrs. The organic layer was separated, dried (MgSO$_4$) and evaporated in vacuo to afford the title compound as a white solid $^1$MR CDCl$_3$, δ7.65(1H, d, J=8 Hz), 7.53(1H, s), 7.15(1H, d, J=8 Hz), 7.04(1H, s), 5.24(2H, s), 3.62(3H, s) and 3.45(2H, s) ppm.

Step D: [1-(4-Cyanobenzyl)-1H-imidazol-5-yl] acetic acid

A solution of [1-(4-cyanobenzyl)-1H-imidazol-5-yl] acetic acid methyl ester (4.44 g, 17.4 mmol) in THF (100 ml) and 1 M lithium hydroxide (17.4 ml, 17.4 mmol) was stirred at room temperature for 18 hrs. 1 M HCl (17.4 ml) was added and the THF removed by evaporation in vacuo. The aqueous solution was lyophilised to afford the title compound containing lithium chloride as a white solid.

$^1$H NMR CD$_3$OD, δ8.22(1H, s), 7.74(1H, d, J=8.4 Hz), 7.36(1H, d, J=8.4 Hz), 7.15(1H, s), 5.43(2H, s) and 3.49(2H, s) ppm.

Step E: N-{[1-(4-Cyanobenzyl)-1H-imidazol-5-yl] acetyl}-4-(3-methylphenyl)-4 hydroxy piperidine To a mixture of the piperidine hydrochloride from example 1 step G (102 mg, 0.447 mmol), [1-(4-cyanobenzyl)-1H-imidazol-5-yl]acetic acid (from step D) (127 mg, 0.447 mmol), HOOBT (73 mg, 0.447 mmol) and triethylamine (0.187 ml, 1.34 mmol) in DMF (3 ml)was added EDC (86 mg, 0.447 mmol) and the reaction stirred at room temperature for 18 hrs. The reaction was diluted with EtOAc and washed with saturated NaHCO$_3$ solution. The organic extracts were dried (Na$_2$SO$_4$) and the solvent evaporated in vacuo. The residue was purified by preparative HPLC (C-18, gradient elution, 95:5 to 5:95 water: acetonitrile containing 0.1% trifluoroacetic acid). Lyophilization afforded the title compound as a white powder.

Anal. Calcd for C$_{25}$H$_{26}$N$_4$O$_2$.1.60 TFA: 0.65H$_2$O: C, 55.65 H, 4.79; N, 9.21. Found: C, 55.68 H, 4.79; N, 8.98.

FAB HRMS exact mass calcd for C$_{25}$H$_{27}$N$_4$O$_2$: 415.213401 (MH$^+$); found 415.212530.

$^1$H NMR CD$_3$OD δ8.95 (1H, d, 1.4 Hz), 7.78 (2H, d, J=8.5 Hz), 7.53 (1H, s), 7.49 (2H, d, J=8.5 Hz), 7.27 (1H, s), 7.30–7.20 (2H, m), 7.07 (1H, d, J=7.0 Hz), 5.53 (2H, s), 4.34 (1H, d, J=11.0Hz), 3.95 (2H, s), 3.76 (1H, d, J=11.0 Hz),3.50 (1H, dt, J=2.3 and 12.5 Hz), 3.13 (1H, dt, J=2.7 and 12.5 Hz), 2.35 (3H, s) and 2.10–1.60 (4H, m) ppm.

Example 5

Preparation of N-{[1-(4-Cyanobenzyl)-1H-imidazol-5-yl]acetyl}-4-(2-methylbenzyl)isonipecotic acid methyl ester The title compound was prepared using the procedure from example 4 step E substituting 4-(2-methylbenzyl)- isonipecotic acid methyl ester for 4-(3-methylphenyl)-4-hydroxypiperidine hydrochloride (from example 3 step E).

¹H NMR CD$_3$OD δ8.94 (1H, d, 1.4 Hz), 7.72 (2H, d, J=8.0 Hz), 7.48 (1H, s), 7.43 (2H, d, J=8.0 Hz), 7.20–6.97 (4H, m), 5.46 (2H, s), 4.28 (1H, d, J=11 Hz), 3.85 (2H, s), 3.76 (1H, d, J=11.0 Hz), 3.67 (3H, s), 3.02 (1H, m), 2.93 (2H, s), 2,57 (1H, dt, J=3.0 and 19.0 Hz), 2.29 (3H, s), 2.20 (2H, d, J=20.0 Hz), and 1.60–1.38 (2H, m)ppm.

Anal. Calcd for C$_{28}$H$_{30}$N$_4$O$_3$.1.70TFA, 0.35H$_2$O: C, 56.23 H, 4.87; N, 8.35. Found: C, 56.21; H, 4.86; N, 8.75.

Example 6

Preparation of N-{[1-(4-Cyanobenzyl)-1H-imidazol-5-yl]acetyl}-4-(4-methylbenzyl))isonipecotic acid methyl ester The title compound was prepared using the procedure above substituting 2-methylbenzyl bromide with 4-methylbenzyl bromide

FAB MS 471 (MH$^+$).

Anal. Calcd for C$_{28}$H$_{31}$N$_4$O$_3$.1.95HCl: 0.05H$_2$O: C, 61.98 H, 5.95; N, 10.33. Found: C, 62.00; H, 5.89; N, 10.38.

Example 7

Preparation of N-{[1-(4-Cyanobenzyl)-1H-imidazol-5-yl]acetyl}-4-(3-methylbenzyl))isonipecotic acid methyl ester The title compound was prepared using the procedure above substituting 2-methylbenzyl bromide with 3-methylbenzyl bromide

FAB MS 471(MH$^+$).

Anal. Calcd for C$_{28}$H$_{31}$N$_4$O$_3$.1.80HCl: 0.05H$_2$O: C, 62.62H, 5.99, N, 10.43. Found: C, 62.59; H, 5.96; N, 10.36.

Example 8

Preparation of N-{[1-(4-Cyanobenzyl)-1H-imidazol-5-yl]acetyl}-4-(2,4-dichlorobenzyl))isonipecotic acid methyl ester The title compound was prepared using the procedure above substituting 2-methylbenzyl bromide with 2,4-dichlorolbenzyl bromide

FAB MS 525(MH$^+$).

Anal. Calcd for C$_{27}$H$_{26}$N$_4$O$_3$Cl$_2$.1.0HCl.1.60H$_2$O: C, 54.90H, 5.15; N, 9.48. Found: C, 54.85; H, 4.76; N, 9.47.

Example 9

Preparation of N-{[1-(4-Cyanobenzyl)-1H-imidazol-5-yl]acetyl}-4-(3-methoxybenzyl)isonipecotic acid methyl ester The title compound was prepared using the procedure above substituting 2-methylbenzyl bromide with 3-methoxybenzyl bromide

FAB MS 487(MH$^+$).

Anal. Calcd for C$_{27}$H$_{26}$N$_4$O$_3$Cl$_2$.1.80HCl: C, 60.90; H, 5.80; N, 10.15. Found: C, 60.90; H, 5.77; N, 10.13.

Example 10

Preparation of N-{[1-(4-Cyanobenzyl)-1H-imidazol-5-yl]acetyl}-4-(1-naphthylmethyl)isonipecotic acid methyl ester The title compound was prepared using the procedure above substituting 2-methylbenzyl bromide with 1-naphthylmethyl bromide.

FAB HRMS exact mass calcd for C$_{27}$H$_{28}$N$_4$O$_3$Cl: 507.239616(MH$^+$); found 507.239124.

Anal. Calcd for C$_{31}$H$_{30}$N$_4$O$_3$.2.25TFA: 0.40H$_2$O: C, 55.35 H, 4.32; N, 7.27. Found: C, 55.36H, 4.30; N, 7.36.

Example 11

Preparation of N-{[1-(4-Cyanobenzyl)-1H-imidazol-5 -yl]acetyl}-4-(4-chlorobenzyl)isonipecotic acid methyl ester The title compound was prepared using the procedure above substituting 2-methylbenzyl bromide with 4-chlorobenzyl bromide.

FAB HRMS exact mass calcd for C$_{27}$H$_{28}$N$_4$O$_3$Cl: 491.184994(MH$^+$); found 491.184736.

Anal. Calcd for C$_{27}$H$_{27}$N$_4$O$_3$Cl.2.30 TFA: 0.15H$_2$O: C, 50.21 H, 3.95; N, 7.41. Found: C, 50.18 H, 3.95; N, 7.46.

Example 12

Preparation of N-{[1-(4-Cyanobenzyl)-1H-imidazol-5-yl]acetyl}-4-(2,3-dichlorobenzyl)isonipecotic acid methyl ester The title compound was prepared using the procedure above substituting 2-methylbenzylbromide with 2,3-dichlorobenzyl bromide.

FAB HRMS exact mass calcd for C$_{27}$H$_{27}$N$_4$O$_3$Cl$_2$: 525.146021 (MH$^+$); found 525.144945.

Anal. Calcd for C$_{27}$H$_{26}$N$_4$O$_3$Cl$_2$.1.85 TFA: 0.45H$_2$O: C, 49.53 H, 3.89; N, 7.53. Found: C, 49.51 H, 3.90; N, 7.73.

Example 13

Preparation of N-{1-(4 Cyanobenzyl)-1H-imidazol-5-yl-aminocarbonyl}4-(2-methylbenzyl) isonipecotic acid methyl ester Step A: 1-(4 Cyanobenzyl)-5-nitro-1H-imidazole A solution of 4-nitroimidazole (2,25 g, 19.9 mmol) and 4-cyanobenzyl bromide (3.90 g, 19.9 mmol) in acetonitrile (10 ml) was stirred at 50° C. for 72 hrs. The reaction was allowed to cool to room temperature and diethyl ether (70 ml) was added. The precipitate was removed by filtration and the filtrate partitioned between EtOAc and NaHCO$_3$ solution. The organic extract was dried (MgSO$_4$) and the solvent evaporated in vacuo. The residue was chromatographed (SiO$_2$, 5% MeOH in CH$_2$Cl$_2$) to afford a solid that was triturated with hot ethanol, and washed with diethyl ether, to afford the product as an off white solid.

Step B: 1-(4 Cyanobenzyl)-5-amino-1H-imidazole hydrochloride

A solution of 1-(4 cyanobenzyl)-5-nitro-1H-imidazole (100 mg, 0.438 mmol) and 10% palladium on carbon was hydrogenated in the presence of 1 equivalent of HCl under Parr conditions for 1 hr. Removal of the catalyst by filtration and evaporation of solvent in vacuo afforded the title compound.

¹HNMR CD$_3$OD, δ8,47(1H, d, J=1.7 Hz), 7.71(2H, d, J=8.4 Hz), 7.50(2H, d, J=8.4 Hz), 6,55(1H, d, J=1.7 Hz) and 5.36(2H, s)ppm.

Step C: N-{1-(4 Cyanobenzyl)-1H-imidazol-5-yl-aminocarbonyl}-4-(2-methylbenzyl) isonipecotic acid methyl ester To a suspension of 4-(2-methylbenzyl)-isonipecotic acid methyl ester hydrochloride (50 mg, 0.176 mmol) in toluene (2 ml) was added phosgene (0.912 ml of a 1.93M solution in toluene, 1.76 mmol) and triethylamine (0.074 ml, 0.528 mmol) and the mixture stirred for 48 hrs at room temperature. The excess phosgene was removed by purging the solution with argon gas for 10 min. The suspension was added to 1-(4-cyanobenzyl)-5-amino-1H-imidazole hydrochloride (100 mg, 0.528 mmol) in $CH_2Cl_2$ (10 ml) and the mixture stirred at 50° C. for 72 hrs. The solvent was evaporated in vacuo and the residue purified by preparative HPLC (C18, 95:5 to 5:95 water: acetonitrile containing 0.1% TFA). The residue after lyophilisation was partitioned between $CH_2Cl_2$ and saturated $NaHCO_3$ solution. The organic extract was dried ($MgSO_4$), and evaporated to dryness

FAB MS 472 ($MH^+$).

$^1$HNMR $CDCl_3$ δ7.60(2H, d, J=8.1 Hz), 7.28–6.90(8H, m), 5.30(2H, s), 3.90(2H, d, J=13.1 Hz), 3.65(3H, s), 2.86 (2H, s), 2.80(2H,d, J=11.9 Hz), 2.30–2.10(5H, m) and 1.80–1.40(2H, m) ppm.

Example 14

2(R,S)-N{-2-{[1-(4-Cyanobenzyl)-1H-imidazol-5-yl]2-(4-cyanobenzyl)}acetyl-4-(2-methylbenzyl)-isonipecotic acid methyl ester Step A: 2-{1-(Triphenylmethyl)-1H-imidazol-4-yl}-2-(4-cyanobenzyl)-acetic acid methyl ester A solution of 1-(triphenylmethyl)-1H-imidazol-4-ylacetic acid methyl ester (977 mg, 2.55 mmol) in THF (25 ml) was cooled to –78° C. Lithium hexamethyldisilazide (2.68 ml, 2.68 mmol) was added dropwise and the reaction stirred 30 min at –78° C. 4-Cyanobenzyl bromide (500.7 mg, 2.68 mmol) was added and the reaction stirred a further 4 hrs at –78° C. and then at –20° C. for 12 hr. The reaction was quenched with water (10 ml) and saturated $NaHCO_3$ solutuon (10 ml) and extracted with EtOAc. The organic extracts were dried ($MgSO_4$) and the solvent evaporated in vacuo. Chromatography of the residue ($SiO_2$, 3% MeOH in $CH_2Cl_2$) afforded the product.

$^1$HNMR $CDCl_3$, δ7.55–6.90(20H, m), 6.55(1H, m), 3.90 (1H, t, J=7.7 Hz), 3.66(3H, s) and 3.31(2H, m) ppm.

Step B: 2-{1-(Triphenylmethyl)-1H-imidazol-4-yl}-2-(4-cyanobenzyl)-acetic acid

A solution of the 2-{1-(triphenylmethyl)-1H-imidazol-4-yl}-2-(4-cyanobenzyl)-acetic acid methyl ester in THF was treated with 1 equivalent of 1M lithium hydroxide solution. Upon consumption of starting material as determined by t.l.c, 1 equivalent of hydrochloric acid was added and the solution evaporated to dryness in vacuo. The material obtained in this manner could be used without further purification.

Step C: 2(R,S)-{1-(Triphenylmethyl)-1H-imidazol-4-yl}-2-(4-cyanobenzyl)-acetyl-4-(2-methylbenzyl) isonipecotic acid methyl ester To a mixture of 4-(2-methylbenzyl)-isonipecotic acid methyl ester hydrochloride (72 mg, 0.25 mmol), and 2-{1-(triphenylmethyl)-1H-imidazol-4-yl}-2-(4-cyanobenzyl)-acetic acid(123 mg, 0.25 mmol), HOOBT (42 mg, 0.25 mmol) and triethylamine (0.088 ml, 0.636 mmol) in DMF (3 ml), was added EDC (54 mg, 0.25 mmol) and the reaction stirred at room temperature for 18 hrs. The reaction was diluted with EtOAc and washed with saturated $NaHCO_3$ solution, the organic extracts were dried ($Na_2SO_4$), and the solvent evaporated in vacuo. The residue was purified by chromatography($SiO_2$, gradient elution, 1–5% MeOH in $CH_2Cl_2$) to afford the product.

Step D: 2(R,S)-N{-2-{[1-(4-Cyanobenzyl)-1H-imidazol-5-yl]-2-(4-cyanobenyl)}acetyl-4-(2-methylbenzyl)-isonipecotic acid methyl ester To a solution of 2(R,S)-2-{{1-(triphenylmethyl)-1H-imidazol-4-yl}-2-(4-cyanobenzyl)}-acetyl-4-(2-methylbenzyl)-isonipecotic acid methyl ester (96 mg, 0.338 mmol) in acetonitrile (2 ml), was added 4-cyanobenyl bromide (24.5 mg, 0.338 mmol) and the mixture heated at 55° C. for 5 hrs. The solvent was evaporated and the residue purified by preparative HPLC (C18, gradient elution, 95:5 to 5:95 water:acetonitrile containing 0.1% TFA) to afford the title compound after lyophilisation.

FAB HRMS exact mass calcd for $C_{36}H_{36}N_5O_3$ 586.281815($MH^+$); found 586.280827.

Example 15

Preparation of N-{[1-(Naphth-2-ylmethyl)-1H-imidazol-5-yl]acetyl}-4-(2-methylbenzyl) isonipecotic acid methyl ester Step A: 2-[1-(Naphth-2-ylmethyl)-1H-imidazol-5-yl)]acetic acid methyl ester To a solution of the product of example 4 step B (4.36 g, 11.4 mmol) in acetonitrile (70 ml) was added 2-(bromomethyl)-naphthalene and heated to 55° C. for 4 hr. The reaction was cooled to room temperature and the resulting white precipitate was collected by filtration. The filtrate was concentrated to 30 ml and heated at 55° C. for 18 hr. After this time, the reaction was cooled to room temperature and the resulting white precipitate collected by filtration. The filtrate was concentrated to 10 ml volume and heated to 55° C. for 1 hr. The reaction was cooled to room temperature and diluted with ethyl acetate (25 ml). The resulting precipitate was collected by filtration and combined with the previous 2 precipitates in methanol (100 ml) and heated to reflux for 30 min. After this time, the solvent was removed in vacuo and the resulting residue was partitioned between methylene chloride (200 ml) and saturated sodium bicarbonate solution (100 ml). The organic layer was evaporated to dryness in vacuo and the residue purified by chromatography ($SiO_2$, gradient elution, 0–6% methanol in methylene chloride) to provide the title compound as an off white solid.

$^1$HNMR $CDCl_3$, δ7.82(2H, m), 7.75(1H, m), 7.70(1H, s), 7.49(3H, m), 7.20(1H, d, J=8.4 Hz), 7.06(1H, s), 5.32(2H, s), 3.57(3H, s) and 3.49(2H, s) ppm.

Step B: 2-[1-(Naphth-2-ylmethyl)-1H-imidazol-5-yl]acetic acid hydrochloride

2-[1-(Naphth-2-ylmethyl)-1H-imidazol-5-yl]acetic acid methyl ester (0.92 g, 3.28 mmol ) was dissolved in 2.5N hydrochloric acid ( 50 ml) and heated to 55° C. for 3 hr. After this time, the solution was concentrated to dryness in vacuo to give the title compound as a white solid.

$^1$HNMR $CD_3OD$, δ8.92(1H, s), 7.94(1H, d, J=8.6 Hz), 7.88(2H, m), 7.83(1H, s), 7.54(3H, m), 7.43(1H, d, J=14.0 Hz), 5.60(2H, s) and 3.82(2H, s) ppm.

Step C: N-{[1-(Naphth-2-ylmethyl)-1H-imidazol-5-yl]acetyl }-4-(2-methylbenzyl)isonipecotic acid methyl ester The title compound was prepared using the procedure from example 4 step E, substituting 4-(2-methylbenzyl)- isonipecotic acid methyl ester hydrochloride for 4-(3-methylphenyl)-4-hydroxypiperidine hydrochloride and the acid from step B. FAB HRMS exact mass calcd for $C_{31}H_{34}N_3O_3$ 496.260017(MH$^+$); found 496.260274.

Anal. Calcd for $C_{31}H_{33}N_3O_3$·2.65HCl: C, 62.87 H, 6.07; N, 7.10. Found: C, 62.85; H, 5.88; N, 7.14.

$^1$H NMR CD$_3$OD δ8.96 (1H, s), 8.00–7.80(3H, m), 7.76 (1H, s), 7.56(2H, m), 7.46(1H, m), 7.35(1H, d, J=6.8 Hz), 7.20–7.00(3H, m), 6.92(1H, d, J=7.0 Hz), 5.56(2H, s), 4.18(1H, m), 3.80(2H, s), 3.62(3H, s), 3.62(1H, m), 3.0–2.70 (3H, m), 2.35(1H, t, J=8.0 Hz), 2.23(3H, s), 2.06(2H, d, J=13.3 Hz) and 1.40–1.20(2H, m)ppm.

Example 16

Preparation of N-{[1-(4-Cyanobenzyl)-1H-imidazol-5-yl]methyl}-4-methoxymethyl-4-(2-methylbenzyl)piperidine Step A: N-t-butoxycarbonyl isonipecotic acid benzyl ester To a solution of N-t-butoxycarbonyl isonipecotic acid (12.0 g, 52.3 mmol) from example 3 step A, in anhydrous CH$_2$Cl$_2$ (100 ml), was added benzyl alcohol (6.0 ml, 58 mmol), followed by EDC (11.04 g, 57.6 mmol), and DMAP (642 mg, 5.25 mmol). The resulting mixture was stirred for 6 hrs, then diluted with CH$_2$Cl$_2$ (150 ml) and washed successively with water, 10% aqueous citric acid, saturated NaHCO$_3$, and brine and dried (MgSO$_4$). Concentration in vacuo afforded a colorless oil which was chromatographed (SiO$_2$, 20% EtOAc in hexanes) to afford the product as a white solid.

Step B: N-t-Butoxycarbonyl-4-(2-methylbenzyl) isonipecotic acid benzyl ester

To a solution of N-t-butoxycarbonyl isonipecotic acid benzyl ester (13.34 g, 41.8 mmol) in THF (100 ml) at −78° C. was added sodium bis-trimethysilylamide (59 ml of a 1.0 M THF solution, 59 mmol) over 15 min. The resulting orange solution was stirred at −78° C. for 1 hr and then treated dropwise with 2-methyl benzyl bromide (6.80 ml, 50.7 mmol) and then allowed to warm slowly to room temperature over 16 hrs. The reaction was quenched with saturated aqueous NH$_4$Cl, diluted with H$_2$O, and extracted with EtOAc. The combined organic extracts were washed with brine, and concentrated in vacuo to an orange gum. Chromatography (SiO$_2$, gradient elution, 20 to 30% EtOAc in hexanes) afforded the product as a white solid.

Step C: N-t-Butoxycarbonyl-4-hydroxymethyl-4-(2-methylbenzyl) piperidine

To a suspension of lithium aluminum hydride (0.32 g, 8.4 mmol) in anhydrous ether (50 ml) was added a solution of 4-(2-methylbenzyl)-N-t-butoxycarbonyl isonipecotic acid benzyl ester (3.0 g, 7.1 mmol) in anhydrous ether (25 ml) over 15 min. The resulting mixture was heated at gentle reflux for 1 hr. The reaction mixture was then quenched with the slow and successive addition of H$_2$O (0.32 ml), 15% aqueous NaOH (0.96 ml), and H$_2$O (0.96 ml). After stirring for 30 min, the mixture was filtered through celite and the filtrate washed with brine, dried (MgSO$_4$), and concentrated in vacuo to a colorless syrup. Purification by chromatography (SiO$_2$, gradient elution, 25 to 50% EtOAc in hexanes), afforded the product as a colorless gum. This material was recrystallized from EtOAc and hexane to afford a white solid. m.p. 104–106° C.

Step D: N-t-Butoxycarbonyl-4-methoxymethyl-4-(2-methylbenzyl)piperidine

To a suspension of sodium hydride (19 mg, 0.80 mmol) in 1.5 ml of THF, at 0° C. was added a solution of N-t-butoxycarbonyl-4-hydroxymethyl-4-(2-methylbenzyl) piperidine (200 mg, 0.63 mmol) in THF (1 ml). The mixture was allowed to warm to room temperature. To this suspension was added anhydrous DMSO (0.35 ml) and the mixture was heated to 60° C. and stirred 5 hrs until the solution was almost homogeneous. The reaction mixture was allowed to cool to room temperature and methyl iodide (0.070 ml, 1.12 mmol) was added. The resulting heterogeneous mixture was stirred at room temperature for 16 hrs. The reaction mixture was treated with 10% aqueous citric acid and extracted with diethylether. The combined etheral extracts were washed successively with saturated aqueous NaHCO$_3$ brine, dried (MgSO$_4$), and concentrated in vacuo to a yellow gum. Chromatography (SiO$_2$, 9% EtOAc in hexanes) afforded the product as a colorless gum.

Step E: 4-Methoxymethyl-4-(2-methylbenzyl)-piperidine hydrochloride salt

N-t-Butoxycarbonyl-4-methoxymethyl-4-(2-methylbenzyl) piperidine was deprotected as in Example 1, Step G to afford the product as a white solid.

Step F: N-{[1-(4-Cyanobenzyl)-1H-imidazol-5-yl]methyl}-4-methoxymethyl-4-(2-methylbenzyl)piperidine The title compound was prepared using the procedure from example 1 step H using 4-methoxymethyl-4-(2-methylbenzyl) piperidine hydrochloride.

FAB HRMS exact mass calcd for $C_{27}H_{33}N_4O$ 429.265437 (MH$^+$); found 429.265817.

$^1$H NMR CD$_3$OD δ8.77 (1H, s), 7.79(2H, d, J=8.4 Hz), 7.78(1H, s), 7.41(2H, d, J=8.4 Hz), 7.20–7.05(4H, m), 5.61(2H, s), 4.36(2H, s), 3.36(3H, s), 3.35–3.10(6H, m), 2.78(2H, m), 2.31(3H, s) and 1.90–1.60(4H, m)ppm.

Example 17

Preparation of N-{[1-(4-Cyanobenzyl)-1H-imidazol-5-yl]acetyl}-4-methoxymethvl-4-(2-methylbenzyl)piperidine The title compound was prepared using the procedure from example 4 step E using 4-methoxymethyl-4-(2-methylbenzyl) piperidine hydrochloride.

FAB HRMS exact mass calcd for $C_{28}H_{33}N_4O_2$ 457.260352 (MH$^+$); found 457.260528.

$^1$H NMR CD$_3$OD δ8.94 (1H, s), 7.69(2H, d, J=8.4 Hz), 7.47(1H, s), 7.41(2H, d, J=8.4 Hz), 7.20–7.05(4H, m), 5.46(2H, s), 3.87(1H, m), 3.80(2H, m), 3.60(1H, m), 3.36 (3H, s), 3.26(2H, m), 3.15(1H, m), 2.77(2H, s), 2.33(3H, s) and 1.70–1.35(4H, m)ppm.

Example 18

Preparation of N-{[1-(4-Cyanobenzyl)-1H-imidazol-5-yl]acetyl}-4-hydroxymethyl-4-(2-methylbenzyl)piperidine The title compound was prepared using the procedure from example 4 step E using 4-hydroxymethyl-4-(2-methylbenzyl) piperidine hydrochloride (which was obtained from treatment of N-t-butoxycarbonyl-4- hydroxymethyl-4-(2-methylbenzyl) piperidine with gaseous HCl in EtOAc and evaporation of solvent.

Anal. Calcd for $C_{27}H_{30}N_4O_2 \cdot 1.75TFA \cdot 0.15H_2O$: C, 56.81; H, 5.01; N, 8.69. Found: C, 56.81; H, 5.02; N, 8.83.

Example 19

Preparation of N-{[1-(4-Cyanobenzyl)-1H-imidazol-5-yl]ethyl}-4-(2-methylbenzyl)isonipecofic acid methyl ester Step A: 5-[1-(4-cyanobenzyl)-1H-imidazolyl] ethanol To a stirred solution of the ester from example 4 step C, (1.50 g, 5.88 mmol), in methanol (20 ml) at 0° C., was added sodium borohydride (1.00 g, 26.3 mmol) portionwise over 5 min. The reaction was stirred at 0° C. for 1 hr and then at room temperature for an additional 1 hr. The reaction was quenched by the addition of saturated $NH_4Cl$ solution and the methanol evaporated in vacuo. The residue was partitioned between EtOAc and saturated $NaHCO_3$ solution and the organic extracts dried, ($MgSO_4$) and evaporated in vacuo. The residue was purified by chromatography ($SiO_2$, gradient elution, 4 to 10% methanol in methylene chloride) to afford the title compound as a white solid.

$^1H$ NMR $CDCl_3 \delta 7.64(2H, d, J=8.2 Hz), 7.57(1H, s), 7.11(2H, d, J=8.2 Hz), 6.97(1H, s), 5.23(2H, s), 3.79(2H, t, J=6.2 Hz), 2.66(2H, t, J=6.2 Hz)$ ppm.

Step B: 5-(-1-(4-Cyanobenzyl)-imidazolyl) ethylmethanesulfonate

A solution of 5-[1-(4-cyanobenzyl)-1H-imidazolyl] ethanol (0.500 g, 2.20 mmol) in methylene chloride (6 ml) at 0° C. was treated with Hunig's base (0.460 ml, 2.64 mmol) and methanesulfonyl chloride (0.204 ml, 2.64 mmol). After 2 hrs, the reaction was quenched by addition of saturated $NaHCO_3$ solution (50 ml) and the mixture extracted with methylene chloride (50 ml), dried ($MgSO_4$) and the solvent evaporated in vacuo. The title compound was used without further purification.

$^1H$ NMR $CDCl_3 \delta 7.69 (1H, s) 7.66(2H, d, J=8.2 Hz), 7.15 (2H, d, J=8.2 Hz), 7.04(1H, s), 5.24(2H, s), 4.31(2H, t, J=6.7 Hz), 2.96(3H, s), $ and $2.88(2H, t, J=6.6 Hz)$ppm.

Step C: N-{[1-(4-Cyanobenzyl)-1H-imidazol-5-yl] ethyl }-4-(2-methylbenzyl)isonipecotic acid methyl ester A solution of 5-(-1-(4-cyanobenzyl)-imidazolyl) ethyl methanesulfonate (223 mg, 0.73 mmol) in DMF (6.0 ml) was added to 4-(2-methylbenzyl isonipecotic acid methyl ester hydochloride (207.2 mg, 0.73 mmol), sodium iodide (438 mg, 2.92 mmol) and $K_2CO_3$ (252 mg, 1.82 mmol). The mixture was stirred at 55° C. for 3 hrs and the solvent evaporated in vacuo. The residue was purified by preparative HPLC (C18, gradient elution, 95:5 to 5:95% water:acetonitrile, containing 0.1 % TFA). Lyophilisation afforded the TFA salt which was converted to the HCl salt, by partioning between $CH_2Cl_2$ and a saturated $NaHCO_3$ solution. The organic extract was dried ($MgSO_4$) and treated with aqueous HCl in acetonitrile and lyophilised.

Anal. Calcd for $C_{28}H_{32}N_4O_2 \cdot 2.55HCl \cdot 2.55H_2O$: C, 56.14; H, 6.74; N, 9.35. Found: C, 56.12; H, 6.74; N, 9.02.

FAB HRMS exact mass calcd for $C_{28}H_{33}N_4O_2 457.260352$ (MH$^+$); found 457.260675.

$^1H$ NMR $CD_3OD \delta 9.05 (1H, s), 7.80(2H, d, J=8.2 Hz), 7.61(1H, s), 7.53(2H, d, J=8.2 Hz), 7.20-7.00(4H, m), 5.66(2H, s), 3.71(3H, s), 3.58(2H, d, J=12.3), 3.38(2H, m), 3.18(2H, m), 2.90(2H, s), 2.90(2H, t, J=13 Hz), 2.40(2H, d, J=12.2 Hz), 2.37(3H, s),$ and $2.10(2H, t, J=12.2 Hz)$ ppm.

Example 20

Preparation of N-{[1-(4-Cyanobenzyl)-1H-imidazol-5-yl]methyl}-trans-4- (3-methylphenyl)-3-hydroxypiperidine Step A: N-t-Butoxycarbonyl-4-(3-methylphenyl)-piperid-3-ene To a solution of N-t-butoxycarbonyl-4-(3-methylphenyl)-4-hydroxy piperidine (from example 1 step F), (1.57 g, 5.40 mmol) in pyridine (25 ml) at 0° C. was added phosphorous oxychloride (1.01 ml, 10.7 mmol) and the reaction stirred 16 hrs at room temperature. The reaction was diluted with water and partitioned between EtOAc and 10% aqueous citric acid solution. The organic extracts were washed with $NaHCO_3$ and brine, dried ($MgSO_4$), and the solvent evaporated in vacuo. Chromatography of the residue ($SiO_2$, 10:90 EtOAc in hexanes) afforded the product as an oil.

$^1H$ NMR $CDCl_3 \delta 7.40-7.00(4H, m), 6.03(1H, s), 4.08 (2H, s), 3.64(2H, t, J=5.5 Hz), 2.52(2H, s), 2.37(3H, s)$ and $1.51(9H, s)$ppm.

Step B: trans-N-t-Butoxycarbonyl-4-(3-methylphenyl)-3 hydroxy piperidine

To a solution of N-t-butoxycarbonyl-4-(3-methylphenyl)-piperid-3-ene, (0.705 g, 2.58 mmol) in THF (3 ml) at 0° C. was added borane (3.09 ml of a 1M solution in THF, 3.09 mmol) and the reaction stirred 4 hrs at room temperature. The reaction was cooled to 0° C. and treated carefully with NaOH (3 ml of a 2.5M solution, and then 30% hydrogen peroxide (10 ml) and the reaction stirred for 2 hrs at room temperature. The reaction was diluted with water and extracted with EtOAc. The organic extracts were washed with $NaS_2O_3$, brine, dried ($MgSO_4$), and the solvent evaporated in vacuo. Chromatography of the residue ($SiO_2$, 25:75 EtOAc in hexanes) afforded the product as an oil.

$^1H$ NMR $CDCl_3 \delta 7.40-7.20(1H, m), 7.20-7.0(3H, m), 4.40(1H, brs), 4.18(1H, brs), 2.75(1H, m), 2.62(1H, m), 2.44(1H, m), 2.35(3H, s), 1.90-1.60(3H, m), 1.49(9H, s)$ ppm.

Step C: trans-4-(3-Methylphenyl)-3 hydroxypiperidine hydrochloride

To a solution of trans -N-t-butoxycarbonyl-4-(3-methylphenyl)-3 hydroxypiperidine, (0.20 g, 0.12 mmol) in EtOAc (50 ml) at 0° C. was bubbled HCl gas until saturated. The reaction was stirred at 0° C. for 10 min and then the solvent evaporated in vacuo to afford the product as a white foam.

$^1H$ NMR $\delta CDCl_3 7.22(1H, t, J=7.3 Hz), 7.20-7.0(3H, m), 3.95(1H, m), 3.54-3.36(2H, m), 3.07(1H, dt, J=3.3$ and $14.6 Hz), 2.84(1H, t, J=10.8 Hz), 2.70(1H, m), 2.34(3H, s), 2.10-1.80(2H, m)$ ppm.

Step D: N-{[1-(4-Cyanobenzyl)-1H-imidazol-5-yl] methyl}-trans-4-(3-methylphenyl)-3 hydroxy piperidine The title compound was prepared by the procedure in example 1 step H using trans-4-(3-methylphenyl)-3 hydroxy piperidine hydrochloride.

Anal. Calcd for $C_{24}H_{26}N_4O \cdot 02.55TFA \cdot 0.05H_2O$: C, 51.54; H, 4.26; N, 8.26. Found: C, 51.53; H, 4.24; N, 8.42.

FAB HRMS exact mass calcd for $C_{24}H_{27}N_4O$ 387.218487 (MH+); found 387.216845.

Example 21

Preparation of N-{[1-(4-Cyanobenzyl)-1H-imidazol-5-yl]methyl}-trans-4-(3-methylphenyl)-3 methoxy piperidine

Step A: trans-N-t-Butoxycarbonyl-4-(3-methylphenyl)-3-methoxy piperidine

To a solution of trans-N-t-butoxycarbonyl-4-(3-methylphenyl)-3 hydroxy piperidine (117 mg, 0.402 mmol), in DMF (2 ml) at 0° C. was added sodium hydride (24 mg of a 60% dispersion in mineral oil, 0.803 mmol). After 10 min, methyl iodide (0.050 ml, 0.803 mmol) was added and the reaction allowed to warm to room temperature over 16 hrs. The reaction was quenched by the addition of saturated $NH_4Cl$ solution (5 ml) and extraction with EtOAc. The organic extracts were washed with brine and dried, ($MgSO_4$) and the solvent evaporated in vacuo. Chromatography of the residue ($SiO_2$, 10–15% EtOAc in hexanes) afforded the title compound as an oil.

$^1$H NMR $CDCl_3$ δ7.20(1H, t, J=7.5 Hz), 7.20–7.0(3H, m), 4.50(1H, brs), 4.12(1H, brs), 3.28(1H, m), 3.17(3H, s), 2.75(1H, t, J=12.3 Hz), 2.60–2.45(2H, m), 2.34(3H, s), 1.85–1.60(2H, m), 1.495(9H, s) ppm.

Step B: trans-4-(3-Methylphenyl)-3 methoxy piperidine hydrochloride

To a solution of trans-N-t-butoxycarbonyl-4-(3-methylphenyl)-3 methoxy piperidine, (0.20 g, 0.65 mmol) in EtOAc (50 ml) at 0° C. was bubbled HCl gas until saturated. The reaction was stirred at 0° C. for 10 min and then the solvent evaporated in vacuo to afford the product as a white foam.

$^1$H NMR δ$CDCl_3$ 7.22(1H, t, J=7.3 Hz), 7.20–7.0(3H, m), 3.80–3.60(2H, m), 3.35(1H, m), 3.15(3H, s), 3.07(1H, m), 2.90–2.70(2H, m), 2.36(3H, s) and 2.10–1.95(2H, m) ppm.

Step C: N-{[1-(4-cyanobenzyl)-1H-imidazol-5-yl]methyl}-trans-4-(3-methylphenyl)-3-methoxy piperidine The title compound was prepared by the procedure in example 1 step H using trans-4-(3-methylphenyl)-3 methoxy piperidine hydrochloride.

Anal. Calcd for $C_{24}H_{26}N_4O.2.65TFA.0.45H_2O$: C, 51.20; H, 4.47; N, 7.88. Found: C, 51.18; H, 4.45; N, 7.90.

FAB HRMS exact mass calcd for $C_{25}H_{29}N_4O$ 401.234137 (MH+); found 401.233036.

Example 22

Preparation of N-{[1-(4-cyanobenzyl)-1H-imidazol-5-yl]methyl}-trans-4-(3-methylphenyl)-3 benzyloxy piperidine

Step A: trans-N-t-Butoxycarbonyl-4-(3-methylphenyl)-3 benzyloxy piperidine

To a solution of trans-N-t-butoxycarbonyl-4-(3-methylphenyl)-3 hydroxy piperidine (131 mg, 0.449 mmol), in DMF (2 ml) at 0° C. was added sodium hydride (27 mg of a 60% dispersion in mineral oil, 0.890 mmol). After 10 min, benzyl bromide (0.107 ml, 0.890 mmol) was added and the reaction allowed to warm to room temperature over 16 hrs. The reaction was quenched by the addition of saturated $NH_4Cl$ solution (5 ml) and extraction with EtOAc. The organic extracts were washed with brine and dried ($MgSO_4$) and the solvent evaporated in vacuo. Chromatography of the residue ($SiO_2$, gradient elution, 10–15% EtOAc in hexanes) afforded the title compound as an oil.

$^1$H NMR $CDCl_3$δ7.30–6.90(9H, m), 4.40(2H, brs), 4.25–4.05(2H, brs), 3.40(1H, m), 2.80–2.55(3H, m), 2.32 (3H, s), 1.85–1.60(2H, m), 1.48(9H, s) ppm.

Step B: trans-4-(3-Methylphenyl)-3-benzloxypiperidine hydrochloride

To a solution of trans-N-t butoxycarbonyl-4-(3-methylphenyl)-3-benzyloxy piperidine, (0.137 g, 3.60mmol) in EtOAc (50 ml) at 0° C. was bubbled HCl gas until saturated. The reaction was stirred at 0° C. for 10 min and then the solvent evaporated in vacuo to afford the product as a white foam.

$^1$H NMR $CD_3OD$ δ7.30–6.90(9H, m), 4.37(1H, d, J=11.5 Hz), 4.17(1H, d, J=11.5 Hz), 3.87(1H, dt, J=4.5 and 10.4 Hz), 3.66(1H, dd, J=4.4 and 13.3 Hz), 3.42(1H, d, J=12.3 Hz), 3.07(1H, dt, 4.0 and 12.3 Hz), 2.93–2.76(2H, m), 2.31(3H, s) and 2.20–1.93(2H, m) ppm.

Step C: N-{[1-(4-Cyanobenzyl)-1H-imidazol-5-yl]methyl}-trans-4-(3-methylphenyl)-3-benzyloxy piperidine The title compound was prepared by the procedure in example 1 step H using trans-4-(3-methylphenyl)-3-benzyloxypiperidine hydrochloride.

FAB HRMS exact mass calcd for $C_{31}H_{33}N_4O$ 477.265437 (MH+); found 477.265776.

Example 23

Preparation of 1-[2(R,S)-Amino-3-(2-tetradecyloxyphenyl)propyl]-4-(2-methylbenzyl) isonipecotic acid methyl ester dihydrochloride salt

Step A: 3-(2-hydroxyphenyl)-2-(N-t-butoxycarbonyl-amino)propanol

To a solution of D,L-N-t-Butoxycarbonyl-ortho-tyrosine methyl ester (1.34 g, 4.54 mmol) in THF (20 mL) at 0° C. was added lithium aluminum hydride (400 mg, 10.5 mmol) portionwise. After 4 hrs at room temperature, $H_2O$ (0.4 ml) was added dropwise followed by 1N NaOH (0.4 ml) and then $H_2O$ (1.2 ml). The slurry was stirred for 1 hour, filtered through celite, rinsed with THF and the solvent was evaporated in vacuo. Chromatography of the residue ($SiO_2$, 50% EtOAc in hexanes) gave the title compound as a solid.

Step B: 3-(2-Tetradecyloxyphenyl)-2(R,S)-(N-t-butoxycarbonyl-amino)propanol A mixture of the alcohol from Step A (218 mg, 0.82 mmol), tetradecyl bromide (170 μL, 0.9 mmol) and $CSCO_3$ (532 mg, 1.63 mmol) in DMF (8 mL) was stirred for 16 hs at room temperature under argon. The mixture was poured into water and extracted with EtOAc. The organic extracts were combined, washed with water and brine, dried ($MgSO_4$), and concentrated in vacuo to give an oil. Purification by chromatography ($SiO_2$, 20% EtOAc in hexanes) gave the title compound as a solid.

Step C: 3-(2-Tetradecyloxyphenyl)-2(R,S)-(N-t butoxycarbonylamino)propanal

To a solution of the alcohol from Step B (135 mg, 0.29 mmol) in $CH_2Cl_2$, (1.0 ml), DMSO, (1.0 ml) and $Et_3N$ (0.2 ml) at room temperature under argon was added pyridine-SO$_3$ complex (185 mg, 1.17 mmol). The mixture was stirred for 3 hrs and then poured into brine, and extracted with EtOAc. The organic extracts were combined, washed with brine, dried (MgSO$_4$) and concentrated in vacuo to give the title compound as an oil.

$^1$H NMR CDCl$_3$δ9.59 (s, 1H), 7.25–7.10 (m, 2H), 6.95–6.80 (mn, 2H), 5.42 (d, 1H), 4.35 (m, 1H), 3.96 (brt, 2H), 3.13 (m, 2H), 1.82 (m, 2H), 1.50–1.20 (m, 31H), 0.89 (brt, 3H).

Step D: 1-[2(R,S)-N-t-Butoxycarbonylamino-3-(2-tetradecyloxyphenyl)propyl]-4-(2-methylbenzyl) isonipecotic acid methyl ester The aldehyde (138 mg, 0.30 mmol) obtained in Step C was dissolved in dichloroethane (2.5 ml) and treated with the piperidine hydrochloride from example 3 step D (75 mg, 0.27 mmol) and Et$_3$N (37.8 ml, 0.27 mmol). The solution was slurried with 4 A molecular sieves and stirred for 30 min at room temperature before adding sodium triacetoxyborohydride (172 mg, 0.81 mmol). After stirring for 18 hrs, the solution was filtered through celite. The filtrate was poured into EtOAc, washed with saturated NaHCO$_3$ solution, brine, dried (MgSO$_4$), and concentrated in vacuo to give an oil. Purification by chromatography (SiO$_2$, 30% EtOAc in hexanes) gave the title compound.

$^1$H NMR CDCl$_3$, δ7.06 (m, 6H), 6.83 (m, 2H), 5.01 (brs, 1H), 3.92 (m, 4H), 3.59 (s, 3H), 2.82 (m, 4H), 2.07 (m, 8H), 1.41 (m, 37H), 0.88 (brt, 3H).

Step E: 1-[2(R,S)-Amino-3-(2-tetradecyloxyphenyl)propyl]-4-(2-methylbenzyl)isonipecotic acid methyl ester dihydrochloride salt A solution of the N-t-butoxycarbonylamine from Step D (186 mg) in EtOAc (20 mL) was treated with HCl gas until saturated. After 15 min, the solvent was removed in vacuo to give the crude product as a solid which was triturated with Et$_2$O/hexane. The solvent was decanted and the residue dried in vacuo to give the title compound. Anal. Calcd. for C$_{38}$H$_{60}$N$_2$O$_3$.2.4 HCl: C, 67.07; H,9.24; N, 4.12. Found: C, 67.10; H, 9.33; N, 4.29.

FAB MS 593 (MH$^+$).

Example 24

Preparation of N-2-(S)-aminolauroyl-4-(1-napthylmethyl) isonipecotic acid methyl ester

Step A: (S)-3-(1-Oxolauroyl)-4-(phenylmethyl-2-oxazolidinone

To a solution of (S)-4-Benzyloxazolidinone (8.85 g, 50 mmol) in 150 mL of anhydrous THF at −78° C. was added a 2.5 M solution of n-Butyllithium (25 mL, 52.5 mmol) over 10 min. After the addition, neat lauroyl chloride (12.7 mL, 55 mmol) was added and the resulting solution stirred at −78° C. for 0.5 hr. and then allowed to warm to room temperature over 0.5 hr. The mixture was quenched with saturated aqueous ammonium chloride and the solvent removed in vacuo. The residue was diluted with water and extracted with methylene chloride. The extracts were combined and washed with 1M aqueous sodium hydroxide, brine, dried over sodium sufate and concentrated in vacuo to afford the product as a viscous yellow oil.

$^1$H NMR CDCl$_3$δ7.20–7.40 (m, 5 H), 4.70 (m, 1 H), 4.20 (m, 2 H), 3.3 ( dd, J=13.3, 3.3 Hz, 1 H), 2.90 (m, 2 H), 2.80 ( dd, J=13.3, 9.7 Hz, 1 H) 1.70 (m, 2 H), 1.30 (m, 18 H), 0.90 (t, J=6.7 Hz, 3 H)

Step B: Preparation of (S)-3-(1-Oxo-(S)-2-azidolauroyl)-4-(phenylmethyl-2-oxazolidinone To a solution of (S)-3-(1-Oxolauroyl)-4-(phenylmethyl-2-oxazolidinone.(3.6 g, 10 mmol) in anhydrous THF (60 ml), at −78° C., was added (21 ml of a 0.5 M solution of potassium hexamethyldisilazide in toluene, 10.5 mmol). The resulting solution was stirred at −78° C. for 15 min. and then treated with a precooled solution of 2,4,6-triisopropylbenzenesulfonyl azide in anhydrous THF (25 ml). Two minutes after the addition, glacial acetic acid (2.3 ml, 40 mmol) was added and the reaction mixture was warmed to 25° C. in a water bath and stirred for 1.5 hrs. The reaction mixture was diluted with chloroform (300 ml) and washed successively with brine and dilute sodium bicarbonate solution. After drying over sodium sulfate the crude chloroform solution was concentrated in vacuo to a yellow oil which was chromatographed on (SiO2, 5% EtOAc in hexanes). Evaporation in vacuo to afforded the product as a pale yellow viscous oil.

$^1$H NMR CDCl$_3$δ7.2–7.4 (m, 5 H), 4.9 (dd, J=8.6, 5.0 Hz, I H), 4.7 ( m, 1 H), 4.2 (m, 2 H), 3.4 ( dd, J=13.4, 3.2 Hz, 1 H), 2.8 ( dd, J=13.4, 9.5 Hz, 1 H) 1.8 (m, 2 H), 1.6–1.2 (m, 18 H), 0.9 (t, J=6.7 Hz, 3 H).

Step C. (S)-3-(1-Oxo-(S)-2-N-t-butoxycarbonylaminolauroyl)-4-(phenylmethyl-2-oxazolidinone To an argon degassed solution of the above azide (2.88 g, 7.2 mmol) in ethyl acetate (150 mL) was added t-butoxycarbonyl anhydride (2.5 g, 11.5 mmol) and 10% palladium on charcoal catalyst (0.3 g). This mixture was vigorously stirred under a balloon of hydrogen for 2 hrs. The catalyst was removed by filtration through celitChromatography (SiO$_2$, 15% EtOAc in hexanes) and evaporation of solventin vacuo, afforded the product as a white solid. m.p. 93.5–94.5° C.

$^1$H NMR CDCl$_3$δ7.2–7.4 (m, 5 H), 5.4 (m, 1 H), 5.2 (br d, J=9 Hz, 1 H), 4.6 (m, 1 H), 4.2 (m, 2 H), 3.3 ( m, 1 H), 2.8 (m, 1 H) 1.8 (m, 1H), 1.6–1.2 (m, 26 H), 0.9 (t, J=6.7 Hz, 3 H).

Step D: Preparation of (S)-2-N-t-Butoxycarbonylaminolauric acid

To an argon degassed solution of the above oxazolidinone in a 3:1 THF: water mixture, under argon at 0° C., was added LiOH monohydrate (0.45 g, 10.7 mmol). After stirring at 0° C. for 1.5 hrs, the mixture was diluted with 0.5 M aqueous sodium bicarbonate and extracted with methylene chloride. The aqueous portion was acidified with 3 M aqueous HCl and extracted with ethyl acetate. The combined extracts were dried (MgSO$_4$) and concentrated in vacuo to afford the product as a viscous oil.

$^1$H NMR (CDCl$_3$) d 5.0 (br d, J=8 Hz, 1 H), 4.3 (m, 1 H), 1.8 (m, 1 H), 1.7 ( m, 1 H), 1.4 ( s, 9 H) 1.4–1.2 ( m, 16 H), 0.9 (t, J=7 Hz, 3 H).

Step E: N-2-(S)-t-Butoxycarbonylaminolauroyl-4-(1-napthylmethyl) isonipecotic acid methyl ester The title compound was prepared according to the procedure in example 10 using the acid prepared in step D.

Step F: N-2-(S)-Aminolauroyl-4-(1-napthylmethyl)-isonipecotic acid methyl ester A solution of the product from Step E (100 mg) in EtOAc (10 ml) was treated with HCl gas until saturated. After 15 mins, the solvent was removed in vacuo to give the crude product which was purified by preparative HPLC (C18, gradient elution, 95:5 to 5:95 water:acetonitrile containing 0.1% TFA) to afford the title compound as a white solid after lyophilisation.

Anal. Calcd for $C_{30}H_{44}N_2O_3 \cdot 1.20TFA$: C, 63.02 H, 7.38; N, 4.54. Found: C, 63.05; H, 7.42; N, 4.43.

Example 25

4-(Benzoxazolidin-2-one-1-yl)-1-[1-(4-cyanobenzyl)-5-imidazolylacetyl]piperidine hydrochloride Step A: Preparation of 1H-Imidazole-4-acetic acid methyl ester hydrochloride A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid.

Step B: Preparation of 1-(Triphenylmethyl)-1H-imidazol-4-ylacetic acid methyl ester To a solution of the product from Step A (24.85 g, 0.141 mol) in dimethyl formamide (DMF) (115 ml) was added triethylamine (57.2 ml, 0.412 mol) and triphenylmethyl bromide(55.3 g, 0.171 mol) and the suspension was stirred for 24 hr. After this time, the reaction mixture was diluted with ethyl acetate (EtOAc) (1l) and water (350 ml). The organic phase was washed with sat. aq. $NaHCO_3$ (350 ml), dried ($Na_2SO_4$) and evaporated in vacuo. The residue was purified by flash chromatography ($SiO_2$, 0–100% ethyl acetate in hexanes; gradient elution) to provide the title compound as a white solid.

$^1H$ NMR ($CDCl_3$, 400 MHz) d 7.35(1H, s), 7.31(9H, m), 7.22(6H, m), 6.76(1H, s), 3.68(3H, s) and 3.60(2H, s) ppm.

Step C: Preparation of [1-(4-cyanobenzyl)-1H-imidazol-5-yl]acetic acid methyl ester To a solution of the product from Step B (8.00 g, 20.9 mmol) in acetonitrile (70 ml) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq $NaHCO_3$ (300 ml) and $CH_2Cl_2$ (300 ml) and stirred at room temperature for 2 hr. The organic layer was separated, dried ($MgSO_4$) and evaporated in vacuo to afford the title compound as a white solid:

Step D: Preparation of [1-(4-cyanobenzyl)-1H-imidazol-5-yl]acetic acid

A solution of [1-(4-cyanobenzyl)-1H-imidazol-5-yl] acetic acid methyl ester (4.44 g, 17.4 mmol ) in THF (100 ml) and 1 M lithium hydoxide (17.4 ml, 17.4 mmol) was stirred at RT for 18 hr. 1 M HCl (17.4 ml) was added and the THF was removed by evaporation in vacuo. The aqueous solution was lyophilised to afford the titled compound containing lithium chloride as a white solid.

Step E: Preparation of 1-(tert-butoxycarbonyl)-4-[(2-hydroxyphenyl)amino]piperidine A 500 mL round bottom flask under inert atmosphere is charged with a magnetic stirring bar, 6.6 g (60 mmol) 2-aminophenol and 12 g (60 mmol) N-t-butyloxycarbonyl-4-piperidone. The solids are suspended in 50 mL each 1,2-dichloroethane and glacial HOAc, treated with 1 g powdered 4 Å molecular sieves, and stirred at room temperature 30 min. 12.8 g (60 mmol) $NaBH(OAc)_3$ is added and the thick slurry stirred at room temperature 30 h. The reaction mixture is diluted with 200 mL $CH_2Cl_2$ and quenched slowly with saturated $NaHCO_3$ solution, approx 100 mL. The layers are separated, the organic layer washed with 1×150 mL saturated $NaHCO_3$ solution, dried over $MgSO_4$, filtered and concentrated to provide a brown oil. Flash chromatography on silica (1 to 3% MeOH in $CH_2Cl_2$ containing 0.5% conc. $NH_4OH$) provided 16.8 g (57 mmol, 95%) of the desired aminoalcohol as a foam.

Step F: Preparation of 1-(tert-butoxycarbonyl)-4-(benzoxaxolidin-2-one-1-yl)piperidine A 1-L round bottom flask under inert atmosphere is charged with a magnetic stirring bar, 16.8 g (57 mmol) of the aminoalcohol from Step E and 500 mL freshly distilled THF, and the flask immersed in an ice-water bath. Stirring is initiated and when the solution becomes homogeneous, 12 mL (69 mmol) N,N-diisopropylethylamine is added followed by 5.7 g (19.2 mmol) triphosgene in one portion. The reaction is stirred at 0° C. 30 min and then the ice-water bath removed and the reaction allowed to stir 15 h, wherein a precipitate is formed. The reaction mixture is filtered, concentrated to an oil and partitioned between 400 mL EtOAc and 200 mL saturated $Na_2CO_3$ solution. The layers are separated, the organic layer washed with 200 mL saturated $Na_2CO_3$ solution, dried over $MgSO_4$, filtered and concentrated to an oil. Flash chromatography on silica (15 to 30 to 40% EtOAc in hexanes) provided 14.6 g (46 mmol, 80%) of the benzoxazolone as an amorphous solid.

Step G: Preparation of 4-(benzoxaxolidin-2-one-1-yl)piperidine hydrochloride

A 1-L round bottom flask is charged with a magnetic stirring bar, 14.6 g (46 mmol) benzoxazolone from Step F and 120 mL isopropanol. 60 mL 8 N HCl is added, the reaction becomes homogeneous and it is stirred 15 h wherein a precipitate forms. The reaction is concentrated by rotary evaporation and the solid dried azeotropically with 2×150 mL toluene and the resulting off white solid dried under vacuum to provide 11.5 g (45 mmol, 99%) of the amine hydrochloride salt.

Step H: Preparation of 4-(benzoxaxolidin-2-one-1-yl)-1-[1-(4-cyanobenzyl)-5-imidazolylacetyl] piperidine hydrochloride To a solution of the acid from Step D (639 mg, 1.77 mmol), the amine hydrochloride salt from Step G (303 mg, 1.18 mmol), and HOOBT (295 mg, 1.81 mmol) in DMF (5 mL) was added EDC (347 mg, 1.81 mmol), followed by triethylamine (0.99 ml, 7.11 mmol). The reaction was stirred at room temperature for 15 hrs, diluted with EtOAc, and the organic layer was washed with sat. aq NaHCO$_3$, brine, and dried (Na$_2$SO$_4$). and evaporated in vacuo. The resulting product was purified by silica gel chromatography (59% acetone/CH$_2$Cl$_2$ with 1% MeOH) to provide the desired amide which was taken up in CH$_2$Cl$_2$ and treated with excess 1 M HCl/ether solution, and concentrated in vacuo. The titled product hydrochloride (391 mg) was isolated as a white solid.

FAB mass spectrum m/e 442 (M+1).

Analysis calculated for C$_{25}$H$_{23}$N$_5$O$_3$.1.0 HCl.0.55 H$_2$O:
C, 61.55; H, 5.19; N, 14.36;
Found: C, 61.51; H, 5.23; N, 15.56.

Example 26

4-(1,2-Dihydro-4(H)-3,1-benzoxazin-2-one-1-yl)-1-[1-(4-cyanobenzyl)-5-imidazolylacetyl]piperidine hydrochloride Step A: Preparation of 1-tert-butoxycarbonyl-4-[(2-hydroxymethyl)phenylamino]piperidine N-t-butoxycarbonyl-4-piperidinone (20 g, 100 mmol), 2-aminobenzyl alcohol (13 g, 110 mmol), and acetic acid (14 mL, 220 mmol) were dissolved in dry toluene (500 mL). The solution was refluxed under inert atmosphere with azeotropic removal of water for 16 h. The solution was cooled to ambient temperature and to it was added NaBH$_3$CN (14 g, 220 mmol) and dry THF (200 mL). The reaction was stirred at ambient temperature for 24 h. The reaction was concentrated under reduced pressure and the residue was dissolved in EtOAc (750 mL). The EtOAc layer was washed with saturated aqueous NaHCO$_3$ (4×500 mL) and brine (250 mL). The EtOAc layer was dried (MgSO$_4$), filtered, and the solvent was removed under reduced pressure. The residue was purified by pressurized silica gel column chromatography, using a gradient elution of 15–30% EtOAc-hexanes. The titled compound was obtained as a gum.

Step B: Preparation of 1-[(1-t-butyloxycarbonyl)piperidin-4-yl]-1,2-dihydro-4(H)-3,1-benzoxazin-2-one The product form Step A (24 g, 78 mmol) was dissolved in dry THF (250 mL) and cooled to 0° C. To the solution was added diisopropylethylamine (41 mL, 240 mmol) and triphosgene (8.54 g, 28.8 mmol). The reaction was stirred at 0° C. for 1 h, and then at ambient temperature for 72 h. Ether (250 mL) was added, the mixture was cooled to 0° C. for 3 h and then filtered to remove the hydrochloride salt of DIEA. The filtrate solvents were removed under reduced pressure and the residue was dissolved in EtOAc (750 mL). The EtOAc solution was washed with 5% aqueous citric acid (2×500 mL), water (250 mL), and saturated aqueous NaHCO$_3$ (2×500 mL). The EtOAc layer was dried (MgSO$_4$), filtered, and the solvent was removed under reduced pressure. The residue was boiled in ether (ca. 200 mL) until the solid had dissolved. Cooling overnight gave the titled product as off-white crystals.

Step C: Preparation of 1-(4-piperidinyl)-1,2-dihydro-4(H)-3,1-benzoxazin-2-one hydrochloride A stirred solution of the product from Step B (19 g, 57 mmol) in EtOAc (500 mL) was cooled to 0° C. HCl gas was bubbled through the solution for 30 min. Stirring was continued at 0° C. for 1 h, during which time a precipitate had formed, and then at ambient temperature for 1 h. The stirred suspension was cooled to 0° C. and cold ether (250 mL) was added. After 1 h at 0° C., the solid was collected by filtration. The solid was dried under reduced pressure for 18 h, giving the titled compound as an off-white solid.

Step D: Preparation of 4-(1,2-dihydro-4(H)-3,1-benzoxazin-2-one-1-yl)-1-[1-(4-cyanobenzyl)-5-imidazolylacetyl]piperidine hydrochloride To a solution of the acid from Step D of Example 25 (435 mg, 1.21 mmol), the amine hydrochloride salt from Step C (215 mg, 0.796 mmol), and HOBT (168 mg, 1.24 mmol) in DMF (6 mL) was added EDC (233 mg, 1.22 mmol), followed by triethylamine (0.66 ml, 4.8 mmol). The reaction was stirred at room temperature for 15 hrs, diluted with EtOAc, and the organic layer was washed with sat. aq NaHCO$_3$, brine, and dried (Na$_2$SO$_4$), and evaporated in vacuo. The resulting product was taken up in CH$_2$Cl$_2$ and treated with excess 1 M HCl/ether solution, and concentrated in vacuo. The titled product hydrochloride (335 mg) was isolated as a white solid.

FAB mass spectrum m/e 456 (M+1).

Analysis calculated for C$_{26}$H$_{25}$N$_5$O$_3$.1.60 HCl.0.85 H$_2$O:

C, 59.05; H, 5.39; N, 13.24;
Found: C, 59.10; H, 5.40; N, 12.76.

Example 27

4-(1,2-Dihydro-4(H)-3,1-benzoxazin-2-one-1-yl)-1-[1-(4-cyanobenzyl)-5-imidazolylmethyl]piperidine hydrochloride Step A: 4-(1,2-dihydro-4(H)-3,1-benzoxazin-2-one-1-yl)-1-[1-(4-cyanobenzyl)-5-imidazolylmethyl]piperidine hydrochloride To a solution of the amine hydrochloride from Step C of Example 26 (135 mg, 0.502 mmol) in 10 mL of 1,2-dichloroethane at 0° C. was added 4 Å powdered molecular sieves (360 mg), followed by sodium triacetoxyborohydride (168 mg, 0.793 mmol). The imidazole carboxaldehyde from Step E of Example 1 (120 mg, 0.570 mmol) was added, and the reaction was stirred at 0° C. After 56 hours, the reaction was poured into EtOAc, washed with dilute aq. NaHCO$_3$, and the aqueous layer was back-extracted with EtOAc. The combined organics were washed with brine, dried (Na$_2$SO$_4$), filtered, and concentrated in vacuo. The resulting product was taken up in 10 mL of CH$_2$Cl$_2$, and propylamine (2 mL) was added. The mixture was stirred for 12 hours, then concentrated in vacuo to afford a pale yellow foam. This material was purified by silica gel chromatography (50–80% % acetone/CH$_2$Cl$_2$), and the resultant white foam was taken up in CH$_2$Cl$_2$ and treated with excess equivalents of 1 M HCl/ether solution. After concentrated in vacuo, the product dihydrochloride was isolated as a white powder.

Example 28

N-[2-{(4-Cyanobenzyl)-5-imidazolyl}ethyl]-4-carbamoyl-1-phenylpiperidine hydrochloride

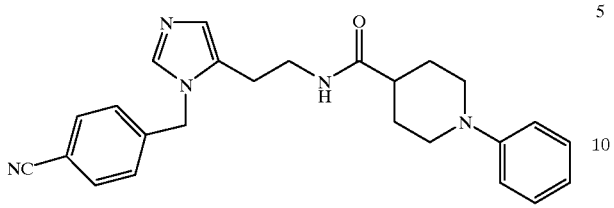

Step A: 4-Cyanobenzyl-Nα-phthaloylhistamine

N$^T$-Pivaloyloxymetbyl-N$^\alpha$-phthaloylhistamine (4.55 g, 12.8 mmol) was prepared as previously described (J. C. Emmett, F. H. Holloway, and J. L. Turner, *J. Chem. Soc., Perkin Trans.* 1, 1341, (1979)). α-Bromo-p-tolunitrile (3.77 g, 19.2 mmol) was dissolved in acetonitrile (70 mL). The solution was heated at 55° C. for 4 h, cooled to room temperature, and filtered to remove the white solid. The acetonitrile (30 mL) was concentrated to ½ its volume under reduced pressure and the solution was heated at 55° C. overnight. The solution was cooled and filtered to give a white solid. The volume of the filtrate was reduced to 10 mL, the solution was heated at 55° C. for 1 hr, then cooled to room temperature, diluted with ethyl acetate (25 mL) and filtered to obtain additional white solid. The solids were combined, dried, and dissolved in methanol (100 mL) which was saturated with ammonia gas while the temperature was maintained below 30° C. The solution was stirred for 1 hr, concentrated to dryness, and extracted with methylene chloride (3×200 mL), dried (MgSO$_4$), concentrated, and chromatographed (silica gel, 10:90:1 MeOH/CH$_2$Cl$_2$/NH$_4$OH) to give the title compound

Step B: 4-Cyanobenzyl histamine

4-Cyanobenzyl-N$^\alpha$-phthaloylhistamine (1.64 g, 4.61 mmol), and hydrazine (1.46 mL, 46.1 mmol) were dissolved in absolute ethanol (70 mL). The solution was concentrated after 1 hr and filtered to remove a white precipitate which was washed several times with ethanol. The filtrate was concentrated and the residue was chromatographed (silica gel, 10:90:1 MeOH/CH$_2$Cl$_2$/NH4OH) to give the title compound.

Step C: 4-Carbethoxy-1-phenylpiperidine

A mixture of ethyl isonipecotate (2.00 mL, 12.97 mmol), triphenylbismuth (8.56 g, 19.46 mmol), copper(II)acetate (3.52 g, 19.46 mmol) and triethylamine (2.70 mL, 19.46 mmol) was stirred for 17 h at 20° C. in dichloromethane (60 mL). The reaction mixture was adsorbed onto silica gel and eluted with 5% ethyl acetate/hexane. The title compound was obtained as an oil.

Step D: 4-Carboxy-1-phenylpiperidine

The product from Step C was dissolved in methanol and 5% aqueous sodium hydroxide added. After 1 h, methanol was removed in vacuo, and the residue partitioned between ethyl acetate and 10% aqueous HCl. The organic layer was washed with saturated brine, and dried over MgSO$_4$. Filtration and concentration provided the title compound.

Step E: N-[2-{1-(4-Cyanobenzyl)-5-imidazolyl}ethyl]-3-carbamoyl-1-phenylpiperidine hydrochloride The product from Step D is dissolved in dimethylformamide. To this solution is added 4-cyanobenzyl histamine dihydrochloride. EDC HCl, and 1-hydroxybenzotriazole. The pH is adjusted to 7.5 with triethylamine. After 16 h, the reaction is poured into water and extracted with ethyl acetate. The organic phase is washed with saturated brine and dried over magnesium sulfate. The crude product is chromatographed on silica gel and the purified product converted to the hydrochloride salt with HCl in methylene chloride. The title compound is isolated by removal of solvent.

Example 29

4-[2-{1-(4-Cyanobenzyl)-5-imidazolyl}ethyl]-1-phenylpiperidine hydrochloride

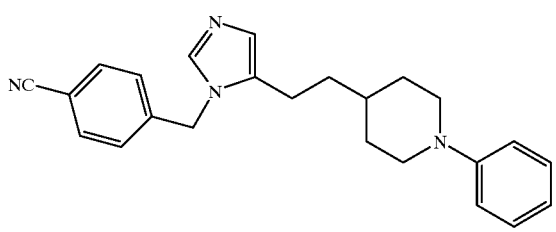

Step A: 4-Formyl-1-phenylpiperidine

The product from Example 28, Step C is dissolved in THF and cooled to −78° C. under nitrogen. A solution of diisobutylaluminum hydride (1 eq.) in toluene is added dropwise. After 30 min, the reaction is quenched with saturated sodium potassium tartrate solution. The mixture is extracted with ethyl acetate, and the organic phase washed with saturated brine, and dried over MgSO$_4$. Filtration and concentration provides the title compound

Step B: 4-Hydroxymethyl-1-triphenylmethylimidazole

To a solution of 4-(hydroxymethyl)imidazole hydrochloride (35.0 g, 260 mmol) in 250 mL of dry DMF at room temperature is added triethylamine (90.6 mL, 650 mmol). A white solid precipitates from the solution. Chlorotriphenylmethane (76.1 g, 273 mmol) in 500 mL of DMF is added dropwise. The reaction mixture is stirred for 20 hours, poured over ice, filtered, and washed with ice water. The resulting product is slurried with cold dioxane, filtered, and dried in vacuo to provide the titled product which is sufficiently pure for use in the next step.

Step C: 4-Chloromethyl-1-triphenylmethylimidazole

The product from Step B is dissolved in chloroform and cooled to 0° C. under nitrogen. Thionyl chloride (molar equivalent) is added slowly via syringe. The reaction is stirred for 30 min, and extracted with sodium bicarbonate solution. The organic phase is dried over magnesium sulfate, filtered and concentrated to provide the title compound.

Step D: 4-Diethylphosphonomethyl-1-triphenylmethylimidazole

The product from Step C is dissolved in acetonitrile and cooled to 0° C. Triethyl phosphite (1 equivalent) and sodium iodide (1 equivalent) are added, and the reaction stirred at room temperature overnight. The reaction is quenched with ammonium chloride, and extracted with ethyl acetate. The organic phase is dried over magnesium sulfate, filtered and concentrated to provide the title compound.

Step E: 4-[2-{1-(Triphenylmethyl)-4-imidazolyl}ethenyl]-1-phenylpiperidine

The product from Step D is dissolved in THF and cooled to −78° C. under nitrogen. A solution of LDA in THF is added dropwise. The reaction was stirred at −78° C. for 1 h, then a solution of 4-formyl-1-phenylpiperidine from Step A is added, and the reaction warmed to room temperature overnight. The reaction is quenched with ammonium chloride solution, and extracted with ethyl acetate. The title compound is obtained after chromatography on silica gel.

Step F: 4-[2-{1-(Triphenylmethyl)-4-imidazolyl}ethyl]-1-phenylpiperidine

The product from Step E is dissolved in methanol and hydrogenated at 60 psi hydrogen with 10% palladium on carbon. When reaction is complete, the catalyst is filtered and the title compound obtained after evaporation of solvent.

Step G: 4-[2-{1-(4-Cyanobenzyl)-5-imidazolyl}ethyl]-1phenylpiperidine hydrochloride The product from Step F is dissolved in acetonitrile and reacted with 4-cyanobenzylbromide (1 equivalent) at room temperature overnight. The reaction is concentrated in vacuo, and the residue dissolved in methanol. The methanol solution is refluxed for 3 h and then concentrated. The residue is partitioned between ethyl acetate and saturated sodium bicarbonate solution. The organic phase is washed with saturated brine, dried over magnesium sulfate, filtered and concentrated. The title compound is obtained after purification by silica gel chromatography, and conversion to the dihydrochloride salt.

Example 30

Preparation of 4-{5-[4-Hydroxymethyl-4-(3-trifluoromethoxybenzyl)-piperidine-1-ylmethyl]imidazol-1-ylmethyl}benzonitrile

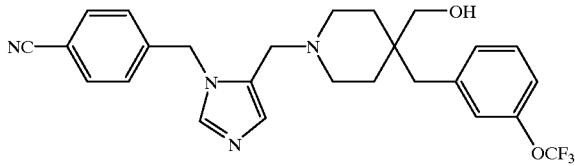

Step A: Preparation of Ethyl N-tert-butoxycarbonylpiperidine-4-carboxylate

To a cold (0° C.) solution of ethyl isonipecotate (39.5 g, 0.251 mol) and triethylamine (38.5 mL, 0.276 mol) in dichloromethane (350 mL), a solution of di-tert-butyl dicarbonate (55.9 g, 0.256 mol) in dichloromethane (50 mL) was added over a period of 30 min. The reacting mixture was stirred at room temp. overnight. The product mixture was washed with aqueous potassium hydrogen sulfate (3 times), and brine (to pH 7). The organic extract was dried over anhydrous sodium sulfate, filtered, and concentrated under vacuum to provide the title compound as clear, colorless, viscous oil.

Step B: Preparation of Ethyl N-tert-butoxycarbonyl-4-(3-trifluoromethoxybenzyl)piperidine-4-carboxylate To a cold (−78° C.) solution of ethyl N-tert-butoxycarbonylpiperidine-4-carboxylate (5.16 g, 20.05 mmol) in anhydrous tetrahydrofuran (60 mL), a solution of sodium bis(trimethylsilyl)amide (28 mL, 1M, 28 mmol) was added over a period of 30 min. The resultant mixture was stirred at −78° C. for 1 h, and 3-(trifluoromethoxy)benzyl bromide (5.90 g, 23.14 mmol) was added. The reacting mixture was allowed to warm to room temp. and stirred overnight. The product mixture was concentrated, and the residue was partitioned between water and ethyl acetate. The organic extract was washed with brine, dried over anhydrous magnesium sulfate, filtered, and concentrated under vacuum. The residue was subjected to column chromatography on silica gel eluting with 20% ethyl acetate in hexane. Collection and concentration of appropriate fractions provided the title compound.

Step C: Preparation of N-tert-butoxycarbonyl-4-(3-trifluoro-methoxybenzyl)-4-hydroxymethylpiperidine To a slurry of lithium aluminum hydride (585 mg, 15.4 mmol) in anhydrous diethyl ether (100 mL) at 0° C., a solution of ethyl N-tert-butoxycarbonyl-4-(3-trifluoromethoxybenzyl)piperidine-4-carboxylate (5.84 g, 14.0 mmol) in diethyl ether (30 mL) was added dropwise with the temp. of the reacting mixture maintained below 10° C. The resulting mixture was stirred at 0° C. for 30 min, and quenched with successive addition of water (0.58 mL), 15% aqueous NaOH (0.58 mL), and water (1.74 mL). The resultant slurry was stirred at room temp. for 30 min., and filtered through a small plug of Celite. The filtrate was washed brine, dried over anhydrous magnesium sulfate, filtered, and concentrated under vacuum to provide the title alcohol.

Step D: Preparation of 4-(3-trifluoromethoxybenzyl)-4-hydroxy-methylpiperidine hydrochloride salt A solution of N-tert-butoxycarbonyl-4-(3-trifluoromethoxy-benzyl)-4-hydroxymethylpiperidine (2.9 g) in dichloromethane (100 mL) at 0° C. was saturated with hydrogen chloride gas. The resultant solution was sealed with a rubber septum and stirred at room temp. for 2.5 h. The product solution was concentrated under vacuum to provide the title compound.

Step E. Preparation of 4-{5-[4-Hydroxymethyl-4-(3-trifluoromethoxybenzyl)piperidine-1-ylmethyl]imidazol-1-ylmethyl}-benzonitrile A mixture of 4-(3-trifluoromethoxybenzyl)-4-hydroxymethylpiperidine hydrochloride salt (0.62 g, 2.0 mmol), 1-(4-cyano-benzyl)imidazole-5-carboxyaldehyde (0.45 g, 2.0 mmol; Example 1, Step E), diisopropylethylamine (0.53 mL, 3.04 mmol), anhydrous magnesium sulfate (650 mg), activated molecular sieves 3 A powder (750 mg), and anhydrous methanol (6 mL) was stirred at room temp. overnight. The pH of the mixture was adjusted to ~5 with addition of glacial acetic acid. To the mixture, a solution of sodium cyanoborohydride in THF (2.2 mL, 1 M, 2.2 mmol) was added slowly over a period of 8 h with a syringe pump, and stirred at room temp. overnight. The product mixture was diluted with chloroform, filtered through Celite. The filtrate was washed with aqueous sodium bicarbonate, brine, dried over anhydrous sodium sulfate, filtered, and concentrated under vacuum. The residue was subjected to column chromatography on silica gel eluting with a 5–10% methanol in chloroform gradient. Collection and concentration of appropriate fractions provided the title compound as white solid.

Anal. Calcd for $C_{26}H_{27}N_4O_2F_3 \cdot 0.38\ H_2O$: C, 63.56; H, 5.69; N, 11.40. Found: C, 63.55; H, 5.72; N, 11.46.

Example 31

Preparation of 4-{5-[4-Hydroxymethyl-4-(3-trifluoromethoxybenzyl)-piperidine-1-ylmethyl]-2-methylimidazol-1-ylmethyl}benzonitrile

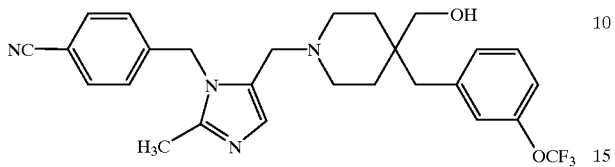

Step A: Preparation of 1-(4-cyanobenzyl)-2-methylimidazole-5-carboxyaldehyde To a cold (0° C.) mixture of 4-formyl-2-methylimidazole (10.0 g, 91 mmol), cesium carbonate (44.4 g, 136 mmol), dimethyl formamide (300 mL) stirred with a mechanical stirred, solid 4-cyanobenzyl bromide (18.7 g, 95 mmol) was added slowly over a period of 5 h using an open end plastic syringe and a syringe pump. The resultant mixture was stirred at 0° C. overnight, concentrated under vacuum. The residue was partitioned between water and ethyl acetate. The organic extract was washed with brine, dried over anhydrous sodium sulfate, filtered, and concentrated under vacuum. The crude product was subjected to column chromatography on silica gel eluting with 4% methanol in chloroform. Collection and concentration of appropriate fractions provided the title compound as white solid.

$^1$H NMR (CDCl$_3$ 300MHz) δ9.67 (1H, s), 7.79 (1H, s), 7.63 (2H, d, J=8.6 Hz), 7.13 (2H, d, J=8.6 Hz), 5,62 (2H, s), and 2.42 (3H, s) ppm.

Step B: Preparation of 4-{5-[4-Hydroxymethyl-4-(3-trifluoromethoxybenzyl)piperidine-1-ylmethyl]-2-methylimidazol-1-ylmethyl}benzonitrile The title compound was prepared as white solid using the protocol described in Example 30- Step E, substituting 1-(4-cyano-benzyl)imidazole-5-carboxyaldehyde with 1-(4-cyanobenzyl)-2-methylimidazole-5-carboxyaldehyde.

Anal. Calcd for $C_{27}H_{29}N_4O_2F_3$: C, 62.05; H, 5.86; N, 11.24. Found: C, 65.06; H, 5.97; N, 11.51.

Example 32

Preparation of 4-{5-[4-Hydroxymethyl-4-(3-trifluoromethylbenzyl)-piperidine-1-ylmethyl]imidazol-1-ylmethyl}benzonitrile

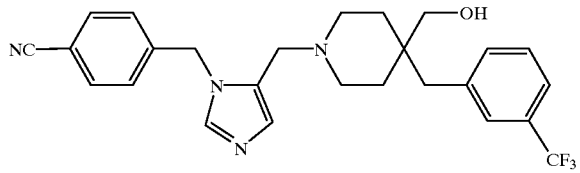

The title compound was prepared as white solid according to the procedure described in Example 30, Step B–E substituting 3-(trifluoromethoxy)benzyl bromide with 3-trifluoromethylbenzyl bromide in Step B.

Anal. Calcd for $C_{26}H_{27}N_4OF_3$: C, 66.65; H, 5.81; N, 11.96. Found: C, 66.74; H, 5.73; N, 12.38.

Example 33

Preparation of 4-{5-[4-Hydroxymethyl-4-(3-trifluoromethylbenzyl)-piperidine-1-ylmethyl]-2-methylimidazol-1-ylmethyl}benzonitrile

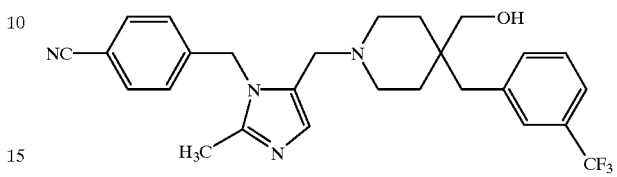

The title compound was prepared as white solid according to the procedure described in Example 30, Step B–E substituting 3-(trifluoromethoxy)benzyl bromide with 3-trifluoromethylbenzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E.

Anal. Calcd for $C_{27}H_{29}N_4OF_3 \cdot 2.85$ TFA: C, 48.64; H, 3.98; N, 6.94.

Found: C, 48.61; H, 4.01; N, 6.91.

Example 34

Preparation of 4-{5-[4-Hydroxymethyl-4-(2-trifluoromethylbenzyl)-1piperidine-1-ylmethyl]imidazol-1-ylmethyl}benzonitrile

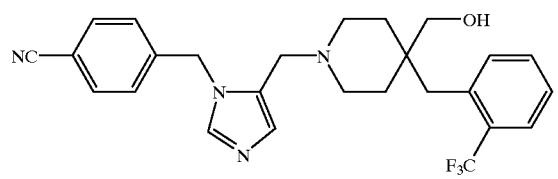

The title compound was prepared as white solid according to the procedure described in Example 30, Step B–E substituting 3-(trifluoromethoxy)benzyl bromide with 2-trifluoromethylbenzyl bromide in Step B.

Anal. Calcd for $C_{26}H_{27}N_4OF_3 \cdot 0.30\ Et_2O$: C, 66.57; H, 6.15; N, 11.42. Found: C, 66.21; H, 5.80; N, 11.22.

Example 35

Preparation of 4-{5-[4-Hydroxymethyl-4-(2-methylbenzyl)piperidine-1-ylmethyl]imidazol-1-ylmethyl}benzonitrile trifluoroacetate salt

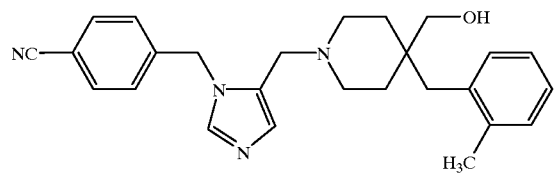

The title compound was prepared as white solid according to the procedure described in Example 30, Step B–E substituting 3-(trifluoromethoxy)benzyl bromide with 2-methylbenzyl bromide in Step B. After column chromatography purification, the final product was dissolved in aqueous TFA and lyophilized.

Anal. Calcd for $C_{26}H_{30}N_4O \cdot 0.75$ TFA $\cdot 0.05$ $H_2O$: C, 51.90; H, 4.54; N, 7.69. Found: C, 51.89; H, 4.52; N, 7.68.

Example 36

Preparation of 4-{5-[4-Hydroxymethyl-4-(3-methylbenzyl)piperidine-1-ylmethyl]imidazol-1-ylmethyl}benzonitrile

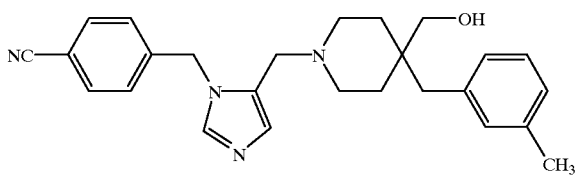

The title compound was prepared as white solid according to the procedure described in Example 30, Step B–E substituting 3-(trifluoromethoxy)benzyl bromide with 3-methylbenzyl bromide in Step B. After column chromatography purification, the final product was triturated in diethyl ether, filtered, and dried under vacuum overnight.

Anal. Calcd for $C_{26}H_{30}N_4O \cdot 0.05$ $Et_2O \cdot 0.25$ $H_2O$: C, 74.44; H, 7.39; N, 13.25. Found: C, 74.43; H, 7.31; N, 13.13.

Example 37

Preparation of 4-{5-[4-Hydroxymethyl-4-(3-methylbenzyl)piperidine-1-ylmethyl]-2-methylimidazol-1-ylmethyl}benzonitrile trifluoroacetate salt

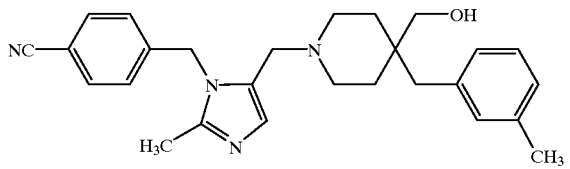

The title compound was prepared as white solid according to the procedure described in Example 30, Step B–E substituting 3-(trifluoromethoxy)benzyl bromide with 3-methylbenzyl bromide in Step B, and substituting 1-(4-cyano-benzyl)imidazole-5-carboxyaldehyde with 1-(4-cyanobenzyl)-2-methylimidazole-5-carboxyaldehyde (Example 31, Step A) in Step E. After column chromatography purification, the final product was dissolved in aqueous TFA and lyophilized.

Anal. Calcd for $C_{27}H_{32}N_4O \cdot 2.45$ TFA $\cdot 1.1$ $H_2O$: C, 52.65; H, 5.08; N, 7.70. Found: C, 52.67; H, 5.07; N, 7.79.

Example 38

Preparation of 4-(5-{2-[4-Hydroxymethyl-4-(3-methylbenzyl)piperidine-1-yl]-2-oxoethyl}imidazol-1-ylmethyl)benzonitrile trifluoroacetate salt

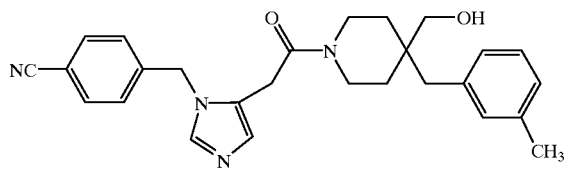

Step A: Preparation of 4-(3-methylbenzyl)-4-hydroxymethylpiperidine hydrochloride salt The title compound was prepared as white solid according to the procedure described in Example 30, Step B–D substituting 3-(trifluoromethoxy)benzyl bromide with 3-methylbenzyl bromide in Step B.

Step B: Preparation of 4-(5-{2-[4-Hydroxymethyl-4-(3-methylbenzyl)-piperidine-1-yl]-2-oxoethyl}imidazol-1-ylmethyl)benzonitrile trifluoroacetate salt A mixture of 4-(3-methylbenzyl)-4-hydroxymethylpiperidine hydrochloride salt (175 mg, 0.52 mmol), 1-(4-cyanobenzyl)imidazole-5-acetic acid.lithium chloride (142 mg, 0.50 mmol), N-ethyl-N'-(3-dimethylaminopropyl)carbodiimide.HCl (105 mg, 0.55 mmol), 1-hydroxy-7-azabenzotriazole (75 mg, 0.55 mmol), diisopropylethylamine (200 µL, 1.1 mmol) in anhydrous dimethylformamide (2.5 mL) was stirred at room temp. overnight. The resultant mixture was concentrated under vacuum, and the residue was partitioned between ethyl acetate and water. The organic extract was washed with brine, dried over anhydrous sodium sulfate, filtered, and concentrated under vacuum. The residue was subjected to high pressure liquid column chromatography on C-18 reverse phase stationary phase. Collection and lyophilization of appropriate fractions provided the title compound as white solid.

Anal. Calcd for $C_{27}H_{32}N_4O \cdot 1.65$ TFA: C, 57.70; H, 5.06; N, 8.88. Found: C, 57.68; H, 5.20; N, 8.83.

Example 39

Preparation of 4-{5-[4-Hydroxymethyl-4-(3-methylbenzyl)piperidine-1-carbonyl]imidazol-1-ylmethyl}benzonitrile

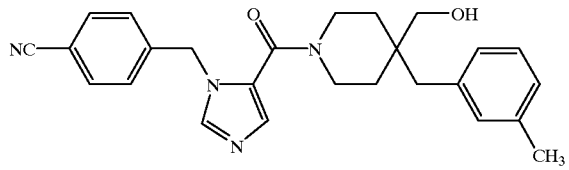

The title compound was prepared as white solid according to the procedure described in Example 38, Step A–B substituting 1-(4-cyanobenzyl)imidazole-5-acetic acid.lithium chloride with 1-(4-cyanobenzyl)imidazole-5-carboxylic acid in Step B. The crude product was purified with column chromatography on silica gel eluting with 2-5% methanol in chloroform.

Anal. Calcd for $C_{26}H_{28}N_4O_2$: C, 72.87; H, 6.59; N, 13.07. Found: C, 72.82; H, 6.67; N, 13.44.

Example 40

Preparation of 4-{5-[4-Hydroxymethyl-4-(2-methylbenzyl)piperidine-1-carbonyl]imidazol-1-ylmethyl}benzonitrile

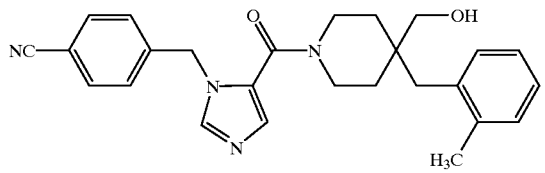

The title compound was prepared as white solid according to the procedure described in Example 38, Step A–B substituting 1-(4-cyanobenzyl)imidazole-5-acetic acid-lithium chloride with 1-(4-cyanobenzyl)imidazole-5-carboxylic acid and 4-(3-methylbenzyl)-4-hydroxymethylpiperidine hydrochloride salt with 4-(2-methylbenzyl)-4-hydroxymethylpiperidine hydrochloride salt (Example 35) in Step B. The crude product was purified with column chromatography on silica gel eluting with 2–5% methanol in chloroform.

Anal. Calcd for $C_{26}H_{28}N_4O_2$: C, 72.87; H, 6.59; N, 13.07. Found: C, 72.82; H, 6.67; N, 13.44.

Example 41

Preparation of 4-{5-[4-Hydroxymethyl-4-(3-chlorobenzyl)-piperidine-1-ylmethyl]-2-methylimidazol-1-ylmethyl}benzonitrile

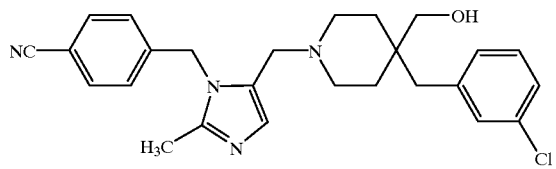

The title compound was prepared as white solid according to the procedure described in Example 30, Step B–E substituting 3-(trifluoromethoxy)benzyl bromide with 3-chlorobenzyl bromide in Step B, and substituting 1-(4-cyanobenzyl)imidazole-5-carboxaldehyde with 1-(4-cyanobenzyl)-2-methylimidazole-5-carboxaldehyde (Example 31, Step A) in Step E.

Anal. Calcd for $C_{26}H_{29}N_4OCl.0.20$ $H_2O$: C, 69.00; H, 6.55; N, 12.38. Found: C, 68.96; H, 6.78; N, 12.49.

Example 42

Preparation of 4-{5-[4-Hydroxymethyl-4-(2-cyanobenzyl)-piperidine-1-ylmethyl]-2-methylimidazol-1-ylmethyl}benzonitrile

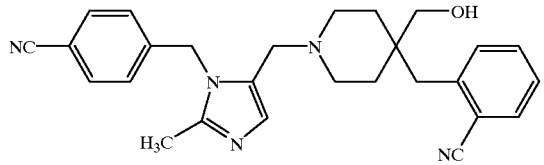

The title compound was prepared as white solid according to the procedure described in Example 30, Step B–E substituting 3-(trifluoromethoxy)benzyl bromide with 2-cyanobenzyl bromide in Step B, and substituting 1-(4-cyanobenzyl)imidazole-5-carboxaldehyde with 1-(4-cyanobenzyl)-2-methylimidazole-5-carboxaldehyde (Example 31, Step A) in Step E. After column chromatography purification, the final product was triturated in diethyl ether, filtered, and dried under vacuum overnight.

Anal. Calcd for $C_{27}H_{29}N_5O.0.05$ $H_2O.0.05$ $Et_2O$: C, 73.55; H, 6.72; N, 15.77. Found: C, 73.51; H, 6.55; N, 15.75.

Example 43

Preparation of 4-{5-[4-Hydroxymethyl-4-(3-cyanobenzyl)-piperidine 1-ylmethyl]-2-methylimidazol-1-ylmethyl}benzonitrile

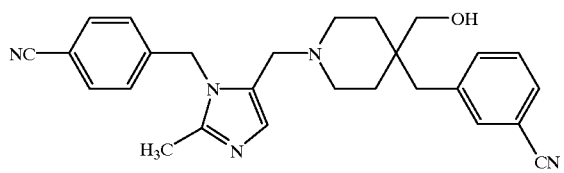

The title compound was prepared as white solid according to the procedure described in Example 30, Step B–E substituting 3-(trifluoromethoxy)benzyl bromide with 3-cyanobenzyl bromide in Step B, and substituting 1-(4-cyanobenzyl)imidazole-5-carboxaldehyde with 1-(4-cyanobenzyl)-2-methylimidazole-5-carboxaldehyde (Example 31, Step A) in Step E. After column chromatography purification, the final product was triturated in diethyl ether, filtered, and dried under vacuum overnight.

Anal. Calcd for $C_{27}H_{29}N_5O.0.35$ $H_2O.0.5$ $Et_2O$: C, 72.12; H, 7.24; N, 14.50. Found: C, 72.13; H, 6.99; N, 14.47.

Example 44

Preparation of 4-{5-[4-Hydroxymethyl-4-(4-cyanobenzyl)piperidine-1-ylmethyl]-2-methylimidazol-1-ylmethyl}benzonitrile

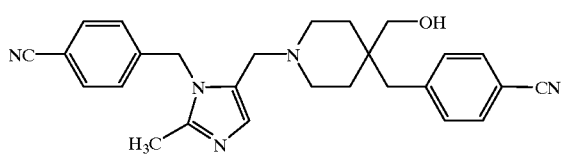

The title compound was prepared as white solid according to the procedure described in Example 30, Step B–E substituting 3-(trifluoromethoxy)benzyl bromide with 4-cyanobenzyl bromide in Step B, and substituting 1-(4-cyano-benzyl)imidazole-5-carboxyaldehyde with 1-(4-cyanobenzyl)-2-methylimidazole-5-carboxyaldehyde (Example 31, Step A) in Step E. After column chromatography purification, the final product was triturated in diethyl ether, filtered, and dried under vacuum overnight.

Anal. Calcd for $C_{27}H_{29}N_5O \cdot 0.1\ H_2O \cdot 0.25\ Et_2O$: C, 73.12; H, 6.95; N, 15.23. Found: C, 73.14; H, 6.83; N, 15.23.

Example 45

Preparation of 4-{5-[4-Hydroxymethyl-4-(2,5-dimethylbenzyl)piperidine-1-ylmethyl]-2-methylimidazol-1-ylmethyl}benzonitrile

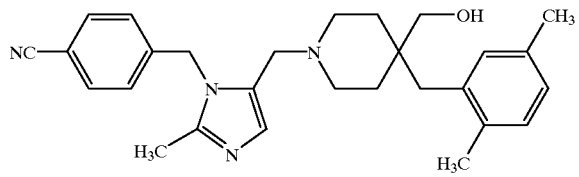

The title compound was prepared as white solid according to the procedure described in Example 30, Step B–E substituting 3-(trifluoromethoxy)benzyl bromide with 2,5-dimethylbenzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E.

Anal. Calcd for $C_{28}H_{34}N_4O \cdot 0.1\ H_2O$: C, 75.68; H, 7.76; N, 12.61.

Found: C, 75.62; H, 7.65; N, 12.60.

Example 46

Preparation of 4-{5-[4-Hydroxymethyl-4-(2,5-dichlorobenzyl)piperidine-1-ylmethyl]-2-methylimidazol-1-ylmethyl}benzonitrile

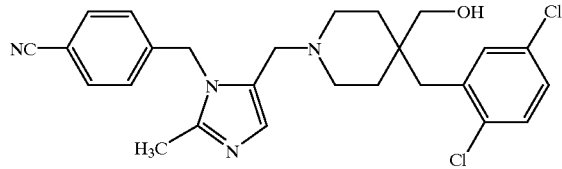

The title compound was prepared as white solid according to the procedure described in Example 30, Step B–E substituting 3-(trifluoromethoxy)benzyl bromide with 2,5-dichlorobenzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E.

Anal. Calcd for $C_{26}H_{28}N_4OCl_2$: C, 64.60; H, 5.84; N, 11.59. Found: C, 65.33; H, 5.70; N, 11.85.

Example 47

Preparation of 4-{5-[4-Hydroxymethyl-4-(3,5-dimethylbenzyl)piperidine-1-ylmethyl]-2-methylimidazol- 1-ylmethyl}benzonitrile

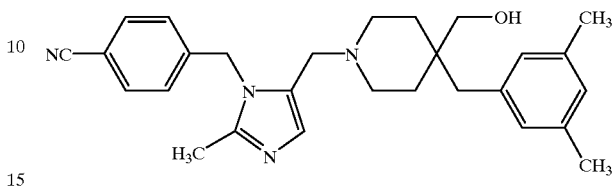

The title compound was prepared as white solid according to the procedure described in Example 30, Step B–E substituting 3-(trifluoromethoxy)benzyl bromide with 3,5-dimethylbenzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E. After column chromatography purification, the final product was triturated in diethyl ether, filtered, and dried under vacuum overnight.

Anal. Calcd for $C_{28}H_{34}N_4O \cdot 0.14\ Et_2O$: C, 75.73; H, 7.88; N, 12.37. Found: C, 75.70; H, 7.88; N, 12.39.

Example 48

Preparation of 4-(5-{4-Hydroxymethyl-4-[3,5-bis (trifluoromethyl)benzyl]-piperidine-1-ylmethyl}-2-methylimidazol-1-ylmethyl)benzonitrile

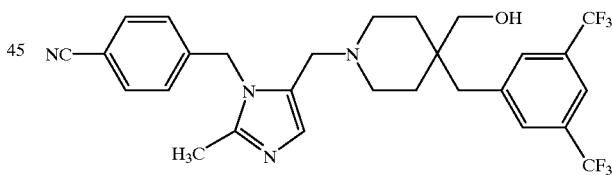

The title compound was prepared as white solid according to the procedure described in Example 30, Step B–E substituting 3-(trifluoromethoxy)benzyl bromide with 3,5-bis (trifluoromethyl)benzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E. After column chromatography purification, the final product was triturated in diethyl ether, filtered, and dried under vacuum overnight.

Anal. Calcd for $C_{28}H_{34}N_4O \cdot 0.14\ Et_2O$: C, 61.01; H, 5.42; N, 9.81. Found: C, 61.01; H, 5.12; N, 9.58.

Example 49

Preparation of 4-{5-[4-Hydroxymethyl-4-(2,3-dichlorobenzyl)piperidine-1-ylmethyl]-2-methylimidazol-1-ylmethyl}benzonitrile

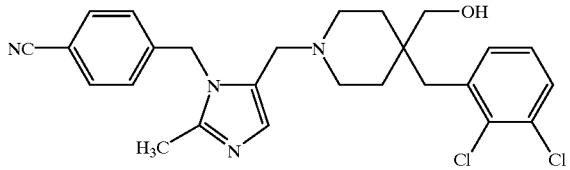

The title compound was prepared as white solid according to the procedure described in Example 30, Step B–E substituting 3-(trifluoromethoxy)benzyl bromide with 2,3-dichlorobenzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E.

Anal. Calcd for $C_{26}H_{28}N_4OCl_2.0.2\ H_2O.0.05\ MeOH$: C, 64.03; H, 5.90; N, 11.47. Found: C, 64.04; H, 5.95; N, 11.75.

Example 50

Preparation of 4-[5-(4-Hydroxymethyl-4-benzylpiperidine-1-ylmethyl)-2-methylimidazol-1-ylmethyl]benzonitrile

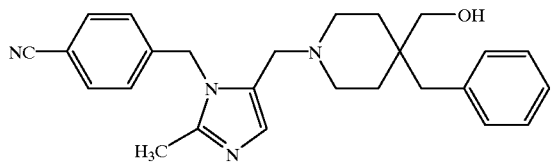

The title compound was prepared as white solid according to the procedure described in Example 30, Step B–E substituting 3-(trifluoromethoxy)benzyl bromide with benzyl bromide in Step B, and substituting 1-(4-cyanobenzyl)imidazole-5-carboxyaldehyde with 1-(4-cyanobenzyl)-2-methylimidazole-5-carboxyaldehyde (Example 31, Step A) in Step E.

Anal. Calcd for $C_{26}H_{28}N_4OCl_2$: C, 75.00; H, 7.31; N, 13.46. Found: C, 75.06; H, 7.20; N, 13.43.

Example 51

Preparation of 4-{5-[4-Hydroxymethyl-4-(3-trifluoromethoxybenzyl)-piperidine-1-ylmethyl]-2-methylimidazol-1-ylmethyl}benzamide

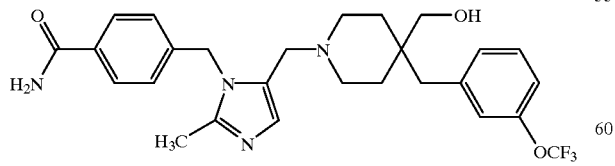

A solution of 4-{5-[4-hydroxymethyl-4-(3-trifluoromethoxy-benzyl)-piperidine-1-ylmethyl]-2-methylimidazol-1-ylmethyl}benzonitrile (71 mg, 0.142 mmol; Example 31) and sodium perborate tetrahydrate (92.8 mg, 0.6 mmol) in a mixture of methanol (2.5 mL) and water (1 mL) was heated at 50° C. for 7 h. The resultant mixture was concentrated under vacuum, and the residue was partitioned between chloroform and dilute hydrochloric acid (0.5 M). The organic extract was washed with brine, dried over anhydrous sodium sulfate, filtered, and concentrated under vacuum. The residue was subjected to column chromatography on silica gel eluting with 10% methanol in chloroform. Collection and concentration of appropriate fractions provided the title compound as white solid.

Anal. Calcd for $C_{27}H_{31}N_4O_3F_3.0.25\ H_2O$: C, 62.24; H, 6.09; N, 10.75. Found: C, 62.20; H, 6.05; N, 11.04.

FAB MS m/e 517 (M+1)

Example 52

Preparation of 4-{5-[4-Methoxymethyl-4-(3-methylbenzyl)-piperidine-1-ylmethyl]imidazol-1-ylmethyl}benzonitrile hydrochloride salt

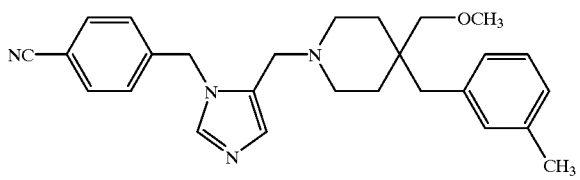

Step A: Preparation of N-tert-butoxycarbonyl-4-(3-methylbenzyl)-4-hydroxymethylpiperidine The title compound was prepared using the protocol described in Example 30, Step A–C, substituting 3-(trifluoromethoxy)benzyl bromide with 3-methylbenzyl bromide in Step B.

Step B: Preparation of N-tert-butoxycarbonyl-4-(3-methylbenzyl)-4-methoxymethylpiperidine To a suspension of potassium hydride (0.40 g, dry weight, 10 mmol; obtained from washing 0.97 g of 35% potassium hydride dispersion in mineral oil with hexanes and drying under a stream of argon) in anhydrous THF (45 mL), N-tert-butoxycarbonyl-4-(3-methylbenzyl)-4-hydroxymethylpiperidine (1.89 g, 5.9 mmol) in THF (15 mL) was added. The resultant mixture was stirred at room temp. for 1 h, and treated with dimethyl sulfate (1.13 mL, 11.9 mmol). The reacting mixture was stirred at room temp. overnight. The product mixture was cooled to 0° C., quenched with water, and diluted with ethyl acetate. The organic extract was washed with brine, dried over anhydrous magnesium sulfate, filtered, and concentrated under vacuum. The residue was subjected to column chromatography on silica gel eluting with 10% ethyl acetate in hexane. Collection and concentration of appropriate fractions provided the title compound.

Step C: Preparation of 4-(3-methylbenzyl)-4-methoxymethyl-piperidine hydrochloride salt To a cold (0° C.) solution of N-tert-butoxycarbonyl-4-(3-methylbenzyl)-4-methoxymethylpiperidine (1.95 g) in ethyl acetate (100 mL), a stream of anhydrous hydrogen chloride gas was bubbled for 20 min. The resultant mixture was stirred at 0° C. for 1 h, purged with argon for 20 min., and concentrated under vacuum to provide the title compound as white solid.

Step D: Preparation of 1-(4-cyanobenzyl)-5-chloromethylimidazole hydrochloride salt A mixture of 1-(4-cyanobenzyl)-5-hydroxymethylimidazole (10.8 g, 50.70 mmol; Example 1, Step D) and thionyl chloride (70 mL, 960 mmol) was stirred at room temp. overnight under a calcium chloride drying tube. The resultant mixture was concentrated under vacuum, and residual thionyl chloride was removed by co-evaporation with toluene. The residue was recrystallized from boiling methanol. After cooling to room temp., the white solid precipitated was obtained by filtration, and residual solvent was removed under vacuum overnight.

Step E: Preparation of 4-{5-[4-Methoxymethyl-4-(3-methylbenzyl)-piperidine-1-ylmethyl]imidazol-1-ylmethyl}benzonitrile hydrochloride salt A solution of 4-(3-methylbenzyl)-4-methoxymethylpiperidine hydrochloride salt (1.57 g, 5.8 mmol), 1-(4-cyanobenzyl)-5-chloromethyl-imidazole hydrochloride salt (1.57 g, 5.8 mmol), and diisopropylethylamine (5.1 mL, 29 mmol) in anhydrous acetonitrile (75 mL) was heated at 60° C. overnight. The resultant mixture was concentrated under vacuum, and the residue was partitioned between saturated aqueous sodium bicarbonate and dichloromethane. The organic extract was washed with brine, dried over anhydrous sodium sulfate, filtered, and concentrated under vacuum. The residue was subjected to column chromatography on silica gel eluting with 3% methanol in chloroform. Collection and concentration of appropriate fractions provided the title compound as free base. The free base obtained was dissolved in anhydrous diethyl ether (50 mL), cooled to 0° C., and bubbled with anhydrous hydrogen chloride gas for 20 second. The resultant mixture was concentrated and the residue solid recrystallized from a mixture of methanol and diethyl ether. The white solid precipitated was filtered, and residual solvent was removed under vacuum overnight to provide the title compound.

Anal. Calcd for $C_{27}H_{32}N_4O.2$ HCl.0.70 $H_2O$: C, 63.08; H, 6.94; N, 10.90. Found: C, 63.06; H, 6.91; N, 10.95.

Example 53

Preparation of 4-{5-[4-Methoxymethyl-4-(3-methylbenzyl)-piperidine-1-ylmethyl]-2-methylimidazol-1-ylmethyl}benzonitrile

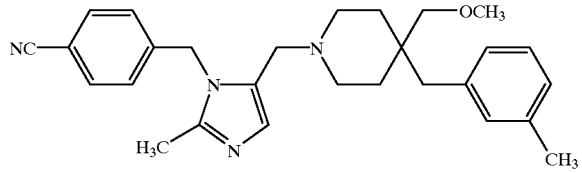

Step A: Preparation of 1-(4-cyanobenzyl)-5-hydroxymethyl-2-methylimidazole

A solution of 1-(4-cyanobenzyl)-2-methylimidazole-5-carboxyaldehyde (4.0 g, 17.76 mmol; Example 31, Step A) in methanol (85 mL) at room temp. was treated with sodium borohydride (0.52 g, 13.7 mmol; added in two portions, 10 min. apart). After stirring at room temp. for 30 min., the resultant slurry was concentrated to about 15 mL. The white solid precipitated was filtered, washed with anhydrous diethyl ether, and residual solvent was removed under vacuum to provide the title compound.

Step B: Preparation of 1-(4-cyanobenzyl)-5-chloromethyl-2-methylimidazole hydrochloride salt A mixture of 1-(4-cyanobenzyl)-5-hydroxymethyl-2-methylimidazole (3.45 g, 15.2 mmol) and thionyl chloride (30 mL, 411 mmol) was stirred at room temp. overnight under a calcium chloride drying tube. The resultant mixture was concentrated under vacuum, and residual thionyl chloride was removed by co-evaporation with toluene. The residue was triturated with anhydrous diethyl ether, filtered, washed with ether to provide the title compound as white solid.

Step C: Preparation of 4-{5-[4-Methoxymethyl-4-(3-methylbenzyl)-piperidine-1-ylmethyl]-2-methylimidazol-1-ylmethyl}-benzonitrile The title compound was prepared using the protocol described in Example 52, Step E substituting 1-(4-cyanobenzyl)-5-chloromethyl-imidazole hydrochloride salt with 1-(4-cyanobenzyl)-5-chloromethyl-2-methylimidazole hydrochloride salt. After column chromatography purification, collection and concentration of appropriate fractions, the residue was triturated with anhydrous diethyl ether. The white solid precipitated was obtained by filtration and provided the title compound.

Anal. Calcd for $C_{28}H_{34}N_4O.0.15$ $Et_2O$ .0.50 $H_2O$: C, 74.24; H, 7.95; N, 12.11. Found: C, 74.22; H, 7.59; N, 12.13.

Example 54

Preparation of 4-{5-[4-Methoxymethyl-4-(3-trifluoromethoxybenzyl)-piperidine-1-ylmethyl]imidazol-1-ylmethyl}benzonitrile hydrochloride salt

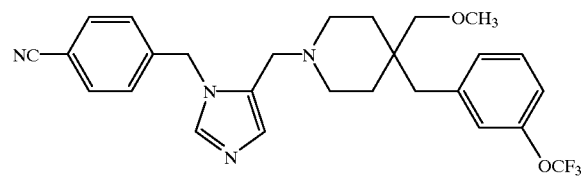

The title compound was prepared using the protocol described in Example 30, Step A–C using 3-(trifluoromethoxy)benzyl bromide in Step B, and in Example 52, Step B–E substituting N-tert-butoxycarbonyl-4-(3-methylbenzyl)-4-hydroxymethylpiperidine with N-tert-butoxy-carbonyl-4-(3-trifluoromethoxybenzyl)-4-hydroxymethylpiperidine in Step B.

Anal. Calcd for $C_{27}H_{29}N_4O_2F_3$.2.6 HCl: C, 54.66; H, 5.37; N, 9.44. Found: C, 54.69; H, 5.37; N, 9.42.

Example 55

Preparation of 4-{5-[4-Methoxymethyl-4-(3-trifluoromethoxybenzyl)-piperidine-1-ylmethyl]-2-methylimidazol-1-ylmethyl}benzonitrile hydrochloride salt

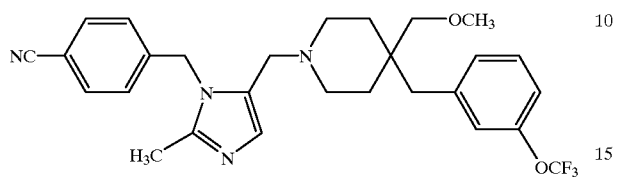

The title compound was prepared using the protocol described in Example 30, Step A–C using 3-(trifluoromethoxy)benzyl bromide in Step B, and in Example 52, Step B–E substituting N-tert-butoxycarbonyl-4-(3-methylbenzyl)-4-hydroxymethylpiperidine with N-tert-butoxy-carbonyl-4-(3-trifluoromethoxybenzyl)-4-hydroxymethylpiperidine in Step B, and substituting 1-(4-cyanobenzyl)-5-chloromethyl-imidazole hydro-chloride salt with 1-(4-cyanobenzyl)-5-chloromethyl-2-methylimidazole hydrochloride salt in Step E.

Anal. Calcd for $C_{28}H_{31}N_4O_2F_3$.2.2 HCl: C, 56.73; H, 5.65; N, 9.45. Found: C, 56.79; H, 5.39; N, 9.40.

Example 56

Preparation of 4-{5-[4-Methoxymethyl-4-(2-trifluoromethoxybenzyl)-piperidine -1-ylmethyl] imidazol-1-ylmethyl}benzonitrile hydrochloride salt

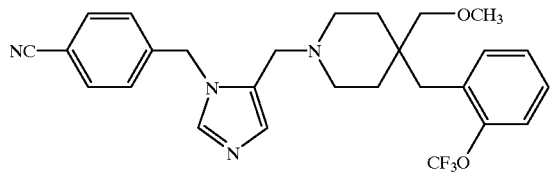

The title compound was prepared using the protocol described in Example 30, Step A–C using 2-(trifluoromethoxy)benzyl bromide in Step B, and in Example 52, Step B–E substituting N-tert-butoxycarbonyl-4-(3-methylbenzyl)-4-hydroxymethylpiperidine with N-tert-butoxy-carbonyl-4-(2-trifluoromethoxybenzyl)-4-hydroxymethylpiperidine in Step B.

Anal. Calcd for $C_{27}H_{29}N_4O_2F_3$.2.45 HCl.0.20 $Et_2O$: C, 55.40; H, 5.59; N, 9.30. Found: C, 55.38; H, 5.52; N, 9.20.

Example 57

Preparation of 4-{5-[4-Methoxymethyl-4-(2-trifluoromethoxybenzyl)-piperidine-1-ylmethyl]-2-methylimidazol-1-ylmethyl}benzonitrile hydrochloride salt

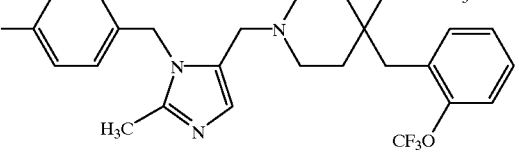

The title compound was prepared using the protocol described in Example 30, Step A–C using 2-(trifluoromethoxy)benzyl bromide in Step B, and in Example 52, Step B–E substituting N-tert-butoxycarbonyl-4-(3-methylbenzyl)-4-hydroxymethylpiperidine with N-tert-butoxy-carbonyl-4-(2-trifluoromethoxybenzyl)-4-hydroxymethylpiperidine in Step B, and substituting 1-(4-cyanobenzyl)-5-chloromethyl-imidazole hydro-chloride salt with 1-(4-cyanobenzyl)-5-chloromethyl-2-methylimidazole hydrochloride salt in Step E.

Anal. Calcd for $C_{28}H_{31}N_4O_2F_3$.2.6 HCl: C, 55.37; H, 5.58; N, 9.22. Found: C, 55.38; H, 5.52; N, 9.20.

Example 58

Preparation of 4-{5-[4-Methoxymethyl-4-(3-cyanobenzyl)-piperidine-1-ylmethyl]-2-methylimidazol-1-ylmethyl}benzonitrile trifluoroacetate salt

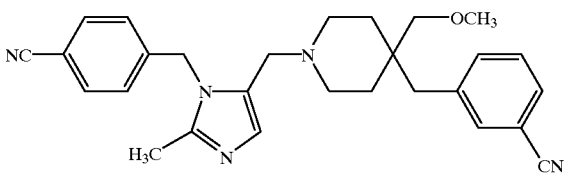

The title compound was prepared using the protocol described in Example 30, Step A–C using 3-cyanobenzyl bromide in Step B, and in Example 52, Step B–E substituting N-tert-butoxycarbonyl-4-(3-methyl-benzyl)-4-hydroxymethylpiperidine with N-tert-butoxycarbonyl-4-(3-cyanobenzyl)-4-hydroxymethylpiperidine in Step B, and substituting 1-(4-cyanobenzyl)-5-chloromethyl-imidazole hydrochloride salt with 1-(4-cyanobenzyl)-5-chloromethyl-2-methylimidazole hydrochloride salt in Step E. The crude product was subjected to high pressure liquid column chromatography on C-18 reverse phase stationary phase. Collection and lyophilization of appropriate fractions provided the title compound as white solid.

Anal. Calcd for $C_{28}H_{31}N_5O$.2 TFA: C, 56.39; H, 4.88; N, 10.27. Found: C, 56.04; H, 5.06; N, 10.26.

Example 59

Preparation of 4-(5-{2-[4-Methoxymethyl-4-(3-methylbenzyl)-piperidine-1-yl]-2-oxoethyl}imidazol-1-ylmethyl)benzonitrile trifluoroacetate salt

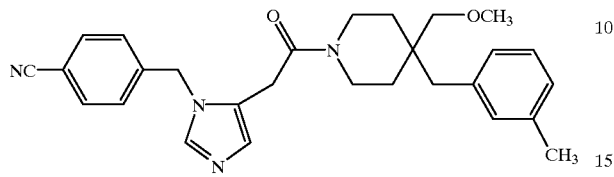

The title compound was prepared according to the procedure described in Example 38, Step B substituting 4-(3-methylbenzyl)-4-hydroxymethylpiperidine hydrochloride salt with 4-(3-methylbenzyl)-4-methoxymethylpiperidine hydrochloride salt (Example 52, Step C). The crude product was subjected to high pressure liquid column chromatography on C-18 reverse phase stationary phase. Collection and lyophilization of appropriate fractions provided the title compound as white solid.

Anal. Calcd for $C_{28}H_{32}N_4O_2 \cdot 1.7$ TFA: C, 57.98; H, 5.22; N, 8.61. Found: C, 57.93; H, 5.30; N, 8.67.

Example 60

Preparation of 4-{5-[4-Methoxymethyl-4-(3-methylbenzyl)piperidine-1-carbonyl]imidazol-1-ylmethyl}benzonitrile trifluoroacetate salt

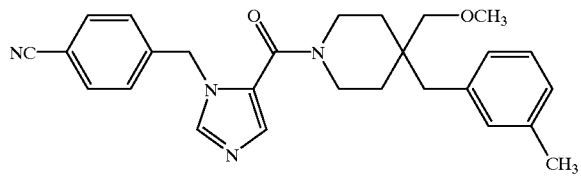

The title compound was prepared according to the procedure described in Example 38, Step B substituting 4-(3-methylbenzyl)-4-hydroxymethylpiperidine hydrochloride salt with 4-(3-methylbenzyl)-4-methoxymethylpiperidine hydrochloride salt (Example 52, Step C), and 1-(4-cyanobenzyl)imidazole-5-acetic acid-lithium chloride with 1-(4-cyanobenzyl)imidazole-5-carboxylic acid. The crude product was subjected to high pressure liquid column chromatography on C-18 reverse phase stationary phase. Collection and lyophilization of appropriate fractions provided the title compound as white solid.

Anal. Calcd for $C_{27}H_{30}N_4O \cdot 1.2$ TFA$\cdot 1.1H_2O$: C, 58.93; H, 5.62; N, 9.35. Found: C, 58.90; H, 5.41; N, 9.74.

Example 61

Preparation of Methyl 1-[3-(4-cyanobenzyl)-3H-imidazol-4-ylmethyl]-4-(3-methylbenzyl)piperidine-4-carboxylate

Step A: Preparation of Methyl N-tert-butoxycarbonyl-4-(3-methyl-benzyl)piperidine-4-carboxylate To a cold (−78° C.) solution of methyl N-tert-butoxycarbonyl-piperidine-4-carboxylate (5.0 g, 20.5 mmol; Example 3, Step B) in anhydrous THF (70 mL), a solution of sodium bis(trimethylsilyl)amide (20.5 mL, 1M, 20.5 mmol) was added over a period of 30 min. The resultant mixture was stirred at −78° C. for 1 h., and 3-methylbenzyl bromide (2.77 mL, 20.5 mmol) was added. The reacting mixture was allowed to warm up to room temp. and stirred overnight. The product mixture was concentrated, and the residue was partitioned between water and ethyl acetate. The organic extract was washed with brine, dried over anhydrous magnesium sulfate, filtered, and concentrated under vacuum. The residue was subjected to column chromatography on silica gel eluting with 10% ethyl acetate in hexane. Collection and concentration of appropriate fractions provided the title compound.

Step B: Preparation of Methyl 4-(3-methylbenzyl)piperidine-4-carboxylate hydrochloride salt To a cold (0° C.) solution of methyl N-tert-butoxycarbonyl-4-(3-methylbenzyl)piperidine-4-carboxylate (1.14 g) in ethyl acetate (75 mL), a stream of anhydrous hydrogen chloride gas was bubbled for 20 min. The resultant mixture was stirred at 0° C. for 1 h, purged with argon for 10 min., and concentrated under vacuum to provide the title compound as white solid.

Step C: Preparation of Methyl 1-[3-(4-cyanobenzyl)-3H-imidazol-4-ylmethyl]-4-(3-methylbenzyl)piperidine-4-carboxylate A solution of methyl 4-(3-methylbenzyl)piperidine-4-carboxylate hydrochloride salt (142 mg, 0.5 mmol), 1-(4-cyanobenzyl)-5-chloromethylimidazole hydrochloride salt (135 mg, 0.5 mmol; Example 52, Step D), and diisopropylethylamine (0.26 mL, 1.5 mmol) in anhydrous acetonitrile (5 mL) was heated under reflux overnight. The resultant mixture was concentrated under vacuum, and the residue was partitioned between saturated aqueous sodium bicarbonate and ethyl acetate. The organic extract was washed with brine, dried over anhydrous sodium sulfate, filtered, and concentrated under vacuum. The residue was subjected to column chromatography on silica gel eluting with 5% methanol in chloroform. After collection and concentration of appropriate fractions, the residue was recrystallized from a mixture of ethyl acetate and hexane to provide the title compound as white solid.

Anal. Calcd for $C_{27}H_{30}N_4O_2 \cdot 0.2$ Hexane: C, 73.66; H, 7.19; N, 12.18. Found: C, 73.68; H, 6.84; N, 11.79.

Example 62

Preparation of Methyl 1-[3-(4-cyanobenzyl)-3H-imidazol-4-ylmethyl]-4-(3-trifluoromethoxybenzyl)piperidine-4-carboxylate trifluoroacetate salt

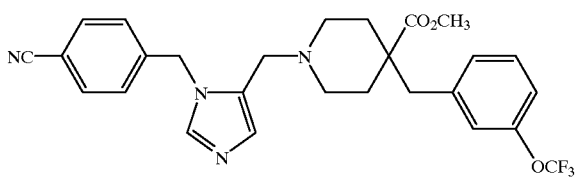

The title compound was prepared using the protocol described in Example 61, Step A–C substituting 3-methylbenzyl bromide with 3-trifluoromethoxybenzyl bromide in Step A. The final product was subjected to high pressure liquid column chromatography on C-18 reverse phase stationary phase. Collection and lyophilization of appropriate fractions provided the title compound as white solid.

Anal. Calcd for $C_{27}H_{27}N_4O_3F_3 \cdot 2.35$ TFA$\cdot 1.05$ H$_2$O: C, 47.62; H, 3.97; N, 7.01. Found: C, 47.61; H, 4.10; N, 6.61.

Example 63

Preparation of Methyl 1-[3-(4-cyanobenzyl)-2-methyl-3H-imidazol-4-ylmethyl]-4-(3-trifluoromethoxybenzyl)piperidine-4-carboxylate trifluoroacetate salt

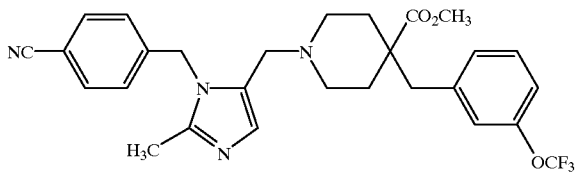

The title compound was prepared using the protocol described in Example 61, Step A–C substituting 3-methylbenzyl bromide with 3-trifluoromethoxybenzyl bromide in Step A, and substituting 1-(4-cyano-benzyl)-5-chloromethylimidazole hydrochloride salt with 1-(4-cyano-benzyl)-5-chloromethyl-2-methylimidazole hydrochloride salt (Example 53, Step B) in Step C. The final product was subjected to high pressure liquid column chromatography on C-18 reverse phase stationary phase. Collection and lyophilization of appropriate fractions provided the title compound as white solid.

Anal. Calcd for $C_{28}H_{29}N_4O_3F_3 \cdot 2.3$ TFA$\cdot 1.05$ H$_2$O: C, 48.47; H, 4.17; N, 6.94. Found: C, 48.48; H, 4.19; N, 6.91.

Example 64

Preparation of Methyl 1-[3-(4-cyanobenzyl)-3H-imidazol-4-ylmethyl]-4-(2-trifluoromethoxybenzyl)piperidine-4-carboxylate trifluoroacetate salt

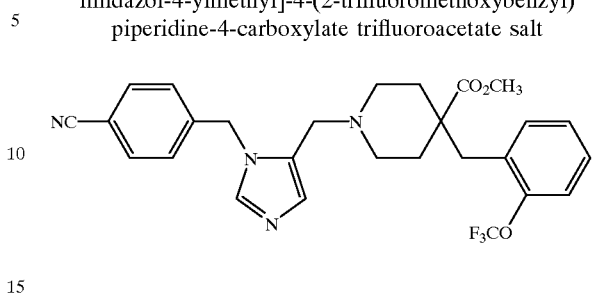

The title compound was prepared using the protocol described in Example 61, Step A–C substituting 3-methylbenzyl bromide with 2-trifluoromethoxybenzyl bromide in Step A. The final product was subjected to high pressure liquid column chromatography on C-18 reverse phase stationary phase. Collection and lyophilization of appropriate fractions provided the title compound as white solid.

Anal. Calcd for $C_{27}H_{27}N_4O_3F_3 \cdot 2.50$ TFA$\cdot 2.30$ H$_2$O: C, 45.81; H, 4.10; N, 6.68. Found: C, 46.11; H, 3.89; N, 6.28.

Example 65

Preparation of Methyl 1-[3-(4-cyanobenzyl)-3H-imidazol-4-ylmethyl]-4-(3-cyanobenzyl)piperidine-4-carboxylate hydrochloride salt

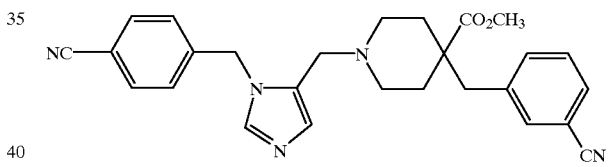

The title compound was prepared using the protocol described in Example 61, Step A–C substituting 3-methylbenzyl bromide with 3-cyanobenzyl bromide in Step A. After column chromatography on silica gel, the free base obtained was dissolved in anhydrous diethyl ether. The ethereal solution was cooled to 0° C., and bubbled with anhydrous hydrogen chloride gas for 20 second. The resultant mixture was concentrated, and the residue solid recrystallized from a mixture of methanol and diethyl ether. The white solid precipitated was filtered, and residual solvent was removed under vacuum overnight to provide the title compound.

Anal. Calcd for $C_{27}H_{27}N_5O_2 \cdot 2.35$ HCl$\cdot 1.80$ MeOH: C, 57.95; H, 6.17; N, 11.73. Found: C, 57.94; H, 6.16; N, 11.72.

Example 66

Preparation of Methyl 1-[3-(4-cyanobenzyl)-3H-imidazol-4-ylmethyl]-4-[3-(benzyloxycarbonylaminomethyl)benzyl]piperidine-4-carboxylate

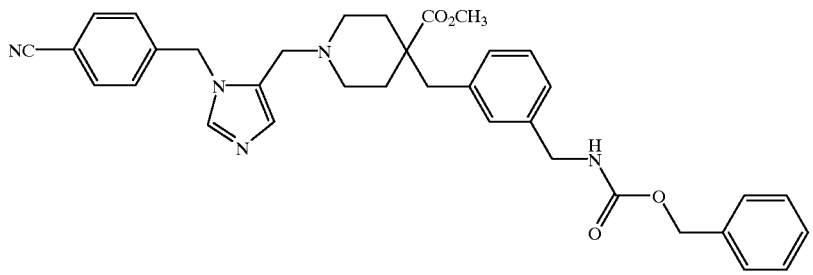

Step A: Preparation of Methyl N-tert-butoxycarbonyl-4-(3-cyano-benzyl)piperidine-4-carboxylate The title compound was prepared using the protocol described in Example 61, Step A substituting 3-methylbenzyl bromide with 3-cyanobenzyl bromide.

Step B: Preparation of Methyl N-tert-butoxycarbonyl-4-(3-amino-methylbenzyl)piperidine-4-carboxylate A mixture of methyl N-tert-butoxycarbonyl-4-(3-cyano-benzyl)piperidine-4-carboxylate (0.6 g, 1.67 mmol), Raney nickel (3 g) in a mixture of ethanol (20 mL) and concentrated aqueous ammonium hydroxide (0.6 mL) was stirred under a balloon of hydrogen gas at room temp. overnight. The slurry was filtered, and the filtrate concentrated under vacuum to provide the title compound.

Step C: Preparation of Methyl N-tert-butoxycarbonyl-4-[3-(benzyl-oxycarbonylaminomethyl)benzyl]piperidine-4-carboxylate A mixture of methyl N-tert-butoxycarbonyl-4-(3-amino-methylbenzyl)piperidine-4-carboxylate (1.67 mmol), benzyl chloroformate (0.48 mL, 3.36 mmol), and diisopropylethylamine (1 mL, 5.74 mmol) in dichloromethane was stirred at room temp. The resultant solution was diluted with dichloromethane, washed with aqueous sodium bicarbonate, and then brine. The organic extract was dried over anhydrous magnesium sulfate, filtered, and concentrated under vacuum. The residue was subjected to column chromatography on silica gel eluting with 40% ethyl acetate in hexane. Collection and concentration of appropriate fractions provided the title compound as clear colorless gum.

Step D: Preparation of Methyl 1-[3-(4-cyanobenzyl)-3H-imidazol-4-ylmethyl]-4-[3-(benzyloxycarbonylaminomethyl)benzyl]-piperidine-4-carboxylate The title compound was prepared using the protocol described in Example 61, Step B–C substituting methyl N-tert-butoxycarbonyl-4-(3-methylbenzyl)piperidine-4-carboxylate with methyl N-tert-butoxycarbonyl-4-[3-(benzyloxycarbonylaminomethyl)-benzyl]piperidine-4-carboxylate in Step B. After column chromatography on silica gel, the free base obtained was triturated with a mixture of dichloromethane and diethyl ether. The white solid precipitated was filtered, and residual solvent was removed under vacuum overnight to provide the title compound.

Anal. Calcd for $C_{35}H_{37}N_5O_4 \cdot 0.2$ $Et_2O \cdot 0.05$ $CH_2Cl_2$: C, 70.50; H, 6.45; N, 11.47. Found: C, 70.39; H, 6.17; N, 11.46.

Example 67

Preparation of Methyl 1-[3-(4-cyanobenzyl)-3H-imidazol-4-ylmethyl]-4-[3-(aminomethyl)benzyl]piperidine-4-carboxylate trifluoroacetate salt

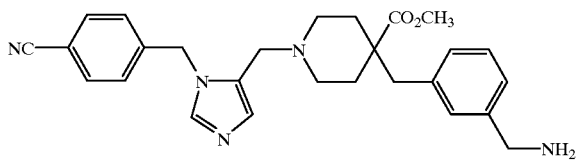

A mixture of methyl 1-[3-(4-cyanobenzyl)-3H-imidazol-4-ylmethyl]-4-[3-(benzyloxycarbonylaminomethyl)benzyl]-piperidine-4-carboxylate (0.13 g, 0.22 mmol; Example 66, Step D) and 30% hydrobromide in acetic acid (4 mL) was stirred at room temp. for 30 min. The resultant mixture was concentrated under vacuum. The residue was partitioned between dichloromethane and aqueous sodium bicarbonate. The organic extract was dried over anhydrous sodium sulfate, filtered, and concentrated under vacuum. The residue was subjected to high pressure liquid column chromatography on C-18 reverse phase stationary phase. Collection and lyophilization of appropriate fractions provided the title compound as white solid.

Anal. Calcd for $C_{27}H_{31}N_5O_2 \cdot 3.35$ TFA$\cdot 1.05$ $H_2O$: C, 47.15; H, 4.28; N, 8.16. Found: C, 47.15; H, 4.24; N, 8.88.

Example 68

Preparation of Ethyl 1-[3-(4-cyanobenzyl)-2-methyl-3H-imidazol-4-ylmethyl]-4-[3-(methanesulfonylaminomethyl)benzyl]piperidine-4-carboxylate

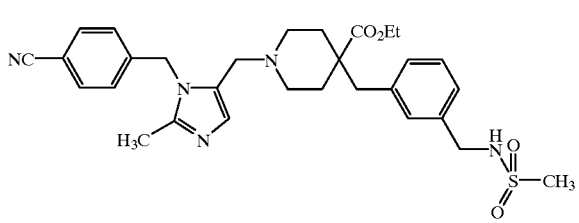

Step A: Preparation of Ethyl N-tert-butoxycarbonyl-4-(3-amino-methylbenzyl)piperidine-4-carboxylate The title compound was prepared using the protocol described in Example 66, Step A–B substituting methyl N-tert-butoxycarbonyl-piperidine-4-carboxylate with ethyl N-tert-butoxycarbonyl-piperidine-4-carboxylate (Example 30, Step A).

Step B: Preparation of Ethyl N-tert-butoxycarbonyl-4-[3-(methane-sulfonylaminomethyl)benzyl]piperidine-4-carboxylate A mixture of ethyl N-tert-butoxycarbonyl-4-(3-aminomethylbenzyl)piperidine-4-carboxylate (400 mg, 0.106 mmol) and methanesulfonyl chloride (99 μL, 0.127 mmol) in anhydrous pyridine (4 mL) was heated at 70° C. for 4 h. The resultant mixture was concentrated, and the residue was subjected to column chromatography on silica gel eluting with 50% ethyl acetate in hexane. Collection and concentration of appropriate fraction provided the title compound.

Step C: Preparation of Ethyl 4-[3-(methanesulfonylaminomethyl)-benzyl]piperidine-4-carboxylate hydrochloride salt A solution of ethyl N-tert-butoxycarbonyl-4-[3-(methanesulfonylaminomethyl)benzyl]piperidine-4-carboxylate (270 mg) in dichloromethane (40 mL) at 0° C. was saturated with hydrogen chloride gas. The resultant solution was sealed with a rubber septum and stirred at room temp. for 2.5 h. The product solution was concentrated under vacuum to provide the title compound

Step D: Preparation of Ethyl 1-[3-(4-cyanobenzyl)-2-methyl-3H-imidazol-4-ylmethyl]-4-[3-(methanesulfonylaminomethyl)-benzyl]piperidine-4-carboxylate The title compound was prepared using the protocol described in Example 61, Step C substituting methyl 4-(3-methylbenzyl)piperidine-4-carboxylate hydrochloride salt with ethyl 4-[3-(methanesulfonylamino-methyl)benzyl]piperidine-4-carboxylate hydrochloride salt, and 1-(4-cyanobenzyl)-5-chloromethylimidazole hydrochloride salt with 1-(4-cyanobenzyl)-5-chloromethyl-2-methylimidazole hydrochloride salt (Example 53, Step B). After column chromatography on silica gel, the free base obtained was triturated with anhydrous diethyl ether. The white solid precipitated was filtered, and residual solvent was removed under vacuum overnight to provide the title compound.

Anal. Calcd for $C_{30}H_{37}N_5O_4$ OS.0.2 $Et_2O$.0.3 $H_2O$: C, 63.35; H, 6.84; N, 11.99. Found: C, 63.34; H, 6.71; N, 11.99.

Example 69

Preparation of Ethyl 1-[3-(4-cyanobenzyl)-2-methyl-3H-imidazol-4-ylmethyl]-4-(3-nitrobenzyl)piperidine-4-carboxylate

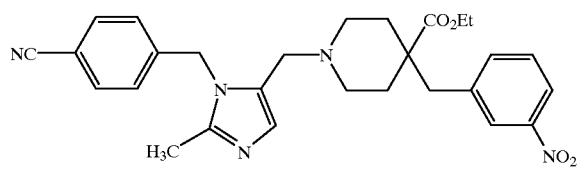

Step A: Preparation of Ethyl N-tert-butoxycarbonyl-4-(3-nitrobenzyl)piperidine-4-carboxylate The title compound was prepared using the protocol described in Example 61, Step A substituting methyl N-tert-butoxycarbonyl-piperidine-4-carboxylate with ethyl N-tert-butoxycarbonyl-piperidine-4-carboxylate (Example 30, Step A), and 3-methylbenzyl bromide with 3-nitrobenzyl bromide.

Step B: Preparation of Ethyl 1-[3-(4-cyanobenzyl)-2-methyl-3H-imidazol-4-ylmethyl]-4-(3-nitrobenzyl)piperidine-4-carboxylate The title compound was prepared using the protocol described in Example 61, Step B–C substituting methyl N-tert-butoxycarbonyl-4-(3-methylbenzyl)piperidine-4-carboxylate with ethyl N-tert-butoxycarbonyl-4-(3-nitrobenzyl)piperidine-4-carboxylate in Step B, and 1-(4-cyano-benzyl)-5-chloromethylimidazole hydrochloride salt with 1-(4-cyano-benzyl)-5-chloromethyl-2-methylimidazole hydrochloride salt (Example 53, Step B) in Step C.

Anal. Calcd for $C_{28}H_{31}N_5O_4$.0.45 $CHCl_3$: C, 61.54; H, 5.71; N, 12.61. Found: 61.39; H, 5.56; N, 12.74.

Example 70

Preparation of Ethyl 1-[3-(4-cyanobenzyl)-2-methyl-3H-imidazol-4-ylmethyl]-4-(3-methanesulfonylaminobenzyl)piperidine-4-carboxylate

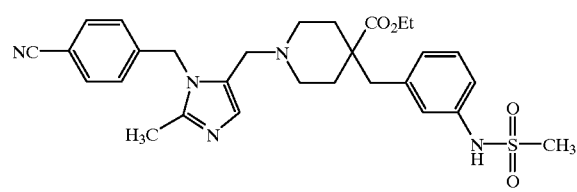

Step A: Preparation of Ethyl N-tert-butoxycarbonyl-4-(3-methane-sulfonylaminobenzyl)piperidine-4-carboxylate A mixture of ethyl N-tert-butoxycarbonyl-4-(3-nitrobenzyl)-piperidine-4-carboxylate (0.85 g, 2.17 mmol; Example 69, Step A) and 5% palladium on charcoal (0.06 g) in ethanol (100 mL) was hydrogenated at room temp. at 50 psi overnight. The resultant mixture was filtered through a plug of Celite, and the filtrate was concentrated under vacuum. The residue was dissolved in pyridine (5 mL), treated with methanesulfonyl chloride (0.24 mL, 3.2 mmol), and heated at 60° C. for 3 h. The product mixture was concentrated under vacuum, and the residue was subjected to column chromatography on silica gel eluting with 2% methanol in chloroform. Collection and concentration of appropriate fractions provided the title compound.

Step B: Preparation of Ethyl 1-[3-(4-cyanobenzyl)-2-methyl-3H-imidazol-4-ylmethyl]-4-(3-methanesulfonylaminobenzyl)-piperidine-4-carboxylate The title compound was prepared using the protocol described in Example 69, Step B substituting ethyl N-tert-butoxycarbonyl-4-(3-nitrobenzyl)piperidine-4-carboxylate with ethyl N-tert-butoxycarbonyl-4-(3-methanesulfonylaminobenzyl)piperidine-4-carboxylate.

Anal. Calcd for $C_{29}H_{35}N_5O_4S$.0.05 $CHCl_3$: C, 62.79; H, 6.36; N, 12.60. Found: 62.87; H, 6.24; N, 12.76.

Example 71

Preparation of Ethyl 1-[3-(4-cyanobenzyl)-3H-imidazol-4-ylmethyl]-4-benzylpiperidine-4-carboxylate

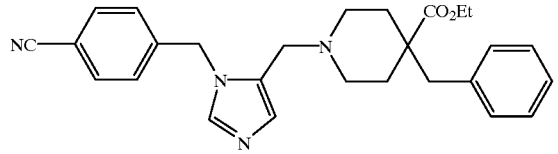

The title compound was prepared using the protocol described in Example 61, Step A–C substituting methyl N-tert-butoxycarbonyl-piperidine-4-carboxylate with ethyl N-tert-butoxycarbonyl-piperidine-4-carboxylate, and 3-methylbenzyl bromide with benzyl bromide.

Anal. Calcd for $C_{27}H_{30}N_4O_2 \cdot 0.1\ CHCl_3 \cdot 0.1\ H_2O$: C, 71.33; H, 6.69;

N, 12.28. Found: 71.35; H, 6.62; N, 12.40.

Example 72

Preparation of methyl 1-[3-(4-cyanobenzyl)-3H-imidazol-4-ylmethyl]-4-cyclopropylmethylpiperidine-4-carboxylate

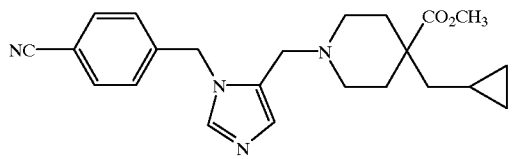

The title compound was prepared using the protocol described in Example 61, Step A–C substituting 3-methylbenzyl bromide with cyclopropylmethyl bromide.

Anal. Calcd for $C_{23}H_{28}N_4O_2$: C, 70.38; H, 7.19; N, 14.27. Found: 70.41; H, 7.13; N, 14.28.

Example 73

Preparation of methyl 1-[3-(4-cyanobenzyl)-3H-imidazol-4-ylcarbonyl]-4-(3-methylbenzyl)piperidine-4-carboxylate

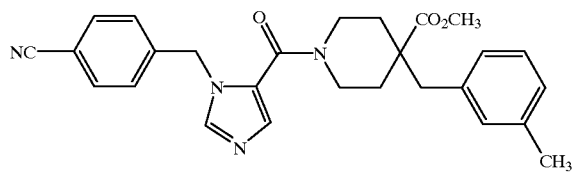

The title compound was prepared according to the procedure described in Example 38, Step B substituting 4-(3-methylbenzyl)-4-hydroxymethylpiperidine hydrochloride salt with methyl 4-(3-methylbenzyl)piperidine-4-carboxylate hydrochloride salt (Example 61, Step B), and 1-(4-cyanobenzyl)imidazole-5-acetic acid.lithium chloride with 1-(4-cyanobenzyl)imidazole-5-carboxylic acid.

Anal. Calcd for $C_{27}H_{28}N_4O_3$: C, 71.03; H, 6.18; N, 12.27. Found: C, 71.10; H, 6.27; N, 12.26.

Example 74

Preparation of methyl 1-[3-(4-cyanobenzyl)-3H-imidazol-4-ylcarbonyl]-4-(2-methylbenzyl)piperidine-4-carboxylate

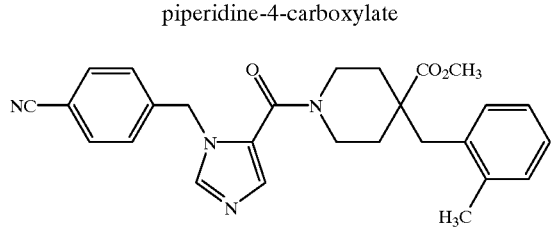

The title compound was prepared according to the procedure described in Example 73, using methyl 4-(2-methylbenzyl)piperidine-4-carboxylate hydrochloride salt (Example 61).

Anal. Calcd for $C_{27}H_{28}N_4O_3 \cdot 0.05\ Et_2O$: C, 70.98; H, 6.24; N, 12.17. Found: C, 71.08; H, 6.62; N, 12.49.

Example 75

Preparation of methyl 1-[3-(4-cyanobenzyl)-3H-imidazol-4-ylacetyl]-4-(3-trifluoromethoxybenzyl)piperidine-4-carboxylate

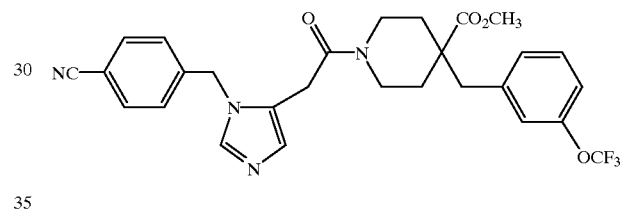

The title compound was prepared using the protocol described in Example 61, Step A–B substituting 3-methylbenzyl bromide with 3-trifluoromethoxybenzyl bromide in Step A, and in Example 38, Step B substituting 4-(3-methylbenzyl)-4-hydroxymethylpiperidine hydrochloride salt with methyl 4-(3-trifluoromethoxybenzyl)piperidine-4-carboxylate hydrochloride salt. The final product was subjected to high pressure liquid column chromatography on C-18 reverse phase stationary phase. Collection and lyophilization of appropriate fractions provided the title compound as white solid.

Anal. Calcd for $C_{28}H_{27}N_4O_4F_3 \cdot 1.2\ TFA \cdot 1.0\ H_2O$: C, 52.50; H, 4.38; N, 8.06. Found: C, 52.51; H, 4.41; N, 7.99.

Example 76

Preparation of methyl 1-[3-(4-cyanobenzyl)-3H-imidazol-4-ylacetyl]-4-(2-trifluoromethoxybenzyl)piperidine-4-carboxylate

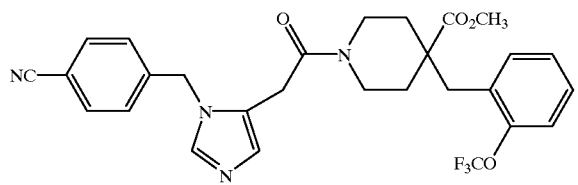

The title compound was prepared according to the procedure described in Example 75, using 3-trifluoromethoxybenzyl bromide.

121

Anal. Calcd for $C_{28}H_{27}N_4O_4F_3 \cdot 1.5$ TFA $\cdot 1.7$ $H_2O$: C, 50.16; H, 4.33; N, 7.55. Found: C, 50.20; H, 4.35; N, 7.38.

Example 77

Preparation of methyl 1-[3-(4-cyanobenzyl)-3H-imidazol-4-ylacetyl]-4-(3-cyanobenzyl)piperidine-4-carboxylate

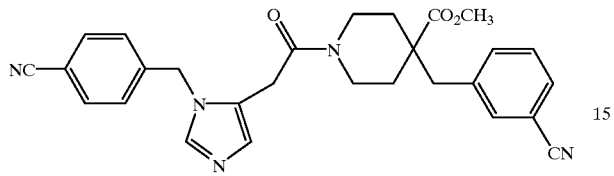

The title compound was prepared according to the procedure described in Example 75, using 3-cyanobenzyl bromide.

Anal. Calcd for $C_{28}H_{27}N_5O_3 \cdot 1.9$ HCl $\cdot 0.6$ toluene: C, 63.80; H, 5.60; N, 11.56. Found: C, 63.83; H, 5.91; N, 11.57.

Example 78

Preparation of methyl 1-[3-(4-cyanobenzyl)-3H-imidazol-4-ylmethyl]-4-(3-methylbenzyl)piperidine-4-carboxylate

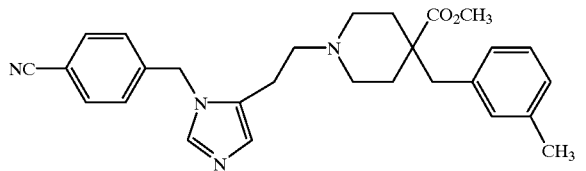

To a cold (−78° C.) solution of 3-(4-cyanobenzyl)-3H-imidazol-4-ylmethyl alcohol (184 mg, 0.81 mmol) and diisopropylethylarnine (155 μL, 0.89 mmol) in dichloromethane (3.8 mL), trifluoromethanesulfonic anhydride (143 μL, 0.85 mmol) was added. The resulting mixture was stirred at −78° C. for 20 min., and was treated with a solution of methyl 4-(3-methylbenzyl)piperidine-4-carboxylate hydrochloride salt (276 mg, 0.97 mmol; Example 61, Step B) and diisopropylethylamine (186 μL, 1.07 mmol) in dichloromethane (1 mL). The reaction mixture was stirred at −78° C. for one h., and at room temp. for two h. The resultant solution was concentrated under vacuum, and the residue was partitioned between dichloromethane and aqueous sodium bicarbonate. The organic extract was washed with brine, dried over anhydrous sodium sulfate, filtered, and concentrated under vacuum. The crude product was subjected to high pressure liquid column chromatography on C-18 reverse phase stationary phase. Collection and lyophilization of appropriate fractions provided the title compound as white solid.

Anal. Calcd for $C_{28}H_{32}N_4O_2 \cdot 2.75$ TFA: C, 52.25; H, 4.55; N, 7.27. Found: C, 52.28; H, 4.66; N, 7.24.

122

Example 79

Preparation of (±) Methyl 2-(n-butyl)-1-[3-(4-cyanobenzyl)-3H-imidazol-4-ylmethyl]-4-(3-methylbenzyl)piperidine-4-carboxylate trifluoroacetate salt

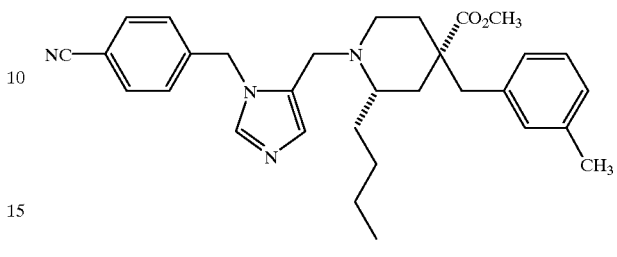

Step A: Preparation of Methyl 2-(n-but-1-ynyl) pyridine-4-carboxylate

A mixture of methyl 2-chloropyridine-4-carboxylate (3.32 g, 19.3 mmol), bis(triphenylphosphine)palladium(II) chloride (0.82 g, 1.1 mmol), copper(I) iodide (0.36 g, 1.9 mmol), triethylamine (30 mL), and n-but-1-yne (~5 g) was heated in a sealed tube at 80° C. overnight. The product mixture was concentrated, and the residue was subjected to column chromatography on silica gel eluting with chloroform. Collection and concentration of appropriate fractions provided the title compound.

Step B: Preparation of Methyl N-tert-butoxycarbonyl-2-(n-butyl)-piperidine-4-carboxylate A mixture of methyl 2-(n-but-1-ynyl)pyridine-4-carboxylate (3.0 g, 15.8 mmol) and platinum (IV) oxide (0.3 g) in methanol (300 mL) acidified with anhydrous hydrochloride gas (~2%) was hydrogenated at room temp. at 55 psi overnight. The resultant mixture was filtered through a plug of Celite, and the filtrate was concentrated under vacuum. The residue was dissolved in mixture of diisopropylethylamine (6.9 mL, 39 mmol) and dichloromethane (60 mL), and treated with di-tert-butyl dicarbonate (4.1 g, 19 mmol). The reaction mixture was stirred at room temp. overnight. The product mixture was concentrated and the residue was partitioned between dichloromethane and aqueous sodium bicarbonate. The organic extract was washed with brine, dried over anhydrous magnesium sulfate, filtered, and concentrated under vacuum. The residue was subjected to column chromatography on silica gel eluting with 15% ethyl acetate in hexane. Collection and concentration of appropriate fractions provided the title compound.

Step C: Preparation of (±) Methyl 2-(n-butyl)-1-[3-(4-cyanobenzyl)-3H-imidazol-4-ylmethyl]-4-(3-methylbenzyl)piperidine-4-carboxylate trifluoroacetate salt The title compound was prepared using the protocol described in Example 61, Step A–C substituting methyl N-tert-butoxycarbonyl-piperidine-4-carboxylate with methyl N-tert-butoxycarbonyl-2-(n-butyl)-piperidine-4-carboxylate in Step A. The final product was subjected to high pressure liquid column chromatography on C-18 reverse phase stationary phase. Collection and lyophilization of appropriate fractions provided the title compound as white solid.

Anal. Calcd for $C_{31}H_{38}N_4O_2 \cdot 2.25$ TFA $\cdot 0.95$ $H_2O$: C, 55.21; H, 5.50; N, 7.25. Found: C, 55.21; H, 5.52; N, 7.44.

Example 81

Preparation of 1-[3-(4-Cyanobenzyl)-3H-imidazol-4-ylmethyl]-4-(3-methylbenzyl)isonipecotamide

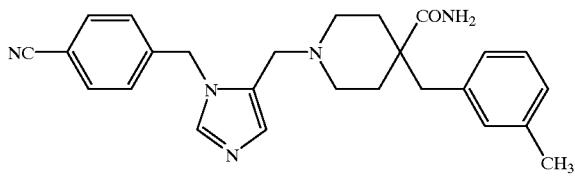

Step A: Preparation of N-tert-butoxycarbonylisonipecotic acid

To a solution of isonipecotic acid (25.8 g, 200 mmol) in 1 M aqueous sodium hydroxide (223 mL, 223 mmol), a solution of di-tert-butyl dicarbonate in tetrahydrofuran (200 mL) was added over a period of one h. The resulting solution was stirred at room temp. overnight. The reaction mixture was concentrated under vacuum. The residual aqueous solution was washed with hexane. The combined organic extract was back extracted with saturated aqueous sodium bicarbonate. The basic aqueous extracts were combined, cooled to 0° C., and acidified with 15% aqueous potassium hydrogen sulfate to a pH of ~2. The resulting thick slurry was extracted with ethyl acetate. The combined organic extract was washed with brine, dried over anhydrous magnesium sulfate, filtered, and concentrated under vacuum to afford the title compound as white solid.

Step B: Preparation of Benzyl N-tert-butoxycarbonylisonipecotate

A mixture of N-tert-butoxycarbonylisonipecotic acid (12.0 g, 52.3 mmol), benzyl alcohol (6.0 mL, 58 mmol), 1-(3-dimethylamino-propyl)-3-ethylcarbodiimide hydrochloride (11.04 g, 57.6 mmol), and 4-dimethylaminopyridine (642 mg, 5.25 mmol) in anhydrous dichloromethane (100 mL) was stirred at room temp. for 6 h. The resultant mixture was diluted with dichloromethane and washed successively with water, 10% aqueous citric acid, saturated sodium bicarbonate, and brine. The organic extract was dried over anhydrous magnesium sulfate, filtered, and concentration under vacuum. The residual oil was subjected to column chromatography on silica eluting with 20% ethyl acetate in hexane. Collection and concentration of appropriate fractions afforded the title product as white solid.

Step C: Preparation of Benzyl N-tert-butoxycarbonyl-4-(3-methyl-benzyl)isonipecotate To a cold (−78° C.) solution of benzyl N-tert-butoxycarbonyl-isonipecotate (8.02 g, 25.11 mmol) in anhydrous THF (80 mL), a solution of sodium bis(trimethysilyl)amide (35 mL, 35 mmol; 1 M) in THF was added over a period of 10 min. The resulting orange solution was stirred at −78° C. for 1 h. and then treated dropwise with 3-methylbenzyl bromide (4.1 mL, 30.6 mmol). The reaction mixture was allowed to warm to room temp., and stirred overnight. The reaction was quenched with saturated aqueous ammonium chloride, diluted with water, and extracted with ethyl acetate. The organic extracts were combined, washed with brine, and concentrated under vacuum. The residual oil was subjected to column chromatography on silica eluting with 20% ethyl acetate in hexane. Collection and concentration of appropriate fractions provided the title product.

Step D: Preparation of N-tert-Butoxycarbonyl-4-(3-methylbenzyl)-isonipecotic acid A mixture of benzyl N-t-butoxycarbonyl-4-(3-methylbenzyl)-isonipecotate (2.36 g, 5.57 mmol), 5% palladium on charcoal (250 mg), and glacial acetic acid (3 mL) in methanol (75 mL), was hydrogenated at 50 psi. in a Parr shaker at room temp. overnight. The reaction mixture was filtered through a pad of Celite and the filtrate was concentrated under vacuum to provide the title product as white solid.

Step E: Preparation of N-tert-butoxycarbonyl-4-(3-methylbenzyl)-isonipecotamide A mixture of N-tert-butoxycarbonyl-4-(3-methylbenzyl)-isonipecotic acid (1.02 g, 3.00 mmol), 1-(3-dimethylaminopropyl)-3-ethylcarbodiimide hydrochloride (0.64 g. 3.36 mmol), 1-hydroxy-benzotriazole hydrate (0.45 g, 3.31 mmol), ammonium chloride (0.33 g, 6.15 mmol), and diisopropylethylamine (1.15 mL, 6.60 mmol) in anhydrous dimethylformamide (10 ml) was stirred at room temp. overnight. The resultant solution was concentrated under vacuum and the residue was partitioned between ethyl acetate and water. The organic extracts were combined, washed with brine, dried over anhydrous magnesium sulfate, filtered, and concentrated under vacuum. The residual oil was subjected to column chromatography on silica eluting with 40% ethyl acetate in hexane. Collection and concentration of appropriate fractions provided the title product.

Step F: Preparation of 4-(3-methylbenzyl) isonipecotamide hydrochloride salt To a cold (0° C.) solution of N-tert-butoxycarbonyl-4-(3-methylbenzyl)isonipecotamide (700 mg) in ethyl acetate (50 mL), a stream of anhydrous hydrogen chloride gas was bubbled for 20 min. The resultant mixture was stirred at 0° C. for 1.5 h, purged with argon for 10 min., and concentrated under vacuum to provide the title compound as white solid.

Step G: Preparation of 1-[3-(4-Cyanobenzyl)-3H-imidazol-4-ylmethyl]-4-(3-methylbenzyl) isonipecotamide A solution of 4-(3-methylbenzyl)isonipecotamide hydrochloride salt (134 mg, 0.5 mmol), 1-(4-cyanobenzyl)-5-chloromethylimidazole hydrochloride salt (134 mg, 0.5 mmol; Example 52, Step D), and diisopropylethylamine (440 mL, 2.5 mmol) in anhydrous acetonitrile (5 mL) was heated under reflux overnight. The resultant mixture was concentrated under vacuum. The residue was subjected to column chromatography on silica gel eluting with 2% methanol in chloroform saturated with ammonia gas. After collection and concentration of appropriate fractions, the residue was triturated with anhydrous diethyl ether. The white solid precipitated was filtered to provide the title compound.

Anal. Calcd for $C_{26}H_{29}N_5O$: C, 70.67; H, 6.67; N, 15.19. Found: C, 70.72; H, 6.54; N, 15.48.

Example 82

Preparation of 1-[3-(4-Cyanobenzyl)-3H-imidazol-4-ylmethyl]-4-(2-methylbenzyl)isonipecotamide

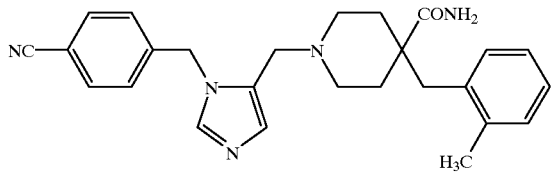

The title compound was prepared using the protocol described in Example 81, Step A–G substituting 3-methylbenzyl bromide with 2-methylbenzyl bromide in Step C.

Anal. Calcd for $C_{26}H_{29}N_5O.0.10\ CH_2Cl_2.0.10\ Et_2O$: C, 71.77; H, 6.86; N, 15.79. Found: C, 71.64; H, 6.70; N, 15.78.

Example 83

Preparation of 1-[3-(4-Cyanobenzyl)-3H-imidazol-4-ylacetyl]-4-(3-methyl-benzyl)isonipecotamide

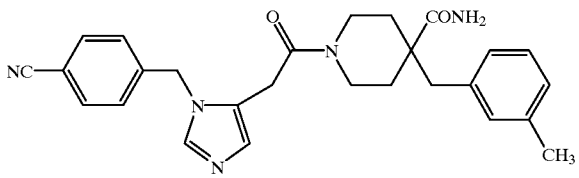

The title compound was prepared using the protocol described in Example 81, Step A–F, and in Example 38, Step B substituting 4-(3-methylbenzyl)-4-hydroxymethylpiperidine hydrochloride salt with 4-(3-methylbenzyl)isonipecotamide hydrochloride salt. Trituration of the purified product with a mixture of dichloromethane and toluene provided the title compound as white solid.

Anal. Calcd for $C_{27}H_{29}N_5O_2.0.35\ EtOAc.0.05$ toluene: C, 70.32; H, 6.61; N, 14.26. Found: C, 70.24; H, 6.59; N, 14.21.

Example 84

Preparation of 1-[3-(4-Cyanobenzyl)-3H-imidazol-4-ylacetyl]-4-(2-methyl-benzyl)isonipecotamide

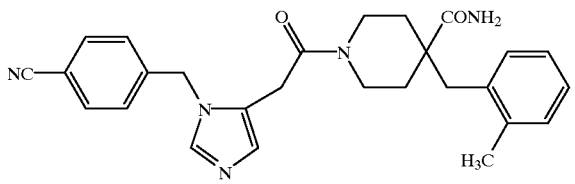

The title compound was prepared using the protocol described in Example 82, and in Example 38, Step B substituting 4-(3-methylbenzyl)-4-hydroxymethylpiperidine hydrochloride salt with 4-(2-methylbenzyl)-isonipecotamide hydrochloride salt. Trituration of the purified product with a mixture of dichloromethane and toluene provided the title compound as white solid.

Anal. Calcd for $C_{27}H_{29}N_5O_2.0.20\ CH_2Cl_2.0.30$ toluene: C, 70.35; H, 6.41; N, 14.00. Found: C, 70.26; H, 6.66; N, 13.88.

Example 85

Preparation of 1-[3-(4-Cyanobenzyl)-3H-imidazol-4-ylcarbonyl]-4-(3-methyl-benzyl)isonipecotamide

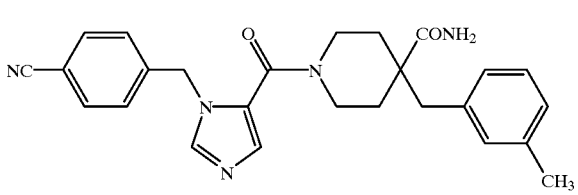

The title compound was prepared using the protocol described in Example 81, and in Example 39, substituting 4-(3-methylbenzyl)-4-hydroxymethylpiperidine hydrochloride salt with 4-(3-methylbenzyl)-isonipecotamide hydrochloride salt. Trituration of the purified product with a mixture of dichloromethane and toluene provided the title compound as white solid.

Anal. Calcd for $C_{26}H_{27}N_5O_2.0.20\ CH_2Cl_2.0.20$ toluene: C, 69.50; H, 6.13; N, 14.68. Found: C, 69.58; H, 6.32; N, 14.62.

Example 86

Preparation of 1-[3-(4-Cyanobenzyl)-3H-imidazol-4-ylcarbonyl]-4-(2-methyl-benzyl)isonipecotamide

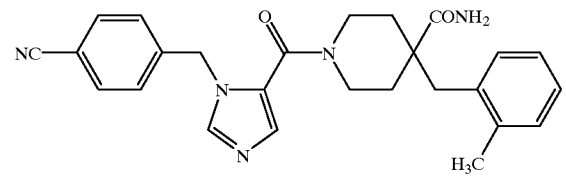

The title compound was prepared using the protocol described in Example 82, and in Example 39, substituting 4-(3-methylbenzyl)-4-hydroxymethylpiperidine hydrochloride salt with 4-(2-methylbenzyl)-isonipecotamide hydrochloride salt. Trituration of the purified product with a mixture of dichloromethane and toluene provided the title compound as white solid.

Anal. Calcd for $C_{26}H_{27}N_5O_2.0.05$ toluene: C, 70.93; H, 6.19; N, 15.70. Found: C, 70.93; H, 6.14; N, 15.73.

Example 87

Preparation of 1-[3-(4-Cyanobenzyl)-3H-imidazol-4-ylmethyl]-4-(3-methylbenzyl)piperidine-4-carbonitrile

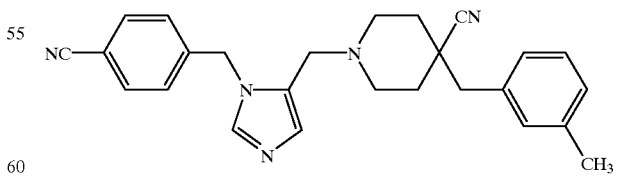

Step A: Preparation of N-tert-butoxycarbonyl-4-hydroxypiperidine

To a solution of 4-hydroxypiperidine (22.9 g, 226.4 mmol), triethylamine (33 mL, 242 mmol) in dichloromethane (250 mL), a solution of di-tert-butyl dicarbonate in dichloromethane (100 mL) was added over a period of over 1 h. The resulting solution was stirred at room temp. overnight. The reaction mixture was washed with aqueous potassium hydrogen sulfate, and brine. The organic extract was dried over anhydrous magnesium sulfate, filtered, and concentrated under vacuum to afford the title compound.

Step B: Preparation of N-tert-butoxycarbonylpiperidine-4-carbonitrile

To a cold (0° C.) solution of N-tert-butoxycarbonyl-4-hydroxypiperidine (1226.4 mmol) and pyridine (24.3 mL, 300 mmol) in anhydrous dichloromethane (300 mL), methanesulfonyl chloride (17.8 mL, 230 mmol) was added. The reaction mixture was stirred at room temp. overnight. The resultant mixture was diluted with dichloromethane and washed successively with 10% aqueous citric acid, saturated aqueous sodium bicarbonate, and brine. The organic extract was dried over anhydrous magnesium sulfate, filtered, and concentration under vacuum. The residue was dissolved in a mixture of potassium cyanide (29 g, 445 mmol) and anhydrous dimethylformamide (800 mL). The reaction mixture was heated at 100° C. overnight. The resultant slurry was filtered through a plug of Celite, and the filtrate concentrated under vacuum. The residue was subjected to column chromatography on silica gel eluting with 0–10% ethyl acetate in chloroform gradient. Collection and concentration of appropriate fractions provided the title nitrile.

Step C: Preparation of N-tert-butoxycarbonyl-4-(3-methyl-benzyl)piperidine-4-carbonitrile To a cold (−78° C.) solution of N-tert-butoxycarbonyl-piperidine-4-carbonitrile (4.01 g, 19.08 mmol) in anhydrous THF (60 mL), a solution of sodium bis(trimethysilyl)amide (20 mL, 20 mmol; 1 M) in THF was added over a period of 8 min. The resultant black solution was stirred at −78° C. for 1 h. and treated dropwise with 3-methylbenzyl bromide (3.08 mL, 22.8 mmol). The reaction mixture was allowed to warm to room temp., and stirred overnight. The product mixture was quenched with saturated aqueous ammonium chloride, diluted with water, and extracted with ethyl acetate. The organic extracts were combined, washed with brine, and concentrated under vacuum. The residual oil was subjected to column chromatography on silica eluting with 20% ethyl acetate in hexane. Collection and concentration of appropriate fractions provided the title product.

Step D: Preparation of 4-(3-methylbenzyl) piperidine-4-carbonitrile hydrochloride salt To a cold (0° C.) solution of N-tert-butoxycarbonyl-4-(3-methylbenzyl)piperidine-4-carbonitrile (1.60 g, 5.1 mmol) in ethyl acetate (100 mL), a stream of anhydrous hydrogen chloride gas was bubbled for 5 min. The resultant mixture was stirred at 0° C. for 45 minute, purged with argon for 10 min., and concentrated under vacuum to provide the title compound as white solid.

Step E: Preparation of 1-[3-(4-Cyanobenzyl)-3H-imidazol-4-ylmethyl]-4-(3-methylbenzyl)piperidine-4-carbonitrile A solution of 4-(3-methylbenzyl)piperidine-4-carbonitrile hydrochloride salt (129 mg, 0.51 mmol), 1-(4-cyanobenzyl)-5-chloro-methylimidazole hydrochloride salt (135 mg, 0.51 mmol; Example 52, Step D), and diisopropylethylamine (440 mL, 2.5 mmol) in anhydrous acetonitrile (5 mL) was heated under reflux overnight. The resultant mixture was concentrated under vacuum. The residue was subjected to column chromatography on silica gel eluting with a 85:15 v/v mixture of chloroform saturated with ammonia gas and hexane. After collection and concentration of appropriate fractions, the residue was triturated with a mixture of ethyl acetate and diethyl ether. The white solid precipitated was filtered to provide the title compound.

Anal. Calcd for $C_{26}H_{27}N_5 \cdot 0.10$ $Et_2O$: C, 76.04; H, 6.77; N, 16.80. Found: C, 76.08; H, 6.80; N, 16.91.

Example 88

Preparation of 1-[3-(4-Cyanobenzyl)-3H-imidazol-4-ylmethyl]-4-(2-methylbenzyl)piperidine-4-carbonitrile

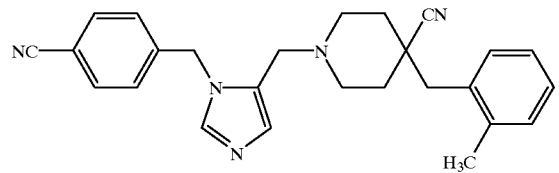

The title compound was prepared using the protocol described in Example 87, Step A–E substituting 3-methylbenzyl bromide with 2-methylbenzyl bromide in Step C.

Anal. Calcd for $C_{26}H_{27}N_5$: C, 76.25; H, 6.65; N, 17.10. Found: C, 76.23; H, 6.79; N, 17.05.

Example 89

Preparation of 1-[3-(4-Cyanobenzyl)-3H-imidazol-4-ylmethyl]-4-(4-mehtylbenzyl)piperidine-4-carbonitrile

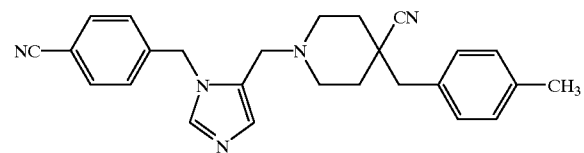

The title compound was prepared using the protocol described in Example 87, Step A–E substituting 3-methylbenzyl bromide with 4-methylbenzyl bromide in Step C.

Anal. Calcd for $C_{26}H_{27}N_5 \cdot 0.15$ $CH_2Cl_2 \cdot 0.15$ $H_2O$: C, 73.90; H, 6.55; N, 16.48. Found: C, 73.86; H, 6.22; N, 17.26.

Example 90

Preparation of 1-[3-(4-Cyanobenzyl)-2-methyl-3 H-imidazol-4-ylmethyl]-4-(3-methylbenzyl)piperidine-4-carbonitrile trifluoroacetate salt

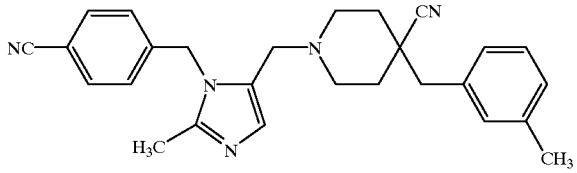

The title compound was prepared using the protocol described in Example 87, Step A–E substituting 1-(4-cyanobenzyl)-5-chloro-methylimidazole hydrochloride salt with 1-(4-cyanobenzyl)-5-chloro-methyl-2-methylimidazole hydrochloride salt (Example 53, Step B) in Step E. The final product was subjected to high pressure liquid column chromatography on C-18 reverse phase stationary phase. Collection and lyophilization of appropriate fractions provided the title compound as white solid.

Anal. Calcd for $C_{27}H_{29}N_5 \cdot 2.25$ TFA$\cdot 1.55$ $H_2O$: C, 53.43; H, 4.89; N, 9.89. Found: C, 53.39; H, 4.87; N, 10.04.

Example 91

Preparation of 1-[3-(4-Cyanobenzyl)-3H-imidazol-4-ylcarbonyl]-4-(3-methylbenzyl)piperidine-4-carbonitrile

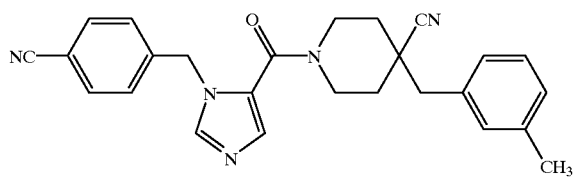

The title compound was prepared using the protocol described in Example 87, Step A–D, and in Example 39 substituting 4-(3-methylbenzyl)-4-hydroxymethylpiperidine hydrochloride salt with 4-(3-methylbenzyl)piperidine-4-carbonitrile hydrochloride salt (Example 87, Step D).

Anal. Calcd for $C_{26}H_{25}N_5O \cdot 0.15 Et_2O$: C, 73.50; H, 6.15; N, 16.11. Found: C, 73.55; H, 6.15; N, 16.17.

Example 92

Preparation of 1-[3-(4-Cyanobenzyl)-3H-imidazol-4-ylcarbonyl]-4-(2-methylbenzyl)piperidine-4-carbonitrile

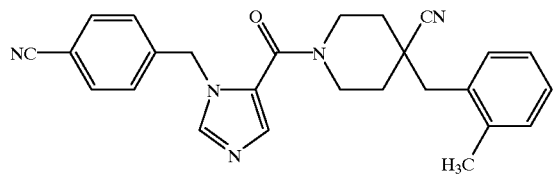

The title compound was prepared using the protocol described in Example 87, Step A–D, substituting 3-methylbenzyl bromide with 2-methylbenzyl bromide in Step C, and in Example 39 substituting 4-(3-methylbenzyl)-4-hydroxymethylpiperidine hydrochloride salt with 4-(2-methylbenzyl)piperidine-4-carbonitrile hydrochloride salt.

Anal. Calcd for $C_{26}H_{25}N_5O \cdot 0.10 Et_2O$: C, 73.58; H, 6.08; N, 16.25. Found: C, 73.67; H, 6.18; N, 16.25.

Example 93

Preparation of 1-[3-(4-Cyanobenzyl)-3H-imidazol-4-ylacetyl]-4-(3-methylbenzyl)piperidine-4-carbonitrile trifluoroacetate salt

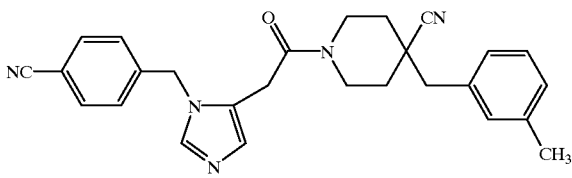

The title compound was prepared using the protocol described in Example 87, Step A–D, and in Example 38 substituting 4-(3-methylbenzyl)-4-hydroxymethylpiperidine hydrochloride salt with 4-(3-methylbenzyl)piperidine-4-carbonitrile hydrochloride salt (Example 87, Step D). The final product was subjected to high pressure liquid column chromatography on C-18 reverse phase stationary phase. Collection and lyophilization of appropriate fractions provided the title compound as white solid.

Anal. Calcd for $C_{27}H_{27}N_5O \cdot 1.6$ TFA$\cdot 0.75$ $H_2O$: C, 57.25; H, 4.79; N, 11.06. Found: C, 57.26; H, 4.75; N, 11.24.

Example 94

Preparation of 1-[3-(4-Cyanobenzyl)-3H-imidazol-4-ylacetyl]-4-(2-methylbenzyl)piperidine-4-carbonitrile

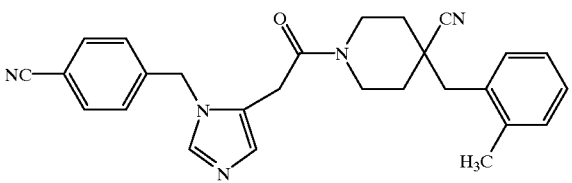

The title compound was prepared using the protocol described in Example 87, Step A–D, substituting 3-methylbenzyl bromide with 2-methylbenzyl bromide in Step C, and in Example 38 substituting 4-(3-methylbenzyl)-4-hydroxymethylpiperidine hydrochloride salt with 4-(2-methylbenzyl)piperidine-4-carbonitrile hydrochloride salt.

Anal. Calcd for $C_{27}H_{27}N_5O \cdot 0.05$ EtOAc$\cdot 0.15$ $Et_2O$: C, 73.69; H, 6.43; N, 15.46. Found: C, 73.71; H, 6.51; N, 15.53.

Example 95

Preparation of 1-[3-(4-Cyanobenzyl)-3H-imidazol-4-ylethyl]-4-(3-methylbenzyl)piperidine-4-carbonitrile trifluoroacetate salt

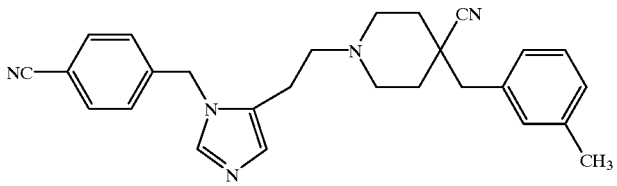

The title compound was prepared using the protocol described in Example 87, Step A–D, and in Example 78 substituting methyl 4-(3-methylbenzyl)piperidine-4-carboxylate hydrochloride salt with 4-(3-methyl-benzyl)piperidine-4-carbonitrile hydrochloride salt (Example 87, Step D). The final product was subjected to high pressure liquid column chromatography on C-18 reverse phase stationary phase. Collection and lyophilization of appropriate fractions provided the title compound as white solid.

Anal. Calcd for $C_{27}H_{29}N_5$.2.6 TFA.0.04 $H_2O$: C, 53.66; H, 4.43; N, 9.72. Found: C, 53.66; H, 4.56; N, 9.32.

Example 96

Preparation of 1-[3-(4-Cyanobenzyl)-3H-imidazol-4-ylethyl]-4-(2-methylbenzyl)piperidine-4-carbonitrile trifluoroacetate salt

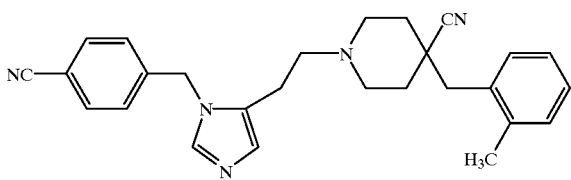

The title compound was prepared using the protocol described in Example 87, Step A–D, substituting 3-methylbenzyl bromide with 2-methylbenzyl bromide in Step C, and in Example 78 substituting methyl 4-(3-methylbenzyl)piperidine-4-carboxylate hydrochloride salt with 4-(2-methylbenzyl)piperidine-4-carbonitrile hydrochloride salt. The crude product was subjected to high pressure liquid column chromatography on C-18 reverse phase stationary phase. Collection and lyophilization of appropriate fractions provided the title compound as white solid.

Anal. Calcd for $C_{27}H_{29}N_5$.2.5 TFA.0.95 $H_2O$: C, 52.93; H, 4.52; N, 10.32. Found: C, 52.96; H, 4.64; N, 9.65.

Example 97

Preparation of 4-{5-[4-Hydroxymethyl-4-(4-methylpyridin-2-ylmethyl)-piperidine-1-ylmethyl]-2-methylimidazol-1-ylmethyl}benzonitrile

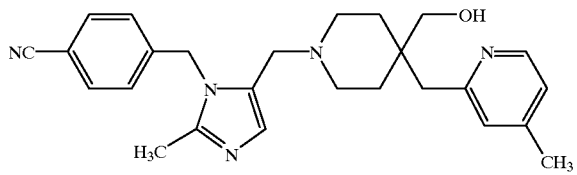

Step A: Preparation of 2-Hydroxymethyl-4-methylpyridine

A mixture of 2,4-dimethylpyridine N-oxide (10.9 g, 88.5 mmol) and trifluoroacetic anhydride (31 mL, 219 mmol) in dichloromethane (75 mL) was stirred at room temp. overnight. The product mixture was concentrated under vacuum. The residue was dissolved in a mixture of dichloromethane (75 mL) and aqueous sodium carbonate (225 mL, 2M), and stirred vigorously for 4 h. The resultant mixture was diluted with dichloromethane. The organic extract was washed with brine, dried over anhydrous sodium sulfate, filtered, and concentrated under vacuum. The residue was subjected to column chromatography on silica gel eluting with 1–2% methanol in chloroform gradient. Collection and concentration of appropriate fractions provided 2-hydroxymethyl-4-methylpyridine as clear oil.

Step B: Preparation of 2-Chloromethyl-4-methylpyridine

A mixture of 2-hydroxymethyl-4-methylpyridine (5.48 g, 44.5 mmol) and thionyl chloride (60 mL, 822 mmol) in benzene (150 mL) was stirred at room temp. overnight. The product mixture was concentrated under vacuum. The residue was partitioned between dichloromethane and aqueous sodium bicarbonate. The organic extract was washed with brine, dried over anhydrous sodium sulfate, and filtered. The filtrate was concentrated under vacuum to provide the title compound as oil. This alkylating reagent was passed through a small plug of activated basic alumina immediately before use.

Step C: Preparation of Ethyl N-tert-butoxycarbonyl-4-(4-methylpyridin-2-ylmethyl)piperidine-4-carboxylate To a cold (−78° C.) solution of ethyl N-tert-butoxycarbonyl-piperidine-4-carboxylate (5.1 g, 19.8 mmol; Example 30, Step A) in anhydrous THF (50 mL), a solution of solution of sodium bis(trimethyl-silyl)amide (20 mL, 1M, 20 mmol) was added over a period of 15 min. The resultant mixture was stirred at −78° C. for 1 h., and 2-chloromethyl-4-methylpyridine (3.5 g, 24.7 mmol) was added. The reacting mixture was allowed to warm to room temp. and stirred overnight. The product mixture was diluted with dichloromethane was washed with brine. The organic extract was dried over anhydrous sodium sulfate, filtered, and concentrated under vacuum. The residue was subjected to column chromatography on silica gel eluting with 25–40% ethyl acetate in hexane gradient. Collection and concentration of appropriate fractions provided the title compound.

Step D: Preparation of N-tert-Butoxycarbonyl-4-(4-methylpyridin-2-ylmethyl)-4-hydroxymethylpiperidine To a slurry of lithium aluminum hydride (280 mg, 7.37 mmol) in anhydrous diethyl ether (30 mL) at 0° C., a solution of ethyl N-tert-butoxycarbonyl-4-(4-methylpyridin-2-ylmethyl)piperidine-4-carboxylate (2.7 g, 7.45 mmol) in diethyl ether (20 mL) was added dropwise with the temperature of the reacting mixture maintained below 10° C.

The resulting mixture was stirred at 0° C. for 30 min, and quenched with successive addition of water (0.28 mL), 15% aqueous NaOH (0.28 mL), and water (0.84 mL). The resultant slurry was stirred at room temp. for 30 min., and filtered through a small plug of Celite. The filtrate was washed brine, dried over anhydrous magnesium sulfate, and filtered. Concentration of the filtrate under vacuum provided the title alcohol.

Step E: Preparation of 4-(4-methylpyridin-2-ylmethyl)-4-hydroxy-methylpiperidine hydrochloride salt A solution of N-tert-butoxycarbonyl-4-(4-methylpyridin-2-ylmethyl)-4-hydroxymethylpiperidine (1.8 g) in dichloromethane (100 mL) at 0° C. was saturated with hydrogen chloride gas. The resultant solution was sealed with a rubber septum and stirred at room temp. for 2.5 h. The product solution was concentrated under vacuum to provide the title compound.

Step F: Preparation of 4-{5-[4-Hydroxymethyl-4-(4-methylpyridin-2-ylmethyl)piperidine-1-ylmethyl]-2-methylimidazol-1-ylmethyl}benzonitrile A mixture of 4-(4-methylpyridin-2-ylmethyl)-4-hydroxymethylpiperidine hydrochloride salt (0.39 g, 1.3 mmol), 1-(4-cyano-benzyl)-2-methylimidazole-5-carboxyaldehyde (0.33 g, 1.5 mol; Example 31, Step A), diisopropylethylamine (0.57 mL, 3.25 mmol), anhydrous magnesium sulfate (0.55 g), activated molecular sieves 3 A powder (0.55 g), and anhydrous methanol (3.5 mL) was stirred at room temp. overnight. The pH of the mixture was adjusted to ~5 with addition of glacial acetic acid. To the this mixture, a solution of sodium cyanoborohydride in THF (1.35 mL, 1M, 1.35 mmol) was added slowly over a period of 8 h with a syringe pump, and stirred at room temp. overnight. The product mixture was diluted with chloroform, filtered through Celite. The filtrate was washed with aqueous sodium bicarbonate, brine, dried over anhydrous sodium sulfate, filtered, and concentrated under vacuum. The residue was subjected to column chromatography on silica gel eluting with 5% methanol in chloroform. Collection and concentration of appropriate fractions provided a gum, which was triturated with anhydrous diethyl ether to provide the title compound as white solid.

Anal. Calcd for $C_{26}H_{31}N_5O$: C, 72.70; H, 7.27; N, 16.30. Found: C, 72.52; H, 7.08; N, 16.18.

Example 98

Preparation of 4-{5-[4-Hydroxymethyl-4-(6-methylpyridin-2-ylmethyl)-piperidine-1-ylmethyl]-2-methylimidazol-1-ylmethyl}benzonitrile

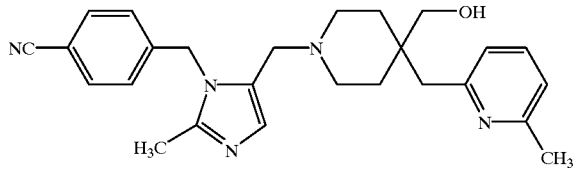

The title compound was prepared using the protocol described in Example 97, Step B–F substituting 2-hydroxymethyl-4-methylpyridine with 6-methyl-2-pyridinemethanol in Step B.

Anal. Calcd for $C_{26}H_{31}N_5O$: C, 72.70; H, 7.27; N, 16.30. Found: C, 72.96; H, 7.34; N, 16.25.

Example 99

Preparation of 4-{5-[4-Hydroxymethyl-4-(2-methylpyridin-4-ylmethyl)-piperidine-1-ylmethyl]-2-methylimidazol-1-ylmethyl}benzonitrile

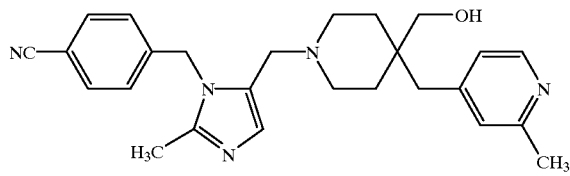

Step A: Preparation of 2-Chloro-4-chloromethyl-6-methylpyridine

To a slurry of lithium aluminum hydride (0.45 g, 11.9 mmol) in anhydrous diethyl ether (40 mL) at 0° C., a solution of 2-chloro-6-methylpyridine-4-carboxylic acid (2.0 g, 11.7 mmol) in diethyl ether (30 mL) was added. The resulting mixture was stirred at room temp. overnight, and quenched with successive addition of water (0.45 mL), 15% aqueous NaOH (0.45 mL), and water (1.35 mL). The resultant slurry was stirred at room temp. for 30 min., and filtered through a small plug of Celite. The filtrate was washed brine, dried over anhydrous magnesium sulfate, filtered, and concentrated under vacuum to provide 2-chloro-4-hydroxymethyl-6-methylpyridine.

The title compound was prepared using the protocol described in Example 97, Step B substituting 2-hydroxymethyl-4-methylpyridine with 2-chloro-4-hydroxymethyl-6-methylpyridine.

Step B: Preparation of Ethyl N-tert-butoxycarbonyl-4-(2-chloro-6-methylpyridin-4-ylmethyl)piperidine-4-carboxylate The title compound was prepared using the protocol described in Example 97, Step C substituting 2-chloromethyl-4-methylpyridine with 2-chloro-4-chloromethyl-6-methylpyridine.

Step C: Preparation of Ethyl N-tert-butoxycarbonyl-4-(2-methylpyridin-4-ylmethyl)piperidine-4-carboxylate A mixture of ethyl N-tert-butoxycarbonyl-4-(2-chloro-6-methylpyridin-4-ylmethyl)piperidine-4-carboxylate (0.32 g, 0.81 mmol) and 5% palladium on charcoal (60 mg) in methanol (10 mL) was stirred under a balloon of hydrogen gas at room temp. for 3 h. The resultant mixture was filtered through a plug of Celite. The filtrate was concentrated under vacuum. The residue was subjected to column chromatography on silica gel eluting with 3–5% methanol in chloroform gradient. Collection and concentration of appropriate fractions provided the title compound.

Step D: Preparation of 4-{5-[4-Hydroxymethyl-4-(2-methylpyridin-4-ylmethyl)-piperidine-1-ylmethyl]-2-methylimidazol-1-ylmethyl}benzonitrile The title compound was prepared using the protocol described in Example 97, Step D–F substituting ethyl N-tert-butoxycarbonyl-4-(4-methylpyridin-2-ylmethyl)piperidine-4-carboxylate with ethyl N-tert-butoxycarbonyl-4-(2-methylpyridin-4-ylmethyl)piperidine-4-carboxylate in Step D. The final product was subjected to high pressure liquid column chromatography on C-18 reverse phase stationary phase. Collection and lyophilization of appropriate fractions provided the title compound as white solid.

Anal. Calcd for $C_{26}H_{31}N_5O.3.35$ TFA: C, 48.39; H, 4.27; N, 8.63. Found: C, 48.42; H, 4.07; N, 8.49.

Example 100

Preparation of 4-{5-[4-Hydroxymethyl-4-(4-chloropyridin-2-ylmethyl)-piperidine-1-ylmethyl]-2-methylimidazol-1-ylmethyl}benzonitrile

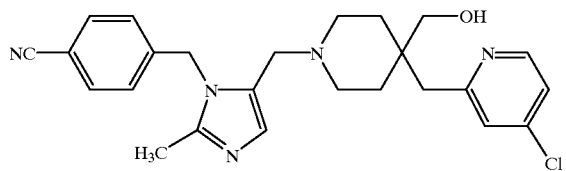

Step A: Preparation of 2-Chloromethyl-4-chloropyridine

To a slurry of lithium aluminum hydride (0.45 g, 11.9 mmol) in anhydrous diethyl ether (40 mL) at 0° C., a solution of methyl 4-chloro-pyridine-2-carboxylate (2.0 g, 11.7 mmol) in diethyl ether (30 mL) was added. The resulting mixture was stirred at room temp. overnight, and quenched with successive addition of water (0.45 mL), 15% aqueous NaOH (0.45 mL), and water (1.35 mL). The resultant slurry was stirred at room temp. for 30 min., and filtered through a small plug of Celite. The filtrate was washed with brine, dried over anhydrous magnesium sulfate, filtered, and concentrated under vacuum to provide 4-chloro-2-hydroxymethylpyridine.

The title compound was prepared using the protocol described in Example 97, Step B substituting 2-hydroxymethyl-4-methylpyridine with 4-chloro-2-hydroxymethylpyridine.

Step B: Preparation of 4-{5-[4-Hydroxymethyl-4-(4-chloropyridin-2-ylmethyl)-piperidine-1-ylmethyl]-2-methylimidazol-1-ylmethyl}benzonitrile The title compound was prepared using the protocol described in Example 97, Step C–F substituting 2-chloromethyl-4-methylpyridine with 2-chloromethyl-4-chloropyridine in Step C.

Anal. Calcd for $C_{25}H_{28}N_5OCl$: C, 66.73; H, 6.27; N, 15.56. Found: C, 66.52; H, 6.19; N, 15.35.

Example 101

Preparation of 4-{5-[4-Methoxymethyl-4-(6-methylpyridin-2-ylmethyl)-piperidine-1-ylmethyl] imidazol-1-ylmethyl}benzonitrile

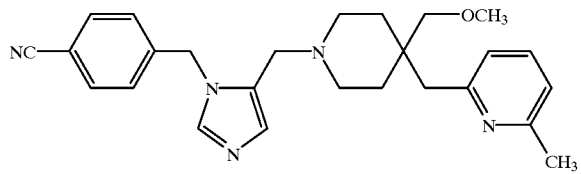

Step A: Preparation of N-tert-Butoxycarbonyl-4-(6-methylpyridin-2-ylmethyl)-4-methoxymethylpiperidine To a suspension of potassium hydride (52 mg, dry weight, 1.3 mmol; obtained from washing 0.15 g of 35% potassium hydride dispersion in mineral oil with hexanes and drying under a stream of argon) in anhydrous THF (10 mL), N-tert-butoxycarbonyl-4-(6-methylpyridin-2-ylmethyl)-4-hydroxymethylpiperidine (0.3 g, 0.9 mmol; Example 98) in THF (2 mL) was added. The resultant mixture was stirred at room temp. for 1 h, and treated with methyl iodide (60 μL, 0.96 mmol). The reacting mixture was stirred at room temp. overnight. The product mixture was cooled to 0° C., quenched with water, and diluted with ethyl acetate. The organic extract was washed with brine, dried over anhydrous magnesium sulfate, filtered, and concentrated under vacuum. The residue was subjected to column chromatography on silica gel eluting with 20–30% ethyl acetate in hexane. Collection and concentration of appropriate fractions provided the title compound.

Step B: Preparation of 4-{5-[4-Methoxymethyl-4-(6-methylpyridin-2-ylmethyl)-piperidine-1-ylmethyl] imidazol-1-ylmethyl}-benzonitrile The title compound was prepared using the protocol described in Example 97, Step E–F substituting N-tert-butoxycarbonyl-4-(4-methylpyridin-2-ylmethyl)-4-hydroxymethylpiperidine with N-tert-butoxycarbonyl-4-(6-methylpyridin-2-ylmethyl)-4-methoxymethyl-piperidine in Step E. The final product was subjected to high pressure liquid column chromatography on C-18 reverse phase stationary phase. Collection and lyophilization of appropriate fractions provided the title compound as white solid.

Anal. Calcd for $C_{26}H_{31}N_5O.3.35$ TFA: C, 48.39; H, 4.27; N, 8.63. Found: C, 48.42; H, 4.07; N, 8.49.

Example 102

Preparation of 4-{5-[4-Hydroxymethyl-4-(6-hydroxypyridin-2-ylmethyl)-piperidine-1-ylmethyl]-2-methylimidazol-1-ylmethyl}benzonitrile

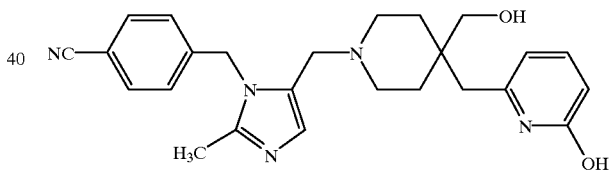

Step A: Preparation of 2-Benzyloxy-6-methylpyridine N-oxide

To a cold (0° C.) solution of 2-chloro-6-methylpyridine (24.6 g, 193 mmol) in dichloromethane (100 mL), a solution of m-chloro-per-benzoic acid (46.2 g, 268 mmol; purified) in dichloromethane (480 mL) was added over a period of 30 min. The reaction mixture was stirred at room temp. overnight, and concentrated to about 100 mL. The slurry was filtered, and the solid washed with ice-cold dichloromethane. The combined filtrate was washed with saturated aqueous sodium bicarbonate, brine, dried over anhydrous magnesium sulfate, and filtered. The filtrate was concentrated under vacuum to provide 2-chloro-6-methylpyridine N-oxide as clear colorless oil.

To a slurry of sodium hydride (4.2 g, 105 mmol; 60% dispersion in mineral oil) in anhydrous dimethyl sulfoxide (70 mL), benzyl alcohol (8.7 mL, 84 mmol) was added over a period of 10 minute. The mixture was stirred at room temp. for 10 h., and treated with a solution of 2-chloro-6-methylpyridine N-oxide (10 g, 70 mmol) in dimethyl sulfoxide (10 mL). The resultant mixture was stirred at room temp. overnight, quenched with water and aqueous hydrochloric acid (to pH 8). The mixture was extracted with chloroform. The organic extract was dried over anhydrous sodium sulfate, filtered, and concentrated under vacuum. The residue was subjected to column chromatography on silica gel eluting with 1–4% methanol in chloroform gradient. Collection and concentration of appropriate fractions provided 2-benzyloxy-6-methylpyridine N-oxide as pale brown oil.

Step B: Preparation of 2-Benzyloxy-6-chloromethylpyridine

A mixture of 2-benzyloxy-6-methylpyridine N-oxide (3.4 g, 15.9 mmol) and acetic anhydride (125 mL) was heated under reflux for 1 h. The resulting solution was concentrated under vacuum, and the residue was partitioned between aqueous sodium bicarbonate and dichloromethane. The organic extract was washed with brine, dried over anhydrous sodium sulfate, filtered, and concentrated under vacuum. The residue was subjected to column chromatography on silica gel eluting with 10–20% ethyl acetate in hexane gradient. Collection and concentration of appropriate fractions provided 2-acetoxymethyl-6-benzyloxypyridine as colorless oil.

A mixture of 2-acetoxymethyl-6-benzyloxypyridine (1.65 g, 6.4 mmol) and aqueous sodium hydroxide (0.58 mL, 40%) in methanol (10 mL) was stirred at room temp. overnight. The resulting solution was concentrated under vacuum, and the residue was partitioned between water and dichloromethane. The organic extract was washed with brine, dried over anhydrous sodium sulfate, filtered, and concentrated under vacuum. The residue was subjected to column chromatography on silica gel eluting with 0–5% ethyl acetate in chloroform gradient. Collection and concentration of appropriate fractions provided 2-benzyloxy-6-hydroxymethylpyridine as colorless oil.

A mixture of 2-benzyloxy-6-hydroxymethylpyridine (1.5 g, 7.0 mmol) and thionyl chloride (10 mL, 137 mmol) in benzene (25 mL) was stirred at room temp. overnight. The product mixture was concentrated under vacuum. The residue was partitioned between chloroform and aqueous sodium bicarbonate. The organic extract was washed with brine, dried over anhydrous sodium sulfate, filtered and concentrated under vacuum. The residue was subjected to column chromatography on silica gel eluting with 5% methanol in chloroform. Collection and concentration of appropriate fractions provided 2-benzyloxy-6-chloromethylpyridine as clear, colorless oil. This alkylating reagent was passed through a small plug of activated basic alumina immediately before use.

Step C: Preparation of N-tert-Butoxycarbonyl-4-(6-benzyloxypyridin-2-ylmethyl)-4-hydroxymethylpiperidine The title compound was prepared using the protocol described in Example 97, Step C–D substituting 2-chloromethyl-4-methylpyridine with 2-benzyloxy-6-chloromethylpyridine in Step C.

Step D: Preparation of N-tert-Butoxycarbonyl-4-(6-hydroxypyridin-2-ylmethyl)-4-hydroxymethylpiperidine A mixture of N-tert-butoxycarbonyl-4-(6-benzyloxypyridin-2-ylmethyl)-4-hydroxymethylpiperidine (0.19 g, 0.5 mmol) and 5% palladium on charcoal (38 mg) in absolute ethanol (10 mL) was stirred under a balloon of hydrogen gas at room temp. for 3 h. The resultant mixture was filtered through a plug of Celite. The filtrate was concentrated under vacuum to provide the title compound as colorless gum.

Step E: Preparation of 4-{5-[4-Hydroxymethyl-4-(6-hydroxypyridin-2-ylmethyl)piperidin-1-ylmethyl]-2-methylimidazol-1-ylmethyl}benzonitrile The title compound was prepared using the protocol described in Example 97, Step E–F substituting N-tert-butoxycarbonyl-4-(4-methylpyridin-2-ylmethyl)-4-hydroxymethylpiperidine with N-tert-butoxycarbonyl-4-(6-hydroxypyridin-2-ylmethyl)-4-hydroxymethyl-piperidine in Step E.

Anal. Calcd for $C_{25}H_{29}N_5O_2 \cdot 1.25\ H_2O \cdot 0.40\ Et_2O$: C, 66.04; H, 7.40; N, 14.48. Found: C, 66.06; H, 7.02; N, 14.18.

Example 102A

Preparation of 4-[5-(4-Hydroxymethyl-4-quinolin-2-ylmethyl-piperidine-1-ylmethyl)-2-methylimidazol-1-ylmethyl]benzonitrile

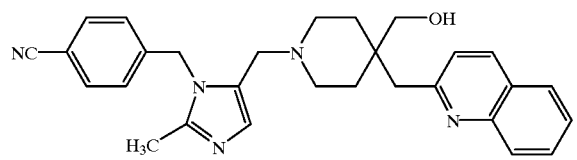

The title compound was prepared using the protocol described in Example 97, Step C–F substituting 2-hydroxymethyl-4-methylpyridine with 2-chloromethylquinoline in Step C. The alkylating reagent, 2-chloromethylquinoline, was generated from 2-chloromethylquinoline hydrochloride salt immediately before use.

Anal. Calcd for $C_{29}H_{31}N_5O$: C, 74.81; H, 6.71; N, 15.04. Found: C, 74.45; H, 6.67; N, 15.07.

Example 103

Preparation of Methyl 1-[3-(4-cyanobenzyl)-3H-imidazol-4-ylmethyl]-4-(3-methylbenzoyl)piperidine-4-carboxylate

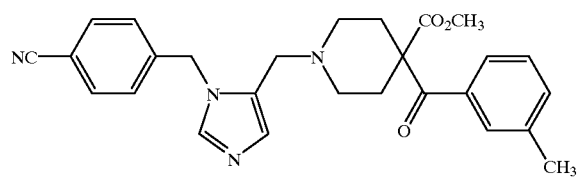

Step A: Preparation of Methyl N-tert-butoxycarbonyl-4-(3-methylbenzoyl)piperidine-4-carboxylate To a cold (−78° C.) solution of methyl N-tert-butoxycarbonyl-piperidine-4-carboxylate (0.25 g, 1.03 mmol; Example 3, Step B) in anhydrous THF (10 mL), a solution of sodium bis(trimethylsilyl)amide (1.2 mL, 1M, 1.2 mmol) was added over a period of 5 min. The resultant mixture was stirred at −78° C. for 1 h., and 3-methylbenzoyl chloride (135 μL, 1.02 mmol) was added. The reacting mixture was allowed to warm up to room temp. and stirred overnight. The product mixture was diluted with ethyl acetate and washed with brine. The organic extract was dried over anhydrous sodium sulfate, filtered, and concentrated under vacuum. The residue was subjected to column chromatography on silica gel eluting with 8–10% ethyl acetate in hexane gradient. Collection and concentration of appropriate fractions provided the title compound.

Step B: Preparation of Methyl 4-(3-methylbenzoyl) piperidine-4-carboxylate hydrochloride salt A solution of methyl N-tert-butoxycarbonyl-4-(3-methylbenzoyl)piperidine-4-carboxylate (77 mg) in ethyl acetate (10 mL) at 0° C. was saturated with hydrogen chloride gas. The resultant solution was stirred at 0° C. for 2.5 h. The product solution was concentrated under vacuum to provide the title compound.

Step C. Preparation of Methyl 1-[3-(4-cyanobenzyl)-3H-imidazol-4-ylmethyl]-4-(3-methylbenzoyl)piperidine-4-carboxylate A solution of methyl 4-(3-methylbenzoyl)piperidine-4-carboxylate hydrochloride salt (58 mg, 0.2 mmol), 1-(4-cyanobenzyl)-5-chloromethylimidazole hydrochloride salt (52 mg, 0.19 mmol), and diisopropylethylamine (174 μL, 1 mmol) in anhydrous acetonitrile (4 mL) was heated at 60° C. overnight. The resultant mixture was concentrated under vacuum, and the residue was partitioned between saturated aqueous sodium bicarbonate and ethyl acetate. The organic extract was washed with brine, dried over anhydrous sodium sulfate, filtered, and concentrated under vacuum. The residue was subjected to column chromatography on silica gel eluting with 2.5% methanol in ethyl acetate. Collection and concentration of appropriate fractions provided the title compound.

Anal. Calcd for $C_{27}H_{28}N_4O_3 \cdot 0.25\ H_2O$: C, 70.34; H, 6.23; N, 12.15. Found: C, 70.27; H, 6.18; N, 12.27.

Example 104

Preparation of 1-[3-(4-Cyanobenzyl)-3H-imidazol-4-ylmethyl]-4-(3-methylbenzoyl)piperidine

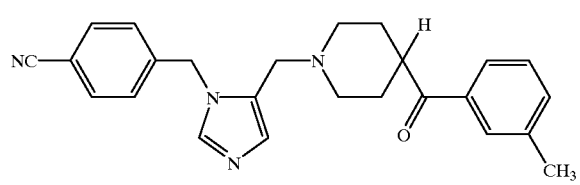

Step A: Preparation of 12-tert-Butoxycarbonyl-4-(3-methyl-benzoyl)piperidine

A mixture of 1-tert-butoxycarbonylisonipecotic acid (5 g, 21.8 mmol; Example 81, Step A), N,O-dimethylhydroxylamine hydrochloride (2.12 g, 21.7 mmol), N-ethyl-N'-(3-dimethylaminopropyl)carbodiimidehydrochloride (4.6 g, 24 mmol), 1-hydroxy-7-azabenzotriazole (0.3 g, 2.2 mmol), and anhydrous dimethylformamide (50 mL) was stirred at room temp. overnight. The resulting mixture was concentrated under vacuum, and the residue was partitioned between ethyl acetate and aqueous sodium bicarbonate. The organic extract was washed with brine, dried over anhydrous magnesium sulfate, filtered, and concentrated under vacuum to provide N-Methoxy-N-methyl 1-tert-butoxycarbonylisonipecotamide.

To a cold (–78° C.) solution of N-Methoxy-N-methyl 1-tert-butoxycarbonylisonipecotamide (1.54 g, 5.65 mmol) in anhydrous THF (25 mL), a solution of 3-methylphenylmagnesium bromide (25 mL, 1M) in THF was added. The reacting mixture was allowed to warm up to room temp. and stirred overnight. The product mixture was quenched with 10% aqueous citric acid and diluted with diethyl ether. The organic extract was washed with aqueous sodium bicarbonate, brine, dried over anhydrous magnesium sulfate, filtered, and concentrated under vacuum. The residue was subjected to column chromatography on silica gel eluting with 10–15% ethyl acetate in hexane gradient. Collection and concentration of appropriate fractions provided the title compound.

Step B: Preparation of 1-[3-(4-Cyanobenzyl)-3H-imidazol-4-ylmethyl]-4-(3-methylbenzoyl)piperidine The title compound was prepared as white solid according to the procedure described in Example 103, Step B–C substituting methyl N-tert-butoxycarbonyl-4-(3-methylbenzoyl)piperidine-4-carboxylate with N-tert-butoxycarbonyl-4-(3-methylbenzoyl)piperidine in Step B.

Anal. Calcd for $C_{25}H_{26}N_4O$: C, 75.35; H, 6.58; N, 14.06. Found: C, 75.38; H, 6.80; N, 14.12.

Example 105

Preparation of 1-[3-(4-Cyanobenzyl)-3H-imidazol-4-ylmethyl]-4-(hydroxy-m-tolylmethyl)piperidine

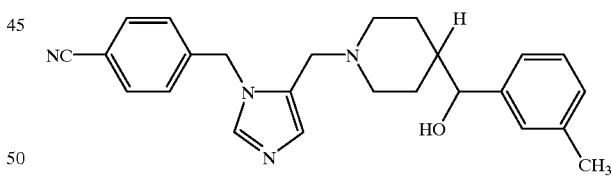

A solution of 1-[3-(4-cyanobenzyl)-3H-imidazol-4-ylmethyl]-4-(3-methylbenzoyl)piperidine (175 mg, 0.44 mmol; Example 104) in methanol (5 mL) was treated with sodium borohydride (12 mg, 0.31 mmol) at room temp. The resultant solution was stirred at room temp. for 30 min., and concentrated under vacuum. The residue was subjected to column chromatography on silica gel eluting with chloroform saturated with ammonia gas. Collection and concentration of appropriate fractions provided the title product.

Anal. Calcd for $C_{25}H_{28}N_4O \cdot 0.25\ Et_2O \cdot 0.55\ H_2O$: C, 72.80; H, 7.43; N, 13.06. Found: C, 72.74; H, 7.06; N, 13.05.

Example 106

Preparation of 4-{5-[4-Hydroxymethyl-4-(3-tolylsulfanyl)piperidine-1-ylmethyl]imidazol-1-ylmethyl}benzonitrile trifluoroacetate salt

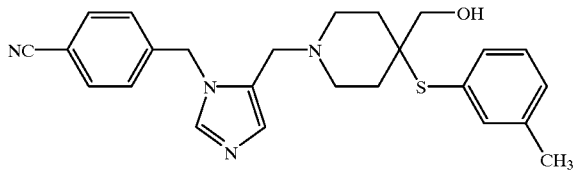

Step A: Preparation of Ethyl N-tert-butoxycarbonyl-4-(3-tolylsulfanyl)piperidine-4-carboxylate To a cold (−78° C.) solution of ethyl N-tert-butoxycarbonyl-piperidine-4-carboxylate (2.6 g, 10 mmol; Example 30, Step A) in anhydrous THF (40 mL), a solution of sodium bis(trimethylsilyl)amide (12 mL, 1M, 12 mmol) was added over a period of 10 min. The resultant mixture was stirred at −78° C. for 1 h., and di-3-methylphenyl disulfide (2.96 g, 12 mmol) was added. The reacting mixture was allowed to warm up to room temp. and stirred overnight. The product mixture was diluted with ethyl acetate and washed with brine. The organic extract was dried over anhydrous magnesium sulfate, filtered, and concentrated under vacuum. The residue was subjected to column chromatography on silica gel eluting with 10–15% ethyl acetate in hexane gradient. Collection and concentration of appropriate fractions provided the title compound.

Step B: Preparation of N-tert-Butoxycarbonyl-4-hydroxymethyl-4-(3-tolylsulfanyl)piperidine To a slurry of lithium aluminum hydride (0.25 g, 6.6 mmol) in anhydrous diethyl ether (60 mL) at 0° C., a solution of ethyl N-tert-butoxycarbonyl-4-(3-tolylsulfanyl)piperidine-4-carboxylate (2.25 g, 5.9 mmol) in diethyl ether (5 mL) was added dropwise with the temperature of the reacting mixture maintained below 10° C. The resulting mixture was stirred at 0° C. for 1 h., and quenched with successive addition of water (0.25 mL), 15% aqueous NaOH (0.25 mL), and water (10.75 mL). The resultant slurry was stirred at room temp. for one h., and filtered through a small plug of Celite. The filtrate was washed brine, dried over anhydrous magnesium sulfate, filtered, and concentrated under vacuum to provide the title alcohol.

Step C: Preparation of 4-hydroxymethyl-4-(3-tolylsulfanyl)piperidine hydrochloride salt A solution of N-tert-butoxycarbonyl-4-hydroxymethyl-4-(3-tolylsulfanyl)piperidine (0.27 g) in dichloromethane (25 mL) at 0° C. was saturated with hydrogen chloride gas. The resultant solution was sealed with a rubber septum and stirred at 0° C. for one h. The product solution was concentrated under vacuum to provide the title compound.

Step D: Preparation of 4-{5-[4-Hydroxymethyl-4-(3-tolylsulfanyl)-piperidine-1-ylmethyl]imidazol-1-ylmethyl}benzonitrile trifluoroacetate salt A mixture of 4-hydroxymethyl-4-(3-tolylsulfanyl) piperidine hydrochloride salt (0.23 g, 0.85 mmol), 1-(4-cyanobenzyl)imidazole-5-carboxyaldehyde (0.20 g, 0.95 mmol; Example 1, Step E), diisopropyl-ethylamine (0.22 mL, 1.3 mmol), anhydrous magnesium sulfate (500 mg), activated powdered molecular sieves 3 Å (500 mg), and anhydrous methanol (3 mL) was stirred at room temp. overnight. The pH of the mixture was adjusted to ~5 with addition of glacial acetic acid. To the this mixture, a solution of sodium cyanoborohydride in THF (0.9 mL, 1M, 0.9 mmol) was added slowly over a period of 3 h. with a syringe pump, and stirred at room temp. overnight. The product mixture was diluted with chloroform, filtered through Celite. The filtrate was washed with aqueous sodium bicarbonate, brine, dried over anhydrous sodium sulfate, filtered, and concentrated under vacuum. The residue was subjected to column chromatography on silica gel eluting with a 3–5% methanol in chloroform gradient. Collection and concentration of appropriate fractions provided the free base. The product was purified with high pressure liquid column chromatography on C-18 reverse phase stationary phase. Collection and lyophilization of appropriate fractions provided the title compound as white solid.

Anal. Calcd for $C_{25}H_{28}N_4OS.2.7$ TFA.0.45 $H_2O$: C, 48.78; H, 4.26; N, 7.48. Found: C, 48.80; H, 4.28; N, 7.37.

Example 107

Preparation of 4-{5-[4-Methoxymethyl-4-(3-tolylsulfanyl)piperidine-1-ylmethyl]imidazol-1-ylmethyl}benzonitrile trifluoroacetate salt

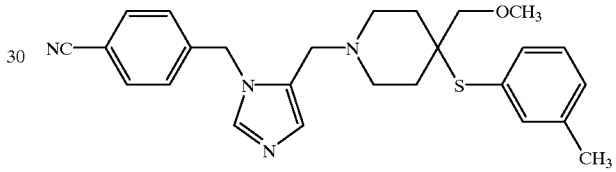

Step A: Preparation of N-tert-Butoxycarbonyl-4-methoxymethyl-4-(3-tolylsulfanyl)piperidine To a suspension of potassium hydride (0.18 g, dry weight, 4.5 mmol; obtained from washing 0.52 g of 35% potassium hydride dispersion in mineral oil with hexanes and drying under a stream of argon) in anhydrous THF (25 mL), N-tert-butoxycarbonyl-4-(3-tolylsulfanyl)-4-hydroxymethylpiperidine (0.96 g, 2.8 mmol; Example 106, Step B) in THF (5 mL) was added. The resultant mixture was stirred at room temp. for 1 h., and treated with methyl iodide (0.31 mL, 4.97 mmol). The reacting mixture was stirred at room temp. overnight. The product mixture was cooled to 0° C., quenched with water, and diluted with ethyl acetate. The organic extract was washed with brine, dried over anhydrous magnesium sulfate, filtered, and concentrated under vacuum to provide the title compound.

Step B: Preparation of 4-Methoxymethyl-4-(3-tolylsulfanyl)piperidine hydrochloride salt A solution of N-tert-butoxycarbonyl-4-methoxymethyl-4-(3-tolylsulfanyl)piperidine (0.18 g) in ethyl acetate (25 mL) at 0° C. was saturated with hydrogen chloride gas. The resultant solution was stirred at 0° C. for one h. The product solution was concentrated under vacuum to provide the title compound.

Step C: Preparation of 4-{5-[4-Methoxymethyl-4-(3-tolylsulfanyl)-piperidine-1-ylmethyl]imidazol-1-ylmethyl}benzonitrile trifluoroacetate salt The title compound was prepared using the protocol described in Example 106, Step D substituting 4-hydroxymethyl-4-(3-tolylsulfanyl)-piperidine hydrochloride salt with 4-methoxymethyl-4-(3-tolylsulfanyl)-piperidine hydrochloride salt.

Anal. Calcd for $C_{26}H_{30}N_4OS.2.45$ TFA.1.1 $H_2O$: C, 49.77; H, 4.68; N, 7.51. Found: C, 49.77; H, 4.68; N, 7.39.

Example 108

Preparation of 4-{5-[4-Methoxymethyl-4-(3-tolylsulfinyl)piperidine-1-ylmethyl]imidazol-1-ylmethyl}benzonitrile

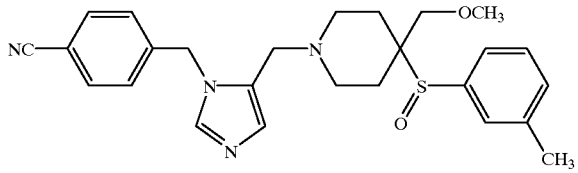

Step A: Preparation of N-tert-Butoxycarbonyl-4-methoxymethyl-4-(3-tolylsulfinyl)piperidine A mixture of N-tert-butoxycarbonyl-4-methoxymethyl-4-(3-tolylsulfanyl)piperidine (0.30 g, 0.85 mmol; Example 107, Step A) and sodium periodate (0.2 g, 0.94 mmol) in a mixture of methanol (6 mL) and water (4 mL) was stirred at room temp. overnight. The reaction mixture was diluted with dichloromethane. The organic extract was washed with brine, dried over anhydrous magnesium sulfate, filtered, and concentrated under vacuum. The residue was subjected to column chromatography on silica gel eluting with 35% ethyl acetate in hexane. Collection and concentration of appropriate fractions provided the title compound.

Step B: Preparation of 4-{5-[4-Methoxymethyl-4-(3-tolylsulfinyl)-piperidine-1-ylmethyl]imidazol-1-ylmethyl}benzonitrile The title compound was prepared using the protocol described in Example 107, Step B substituting N-tert-butoxycarbonyl-4-methoxy-methyl-4-(3-tolylsulfanyl)piperidine with N-tert-butoxycarbonyl-4-methoxymethyl-4-(3-tolylsulfinyl)piperidine, and in Example 103, Step C substituting 4-(3-methylbenzoyl)piperidine-4-carboxylate hydrochloride salt with 4-methoxymethyl-4-(3-tolylsulfinyl)piperidine hydrochloride salt.

Anal. Calcd for $C_{26}H_{30}N_4O_2S.0.8$ $H_2O$: C, 65.47; H, 6.68; N, 11.75. Found: C, 65.53; H, 6.35; N, 11.66.

Example 109

Preparation of 4-{5-[4-Methoxymethyl-4-(3-tolylsulfonyl)piperidine-1-ylmethyl]imidazol-1-ylmethyl}benzonitrile

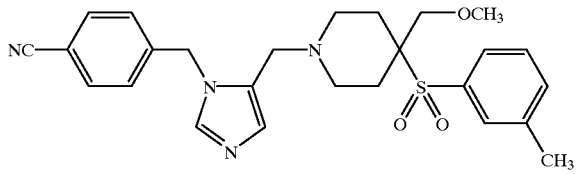

Step A: Preparation of N-tert-Butoxycarbonyl-4-methoxymethyl-4-(3-tolylsulfinyl)piperidine A solution of N-tert-Butoxycarbonyl-4-methoxymethyl-4-(3-tolylsulfanyl)piperidine (0.26 g, 0.73 mmol; Example 107, Step A) in acetonitrile (10 mL) was treated with a solution of Oxone (0.99 g, 1.6 mmol) in water (10 mL) and potassium bicarbonate (0.56 g, 5.6 mmol) in water (10 mL), and stirred at room temp. for 1 h. The reaction mixture was diluted with dichloromethane and water. The organic extract was washed with brine, dried over anhydrous magnesium sulfate, filtered, and concentrated under vacuum. The residue was subjected to column chromatography on silica gel eluting with 25% ethyl acetate in hexane. Collection and concentration of appropriate fractions provided the title compound.

Step B: Preparation of 4-{5-[4-Methoxymethyl-4-(3-tolylsulfonyl)-piperidine-1-ylmethyl]imidazol-1-ylmethyl}benzonitrile The title compound was prepared using the protocol described in Example 107, Step B substituting N-tert-butoxycarbonyl-4-methoxy-methyl-4-(3-tolylsulfanyl)piperidine with N-tert-butoxycarbonyl-4-methoxymethyl-4-(3-tolylsulfonyl)piperidine, and in Example 103, Step C substituting 4-(3-methylbenzoyl)piperidine-4-carboxylate hydrochloride salt with 4-methoxymethyl-4-(3-tolylsulfonyl)piperidine hydrochloride salt.

Anal. Calcd for $C_{26}H_{30}N_4O_3S.0.6$ $H_2O$: C, 63.81; H, 6.43; N, 11.45. Found: C, 63.86; H, 6.11; N, 11.32.

Example 110

Preparation of 1-[3-(4-Cyanobenzyl)-3H-imidazol-4-ylmethyl]-4-(3-methylphenylamino) isonipecotamide

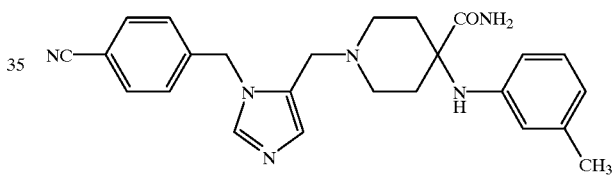

Step A: Preparation of 1-Benzyl-4-cyano-4-(3-methylphenylamino)-piperidine

To a solution of 1-benzyl-4-piperidone (18.9 g, 0.1 mol) and 3-methylaniline (10.7 g, 0.1 mol) in glacial acetic acid (100 mL), trimethylsilyl cyanide (6.7 mL, 0.1 mol; Journal of Organic Chemistry, vol.55, page 4207, year 1990) was added dropwise with the temp. of the reaction maintained <40° C. with a ice-water bath. After the addition was complete, the reaction mixture was stirred at room temp. for 30 min, and poured into a mixture of ice (140 g) and concentrated ammonium hydroxide (168 g). The resultant mixture was extracted with chloroform (3 times). The organic extract was washed with brine, dried over anhydrous sodium sulfate, filtered, and concentrated under vacuum. The residual oil was triturated with diisopropyl ether (300 mL) and stirred at room temp. overnight. The white solid precipitated was filtered to provide the title compound.

Step B: Preparation of 1-Benzyl-4-(3-methylphenylamino)-isonipecotamide

A mixture of 1-benzyl-4-cyano-4-(3-methylphenylamino)-piperidine (7.6 g) and 90% sulfuric acid (53 mL) was heated 70° C. until all the solid dissolved (~1 h). The resultant mixture was stirred at the temp. for 30 min., and poured into a mixture of ice (80 g) and concentrated ammonium hydroxide (75 g). The solution was basified with ammonium hydroxide, and extracted with chloroform. The organic extract was washed with brine, dried over anhydrous sodium sulfate, filtered, and concentrated under vacuum to provide the title compound.

Step C: Preparation of 4-(3-methylphenylamino) isonipecotamide hydrochloride salt A mixture of 1-benzyl-4-(3-methylphenylamino)-isonipecotamide (0.42 g, 1.3 mmol) and 10% palladium on charcoal (0.88 g) in a mixture of ethanol (40 mL) and ethanol saturated with anhydrous hydrochloride gas (10 mL) was shaken in a Parr hydrogenator at 60 psi for 48 h. The resultant mixture was filtered through a plug of Celite, and the filtrate concentrated to provide the title compound.

Step D: Preparation of 1-[3-(4-Cyanobenzyl)-3H-imidazol-4-ylmethyl]-4-(3-methylphenylamino) isonipecotamide The title compound was prepared using the protocol described in Example 106, Step D substituting 4-hydroxymethyl-4-(3-tolylsulfanyl)-piperidine hydrochloride salt with 4-(3-methylphenylamino)-isonipecotamide hydrochloride salt.

Anal. Calcd for $C_{25}H_{28}N_6O.0.15$ $Et_2O.0.65$ $H_2O$: C, 68.12; H, 6.88; N, 18.62. Found: C, 68.14; H, 6.73; N, 18.65.

Example 111

Preparation of Ethyl 1-[3-(4-Cyanobenzyl)-3H-imidazol-4-ylmethyl]-4-(3-methylphenylamino) piperidine-4-carboxylate

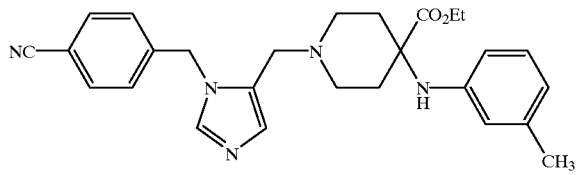

Step A: Preparation of Ethyl 1-Benzyl-4-(3-methylphenylamino)-piperidine-4-carboxylate A solution of 1-benzyl-4-(3-methylphenylamino)-isonipecotamide (4.5 g, 13.9 mmol) and potassium hydroxide (3. g, 53.5 mmol) in ethylene glycol (35 mL) was heated under reflux. The resulting mixture was diluted with water and neutralized with acetic acid. The white solid precipitated was filtered, washed with chloroform to provide 1-benzyl-4-(3-methylphenylamino)piperidine-4-carboxylic acid.

A mixture of 1-benzyl-4-(3-methylphenylamino) piperidine-4-carboxylic acid (3.81 g, 11.7 mmol) and concentrated sulfuric acid (2 mL) in absolute ethanol (80 mL) was heated under reflux overnight. The resultant solution was concentrated under vacuum, and the residue was treated with chloroform saturated with ammonia gas. The mixture was filtered, and the filtrate concentrated. The residue was passed through a small plug of silica gel eluting with chloroform saturated with ammonia gas. Collection and concentration of the eluent under vacuum provided the title compound.

Step B: Preparation of Ethyl 1-[3-(4-Cyanobenzyl)-3H-imidazol-4-ylmethyl]-4-(3-methylphenylamino) piperidine-4-carboxylate The title compound was prepared using the protocol described in Example 110, Step C–D substituting 1-benzyl-4-(3-methylphenyl-amino)isonipecotamide with ethyl 1-benzyl-4-(3-methylphenylamino)-piperidine-4-carboxylate.

Anal. Calcd for $C_{27}H_{31}N_5O.0.3$ $Et_2O$: C, 70.59; H, 7.14; N, 14.60. Found: C, 70.57; H, 7.07; N, 14.56.

Example 112

Preparation of 1-[3-(4-Cyanobenzyl)-3H-imidazol-4-ylmethyl]-4-hydroxymethyl-4-(3-methylphenylamino)piperidine

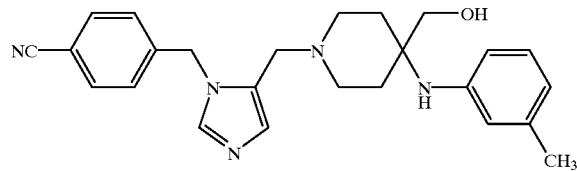

Step A: Preparation of 1-Benzyl-4-hydroxymethyl-4-(3-methylphenylamino)piperidine To a slurry of lithium aluminum hydride (330 mg, 8.7 mmol) in anhydrous diethyl ether (25 mL) at 0° C., a solution of ethyl 1-benzyl-4-(3-methylphenylamino) piperidine-4-carboxylate (2.8 g, 7.94 mmol) in diethyl ether (10 mL) was added dropwise with the temp. of the reacting mixture maintained below 10° C. The resulting mixture was stirred at 0° C. for 30 min, and quenched with successive addition of water (0.33 mL), 15% aqueous NaOH (0.33 mL), and water (1 mL). The resultant slurry was stirred at room temp. for 30 min., and was filtered through a small plug of Celite. The filtrate was washed brine, dried over anhydrous sodium sulfate, filtered, and concentrated under vacuum to provide the title alcohol as white solid.

Step B: Preparation of 4-hydroxymethyl-4-(3-methylphenylamino)-piperidine hydrochloride salt A mixture of 1-benzyl-4-hydroxymethyl-4-(3-methylphenylamino)piperidine (0.2 g, 0.64 mmol) and 10% palladium on charcoal (0.4 g) in a mixture of methanol (15 mL) and methanol saturated with anhydrous hydrochloride gas (10 mL) was shaken in a Parr hydrogenator at 60 psi for 24 h. The resultant mixture was filtered through a plug of Celite, and the filtrate was concentrated to provide the title compound.

Step C: Preparation of 1-[3-(4-Cyanobenzyl)-3H-imidazol-4-ylmethyl]-4-hydroxymethyl-4-(3-methylphenyl-amino)piperidine The title compound was prepared using the protocol described in Example 110, Step D substituting 4-(3-methylphenylamino)-isonipecotamide hydrochloride salt with 4-hydroxymethyl-4-(3-methylphenylamino)piperidine hydrochloride salt.

Anal. Calcd for $C_{25}H_{29}N_5O.0.1$ $H_2O$: C, 71.94; H, 7.05; N, 16.78. Found: C, 71.76; H, 7.09; N, 17.17.

Example 112A

Preparation of O-{1-[3-(4-Cyanobenzyl)-3H-imidazol-4-ylmethyl]-4-(3-methylphenylamino)piperidyl-4-methyl}carbamate

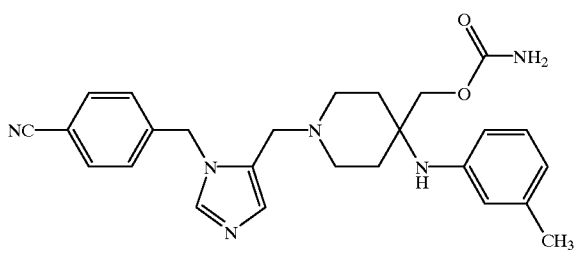

Step A: Preparation of O-[1-Benzyl-4-(3-methylphenylamino)piperidyl-4-methyl]carbamate A mixture of 1-benzyl-4-hydroxymethyl-4-(3-methylphenyl-amino)piperidine (0.25 g, 0.81 mmol; Example 112, Step A), 1,1'-carbonyldiimidazole (0.14 g, 0.89 mmol) and dichloromethane (2 mL) was stirred at room temp. overnight. The resultant solution was concentrated, and the residue subjected to column chromatography on silica gel eluting with 5% methanol in chloroform. Collection and concentration of appropriate fraction provided 1-[1-benzyl-4-(3-methylphenylamino)-piperidylmethyloxy]carbonyl-1'-imidazole. This material was dissolved in chloroform saturated with ammonia gas. The reaction mixture was sealed with a rubber septum, and stirred at room temp. for 2 days. The resultant mixture was concentrated, and the residue subjected to column chromatography on silica gel eluting with 8% methanol in chloroform. Collection and concentration of appropriate fraction provided the title compound.

Step B: Preparation of O-{1-[3-(4-Cyanobenzyl)-3H-imidazol-4-ylmethyl]-4-(3-methylphenylamino)piperidyl-4-methyl}carbamate The title compound was prepared using the protocol described in Example 110, Step C–D substituting 1-benzyl-4-(3-methylphenyl-amino)isonipecotamide with O-[1-Benzyl-4-(3-methylphenylamino)-piperidyl-4-methyl]carbamate.

Anal. Calcd for $C_{26}H_{30}N_6O_2 \cdot 0.2 H_2O$: C, 67.56; H, 6.63; N, 18.18. Found: C, 67.60; H, 6.28; N, 18.13.

Example 112B

Preparation of 1-[3-(4-Cyanobenzyl)-3H-imidazol-4-ylmethyl]-4-(3-methylphenylamino)piperidyl-4-methylurea

Step A: Preparation of 1-Benzyl-4-(3-methylphenylamino)-4-aminomethylpiperidine A mixture of 1-benzyl-4-cyano-4-(3-methylphenylamino)-piperidine (4.0 g; Example 110, Step A) and 5% rhodium on alumina (4 g) in absolute ethanol (100 mL) treated with anhydrous ammonia gas (8 g) was hydrogenated at 55 psi at room temp. for 24 h. The resultant mixture was filtered through a plug of Celite, and the filtrate concentrated under vacuum. The residue was subjected to column chromatography on silica gel eluting with a 1:1 mixture of 5 % methanol in chloroform and chloroform saturated with ammonia gas. Collection and concentration of appropriate fractions provided the title triamine as clear, colorless, viscous oil.

FAB MS m/e 310(M+1)

Step B: Preparation of [1-Benzyl-4-(3-methylphenylamino)piperidin-4-ylmethyl]urea A mixture of 1-benzyl-4-(3-methylphenylamino)-4-aminomethylpiperidine (247 m g, 0.79 mmol) and nitrourea (253 mg, 2.4 mmol) in mixture of acetonitrile (1 mL) and water (10 drops) was stirred at room temp. for 48 hrs. The resultant mixture was concentrated under vacuum, and the residue was subjected to column chromatography on silica gel eluting with a 1:1 mixture of 15% methanol in chloroform and chloroform saturated with ammonia gas. Collection and concentration of appropriate fractions provided the title compound.

Step C: Preparation of 1-[3-(4-Cyanobenzyl)-3H-imidazol-4-ylmethyl]-4-(3-methylphenylamino)piperidyl-4-methylurea The title compound was prepared using the protocol described in Example 110, Step C–D substituting 1-benzyl-4-(3-methylphenylamino)isonipecotamide with [1-benzyl-4-(3-methylphenylamino)piperidin-4-ylmethyl]urea.

Example 112C

Preparation of 1-[3-(4-Cyanobenzyl)-3H-imidazol-4-ylmethyl]-4-(3-methylphenylamino)piperidyl-4-methylsulfamide

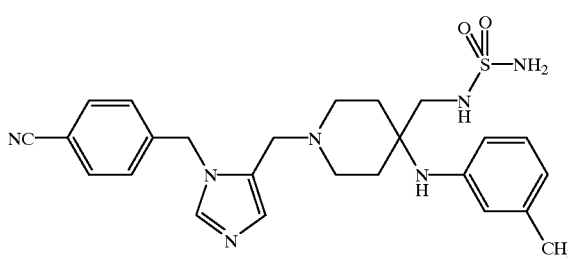

Step A: Preparation of [1-Benzyl-4-(3-methylphenylamino)piperidin-4-ylmethyl]sulfamide To a cold (5° C.) solution of chlorosulfonyl isocyanate in THF, anhydrous formic acid is added (Journal of Organic Chemistry, vol 54, page 5825,(1989)). The resultant mixture is stirred until gas evolution ceased, and treated with a solution of 1-benzyl-4-(3-methylphenylamino)-4-aminomethylpiperidine in THF. The mixture is stirred at room temp. overnight to provide the title compound.

Step B: Preparation of 1-[3-(4-Cyanobenzyl)-3H-imidazol-4-ylmethyl]-4-(3-methylphenylamino)piperidyl-4-methylsulfamide The title compound is prepared using the protocol described in Example 110, Step C–D substituting 1-benzyl-4-(3-methylphenylamino)-isonipecotamide with [1-benzyl-4-(3-methylphenylamino)piperidin-4-ylmethyl]sulfamide.

Example 113

Preparation of 4-{5-[4-(Hydroxydiphenylmethyl)piperidin-1-ylmethyl]imidazol-1-ylmethyl}benzonitrile

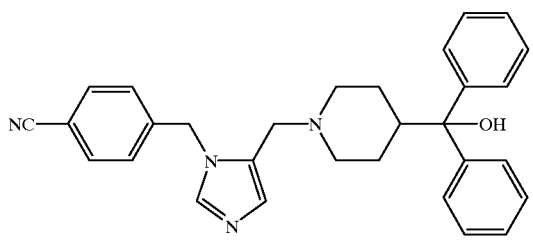

The title compound was prepared as white solid according to the procedure described in Example 103, Step C substituting methyl 4-(3-methylbenzoyl)piperidine-4-carboxylate hydrochloride salt with α,α-diphenyl-4-piperidinemethanol in Step B.

Anal. Calcd for $C_{30}H_{30}N_4O$: C, 77.59; H, 6.70; N, 11.83. Found: C, 77.39; H, 6.69; N, 12.00.

Example 114

Preparation of 4-{5-[4-(Hydroxydiphenylmethyl)piperidine-1-carbonyl]imidazol-1-ylmethyl}benzonitrile

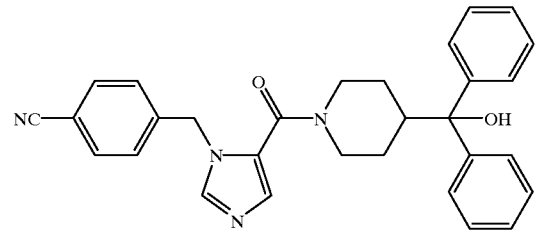

The title compound was prepared as white solid according to the procedure described in Example 39 substituting 4-(3-methylbenzyl)-4-hydroxymethylpiperidine hydrochloride salt with α,α-diphenyl-4-piperidinemethanol in Step B.

Anal. Calcd for $C_{30}H_{28}N_4O.0.8\ H_2O.0.35\ Et_2O$: C, 72.96; H, 6.45; N, 10.84. Found: C, 73.00; H, 6.36; N, 10.83.

Example 115

Preparation of 4-(5-{2-[4-(Hydroxydiphenylmethyl)piperidin-1-yl]-2-oxoethyl}-3H-imidazol-1-ylmethyl)benzonitrile The title compound was prepared as white solid according to the procedure described in Example 38, Step B substituting 4-(3-methylbenzyl)-4-hydroxymethylpiperidine hydrochloride salt with α,α-diphenyl-4-piperidinemethanol in Step B.

Anal. Calcd for $C_{31}H_{30}N_4O_2$: C, 75.89; H, 6.16; N, 11.42. Found: C, 75.60; H, 6.20; N, 11.25.

Example 116

1-(Piperidin-4-ylmethyl)-5-(4-cyanobenzyl)imidazole bis hydrochloride

Step A: 1-Trityl-4-(4-cyanobenzyl)-imidazole

To a suspension of activated zinc dust (3.57 g, 54.98 mmol) in THF (50 mL) was added dibromoethane (0.315 mL, 3.60 mmol) and the reaction stirred under argon for 45 minutes, at 20° C. The suspension was cooled to 0° C. and a-bromo-p-tolunitrile (9.33 g, 47.6 mmol) in THF (100 mL) was added dropwise over a period of 10 minutes. The reaction was then allowed to stir at 20° C. for 6 hours and bis(triphenylphosphine) Nickel II chloride (2.40 g, 3.64 mmol) and 4-iodo-1-tritylimidazole (15.95 g, 36.6 mmol, S. V. Ley, et al., J. Org. Chem. 56, 5739(1991)) were added in one portion. The resulting mixture was stirred 16 hours at 20° C. and then quenched by addition of saturated NH$_4$Cl solution (100 mL) and the mixture stirred for 2 hours. Saturated aq. NaHCO$_3$ solution was added to give a pH of 8 and the solution was extracted with EtOAc (2×250 mL), dried (MgSO$_4$) and the solvent evaporated in vacuo. The residue was chromatographed (Silica gel, 0–20% EtOAc in CH$_2$Cl$_2$) to afford the title compound as a white solid.

$^1$H NMR (CDC$_{13}$, 400 Mz) δ(7.54(2H, d, J=7.9 Hz), 7.38(1H, s), 7.36–7.29(11H, m), 7.15–7.09(6H, m), 6.58 (1H, s) and 3.93(2H, s) ppm.

Step B: N-t-butoxycarbonyl-4-hydroxymethyl piperidine.

To a solution of N-t-butoxycarbonyl isonipecotic acid (15.0 g, 65.4 mmol) from example 3 step A, in anhydrous THF (50 ml), was added borane (65.4 ml of a 1M solution in THF, 65.4 mmol) at room temperature. After 72 hours methanol (50 ml) was added and the solvent evaporated in vacuo. The residue was dissolved in methanol (100 ml) and the solvent evaporated in vacuo. The eesidue was partitioned between EtOAc and NaHCO$_3$, the organic layer separated and washed with brine, dried (MgSO$_4$) and evaporated in vacuo. The residue was purified by chromatography (Silica gel, eluting with 50% EtOAc in hexanes ) to afford the title compound.

Step C: 1-(N-t- Butoxycarbonyl-piperidin-4-ylmethyl)-5-(4-cyanobenzyl)imidazole

To 1-trityl-4-(4-Cyanobenzyl)-imidazole (1.99 g, 4.64 mmol) in CH$_2$Cl$_2$ (9.3 mL), Hunigs base (1.62 mL, 9.28 mmol) and the product from step B (1.0 g 4.64 mmol) at −78° C. was added trifluoromethanesulfonic anhydride (0.78 mL, 4.64 mmol). After 45minutes the reaction was allowed to warm to room temperature. The solvent was evaporated and the residue was dissolved in methanol (50 ml) and heated at reflux for 1 hour, cooled and evaporated to dryness. The residue was partitioned between sat. aq. NaHCO$_3$ solution and CH$_2$Cl$_2$. The organic layer was dried, (MgSO$_4$) and the solvent evaporated in vacuo. The residue was chromatographed (Silica gel, 3% MeOH in CH$_2$Cl$_2$) to afford the title compound.

$^1$H NMR CD$_3$OD δ7.69(2H, d, J=8.05 Hz), 7.61(1H,s), 7.41(2H,d, J=8.05 Hz), 6.75(1H,s), 4.10(2H,s), 4.03(2H,brd, J=13.4 Hz), 3.73(2H,d, J=7.3 Hz), 3.50–3.30(2H,m), 2.60 (2H,m), 1.80–1.55(2H,m), 1.43(9H,s) and 1.10–1.00(2H,m) ppm.

Step D: 1-(Piperidin-4-ylmethyl)-5-(4-cyanobenzyl) imidazole bis hydrochloride

Into a solution of the product from step C (0.843 g, 2.21 mmol) in EtOAc (200 mL) at 0° C. was bubbled HCl gas. After 10 minutes the solvent was evaporated in vacuo to afford the title compound as a foam.

Anal. Calcd for C$_{17}$H$_{20}$N$_4$.2.15 HCl.0.55 H$_2$O C, 55.38; H, 6.36; N, 15.2. Found: C, 55.39; H, 6.36; N, 14.82.

Example 117

1-(1-Phenylpiperidin-4-ylmethyl)-5-(4-cyanobenzyl) imidazole hydrochloride salt

The amine from Example 116, step D (0.16 g, 0.566 mmol) and triethylamine (0.158 mL 1.32 mmol) in CH$_2$Cl$_2$ (2.5 mL) at room temperature was added triphenyl bismuth (0.409 g, 8.49 mmol) and Copper (II) acetate (0.154 g, 0.849 mmol) and the reaction was stirred for 12 hours. The reaction was quenched by the addition of sat NH40H and CH$_2$Cl$_2$. The mixture was filtered and the filtrate extracted with CH$_2$Cl$_2$ dried, (MgSO$_4$) and the solvent evaporated in vacuo. The residue was chromatographed (Silica Gel, eluting with 3% MeOH in CH$_2$Cl$_2$). The product was converted to the hydrochloride salt.

$^1$H NMR CD$_3$OD δ9.11(1H,s), 7.78(2H,d, J=8.2 Hz), 7.71(2H,d, J=7.9 Hz), 7.70–7.50(5H,m), 7.28(1H,s), 4.33 (2H,s), 4.21(2H,d, J=7.5 Hz), 3.80–3.50(4H,m), 2.38(1H,m) and 2.05–1.85(4H,m) ppm.

Anal. Calcd for C$_{23}$H$_{24}$N$_4$.2.15 HCl.1.40 H$_2$O C, 60.05; H, 6.34; N, 12.18. Found: C, 60.07; H, 6.34; N, 12.35.

FAB HRMS exact mass calcd for C$_{23}$H$_{25}$N$_4$: 357.2073724(MH$^+$); found 3572079910.

Example 118

1-(1-(2-methylphenyl)piperidin-4-ylmethyl)-5-(4-cyanobenzyl)imidazole hydrochloride salt The amine from Example 116, step D (0.16 g, 0.566 mmol) and triethylamine (0.158 mL 1.32 mmol) in CH$_2$Cl$_2$ (2.5 mL) at room temperature was added tris-2-methylphenyl bismuth (0.440 g, 8.49 mmol) and Copper (II) acetate (0.154 g, 0.849 mmol) and the reaction was stirred for 12 hours. The reaction was quenched by the addition of sat NH$_4$OH and CH$_2$Cl$_2$. The mixture was filtered and the filtrate extracted with CH$_2$Cl$_2$ dried, (MgSO$_4$) and the solvent evaporated in vacuo. The residue was chromatographed (Silica Gel, eluting with 3% MeOH in CH$_2$Cl$_2$). The product was converted to the hydrochloride salt.

$^1$H NMR CD$_3$OD δ9.11(1H,s), 7.78(2H,d, J=7.8 Hz), 7.60(1H,m), 7.55(2H,d, J=7.9 Hz), 7.50–7.35(3H,m), 7.29 (1H,s), 4.33(2H,s), 4.21(2H,d, J=7.1 Hz), 3.80–3.40(4H,m), 2.57(3H,s), 2.31(1H,m) and 2.05–1.85(4H,m) ppm.

Anal. Calcd for C$_{24}$H$_{26}$N$_4$.2.45 HCl.1.55 H$_2$O C, 59.10; H, 6.52; N, 11.49. Found: C, 59.16; H, 6.51; N, 11.26.

Example 119

1-(1-(2-chlorobenzoyl)piperidin-4-ylmethyl)-5-(4-cyanobenzyl)imidazole hydrochloride salt The amine hydrochloride from Example 116, step D (0.061 g, 0.194 mmol) and triethylamine (0.108 mL 0.775 mmol) in CH$_2$Cl$_2$(2.0 mL) at 0° C. was added 2 chlorobenzoyl chloride (0.025 mL, 0.203 mmol) and the reaction was allowed to warm to room temperature and stirred for 12 hours. The reaction was quenched by the addition of sat Na2CO3 and extracted into EtOAcThe organic extracts were washed with brine, dried, (MgSO$_4$) and the solvent evaporated in vacuo. The residue was chromatographed (Silica gel, eluting with 3% MeOH in CH$_2$Cl$_2$). The product was converted to the hydrochloride salt.

FAB MS 419(MH$^+$)

Anal. Calcd for C$_{24}$H$_{22}$N$_4$OCl.1.35 HCl.0.35 CH$_3$CN C, 61.58; H, 5.13; N, 12.84. Found: C, 61.48; H, 5.47; N, 12.84.

Example 120

1-(1-(3-chlorobenzoyl)piperidin-4-ylmethyl)-5-(4-cyanobenzyl)imidazole hydrochloride salt The amine hydrochloride from Example 116, step D (0.059 g, 0.189 mmol) and triethylamine (0.105 mL 0.775 mmol) in CH$_2$Cl$_2$(2.0 mL) at 0° C. was added 3-chlorobenzoyl chloride (0.025 mL, 0.198 mmol) and the reaction was allowed to warm to room temperature and stirred for 12 hours. The reaction was quenched by the addition of sat Na$_2$CO$_3$ and extracted into EtOAcThe organic extracts were washed with brine, dried, (MgSO$_4$) and the solvent evaporated in vacuo. The residue was chromatographed (Silica gel, eluting with 3% MeOH in CH$_2$Cl$_2$). The product was converted to the hydrochloride salt. FAB MS 419(MH$^+$)

Anal. Calcd for C$_{24}$H$_{22}$N$_4$OCl.1.35 HCl.0.25 CH$_3$CN C, 61.63; H, 5.09; N, 12.47. Found: C, 61.68; H, 5.42; N, 12.44.

Example 121

1-(1-(3-chlorobenzenesulfonyl)piperidin-4-ylmethyl)-5-(4-cyanobenzyl)imidazole hydrochloride salt The amine hydrochloride from Example 116, step D (0.066 g, 0.187 mmol) and triethylamine (0.84 mL 0.60 mmol) in CH$_2$Cl$_2$(2.0 mL) at 0° C. was added 3-chlorobenzenesulfonyl chloride (0.043 g, 0.21 mmol) and the reaction was allowed to warm to room temperature and stirred for 1 hour. The reaction was quenched by the addition of sat Na$_2$CO$_3$ and extracted into EtOAcThe organic extracts were washed with brine, dried, (MgSO$_4$) and the solvent evaporated in vacuo. The residue was chromatographed (Silica gel, eluting with 3% MeOH in CH$_2$Cl$_2$). The product was converted to the hydrochloride salt.

Anal. Calcd for C$_{23}$H$_{23}$N$_4$O$_2$ClS.1.00 HCl.0.35 H$_2$O C, 55.50; H, 5.00; N, 11.26. Found: C, 55.51; H, 4.99; N, 11.31.

$^1$H NMR CD$_3$OD δ8.91(1H,s), 7.75–7.55(6H,m), 7.44 (2H,d, J=8.6 Hz), 7.27(1H,s), 4.21(2H,s), 4.02(2H,d, J=7.1 Hz), 3.79(2H,d, J=11.9 Hz), 2.16(2H,dd, J=12.1 and 10.2 Hz), 1.70–1.50(3H,m), and 1.40–1.20(2H,m) ppm.

Example 122

1-(1-(3-chlorobenzyl)piperidin-4-ylmethyl)-5-(4-cyanobenzyl)imidazole hydrochloride salt To the amine hydrochloride from Example 116, step D (0.092 g, 0.261 mmol) and 3A molecular sieves (0.30 g) in MeOH (5.0 mL) at room temperature was added 3-chlorobenzaldehyde (0.043 g, 0.21 mmol) and the reaction was stirred for 30 minutes. sodium cyanoborohydride (24.5 mg was added in one portion and the reaction stirred for a further 16 hours, The reaction was filtered and the filtrate evaporated in vacuo. The residue was partitio between CH$_2$Cl$_2$ and sat Na$_2$CO$_3$ and extracted into CH$_2$Cl$_2$. The organic extracts were dried, (MgSO$_4$) and the solvent evaporated in vacuo. The residue was chromatographed (Silica gel, gradient elution with 2–5% MeOH in CH$_2$Cl$_2$). The product was converted to the hydrochloride salt.

Anal. Calcd for C$_{23}$H$_{23}$N$_4$O$_2$ClS.2.50 HCl.0.65 H$_2$O C, 56.77; H, 5.72; N, 11.03. Found: C, 56.74; H, 5.71; N, 10.81.

$^1$H NMR CD$_3$OD δ9.04(1H,s), 7.75(2H,d, J=7.9 Hz), 7.65(1H,s), 7.60–7.40(5H), 7.26(1H,s), 4.33(2H,s), 4.27 (2H,s), 4.11(2H,d, J=7.1 Hz 3.50(2H,d, J=8.1 Hz), 3.00(2H, t, 11.9 Hz), 2.17(1H,m), 1.90–1.80(2H,m), 1.80–1.60(2H,m) ppm.

Example 123

2-[3-(4-cyanobenzyl)-3H-imidazol-1-yl]-N-(1-phenylpiperidin-4-yl)acetamide hydrochloride Step A: 8-Phenyl-1 4-dioxa-8-azaspiro[4.5]decane Palladium (II) chloride (1.40 g, 7.9 mmol) and tri-o-tolylphosphine (4.80 g, 15.8 mmol) were stirred in dry toluene (60 mL) at room temperature under an argon atmosphere for 30 min. The solution was then diluted with dry toluene (800 mL) and to this was added 1,4-dioxa-8-azaspiro[4.5]decane (27.4 g, 191 mmol); sodium tert-butoxide (21.4 g, 223 mmol); and bromobenzene (25.0 g, 159 mmol). The mixture was heated to 100° C. for 18 hrs then allowed to cool. Ether (300 mL) was added and the mixture was washed with brine (800 mL). The brine was extracted with a further portion of ether (200 mL) and the combined organic extracts were dried over MgSO$_4$, filtered, and concentrated in vacuo to give a dark oil. The crude product was purified by flash column chromatography on silica, eluting with hexane—10% ethyl acetate to yield the product as a pale yellow oil.

$^1$H NMR (CDCl$_3$) δ7.25(2H, dd, J=8,7 Hz); 6.95(2H, d, J=8 Hz); 6.83 (1H, t, J=7 Hz); 3.99(4H, s); 3.32(4H, m); 1.84(4H, m).

Step B: 1-Phenylpiperidin-4-one

8-Phenyl-1,4-dioxa-8-azaspiro[4.5]decane (18.1 g, 82.5 mmol) was dissolved in a mixture of acetic acid (150 mL), water (150 mL), and conc. hydrochloric acid (38 mL) and the resulting solution was heated to 50° C. for 18 hrs. The reaction mixture was cooled in an ice-water bath, and sodium hydroxide pellets were added in portions until the mixture was neutralized. This mixture was extracted with dichloromethane (3×300 mL) and the combined organic extracts were dried over MgSO$_4$, filtered, and concentrated in vacuo to give a dark oil. Chromatography on silica gel, eluting with hexane—10% ethyl acetate gave the product as a pale yellow oil.

$^1$H NMR (CDCl$_3$) δ7.30(2H, dd, J=9,7 Hz); 6.99(2H, dd, J=9,1 Hz); 6.89(1H, tt, J=7,1 Hz); 3.61(4H, t, J=6 Hz); 2.56(4H, t, J=6 Hz).

Step C: 1-Phenylpiperidin-4-ylamine

1-Phenylpiperidin-4-one (3.0 g, 17.1 mmol) was dissolved in methanol (250 mL) and acetic acid (147 mL), and ammonium acetate (67 g, 870 mmol) was added portionwise. The mixture was stirred for 4 hrs at room temperature, then cooled to 0° C. (ice-water) and sodium cyanoborohydride (1.6 g, 25 mmol) was added, then the reaction mixture was stirred at room temperature for 18 hrs. Water (20 mL) was added, and the mixture was concentrated under reduced pressure. The residue was adjusted to pH 12 with 15% aqueous NaOH and the resulting mixture was extracted with dichloromethane (3×100 mL). The combined organic extracts were dried over MgSO$_4$, filtered, and concentrated in vacuo. The residue was chromatographed on silica gel, eluting with dichloromethane—3% methanol—0.3% NH$_4$OH to give the product as a pale solid.

$^1$H NMR (CDCl$_3$) δ7.26(2H, m); 6.96(2H, m); 6.83(1H, m); 3.65(2H, m); 2.87–2.75(3H, m); 1.92(2H, m); 1.50(2H, m); 1.32(2H, br s).

FAB MS: 177(MH$^+$).

Step D: 2-[3-(4-Cyanobenzyl)-3H-imidazol-1-yl]-N-(1-phenylpiperidin-4-yl)acetamide hydrochloride 1-Phenylpiperidin-4-ylamine (40 mg, 0.227 mmol), lithium [3-(4-cyanobenzyl)-3H-imidazol-4-yl]acetate (56 mg, 0.227 mmol), 1-hydroxybenzotriazole hydrate (46 mg, 0.34 mmol), 1-(3-dimethylaminopropyl)-3-ethylcarbodiimide hydrochloride (87 mg, 0.45 mmol), and N,N-diisopropylethylamine (99 μL, 0.57 mmol) were added to degassed DMF (2 mL) and the mixture was stirred for 18 hrs at room temperature then concentrated in vacuo. The residue was added to sat. NaHCO$_3$(aq) (5 mL) and extracted with dichloromethane (3×3 mL). The combined organic extracts were dried over MgSO$_4$, filtered, and concentrated under reduced pressure. The residue was chromatographed on silica gel, eluting with dichloromethane—5% methanol—0.05% NH$_4$OH to give the product as a free base. This was lyophilized from HCl (aq)—acetonitrile to give the title compound as a white solid.

Elemental analysis calculated for C$_{24}$H$_{25}$N$_5$O.1.2 HCl.0.5 H$_2$O.0.15 CH$_2$C$_{12}$:

C: 62.37; H: 5.96; N: 15.06

Found: C: 62.64; H: 6.35; N: 14.67

$^1$H NMR (CD$_3$OD) δ8.79(1H, d, J=1 Hz); 7.79(2H, d, J=8 Hz); 7.47–7.40(3H, m); 7.23(2H, dd, J=7,9 Hz); 7.00(2H, d, J=8 Hz); 6.86(1H, t, J=7 Hz); 5.55(2H, s); 3.70–3.57(3H, m); 3.60(2H, s); 2.83(2H, td, J=12,2 Hz); 1.92(2H, dd, J=14,4 Hz); 1.59(2H, qd, J=12,4 Hz).

FAB MS: 400(MH$^+$).

Example 124

2-[3-(4-cyanobenzyl)-3H-imidazol-1-yl]-N-benzyl-N-(1-phenylpiperidin-4-yl)acetamide hydrochloride Step A: Benzyl(1-phenylpiperidin-4-yl)amine 1-Phenylpiperidin-4-one (2.0 g, 11.4 mmol) (from Example 123) and benzylamine (1.33 g, 12.5 mmol) were dissolved in 1,2-dichloroethane (35 mL) and acetic acid (1.36 g, 22.6 mmol) was added. The mixture was stirred for 2 hrs at room temperature, then cooled to 0° C. (ice-water) and sodium triacetoxyborohydride (3.14 g, 14.8 mmol) was added, then the reaction mixture was stirred at room temperature for 18 hrs. Sat. NaHCO$_3$(aq) (30 mL) was added, and the organic layer was extracted. The aqueous phase was extracted with dichloromethane (2×50 mL). The combined organic extracts were dried over MgSO$_4$, filtered, and concentrated in vacuo. The residue was chromatographed on silica gel, eluting with hexane—30% ethyl acetate to give the product as a white solid.

$^1$H NMR (CDCl$_3$) δ7.35–7.21(7H, m); 6.94(2H, dd, J=9,1 Hz); 6.82 (1H, tt, J=7,1 Hz); 3.86(2H, s); 3.66(2H, dt, J=13,3 Hz); 2.78(2H, td, J=12,2 Hz); 2.68(1H, tt, J=10,4 Hz); 2.01(2H, m); 1.55(2H, qd, J=12,4 Hz); 1.35(1H, br s).

Step B: 2-[3-(4-cyanobenzyl)-3H-imidazol-1-yl]-N-benzyl-N-(1-phenylpiperidin-4-yl)acetamide hydrochloride Benzyl(1-phenylpiperidin-4-yl)amine (50 mg, 0.188 mmol), lithium [3-(4-cyanobenzyl)-3H-imidazol-4-yl] acetate (51 mg, 0.206 mmol), 1-hydroxybenzotriazole hydrate (38 mg, 0.28 mmol), 1-(3-dimethylaminopropyl)-3-ethylcarbodiiunide hydrochloride (72 mg, 0.38 mmol), and N,N-diisopropylethylamine (82 μL, 0.47 mmol) were added to degassed DMF (2 mL) and the mixture was stirred for 18 hrs at room temperature then concentrated in vacuo. The residue was added to sat. NaHCO$_3$(aq) (5 mL) and extracted with dichloromethane (3×3 mL). The combined organic extracts were dried over MgSO$_4$, filtered, and concentrated under reduced pressure. The residue was chromatographed on silica gel, eluting with dichloromethane—4% methanol—0.01% NH$_4$OH to give the product as a free base. This was lyophilized from HCl (aq)—acetonitrile to give the title compound as a white solid.

Elemental analysis calculated for C$_3$H$_{31}$N$_5$O.1.2 HCl.0.35 H$_2$O.0.15 CH$_2$Cl$_2$:

C: 67.72; H: 6.06; N: 12.68

Found: C: 67.87; H: 6.39; N: 12.28

$^1$H NMR (CD$_3$OD) δ8.88–8.86(1H, m); 7.81–7.69(2H, m); 7.55–7.19 (10H, m); 7.00–6.97(2H, m); 6.86(1H, t, J=7 Hz); 5.51–5.46(2H, m); 4.63–4.59(2H, m); 4.52–3.67(5H, m); 2.86–2.76(2H, m); 1.95–1.73 (4H, m).

FAB MS: 490(MH$^+$).

Example 125

2-[3-(4-Cyanobenzyl)-3H-imidazol-1-yl]-N-(1-phenylpiperidin-4-yl)-N-pyridin-4-ylmethylacetamide hydrochloride The title compound was prepared according to the procedure in Example 124, Steps A & B, with 4-(aminomethyl) pyridine replacing benzylamine in Step A. The product was treated with HCl in ethyl acetate—ethanol to give the hydrochloride salt. Elemental analysis calculated for C$_{30}$H$_{30}$N$_6$O.3 HCl.0.5 EtOH.0.5 CH$_2$Cl$_2$:

C: 56.85; H: 5.60; N: 12.63

Found: C: 57.00; H: 5.92; N: 12.80

FAB MS: 491(MH$^+$).

Example 126

2-[3-(4-cyanobenzyl)-3H-imidazol-1-yl]-N-phenethyl-N-(1-phenylpiperidin-4-yl)acetamide hydrochloride The title compound was prepared according to the procedure in Example 124, Steps A & B, with phenethylamine replacing benzylamine in Step A. The product was treated with HCl in ethyl acetate to give the hydrochloride salt.

Elemental analysis calculated for C$_{32}$H$_{33}$N$_5$O.2 HCl.0.2 H$_2$O:

C: 66.24; H: 6.15; N: 12.07

Found: C: 66.24; H: 5.91; N: 11.84

FAB MS: 504(MH$^+$).

Example 127

4-{5-[(1-Phenylpiperidin-4-ylamino)methyl] imidazol-1-ylmethyl}benzonitrile hydrochloride Step A: 4-{5-[(1-Phenylpiperidin-4-ylamino)methyl] imidazol-1-ylmethyl}benzonitrile hydrochloride 1-Phenylpiperidin-4-ylamine (75 mg, 0.43 mmol) (from Example 123) and 4-(5-formylimidazol-1-ylmethyl) benzonitrile (99 mg, 0.47 mmol) were dissolved in 1,2-dichloroethane (2 mL) and acetic acid (49 μL, 0.86 mmol) was added. The mixture was stirred for 2 hrs at room temperature, then sodium triacetoxyborohydride (117 mg, 0.55 mmol) was added, then the reaction mixture was stirred at room temperature for 18 hrs. Sat. NaHCO$_3$(aq) (30 mL) was added, and the organic layer was extracted. The aqueous phase was extracted with dichloromethane (2×5 mL). The combined organic extracts were dried over MgSO$_4$, filtered, and concentrated in vacuo. The residue was chromatographed on silica gel, eluting with dichloromethane—5% methanol—0.5% NH$_4$OH to give the product as a free base. This was lyophilized from HCl (aq)—acetonitrile to give the title compound as a white solid.

Elemental analysis calculated for C$_{23}$H$_{25}$N$_5$.2 HCl:

C: 62.41; H: 6.14; N: 15.82

Found: C: 62.43; H: 6.02; N: 15.63

$^1$H NMR (CD$_3$OD) δ8.62(1H, s); 7.82(2H, d, J=8 Hz); 7.69(1H, s); 7.46(2H, d, J=8 Hz); 7.27(2H, t, J=8 Hz); 7.06(2H, d, J=8Hz); 6.92 (1H, t, J=8 Hz); 5.67(2H, s);

4.32(2H, s); 3.82(2H, d, J=13 Hz); 3.40(1H, tt, J=12,4 Hz); 2.88(2H, t, J=12 Hz); 2.23(2H, d, J=12 Hz); 1.84(2H, qd, J=12,4 Hz).

FAB MS: 372(MH$^+$).

Example 128

4-(5-{[Benzyl(1-phenylpiperidin-4-yl)amino]methyl}imidazol-1-ylmethyl)benzonitrile hydrochloride

The title compound was prepared according to the procedure in Example 127, Step A, with benzyl(1-phenylpiperidin-4-yl)amine (from Example 124) replacing 1-phenylpiperidin-4-ylamine. The product was lyophilized from HCl (aq)—acetonitrile to give the title compound as a white solid.

Elemental analysis calculated for $C_{30}H_{31}N_5 \cdot HCl \cdot 0.4$ EtOAc:

C: 71.16; H: 6.65; N: 13.13
Found: C: 71.25; H: 6.47; N: 12.84
FAB MS: 462(MH$^+$).

Example 129

4-(5-{[(1-phenylpiperidin-4-yl)pyridin-4-ylmethylamino]methyl}imidazol-1-ylmethyl) benzonitrile hydrochloride

The title compound was prepared according to the procedure in Example 127, Step A, with (1-phenylpiperidin-4-yl)pyridin-4-ylmethylamine (from Example 125) replacing 1-phenylpiperidin-4-ylamine. The product was treated with HCl in ethyl acetate—ethanol to give the title compound as a white solid.

Elemental analysis calculated for $C_{29}H_{30}N_6 \cdot 4 \text{ HCl} \cdot 0.65$ EtOAc $\cdot 0.6 \text{ H}_2\text{O}$:

C: 56.10; H: 6.02; N: 12.42
Found: C: 56.11; H: 6.02; N: 12.40
FAB MS: 463(MH$^+$).

Example 130

4-(5-{[Phenethyl(1-phenylpiperidin-4-yl)amino]methyl}imidazol-1-ylmethyl)benzonitrile hydrochloride

The title compound was prepared according to the procedure in Example 127, Step A, with phenethyl(1-phenylpiperidin-4-yl)amine (from Example 126) replacing 1-phenylpiperidin-4-ylamine. The product was treated with HCl in ethyl acetate to give the title compound as a white solid.

Elemental analysis calculated for $C_{31}H_{33}N_5 \cdot 3 \text{ HCl} \cdot 0.65 \text{ H}_2\text{O} \cdot 0.3$ EtOAc:

C: 61.42; H: 6.82; N: 11.60
Found: C: 61.42; H: 6.68; N: 11.53
FAB MS: 476(MH$^+$).

Example 131

4-{5-[2-(1-Phenylpiperidin-4-ylamino)ethyl]imidazol-1-ylmethyl}benzonitrile hydrochloride

Step A: 4-{5-[2-(1-Phenylpiperidin-4-ylamino)ethyl]imidazol-1-ylmethyl}benzonitrile hydrochloride 1-Phenylpiperidin-4-one (150 mg, 0.86 mmol) (from Example 123) and 4-[5-(2-aminoethyl)imidazol-1-ylmethyl] benzonitrile (213 mg, 0.94 mmol) were dissolved in 1,2-dichloroethane (4 mL) and acetic acid (49 µL, 0.86 mmol) was added. The mixture was stirred for 30 min at room temperature, then sodium triacetoxyborohydride (272 mg, 1.28 mmol) was added and the reaction mixture was stirred at room temperature for 18 hrs. Sat. Na$_2$CO$_3$(aq) (5 mL) was added, and the mixture was extracted with dichloromethane (3×10 mL). The combined organic extracts were dried over Na$_2$SO$_4$, filtered, and concentrated in vacuo. The residue was purified by flash column chromatography on silica gel, eluting with a gradient of dichloromethane—0.5% NH$_4$OH—1 to 8% methanol to yield the product.

$^1$H NMR (CDCl$_3$) δ7.63(2H, d, J=8 Hz); 7.51(1H, s); 7.24(2H, dd, J=9,7 Hz); 7.12(2H, d, J=8 Hz); 6.93(1H, s); 6.92(2H, d, J=9 Hz); 6.82 (1H, t, J=7 Hz); 5.20(2H, s); 3.63(2H, dt, J=13,3 Hz); 2.86(2H, t, J=7 Hz); 2.74(2H, td, J=12,2 Hz); 2.61(2H, t, J=7 Hz); 2.60–2.54(1H, m); 2.10 (1H, br s); 1.92(2H, d, J=13 Hz); 1.46(2H, qd, J=12,4 Hz).

Treatment with HCl in ethyl acetate gave the title compound as a white solid.

Elemental analysis calculated for $C_{24}H_{27}N_5 \cdot 3 \text{ HCl} \cdot 0.5$ EtOAc:

C: 57.94; H: 6.36; N: 13.00
Found: C: 57.80; H: 6.42; N: 13.00
FAB MS: 386(MH$^+$).

Example 132

4-(5-{2-[Benzyl(1-phenylpiperidin-4-yl)amino]ethyl}imidazol-1-ylmethyl)benzonitrile hydrochloride

Step A: 4-(5-{2-[Benzyl(1-phenylpiperidin-4-yl)amino]ethyl}imidazol-1-ylmethyl)benzonitrile hydrochloride Benzaldehyde (15 µL, 0.14 mmol) and 4-{5-[2-(1-phenylpiperidin-4-ylamino)ethyl]imidazol-1-ylmethyl}benzonitrile (50 mg, 0.13 mmol) (from Example 131) were dissolved in 1,2-dichloroethane (0.8 mL) and acetic acid (7 µL, 0.13 mmol) was added. The mixture was stirred for 30 min at room temperature, then sodium triacetoxyborohydride (41 mg, 0.20 mmol) was added and the reaction mixture was stirred at room temperature for 18 hrs. Sat. Na$_2$CO$_3$(aq) (3 mL) was added, and the mixture was extracted with dichloromethane (3×5 mL). The combined organic extracts were dried over Na$_2$SO$_4$, filtered, and concentrated in vacuo. The residue was purified by chromatography on silica gel, eluting with a gradient of ethyl acetate—0 to 10% methanol to yield the product.

$^1$H NMR (CDCl$_3$) δ7.55(2H, d, J=8 Hz); 7.40(1H, d, J=1 Hz); 7.29–7.21 (7H, m); 6.94–6.90(4H, m); 6.86(1H, s); 6.83(1H, tt, J=7,1 Hz); 4.86 (2H, s); 3.72(2H, d, J=12 Hz); 3.62(2H, s); 2.71–2.60(5H, m); 2.39 (2H, t, J=8 Hz); 1.83 (2H, d, J=12 Hz); 1.68(2H, qd, J=12,4 Hz).

Treatment with HCl in ethyl acetate gave the title compound as a white solid.

Elemental analysis calculated for $C_{31}H_{33}N_5 \cdot 3 \text{ HCl} \cdot 0.3 \text{ H}_2\text{O} \cdot 0.15$ EtOAc:

C: 62.87; H: 6.31; N: 11.60
Found: C: 62.87; H: 6.14; N: 11.60
FAB MS: 476(MH$^+$).

Example 133

2-[3-(4-cyanobenzyl)-3H-imidazol-1-yl]-N-(4-cyanobenzyl)-N-(1-phenylpiperidin-4-yl)acetamide hydrochloride

Step A: 4-Cyanobenzyl(1-phenylpiperidin-4-yl)amine

1-Phenylpiperidin-4-ylamine (0.50 g, 2.84 mmol) (from Example 123) and 4-cyanobenzaldehyde (0.74 g, 5.64 mmol) were dissolved in anhydrous methanol (10 mL) and acetic acid (0.97 mL, 17 mmol) was added. The mixture was stirred for 2 hrs at room temperature, then cooled to 0° C. (ice-water) and sodium cyanoborohydride (0.267 g, 4.25 mmol) was added, then the reaction mixture was stirred at room temperature for 2 hrs. The solvent was evaporated under reduced pressure and the residue was partitioned between sat. NaHCO$_3$(aq) (50 mL) and dichloromethane (25 mL), and the organic layer was extracted. The aqueous phase was extracted with dichloromethane (2×25 mL). The combined organic extracts were dried over MgSO$_4$, filtered, and concentrated in vacuo. The residue was chromatographed on silica gel, eluting with hexane—30% ethyl acetate to give the product as a white solid.

$^1$H NMR (CDCl$_3$) δ7.62(2H, d); 7.48(2H, d); 7.25(2H, t); 6.94(2H, d); 6.83(1H, t); 3.93(2H, s); 3.65(2H, dt); 2.78(2H, td); 2.65(1H, tt); 1.99(2H, d); 1.54(2H, qd); 1.41(1H, br s).

Step B: 2-[3-(4-cyanobenzyl)-3H-imidazol-1-yl]-N-(4-cyanobenzyl)-N-(1-phenylpiperidin-4-yl) acetamide hydrochloride 4-Cyanobenzyl(1-phenylpiperidin-4-yl)amine (75 mg, 0.26 mmol), lithium [3-(4-cyanobenzyl)-3H-imidazol-4-yl]acetate (70 mg, 0.28 mmol), 1-hydroxybenzotriazole hydrate (52 mg, 0.38 mmol), 1-(3-dimethylaminopropyl)-3-ethylcarbodiimide hydrochloride (99 mg, 0.52 mmol), and N,N-diisopropylethylamine (67 µL, 0.38 mmol) were added to degassed DMF (3 mL) and the mixture was stirred for 18 hrs at room temperature then concentrated in vacuo. The residue was added to sat. NaHCO$_3$(aq) (5 mL) and extracted with dichloromethane (3×3 mL). The combined organic extracts were dried over MgSO$_4$, filtered, and concentrated under reduced pressure. The residue was chromatographed on silica gel, eluting with dichloromethane—2% methanol to give the product as a free base. This was lyophilized from HCl (aq)—acetonitrile to give the title compound as a white solid.

Elemental analysis calculated for C$_{32}$H$_{30}$N$_6$O.2.5 HCl.1.85 H$_2$O:
 C: 60.04; H: 5.86; N: 13.13
 Found: C: 60.08; H: 5.66; N: 13.09
$^1$H NMR (CD$_3$OD) δ8.99–8.92(1H, m); 7.81–7.40(14H, m); 5.59–5.53 (2H, m); 4.86–4.66(3H, m); 4.40–3.69(6H, m); 2.55–2.42(2H, m); 2.15–2.02(2H, m).
 FAB MS: 515(MH$^+$).

Example 134

N-(1-benzylpiperidin-4-yl)-2-[3-(4-cyanobenzyl)-3H-imidazol-4-yl]acetamide hydrochloride The title compound was prepared according to the procedure in Example 123, Steps C & D, with 1-benzylpiperidin-4-one replacing 1-phenylpiperidin-4-one in Step C. The product was treated with HCl in ethyl acetate—ethanol to give the hydrochloride salt.

Elemental analysis calculated for C$_{25}$H$_{27}$N$_5$O.2 HCl.1 MeOH:
 C: 60.22; H: 6.42; N: 13.51
 Found: C: 60.07; H: 6.53; N: 13.27
 FAB MS: 414(MH$^+$).

Example 135

4-{5-[(1-benzylpiperidin-4-ylamino)methyl]imidazol-1-ylmethyl}benzonitrile hydrochloride To a stirred solution of 1-benzylpiperidin-4-ylamine (38 mg, 0.20 mmol) (from Example 134) and 4-(5-formylimidazol-1-ylmethyl)benzonitrile (42 mg, 0.20 mmol) in methanol (1 mL) was added sodium cyanoborohydride (12 mg, 0.20 mmol). Acetic acid was added to adjust the mixture to pH 5.5, as judged by analyzing the solution with moist indicator paper. The resulting solution was stirred for 18 hrs, then sat. Na$_2$CO$_3$(aq) (5 mL) was added and the mixture was extracted with ethyl acetate (3×10 mL). The combined organic extracts were washed with water (10 mL), then brine (10 mL), then dried over Na$_2$SO$_4$, filtered and concentrated in vacuo. The residue was chromatographed on silica, eluting with ammonia-saturated chloroform to give the product as a free base.

$^1$H NMR (CDCl$_3$) δ7.61(2H, d); 7.49(1H, s); 7.48(2H, d); 7.33–7.22 (5H, m); 7.15(2H, d); 6.95(1H, s); 5.37(2H, s); 3.59(2H, s); 3.47(2H, s); 2.78(2H, d); 2.39(1H, tt); 1.98(2H, td); 1.73(2H, d); 1.32(2H, m); 1.41(1H, br s).

Treatment of this with HCl in ethyl acetate—ethanol gave the hydrochloride salt.

Elemental analysis calculated for C$_{24}$H$_{27}$N$_5$.3 HCl.1 EtOH.0.4 CH$_2$Cl$_2$:
 C: 55.15; H: 6.45; N: 12.18
 Found: C: 55.29; H: 6.59; N: 12.02
 FAB MS: 386(MH$^+$).

Example 136

In vitro inhibition of ras farnesyl transferase

Assays of farnesyl-protein transferase. Partially purified bovine FPTase and Ras peptides (Ras-CVLS, Ras-CVIM and Ras-CAIL) were prepared as described by Schaber et al. *J. Biol. Chem.* 265:14701–14704(1990), Pompliano, et al., *Biochemistry* 31:3800(1992) and Gibbs et al., *PNAS* U.S.A. 86:6630–6634(1989), respectively. Bovine FPTase was assayed in a volume of 100 µl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 MM [$^3$H]-farnesyl diphosphate ([$^3$H]-FPP; 740 CBq/mmol, New England Nuclear), 650 nM Ras-CVLS and 10 µg/ml FPTase at 31° C. for 60 min. Reactions were initiated with FPTase and stopped with 1 ml of 1.0 M HCL in ethanol. Precipitates were collected onto filter-mats using a TomTec Mach II cell harvester, washed with 100% ethanol, dried and counted in an LKB r-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176(1993). Human FPTase activity was assayed as described above with the exception that 0.1% (w/v) polyethylene glycol 20,000, 10 µM ZnCl$_2$ and 100 nm Ras-CVIM were added to the reaction mixture. Reactions were performed for 30 min., stopped with 100 µl of 30% (v/v) trichloroacetic acid (TCA) in ethanol and processed as described above for the bovine enzyme.

The compounds of the instant invention described in above Examples 1–135, except for Example 112C, were tested for inhibitory activity against human FPTase by the assay described above and were found to have IC$_{50}$ of ≦50 µM.

Example 31

In vivo ras farnesylation assay

The cell line used in this assay is a v-ras line derived from either Rati or NIH$_3$T3 cells, which expressed viral Ha-ras p21. The assay is performed essentially as described in DeClue, J. E. et al., *Cancer Research* 51:712–717,(1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259(Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/ SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 32

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound.

Photomicrographs are taken 16 days after the cultures are seeded and comparisons are made.

What is claimed is:

1. A compound which inhibits farnesyl-protein transferase of the formula B:

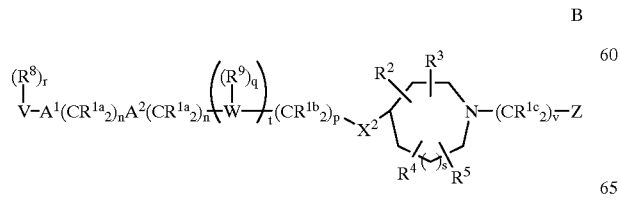

B wherein:

$R^{1a}$ and $R^{1b}$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, NO$_2$, $(R^{10})_2N$—C(NR$^{10}$)—, $R^{10}C(O)$—, N$_3$, —N($R^{10}$)$_2$, or $R^{11}$ OC(O)NR$^{10}$—, c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, N$_3$, —N($R^{10}$)$_2$, and $R^{11}OC(O)$—NR$^{10}$—;

$R^{1c}$ is selected from:

a) hydrogen, b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, N$_3$, —N($R^{10}$)$_2$, and $R^{11}OC(O)$—NR$^{10}$—, and c) unsubstituted or substituted aryl;

$R^2$ and $R^3$ are independently selected from: H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or

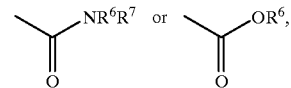

substited heterocycle, OR$^{10}$, wherein the substituted group is substituted with one or more of:
1) aryl or heterocycle, unsubstituted or substituted with:
   a) $C_{1-4}$ alkyl,
   b) (CH$_2$)$_p$OR$^6$,
   c) (CH$_2$)$_p$NR$^6$R$^7$,
   d) halogen,
   e) CN,
   f) aryl or heteroaryl,
   g) perfluoro-$C_{1-4}$ alkyl,
   h) SR$^{6a}$, S(O)R$^{6a}$, SO$_2$R$^{6a}$,
2) $C_{3-6}$ cycloalkyl,
3) OR$^6$,
4) SR$^{6a}$, S(O)R$^{6a}$, or SO$_2$R$^{6a}$,
5) —NR$^6$R$^7$,
6)

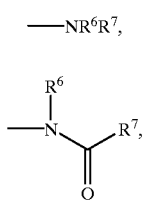

-continued

7) 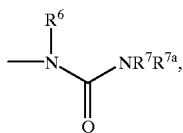

8) 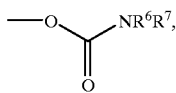

9) 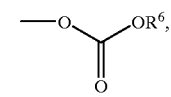

10) 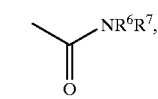

11) —SO$_2$—NR$^6$R$^7$,

12) 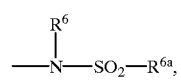

13) 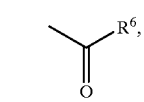

14) 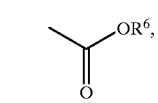

15) N$_3$,

16) F, or 17) perfluoro-C$_{1-4}$-alkyl; or

R$^2$ and R$^3$ are attached to the same C atom and are combined to form —(CH$_2$)$_u$— wherein one of the carbon atoms is optionally replaced by a moiety selected from: O, S(O)$_m$, —NC(O)—, and —N(COR$^{10}$)—;

R$^4$ and R$^5$ are independently selected from H and CH$_3$;

and any two of R$^2$, R$^3$, R$^4$ and R$^5$ are optionally attached to the same carbon atom;

R$^6$, R$^7$ and R$^{7a}$ are independently selected from: H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:

a) C$_{1-4}$ alkoxy,
b) unsubstituted aryl, substituted aryl, unsubstituted heteroaryl or substituted heteroaryl,
c) halogen,
d) HO, e) 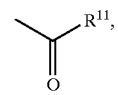

f) —SO$_2$R$^{11}$, or
g) N(R$^{10}$)$_2$; or

R$^6$ and R$^7$ may be joined in a ring;
R$^7$ and R$^{7a}$ may be joined in a ring;
R$^{6a}$ is selected from: C$_{1-4}$ alkyl, C$_{3-6}$ cycloalkyl, heterocycle, aryl, unsubstituted or substituted with:

a) C$_{1-4}$ alkoxy,
b) aryl or heterocycle,
c) halogen,
d) HO,
e)

f) —SO$_2$R$^{11}$, or
g) N(R$^{10}$)$_2$;

R$^8$ is independently selected from:
a) hydrogen,
b) aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by aryl, cyanophenyl, heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{10}$OC(O)NH—;

R$^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, or R$^{11}$OC(O)NR$^{10}$—;

R$^{10}$ is independently selected from hydrogen, C$_1$–C$_{14}$ alkyl, substituted or unsubstituted benzyl and substituted or unsubstituted aryl;

R$^{11}$ is independently selected from C$_1$–C$_6$ alkyl and substituted or unsubstituted aryl;

A$^1$ and A$^2$ are independently selected from: a bond, —CH═CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) C$_1$–C$_{20}$ alkyl wherein from 0 to 4 carbon atoms are replaced with a heteroatom selected from O, S, and N, and
e) C$_2$–C$_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

$X^2$ is a bond, —CH$_2$—, —C(=O)—, —NR$^6$C(=O)—, —C(=O)NR$^6$—, —NR$^6$—, —O— or —S(=O)$_m$—;

Z is an unsubstituted or substituted group selected from aryl and heterocycle, wherein the substituted group is substituted with one or more of the following:
1) $C_{1-4}$ alkyl, unsubstituted or substituted with:
   a) $C_{1-4}$ alkoxy,
   b) NR$^6$R$^7$,
   c) $C_{3-6}$ cycloalkyl,
   d) aryl, substituted aryl or heterocycle,
   e) HO,
   f) —S(O)$_m$R$^{6a}$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$;
9) —S(O)$_m$R$^{6a}$,
10) —C(O)NR$^6$R$^7$, or
11) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5, provided that r is 0 when V is hydrogen;
s is 0 or 1;
t is 0 or 1;
u is 4 or 5; and
v is 0, 1 or 2;

or a pharmaceutically acceptable salt thereof.

2. The compound according to claim 1 of the formula B:

$$(R^8)_r\text{—}V\text{—}A^1(CR^{1a}_2)_nA^2(CR^{1a}_2)_n\text{—}W\text{—}((R^9)_q)\text{—}((CR^{1b}_2)_p)\text{—}X^2\text{—}\begin{pmatrix}R^2 & R^3 \\ R^4 & R^5\end{pmatrix}_s\text{N—}(CR^{1c}_2)_v\text{—}Z$$

B wherein:

$R^{1a}$ is independently selected from: hydrogen or $C_1$–$C_6$ alkyl;

$R^{1b}$ is independently selected from:
a) hydrogen,
b) aryl, heterocycle, cycloalkyl, R$^{10}$O—, —N(R$^{10}$)$_2$ or $C_2$–$C_6$ alkenyl,
c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, R$^{10}$O— and —N(R$^{10}$)$_2$;

$R^{1c}$ is selected from:
a) hydrogen,
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—, and
c) unsubstituted or substituted aryl;

$R^3$, $R^4$ and $R^5$ are independently selected from H and CH$_3$;

$R^2$ is H;

or $C_{1-5}$ alkyl, unbranched or branched, unsubstituted or substituted with one or more of:
1) aryl,
2) heterocycle,
3) OR$^6$,
4) SR$^{6a}$, SO$_2$R$^{6a}$, or
5)

and any two of $R^2$, $R^3$, $R^4$, and $R^5$ are optionally attached to the same carbon atom;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^{6a}$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl unsubstituted or substituted by $C_1$–$C_6$ perfluoroalkyl, F, Cl, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, —N(R$^{10}$)$_2$, or R$^{11}$OC(O)NR$^{10}$—;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

$X^2$ is a bond, —$CH_2$—, —C(↑O)—, —$NR^6$C(↑O)—, —C(=O)$NR^6$—, —$NR^6$—, —O— or —$S(=O)_m$—;

Z is an unsubstituted or substituted aryl, wherein the substituted aryl is substituted with one or more of the following:
  1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl, substituted aryl or heterocycle,
    e) HO,
    f) —$S(O)_m$ $R^{6a}$, or
    g) —C(O)$NR^6R^7$,
  2) aryl or heterocycle,
  3) halogen,
  4) $OR^6$,
  5) $NR^6R^7$,
  6) CN,
  7) $NO_2$,
  8) $CF_3$;
  9) —$S(O)_m$ $R^{6a}$,
  10) —C(O)$NR^6R^7$, or
  11) $C_3$–$C_6$ cycloalkyl;

m is 0, 1 or 2;
n is 0, 1, 2, 3 or 4;
p is 0, 1, 2, 3 or 4;
r is 0 to 5, provided that r is 0 when V is hydrogen;
s is 0 or 1;
t is 1; and
v is 0, 1 or 2;
or a pharmaceutically acceptable salt thereof.

3. The compound according to claim 1 of the formula D:

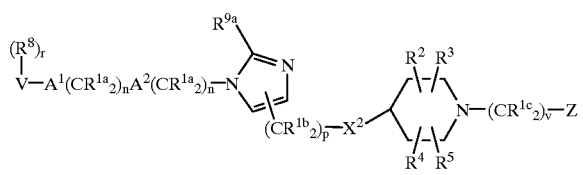

D wherein:
$R^{1a}$ is selected from: hydrogen or $C_1$–$C_6$ alkyl;
$R^{1b}$ is independently selected from:
  a) hydrogen,
  b) aryl, heterocycle, cycloalkyl, $R^{10}O$—, —$N(R^{10})_2$ or $C_2$–$C_6$ alkenyl,
  c) $C_1$–$C_6$ alkyl unsubstituted or substituted by unsubstituted or substituted aryl, heterocycle, cycloalkyl, alkenyl, $R^{10}O$—, or —$N(R^{10})_2$;
$R^{1c}$ is selected from:
  a) hydrogen,
  b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{10}OC(O)$—$NR^{10}$—, and
  c) unsubstituted or substituted aryl;

$R^3$ and $R^4$ independently selected from H and $CH_3$;
$R^2$ is selected from H; $OR^{10}$;

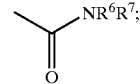

or $C_{1-5}$ alkyl, unbranched or branched, unsubstituted or substituted with one or more of:
  1) aryl,
  2) heterocycle,
  3) $OR^6$,
  4) $SR^{6a}$, $SO_2R^{6a}$, or
  5)

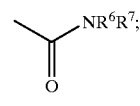

and $R^2$, $R^3$ and $R^4$ are optionall attached to the same carbon atom;

$R^6$ and $R^7$ are independently selected from:
  H; $C_{1-4}$ alkyl, $C_{3-6}$ cycloalkyl, aryl, heterocycle, unsubstituted or substituted with:
    a) $C_{1-4}$ alkoxy,
    b) halogen, or
    c) aryl or heterocycle;

$R^{6a}$ is selected from:
  $C_{1-4}$ alkyl or $C_{3-6}$ cycloalkyl, unsubstituted or substituted with:
    a) $C_{1-4}$ alkoxy,
    b) halogen, or
    c) aryl or heterocycle;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—C(NR10)—, $R^{10}C(O)$—, —$N(R^{10})_2$, or $R^{11}OC(O)NR^{10}$—;

$R^{9a}$ is hydrogen or methyl;
$R^{10}$ is independently selected from hydrogen, $C_1$–$C_{14}$ alkyl, substituted or unsubstituted benzyl and substituted or unsubstituted aryl;
$R^{11}$ is independently selected from $C_1$–$C_6$ alkyl and substituted or unsubstituted aryl;
$A^1$ and $A^2$ are independently selected from: a bond, —CH=CH—, —C≡C—, —C(O)—, —C(O)$NR^{10}$—, —$NR^{10}C(O)$—, O, —$N(R^{10})$—, or $S(O)_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

$X^2$ is a bond, —$CH_2$—, —$C(=O)$—, —$NR^6C(=O)$—, —$C(=O)NR^6$—, —$NR^6$—, or —$S(=O)_m$—;

Z is an unsubstituted or substituted aryl, wherein the substituted aryl is substituted with one or more of the following:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl, substituted aryl or heterocycle,
   e) HO,
   f) —$S(O)_mR^{6a}$, or
   g) —$C(O)NR^6R^7$,
2) aryl or heterocycle,
3) halogen,
4) $OR^6$,
5) $NR^6R^7$,
6) CN,
7) $NO_2$,
8) $CF_3$;
9) —$S(O)_m R^{6a}$,
10) —$C(O)NR^6R^7$, or
11) $C_3$–$C_6$ cycloalkyl;

m is 0, 1 or 2;
n is 0, 1, 2, 3 or 4;
p is 0, 1, 2, 3 or 4; and
r is 0 to 5, provided that r is 0 when V is hydrogen; and
v is 0, 1 or 2;
or a pharmaceutically acceptable salt thereof.

4. The compound according to claim 1 of the formula F:

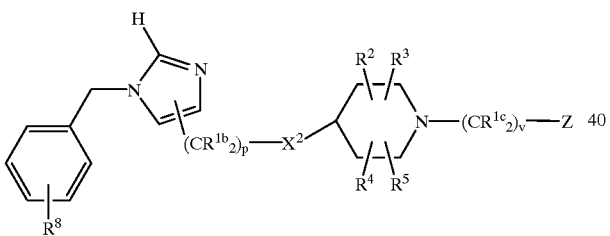

wherein:
$R^{1b}$ is independently selected from:
a) hydrogen,
b) aryl, heterocycle, cycloalkyl, $R^{10}O$—, —$N(R^{10})_2$ or $C_2$–$C_6$ alkenyl,
c) $C_1$–$C_6$ alkyl unsubstituted or substituted by unsubstituted or substituted aryl, heterocycle, cycloalkyl, alkenyl, $R^{10}O$—, or —$N(R^{10})_2$;

$R^{1c}$ is selected from:
a) hydrogen,
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—, and
c) unsubstituted or substituted aryl;

$R^3$ and $R^4$ independently selected from H and $CH_3$;

$R^2$ is selected from H; $OR^{10}$;

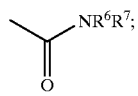

or $C_{1-5}$ alkyl, unbranched or branched, unsubstituted or substituted with one or more of:
1) aryl,
2) heterocycle,
3) $OR^6$,
4) $SR^{6a}$, $SO_2R^{6a}$, or
5)

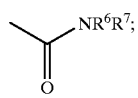

and $R^2$, $R^3$ and $R^4$ are optionally attached to the same carbon atom;

$R^6$, $R^7$ and $R^{7a}$ are independently selected from:
H; $C_{1-4}$ alkyl, $C_{3-6}$ cycloalkyl, aryl, heterocycle, unsubstituted or substituted with:
  a) $C_{1-4}$ alkoxy,
  b) halogen, or
  c) aryl or heterocycle;

$R^{6a}$ is selected from:
$C_{1-4}$ alkyl or $C_{3-6}$ cycloalkyl, unsubstituted or substituted with:
  a) $C_{1-4}$ alkoxy,
  b) halogen, or
  c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$X^2$ is —$CH_2$—, —$C(=O)$—, —$C(=O)NR^6$— or —$NR^6$—;

Z is an unsubstituted or substituted aryl, wherein the substituted aryl is substituted with one or more of the following:
1) $C_{1-4}$ alkyl, unsubstituted or substituted with:
   a) $C_{1-4}$ alkoxy,
   b) $NR^6R^7$,
   c) $C_{3-6}$ cycloalkyl,
   d) aryl, substituted aryl or heterocycle,
   e) HO,
   f) —$S(O)_mR^{6a}$, or
   g) —$C(O)NR^6R^7$,
2) aryl or heterocycle,
3) halogen,
4) $OR^6$,
5) $NR^6R^7$,
6) CN, 7) $NO_2$,
8) $CF_3$;
9) —$S(O)_m R^{6a}$,
10) —$C(O)NR^6 R^7$, or
11) $C_3$–$C_6$ cycloalkyl;
m is 0, 1 or 2;
p is 0, 1, 2, 3 or 4; and
v is 0, 1 or 2;
or a pharmaceutically acceptable salt thereof.

5. The compound according to claim 1 wherein $X^2$ is a bond, —$CH_2$—, —$C(=O)$—, —$NR^6C(=O)$—, —$C(=O)NR^6$— or —$S(=O)_m$—.

6. The compound according to claim 1 which is:
1-(1-(3-chlorobenzoyl)piperidin-4-ylmethyl)-5-(4-cyanobenzyl)imidazole

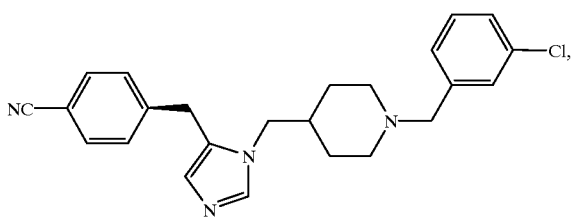

or a pharmaceutically acceptable salt or optical isomer thereof.

7. The compound according to claim 1 which is:
4-{5-[(1-benzylpiperidin-4-ylamino)$_m$ ethyl]imidazol-1-ylmethyl}benzonitrile

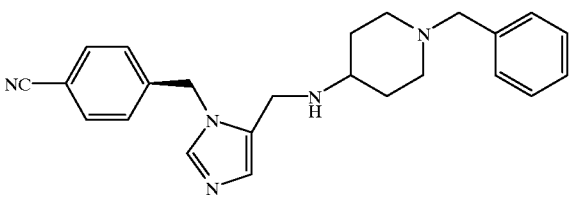

or a pharmaceutically acceptable salt or optical isomer thereof.

8. A compound which inhibits farnesyl-protein transferase which is:
1-(piperidin-4-ylmethyl)-5-(4-cyanobenzyl)imidazole;
1-(1-phenylpiperidin-4-ylmethyl)-5-(4-cyanobenzyl)imidazole;
1-(1-(2-methylphenyl)piperidin-4-ylmethyl)-5-(4-cyanobenzyl)imidazole;
1-(1-(2-chlorobenzoyl)piperidin-4-ylmethyl)-5-(4-cyanobenzyl)imidazole;
1-( 1-(3-chlorobenzoyl)piperidin-4-ylmethyl)-5-(4-cyanobenzyl)imidazole;
1-(1-(3-chlorobenzenesulfonyl)piperidin-4-ylmethyl)-5-(4-cyanobenzyl)imidazole;
1-(1-(3-chlorobenzyl)piperidin-4-ylmethyl)-5-(4-cyanobenzyl)imidazole;
2-[3-(4-cyanobenzyl)-3H-imidazol-1-yl]-N-(1-phenylpiperidin-4-yl)acetamide;
2-[3-(4-cyanobenzyl)-3H-imidazol-1-yl]-N-benzyl-N-(1-phenylpiperidin-4-yl)acetamide;
2-[3-(4-cyanobenzyl)-3H-imidazol-1-yl]-N-phenethyl-N-(1-phenylpiperidin-4-yl)acetamide;
4-{5-[(1-phenylpiperidin-4-ylamino)methyl]imidazol-1-ylmethyl}benzonitrile;
4-(5-{[benzyl(1-phenylpiperidin-4-yl)amino]methyl}imidazol-1-ylmethyl)benzonitrile;
4-(5-{[phenethyl(1-phenylpiperidin-4-yl)amino]methyl}imidazol-1-ylmethyl)benzonitrile;
4-{5-[2-(1-phenylpiperidin-4-ylamino)ethyl]imidazol-1-ylmethyl}benzonitrile;
4-(5-{2-[benzyl(1-phenylpiperidin-4-yl)amino]ethyl}imidazol-1-ylmethyl)benzonitrile;
2-[3-(4-cyanobenzyl)-3H-imidazol-1-yl]-N-(4-cyanobenzyl)-N-(1-phenylpiperidin-4-yl)acetamide;
N-(1-benzylpiperidin-4-yl)-2-[3-(4-cyanobenzyl)-3H-imidazol-4-yl]acetamide; or
4-{5-[(1-benzylpiperidin-4-ylamino)methyl]imidazol-1-ylmethyl}benzonitrile;
or a pharmaceutically acceptable salt or optical isomer thereof.

9. A pharmaceutical composition comprising a pharmaceutical carrier, and dispersed therein, a therapeutically effective amount of a compound of claim 1.

10. A pharmaceutical composition comprising a pharmaceutical carrier, and dispersed therein, a therapeutically effective amount of a compound of claim 4.

11. A pharmaceutical composition comprising a pharmaceutical carrier, and dispersed therein, a therapeutically effective amount of a compound of claim 8.

* * * * *